(12) United States Patent
Dumont et al.

(10) Patent No.: US 10,010,622 B2
(45) Date of Patent: Jul. 3, 2018

(54) FACTOR VIII CHIMERIC AND HYBRID POLYPEPTIDES, AND METHODS OF USE THEREOF

(75) Inventors: Jennifer A. Dumont, Groton, MA (US); Susan Low, Pepperill, MA (US); Alan J. Bitoni, Acton, MA (US); Glenn Pierce, Rancho Santa Fe, CA (US); Alvin Luk, Boston, MA (US); Haiyan Jiang, Belmont, MA (US); Byron McKinney, San Diego, CA (US); Matt Ottmer, Newton, MA (US); Jurg Sommer, Wayland, MA (US); Karen Nugent, Owlswick (GB); Lian Li, Lexington, MA (US); Robert Peters, Needham, MA (US)

(73) Assignee: Bioverativ Therapeutics Inc., Waltham, MA (US)

( * ) Notice: Subject to any disclaimer, the term of this patent is extended or adjusted under 35 U.S.C. 154(b) by 1058 days.

(21) Appl. No.: 14/131,600

(22) PCT Filed: Jul. 6, 2012

(86) PCT No.: PCT/US2012/045784
§ 371 (c)(1),
(2), (4) Date: Jun. 13, 2014

(87) PCT Pub. No.: WO2013/009627
PCT Pub. Date: Jan. 17, 2013

(65) Prior Publication Data
US 2014/0294821 A1 Oct. 2, 2014

Related U.S. Application Data

(60) Provisional application No. 61/506,015, filed on Jul. 8, 2011, provisional application No. 61/522,647, filed on Aug. 11, 2011, provisional application No. 61/541,561, filed on Sep. 30, 2011, provisional application No. 61/569,158, filed on Dec. 9, 2011, provisional application No. 61/586,443, filed on Jan. 13, 2012, provisional application No. 61/622,789, filed on Apr. 11, 2012, provisional application No. 61/657,641, filed on Jun. 8, 2012.

(51) Int. Cl.
| C07K 14/755 | (2006.01) |
| A61K 47/48 | (2006.01) |
| A61K 38/37 | (2006.01) |
| G01N 33/86 | (2006.01) |
| A61K 47/60 | (2017.01) |
| A61K 47/68 | (2017.01) |

(52) U.S. Cl.
CPC ........ *A61K 47/48369* (2013.01); *A61K 38/37* (2013.01); *A61K 47/60* (2017.08); *A61K 47/68* (2017.08); *C07K 14/755* (2013.01); *G01N 33/86* (2013.01); *C07K 2319/00* (2013.01); *C07K 2319/31* (2013.01)

(58) Field of Classification Search
None
See application file for complete search history.

(56) References Cited

U.S. PATENT DOCUMENTS

| 4,757,006 A | 7/1988 | Toole, Jr. et al. |
| 4,868,112 A | 9/1989 | Toole, Jr. |
| 4,965,199 A | 10/1990 | Capon et al. |
| 4,994,371 A | 2/1991 | Davie et al. |
| 5,004,803 A | 4/1991 | Kaufman et al. |
| 5,112,950 A | 5/1992 | Meulien et al. |
| 5,171,844 A | 12/1992 | Van Ooyen et al. |
| 5,364,771 A | 11/1994 | Lollar et al. |
| 5,543,502 A | 8/1996 | Nordfang et al. |
| 5,563,045 A * | 10/1996 | Pittman ............... C07K 14/755 435/252.3 |
| 5,595,886 A | 1/1997 | Chapman et al. |
| 5,610,278 A | 3/1997 | Nordfang et al. |
| 5,712,122 A | 1/1998 | Boime et al. |
| 5,789,203 A | 8/1998 | Chapman et al. |
| 5,859,204 A | 1/1999 | Lollar |
| 5,972,885 A | 10/1999 | Spira et al. |
| 6,048,720 A | 4/2000 | Dalborg et al. |
| 6,060,447 A | 5/2000 | Chapman et al. |
| 6,228,620 B1 | 5/2001 | Chapman et al. |

(Continued)

FOREIGN PATENT DOCUMENTS

| EP | 0154316 A2 | 9/1985 |
| EP | 0295597 A2 | 12/1988 |

(Continued)

OTHER PUBLICATIONS

Jefferis et al., Nat Rev Drug Discov. Mar. 2009;8(3):226-34. doi: 10.1038/nrd2804.*
McCue et al., J Chromatogr A. Nov. 6, 2009;1216(45):7824-30. doi: 10.1016/j.chroma.2009.09.045.*
Mols et al., In Vitro Cell Dev Biol Anim. Mar.-Apr. 2005;41(3-4):83-91.*
Pillay et al., In Vitro Cell Dev Biol Anim. Mar.-Apr. 2005;41(3-4):83-91.*
Pittman, D., et al. "Post-translational Requirements for Functional Factor V and Factor VIII Secretion in Mammalian Cells," *Journal of Biological Chemistry* 269:17329-17337, American Society for Biochemistry and Molecular Biology Inc., United States (1994).

(Continued)

*Primary Examiner* — Michael Szperka
(74) *Attorney, Agent, or Firm* — Sterne, Kessler, Goldstein & Fox P.L.L.C.

(57) ABSTRACT

The present invention provides methods of administering Factor VIII (processed FVIII, single chain FVIII, or a combination thereof); methods of administering chimeric and hybrid polypeptides comprising Factor VIII; chimeric and hybrid polypeptides comprising Factor VIII; polynucleotides encoding such chimeric and hybrid polypeptides; cells comprising such polynucleotides; and methods of producing such chimeric and hybrid polypeptides using such cells.

22 Claims, 28 Drawing Sheets

(56) References Cited

U.S. PATENT DOCUMENTS

Figure 1:
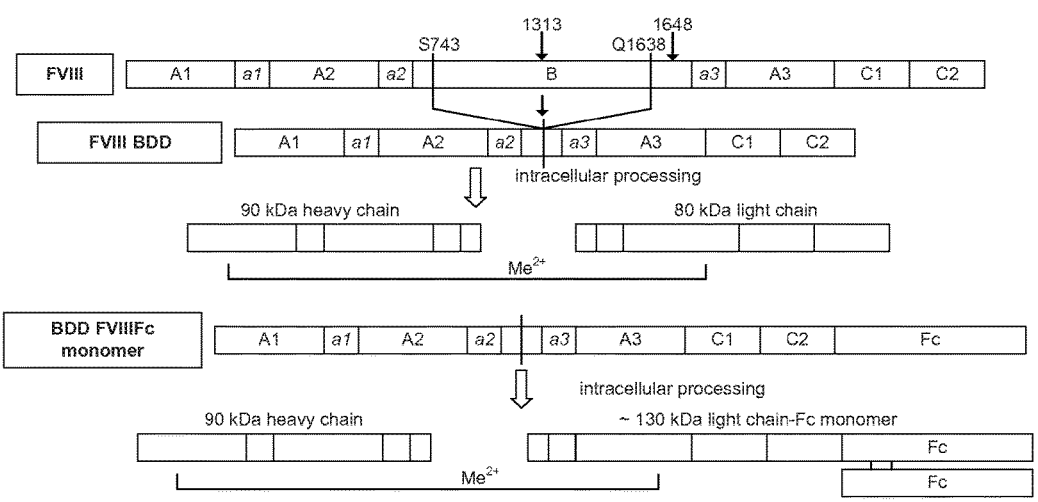

| | | | |
|---|---|---|---|
| 6,251,632 | B1 | 6/2001 | Lillicrap et al. |
| 6,316,226 | B1 | 11/2001 | Van Ooyen et al. |
| 6,346,513 | B1 | 2/2002 | Van Ooyen et al. |
| 6,376,463 | B1 | 4/2002 | Lollar |
| 6,458,563 | B1 | 10/2002 | Lollar |
| 6,686,179 | B2 | 2/2004 | Fleer et al. |
| 7,041,635 | B2 | 5/2006 | Kim et al. |
| 7,348,004 | B2 * | 3/2008 | Peters .................. C07K 5/0806 424/178.1 |
| 7,404,956 | B2 | 7/2008 | Peters et al. |
| 7,592,010 | B2 | 9/2009 | Rosen et al. |
| 7,632,921 | B2 | 12/2009 | Pan et al. |
| 7,862,820 | B2 * | 1/2011 | Peters .................. C07K 14/475 424/133.1 |
| 8,329,182 | B2 | 12/2012 | Peters et al. |
| 8,815,250 | B2 | 8/2014 | Rivera et al. |
| 9,611,310 | B2 * | 4/2017 | Low ...................... C07K 14/755 |
| 2005/0100990 | A1 | 5/2005 | Saenko et al. |
| 2005/0118684 | A1 * | 6/2005 | Lollar .................. C07K 14/755 435/69.6 |
| 2009/0087411 | A1 | 4/2009 | Fares et al. |
| 2009/0092582 | A1 | 4/2009 | Bogin et al. |
| 2009/0163699 | A1 | 6/2009 | Chamberlain et al. |
| 2009/0264627 | A1 | 10/2009 | Gillies et al. |
| 2010/0120664 | A1 * | 5/2010 | Schulte ................ C07K 14/745 514/13.7 |
| 2010/0189682 | A1 | 7/2010 | Schellenberger et al. |
| 2010/0292130 | A1 | 11/2010 | Skerra et al. |
| 2013/0108629 | A1 | 5/2013 | Dumont et al. |
| 2013/0274194 | A1 | 10/2013 | Dumont et al. |

FOREIGN PATENT DOCUMENTS

| | | | | |
|---|---|---|---|---|
| EP | | 0401384 A1 | 12/1990 | |
| EP | | 2173890 B1 | 3/2011 | |
| WO | | WO-8704187 A1 | 7/1987 | |
| WO | | WO-8800831 A1 | 2/1988 | |
| WO | | WO-8803558 A1 | 5/1988 | |
| WO | | WO-8808035 A1 | 10/1988 | |
| WO | | WO-9109122 A1 | 6/1991 | |
| WO | | WO-9216221 A1 | 10/1992 | |
| WO | | WO-9320093 A1 | 10/1993 | |
| WO | | WO-9411503 A2 | 5/1994 | |
| WO | | WO-9534326 A1 | 12/1995 | |
| WO | | WO-2004101740 A2 | 11/2004 | |
| WO | | WO-2006071199 A1 | 7/2006 | |
| WO | | WO-2007103515 A2 | 9/2007 | |
| WO | | WO-2008155134 A1 | 12/2008 | |
| WO | | WO-2009023270 A2 | 2/2009 | |
| WO | | WO-2010091122 A1 | 8/2010 | |
| WO | | WO-2011069164 A2 | 6/2011 | |
| WO | | WO-2012006623 A1 * | 1/2012 | ........... C07K 14/755 |
| WO | | WO 2012006635 A1 * | 1/2012 | ........... C07K 14/745 |

OTHER PUBLICATIONS

Donath, M.J., et al. "Characterization of des-(741-1668)-factor VIII, a single-chain factor VIII variant with a fusion site susceptible to proteolysis by thrombin and factor Xa," *Biochemical Journal* 312:49-55, Portland Press, United States (1994).

Aledort, L.M., et al., "A longitudinal study of orthopaedic outcomes for severe factor-VIII-deficient haemophiliacs," Journal of Internal Medicine 236(4):391-399, Blackwell Scientific Publications, England (1994).

Armour, K.L., et al., "Recombinant human IgG molecules lacking Fcgamrna receptor I binding and monocyte triggering activities," European Journal of Immunology 29(8):2613-2624, Wiley-VCH Verlag GmbH, Germany (1999).

Aznar, J.A., et al., "The orthopaedic status of severe haemophiliacs in Spain," Haemophilia 6(3):170-176, Blackwell Publishing Ltd., England (2000).

Bai, Y., et al., "Recombinant granulocyte colony-stimulating factor-transferrin fusion protein as an oral myelopoietic agent," Proceedings of the National Academy of Sciences USA 102(20):7292-7296, National Academy of Sciences, United States (2005).

Brandsma, M.E., et al., "Recombinant human transferrin: Beyond iron binding and transport," Biotechnology Advances 29(2):230-238, Elsevier, United States (2011, available online on Dec. 13, 2010).

Brutlag, D.L., et al., "Improved sensitivity of biological sequence database searches," Computer Applications in the Biosciences 6(3):237-245, Oxford University Press, England (1990).

Burmeister, W.P., et al., "Crystal structure of the complex of rat neonatal Fc receptor with Fc," Nature 372(6504):379-383, Nature Publishing Group, England (1994).

Cameron, C., et al., "The canine factor VIII cDNA and 5' flanking sequence," Thrombosis and Haemostasis 79(2):317-322, Schattauer Verlag, Germany (1998).

Coppola, A., et al., "Primary Prophylaxis in Children with Haemophilia," Blood Transfusion Prophylaxis in Congenital Coagulation Disorders 6(Suppl 2):s4-s11, Society of Transfusion Medicine and Immunohaematology, Italy (2008).

Cutler, J.A., et al., "The Identification and Classification of 41 Novel Mutations in the Factar VIII Gene (F8C)," Human Mutation 19(3):274-278, Wiley-Liss, Inc., England (2002).

Dennis, M.S., et al., "Albumin Binding as a General Strategy for Improving the Pharmacokinetics of Proteins," The Journal of Biological Chemistry 277(38):35035-35043, The American Society for Biochemistry and Molecular Biology, Inc., United States, (2002).

Dobeli, H., et al., "Role of the carboxy-terminal sequence on the biological activity of human immune interferon (IFN-γ)," Journal of Biotechnology 7:199-216, Elsevier Science Publishers B.V., Netherlands (1988).

Dumont, J.A., et al., "Factor VIII-Fc Fusion Protein Shows Extended Half-life and Hemostatic Activity in Hemophilia A Dogs," Blood 116(21): Abstract 545, The American Society of Hematology, United States (2009).

Dumont, J.A., et al., "Monomeric Fc Fusions: Impact on Pharmacokinetic and Biological Activity of Protein Therapeutics," BioDrugs 20(3):151-160, Adis Data Information B.V., New Zealand (2006).

Dumont, J.A., et al., "Monomeric Fc fusion technology: an approach to create long lasting clotting factors," in: Kontermann R., ed., Therapeutic Proteins-Strategies to Modulate Half-Life, Chapter 11, Wiley VCH publisher.

Eaton, D.L., et al., "Construction and Characterization of an Active Factor VIII Variant Lacking the Central One-Third of the Molecule," Biochemistry 25(26):8343-8347, The American Chemical Society, United States (1986).

Fatouros, A., et al., "Recombinant factor VIII SQ—influence of oxygen, metal ions, pH and ionic strength on its stability in aqueous solution," International Journal of Pharmaceutics 155(1):121-131, Elsevier Science B.V., Netherlands (1997).

Feldman, B.M., et al., "Tailored prophylaxis in severe hemophilia A: interim results from the first 5 years of the Canadian Hemophilia Primary Prophylaxis Study," Journal of Thrombosis and Haemostasis 4(6):1228-1236, International Society on Thrombosis and Haemostasis, England (2006).

Francis, G.E., "Protein Modification and Fusion Proteins," Focus on Growth Factors 3(2):4-10, Mediscript, England (1992).

Friend, P.J., et al., "Phase I study of an engineered aglycosyiated humanized CD3 antibody in renal transplant rejection," Transplantation 68(11):1632-1637, Lippincott Williams & Wilkins, Inc., United States (1999).

Gayle, R.B. III., et al., "Identification of Regions in Interleukin-1α Important for Activity," The Journal of Biological Chemistry 268(29):22105-22111, The American Society for Biochemistry and Molecular Biology, Inc., United States (1993).

GenBank, "*Homo sapiens* coagulation factor VIII, procoagulant component (F8), transcript variant 1, mRNA", Accession No. NM_000132.3, accessed at http://www.ncbi.nlm.nih.gov/nuccore/NM_000132.3, May 11, 2014, 12 pages.

GenBank, "*Home sapiens* transferrin (TF), mRNA", Accession No. NM001063.1, accessed at http://www.ncbi.nlm.nih.gov/nuccore/NM_001063, May 25, 2014, 5 pages.

(56) References Cited

OTHER PUBLICATIONS

GenBank, "*Homo sapiens* transferrin (TF), mRNA,"Accessien No. XM002793 accessed at https://www.ncbi.nlm.nih.gov/nuccore/XM_002793.7?report=genbank, May 13, 2002, 2 pages.

GenBank, "*Homo sapiens* transferrin (TF), mRNA," Accession No. XM039845 accessed at https://www.ncbi.nlm.nih.gov/nuccore/XM_039845.1?report=genbank, Jul. 16, 2001, 2 pages.

GenBank, "*Homo sapiens* transferrin (TF), mRNA," Accession No. XM039847 accessead at http://www.ncbi.nlm.nih.gov/nuccore/XM_039847.1?report=genbank, Jul. 16, 2001, 2 pages.

GenBank, "Human transferrin mRNA, complete cds", Accession No. M12530.1, accessed at http://www.ncbi.nlm.nih.gov/nuccore/M12530.1, Jan. 14, 1995, 2 pages.

GenBank, "Transferrin [human, liver, mRNA, 2347 nt]", Accessian No. S95936.1, accessed at http://www.ncbi.nlm.nih/gov/nuccore/S95936, May 7, 1993, 2 pages.

Geraghty, S., et al., "Practice patterns in haemophilia A therapy—global progress towards optimal care," Haemophilia 12(1):75-81, Blackwell Publishing Ltd., England (2006).

Gitschier, J., et al. "Characterization of the human factor VIII gene,"Nature 312(5992):326-330, Nature Publishing Group, England (1984).

Hacker, M.R., et al., "Barriers to campliance with prophylaxis therapy in haemophilia," Haemophilia 7(4):392-396, Blackwell Publishing Ltd., England (2001).

Healey, J.F., et al., "The cDNA and Derived Amino Acid Sequence of Porcine Factor VIII," Blood 88(11):4209-4214, The American Society of Hematology, United States (1996).

Hoeben, R.C., et al., "Expression of Functional Factor VIII in Primary Human Skin Fibroblasts after Retrovirus-mediated Gene Transfer," The Journal of Biological Chemistry 265(13):7318-7323, The American Society for Biochemistry and Molecular Biology, Inc., United States (1990).

Holt, L.J., et al., "Anti-serum albumin domain antibodies for extending the half-lives of short lived drugs," Protein Engineering, Design & Selection 21(5):283-288, Oxford University Press, England, (2008).

Huang, C., "Receptor-Fc fusion therapeutics, traps, and MIMETIBODY technology," Current Opinion in Biotechnology 20(6):692-699, Elsevier Ltd., England (2009).

International Search Report and Written Opinion for Application No. PCT/US2012/045784, dated Dec. 21, 2012, 13 pages.

Kim, B.J., et al., "Transferrin Fusion Technology: a Novel Approach to Prolonging Biological Half-Life of Insulinotropic Peptides," The Journal of Pharmacology and Experimental Therapeutics 334(3):682-692, American Society for Pharmacology and Experimental Therapeutics, United States (2010).

Kraulis, P.J., et al., "The serum albumin-binding domain of streptococcal protein G is a three-helical bundle: a heteronuclear NMR study," FEBS Letters 378(2):190-194, Federation of European Biochemical Societies, Netherlands (1996).

Kreljz, W., et al., "When should prophylactic treatment in patients with haemophilia A and B start?—The German experience." Haemophilia 4(4):413-417, Blackwell Science Ltd., England (1998).

Langner, K.D., et al., "Synthesis of Biologically Active Deletion Mutants of Human Factor VIII:C," Behring Institute Mitteilungen 82:16-25, Behringwerke AG, Germany, (1988).

Lee, C.A., et al., "Pharmacokinetics of Recombinant Factor VIII (Recombinate) Using One-Stage Clotting and Chromogenic Factor VIII Assay" Thrombosis and Haemostasis 82(6):1644-1647,, Schattauer Verlag, Germany (1999).

Lencer, W.I. and Blumberg, R.S., "A passionate kiss, then run: exocytosis and recycling of IgG by FcRn," TRENDS in Cell Biology 15(1):5-9, Elsevier Science Publishers, England (2005).

Lenting, P.J., et al., "Clearance mechanisms of von Willebrand factor and factor VIII," Journal of Thrombosis and Haemostasis 5(7):1353-1360, International Society on Thrombosis and Haemostasis, England (2007).

Li, H., et al., "The role of the transferrin-transferrin-receptor system in drug delivery and targeting," TRENDS in Pharmacological Sciences 23(5):206-209, Elsevier Science Ltd., England (2002).

Liesner, R.J., et al., "The impact of prophylactic treatment on children with severe haemophilia," British Journal of Haematology 92(4):973-978, Blackwell Science Ltd., England (1996).

Lillicrap, D., "Improvements in factor concentrates," Current Opinion in Hematology 17(5):393-397, Wolters Kluwer Health and Lippincott Williams & Wilkins, United States (2010).

Linhult, M., et al., "Mutational analysis of the interaction between albumin-binding domain from streptococcal protein G and human serum albumin," Protein Science 11(2):206-213, Cold Spring Harbor Laboratory Press, United States (2002).

Liu, T., et al., "Recombinant FVIII Fc fusion protein is fully active in treating acute injury and demonstrates prolonged prophylactic efficacy in hemophilia a mice," Journal of Thrombosis and Haemostasis 9(Suppl 2):561,International Society on Thrombosis and Haemostasis, United States (Jul. 23-28, 2011) (Abstract P-WE-131).

Ljung, R.C.R., "Prophylactic treatment in Sweden—overtreatment or optimal model?," Haemophilia 4(4):409-412, Blackwell Science Ltd., England (1998).

Lofqvist, T., et al., "Haemophilia prophylaxis in young patients—a long-term follow-up," Journal of Internal Medicine 241(5):395-400, Blackwell Scientific Ltd., England (1997).

Lollar, P. and Parker, E.T., "Structural Basis for the Decreased Procoagulant Activity of Human Factor VIII Compared to the Porcine Homolog," Journal of Biological Chemistry 266(19):12481-12486, The American Society for Biochemistry and Molecular Biology, Inc., United States (1991).

Lollar, P., et al., "Coagulant Properties of Hybrid Human/Porcine Factor VIII Molecules," Journal of Biological Chemistry 267(33):23652-23657, The American Society for Biochemistry and Molecular Biology, Inc., United States (1992).

Malik, F., et al., "Polyethylene Glycol (PEG)-modified Granulocyte-Macrophage Colony-stimulating Factor (GM-CSF) with Conserved Biological Activity," Experimental Hematology 20(8):1028-1035, International Society for Experimental Hematology, United States (1992).

Manco-Johnson, M.J., et al., "Prophylaxis versus Episodic Treatment to Prevent Joint Disease in Boys with Severe Hemophilia," New England Journal of Medicine 357(6):535-544, Massachusetts Medical Society, United States (2007).

Mannucci, P.M,, et al., "The hemophilias—from royal genes to gene therapy," The New England Journal of Medicine 344(23):1773-1779, Massachusetts Medical Society, United States (2001).

McCue, J.T., et al., "Application of a Novel Affinity Adsorbent for the Capture and Purification of Recombinant Factor VIII Compounds," Journal of Chromatography 1216(45):7824-7830, Elsevier, United States (2009).

McCue, J.T., et al., "Application of a novel affinity adsorbent for the capture and purification of recombinant Factor VIII compounds," Journal of Chromatography A 1216:7824-7830, Elsevier B.V., Netherlands (2009).

Mei, B., et al., "Rational design of a fully active, long-acting PEGylated factor VIII for hemophilia A Treatment," Blood 116(2):270-279, The American Society of Hematology, United States (2010).

Metzner, H.J., et al., "Characterization of factor VIII/von Willebrand factor concentrates using a modified method of von Willebrand factor multimer analysis," Haemophilia 4(3):25-32, Blackwell Science Ltd., England (1998).

Meulien, P., et al., "A new recombinant procoagulant protein derived from the cDNA encoding human factor VIII," Protein Engineering 2(4):301-306, IRL Press Ltd, England (1988).

Mikaelsson, M. and Oswaldsson, U., "Assaying the Circulating Factor VIII Activity in Hemophilia A Patients Treated with Recombinant Factor VIII Products," Seminars in Thrombosis and Hemostasis 28(3):257-264, Thieme Medical Publishers, New York, (2002).

Molho, P., et al., "Epidemiological survey of the orthopaedic status of severe haemophilia A and B patients in France," Haemophilia 6(1):23-32, Blackwell Science Ltd., England (2000).

(56) References Cited

OTHER PUBLICATIONS

Morfini, M., "Pharmacokinetics of Factor VIII and factor IX," Haemophilia 9(Suppl 1):94-100, Blackwell Publishing Ltd., England (2003).

Muller, D. and Kontermann, R.E., "Recombinant bispecific antibodies for cellular cancer immunotherapy." Current Opinion in Molecular Therapeutics 9(4):319-326, The Thomson Corporation, England (2007).

Nilsson, I.M., et al., "Twenty-five years' experience of prophylactic treatment in severe haemophilia A and B," Journal of Internal Medicine 232(1):25-32, Blackwell Scientific Publications, England (1992).

Oganesyan, V., et al.. "Structural characterization of a human Fc fragment engineered for extended serum half-life," Molecular Immunology 46(8-9):1750-1755, Elsevier Ltd., United States (2009).

Petrini, P., et al., "Prophylaxis with Factor Concentrates in Preventing Hemophilic Arthropathy," The American Society of Pediatric Hematology/Oncology 13(3):280-287, Raven Press, Ltd., United States (1992).

Peyvandi, F., et al., "Genetic diagnosis of haemophilia and other inherited bleeding disorders," Haemophilia 12(Suppl 3):82-89, Blackwell Publishing, Ltd., England (2006).

Risebrough, N., et al., "Cost-utility analysis of Canadian tailored prophylaxis, primary prophylaxis and on-demand therapy in young children with severe haemophilia A," Haemophilia 14(4):743-752, Blackwell Publishing Ltd., England (2008).

Rodriguez-Merchan, E.C. "Management of Musculoskeletal Complications of Hemophilia," Seminars in Thrombosis and Hemostasis 29(1):87-98, Thieme Medical Publishers, Inc., United States (2003).

Ron, D., et al., "Expression of Biologically Active Recombinant Keratinocyte Growth Factor: Structure/function analysis of amino-terminal truncation mutants," The Journal of Biological Chemistry 268(4):2984-2988. American Society for Biochemistry and Molecular Biology, United States (1993).

Roopenian, D.C. and Akilesh, S., "FcRn: the neonatal Fc receptor comes of age," Nature Reviews Immunology 7(9):715-725, Nature Publishing Group, England (2007).

Roovers, R.C., et al., "Efficient inhibition of EGFR signaling and of tumour growth by antagonistic anti-EFGR Nanobodies," Cancer Immunology, Immunotherapy 56(3):303-317, Springer Verlag, Germany (2007).

Rosen, S., "Assay of Factor VIII:C with a Chromogenic Substrate," Scandinavian Journal of Haematology 33(Suppl 40):139-145, Munksgaard International Publishers, Denmark (1984).

Routledge, E.G., et al., "The effect of aglycosylation on the immunogenicity of a humanized therapeutic CD3 monoclonal antibody." Transplanation 60(8):847-853, Williams & Wilkins, United States (1995).

Sarver, N., et al., "Stable Expression of Recombinant Factor VIII Molecules Using a Bovine Papillomavirus Vector," DNA 6(6):553-564, Mary Ann Liebert, Inc., United States (1987).

Schellenberger, V., et al., "A recombinant polypeptide extends the in vivo half-life of peptides and proteins in a tunable manner," Nature Biotechnology 27(12):1186-1190, Nature America, Inc., United States (2009).

Schmidt, S.R., "Fusion-proteins as biopharmaceuticals—Applications and challenges," Current Opinion in Drug Discovery & Development 12(2):284-295, Thomson Reuters (Scientific) Ltd., England (2009).

Schulte, S., "Half-life extension through albumin fusion technologies," Thrombosis Research 124(2):S6-S8, Elsevier Ltd., United States (2009).

Shields, R.L., et al., "High Resolution Mapping of the Binding Site on Human IgG1 for FcγRI, FcγRII, FcγRIII, and FcRn and Design of IgG1 Variants with Improved Binding to the FcγR," The Journal of Biological Chemistry 276(9):6591-6604, The American Society for Biochemistry and Molecular Biology, Inc., United States (2001).

Siedlecki, C.A., et al., "Shear-Dependent Changes in the Three-Dimensional Structure of Human von Willebrand Factor," Blood 88(8):2939-2950, The American Society of Hematology, United States (1996).

Smith, N.L., et al., "Novel associations of multiple genetic loci with plasma levels of factor VII, factor VIII, and von Willebrand factor: The CHARGE Consortium," Circulation 121(12):1382-1392, American Heart Association, Inc., USA (2010).

Sommermeyer, V.K., et al., "Klinisch verwendete Hydroxyethylstarke: Physikalisch-chemische Charakterisierung," Krankenhauspharmazie 8(8):271-278, German pharmacist Publisher, Birkenwaldstr, Germany (1987).

Soucie, J.M., et al., "Mortality among males with hemophilia: relations with source of medical care," Blood 96(2):437-442, The American Society of Hematology, United States (2000).

Story, C.M., et al., "A Major Histocompatibility Complex Class I-like Fc Receptor Cloned from Human Placenta: Possible Role in Transfer of Immunoglobulin G from Mother to Fetus," The Journal of Experimental Medicine 180(6):2377-2381, The Rockefeller University Press, United States (1994).

Stroobants, A.K. et al., "Differences between one stage clotting and chromogenic factor VIII assay results," Journal of Thrombosis and Haemostasis 9(Suppl 2): 381-, International Society on Thrombosis and Haemostasis, Blackwell Pub., England (Jul. 23-28, 2011) (Abstract P-TU-230).

Tools, J.J., et al., "Molecular cloning of a cDNA encoding human antihaemophilic factor," Nature 312(5992):342-347, Nature Publishing Group, England (1984).

Toole, J.J., et al., "A large region (approximately equal to 95 kDa) of human factor VIII is dispensable for in vitro procoagulant activity," Proceedings of the National Academy of Sciences USA 83(16):5939-5942, National Academy of Sciences, United States (1986).

Trussel, S., et al., "New Strategy for the Extension of the Serum Half-Life of Antibody Fragments," Bioconjugate Chemistry 20(12):2286-2292, American Chemical Society, United States (2009).

Vaccaro, C., et al., "Engineering the Fc region of immunoglobulin G to modulate in vivo antibody levels," Nature Biotechnology 23(10):1283-1288, Nature America Publishing, United States (2005).

Van Den Berg, H.M., et al., "Comparing outcomes of different treatment regimens for severe haemophilia," Haemophilia 9(Suppl 1):27-31, Blackwell Publishing Ltd., England (2003).

Van Den Berg, H.M., et al., "Issues surrounding therapeutic choices for hemophilia patients," Haematologica 89(6):645-650, Blackwell Publishing Ltd., England (2004).

Vehar, G.A., et al., "Structure of human factor VIII," Nature 312(5992):337-342, Nature Publishing Group, England (1984).

Wakabayashi, H., et al., "Residues 110-126 in the A1 Domain of Factor VIII Contain a Ca2+ Binding Site Required for Cofactor Activity," The Journal of Biological Chemistry 279(13):12677-12684, The American Society for Biochemistry and Molecular Biology, Inc., United States (2004).

Wang, Y., et al., "Receptor-Mediated Activation of a Proinsulin-Transferrin Fusion Protein in Hepatoma Cells," Journal of Controlled Release 155(3):386-392, Elsevier B.V., Netherlands (Nov. 7, 2011).

Ward, E.S., and Ghetie, V., "The effector functions of immunoglobulins: implications for therapy," Therapeutic Immunology 2(2):77-94, Blackwell Science Ltd., England (1995).

Weidler, B., et al., "Pharmacokinetic parameters as criteria for clinical use of hydroxyethyl starch preparations," Arzneimittel-Forschung 41(5):494-498 Editio Cantor, Germany (1991).

White, G.C. II, et al., "Recombinant Factor IX," Thrombosis and Haemostasis 78(1):261-265, F.K. Schattauer Verlagsgesellschaft mbH, Germany (1997).

Wood, W.I., et al., "Expression of active human factor VIII from recombinant DNA Clones," Nature 312(5992):330-337, Nature Publishing Group, England (1984).

International Search Report in International Patent Application No. PCT/US2010/059136, United States Patent Office, Alexandria, Virginia, dated Jun. 2, 2011.

(56) References Cited

OTHER PUBLICATIONS

Co-pending U.S. Appl. No. 14/530,256 inventors Peters, R., et al., filed Oct. 31, 2014 (Not Yet Published)
English Language Abstract of Sommermeyer, V.K., et al., "Klinisch verwendete Hydroxyethylstarke: Physikalisch-chemische Charakterisierung," Krankenhauspharmazie 8(8):271-278, German pharmacist Publisher, Birkenwaldstr, Germany (1987) (listed as document NPL83).

\* cited by examiner

Figure 2
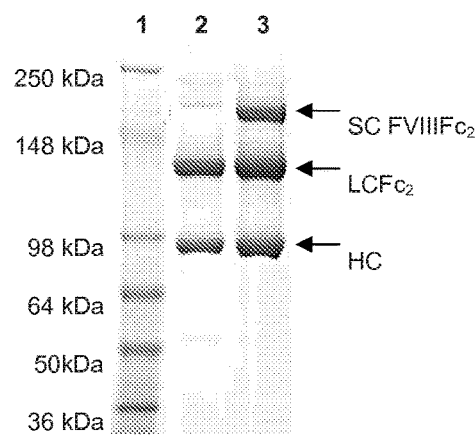
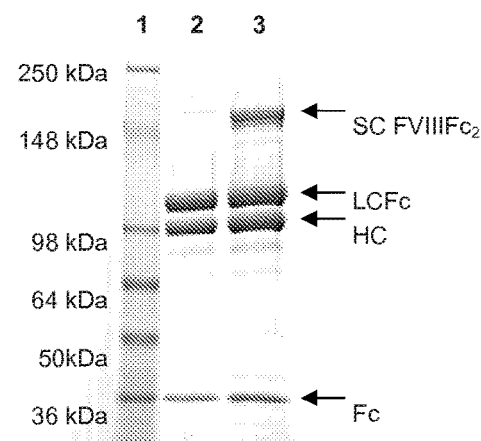
1. SeeBlue MW Marker
2. rFVIIIFc/PC5
3. rFVIIIFc
Figure 2C
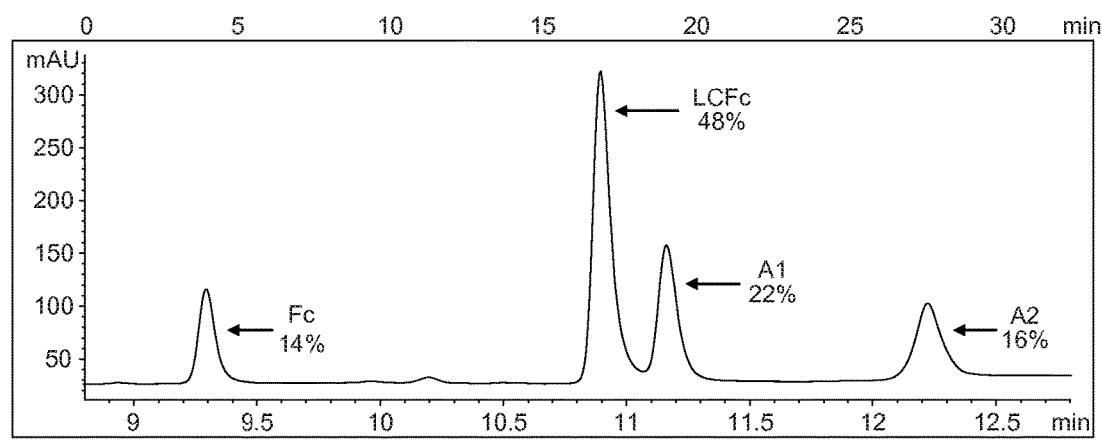

Figure 3
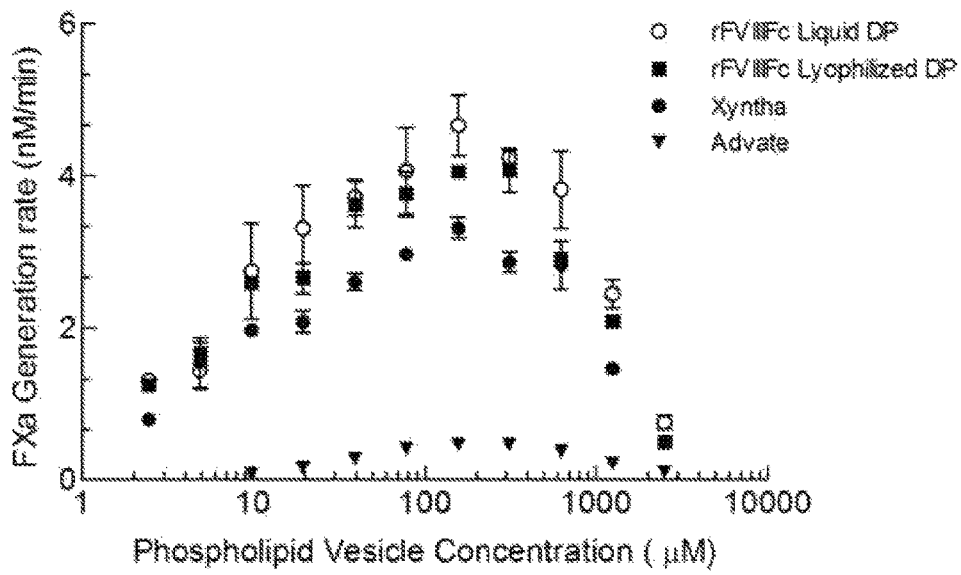
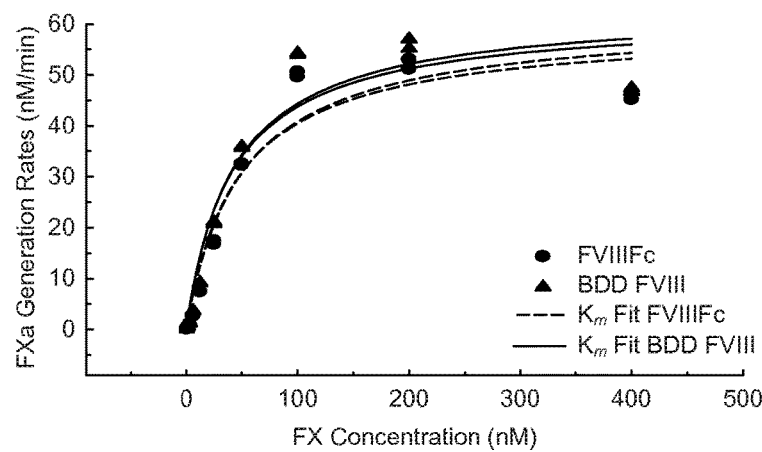
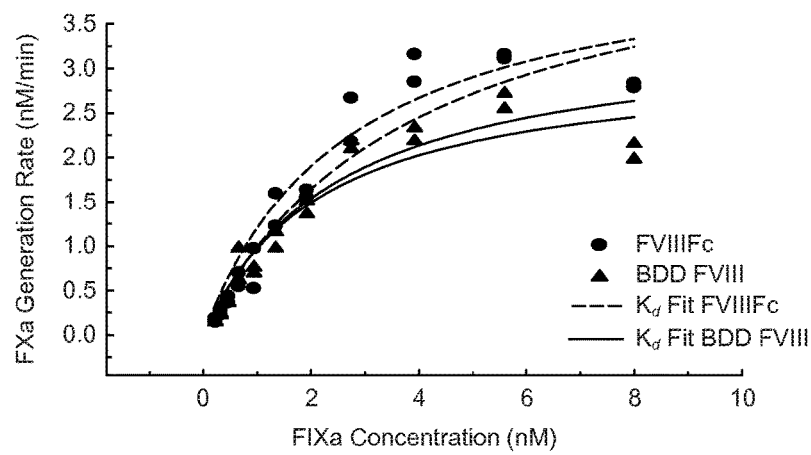

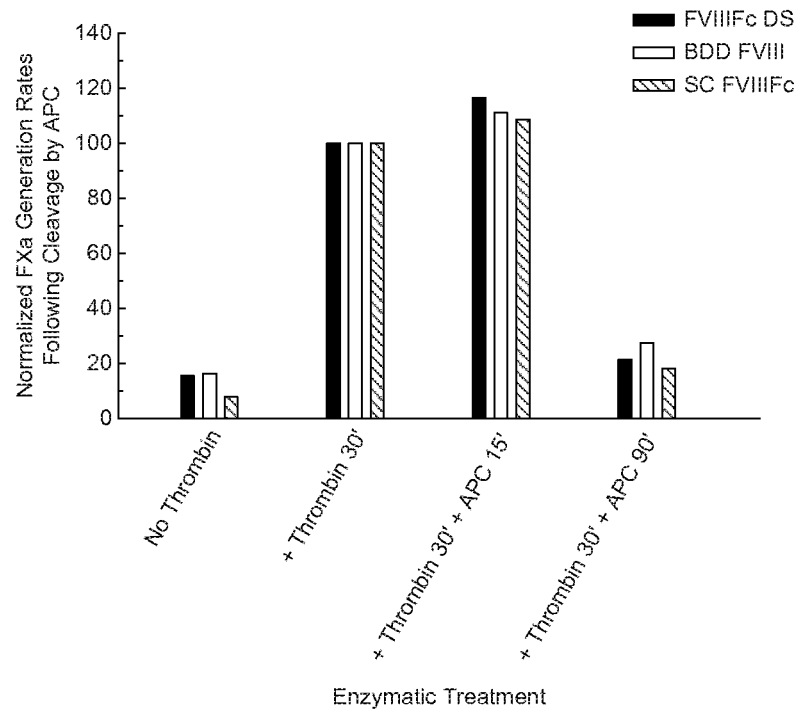

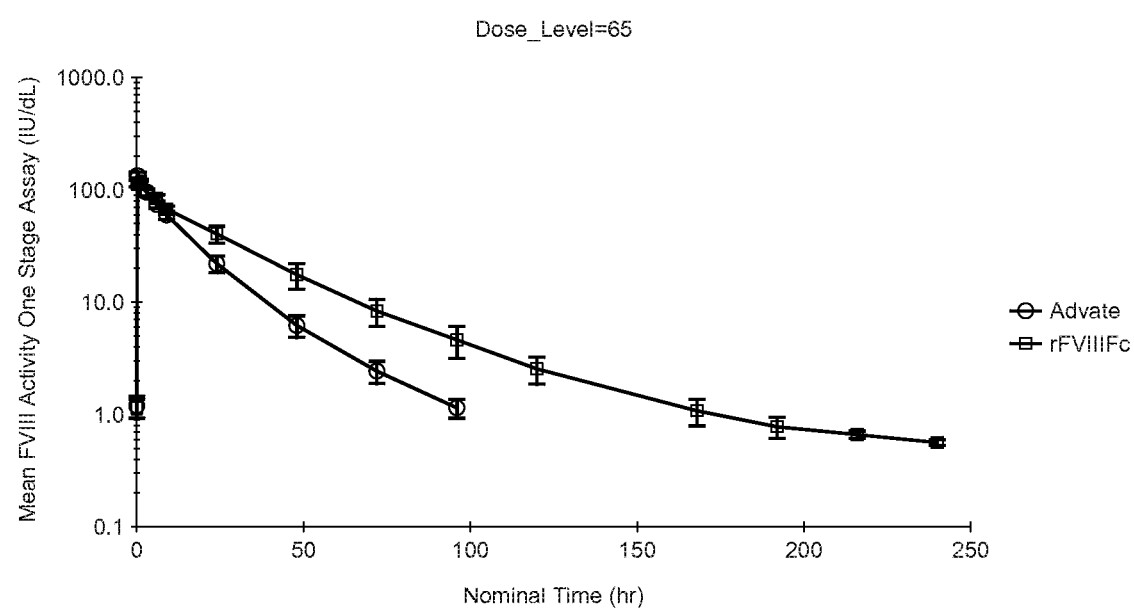

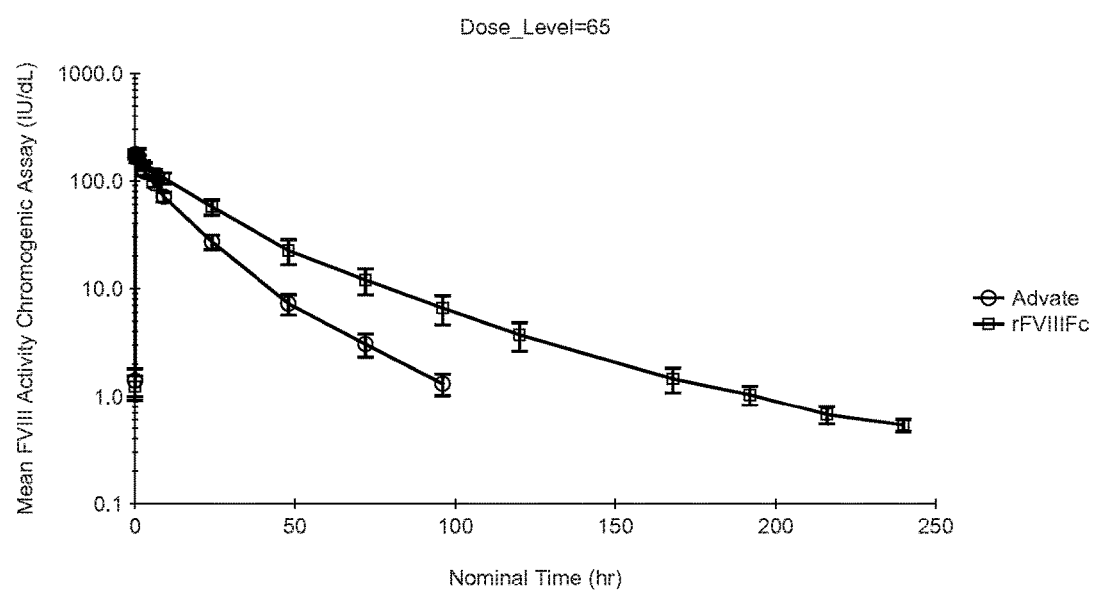

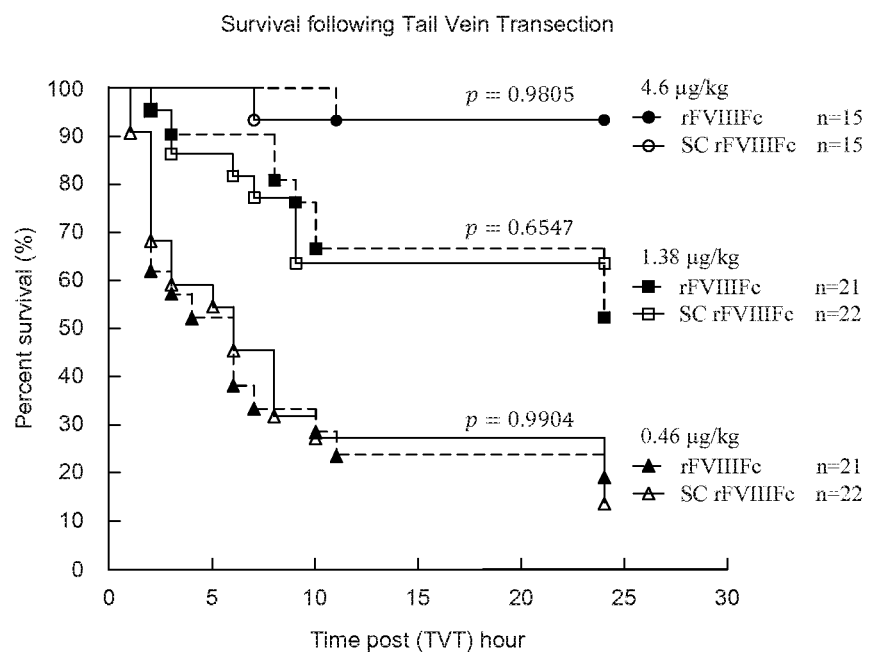

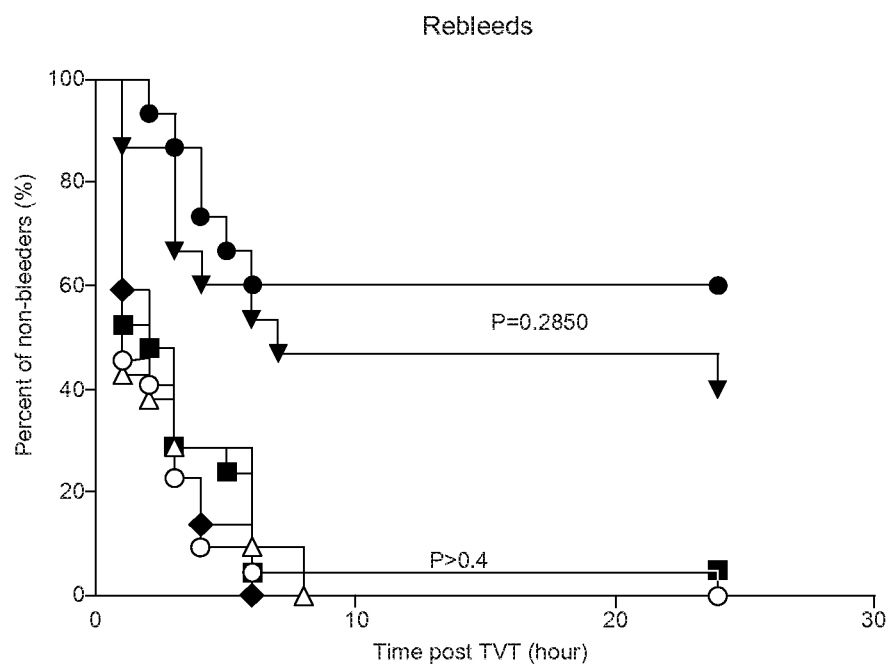

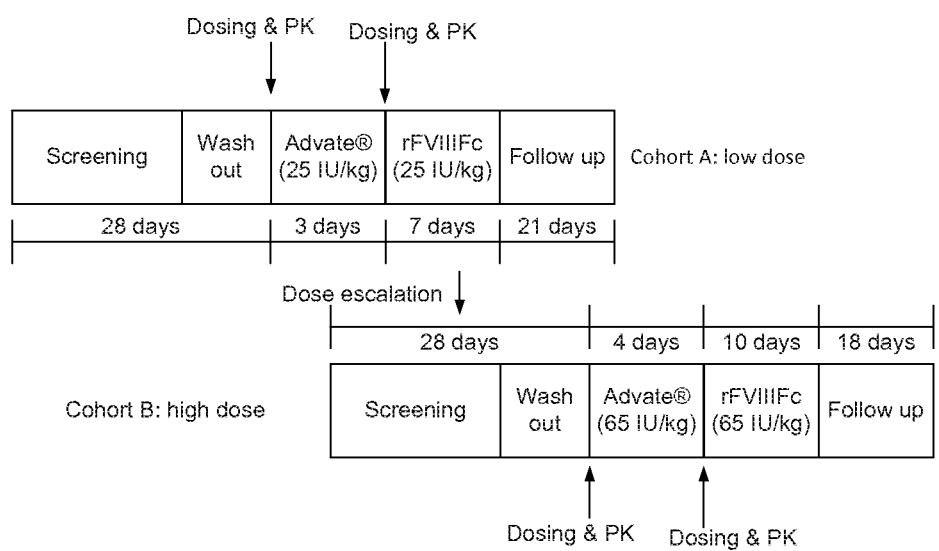
Figure 8 Study Design

Figure 12
(A)
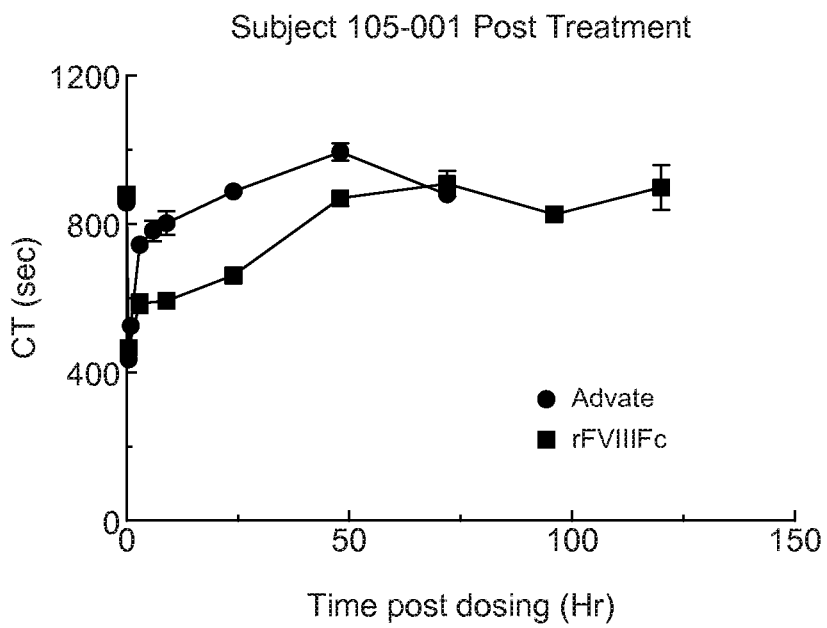
(B)
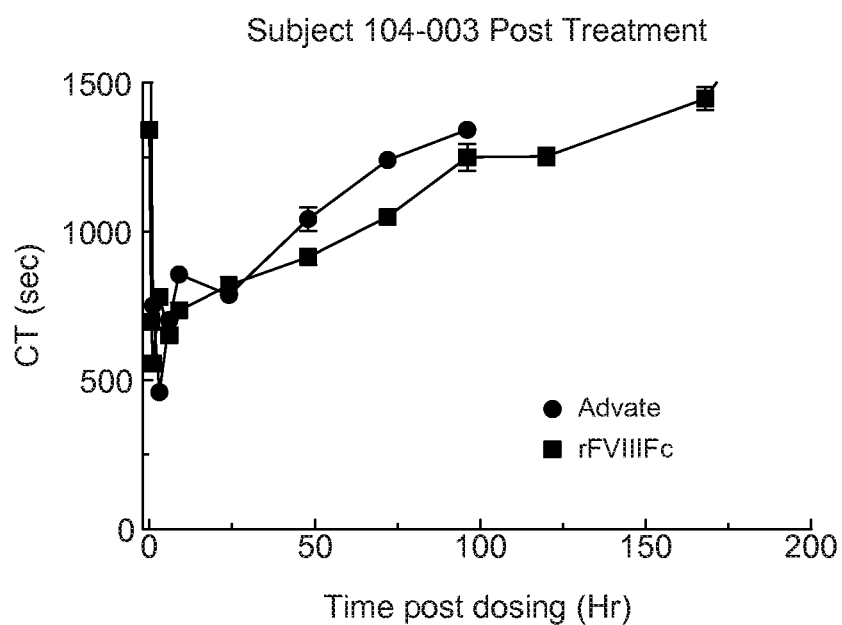

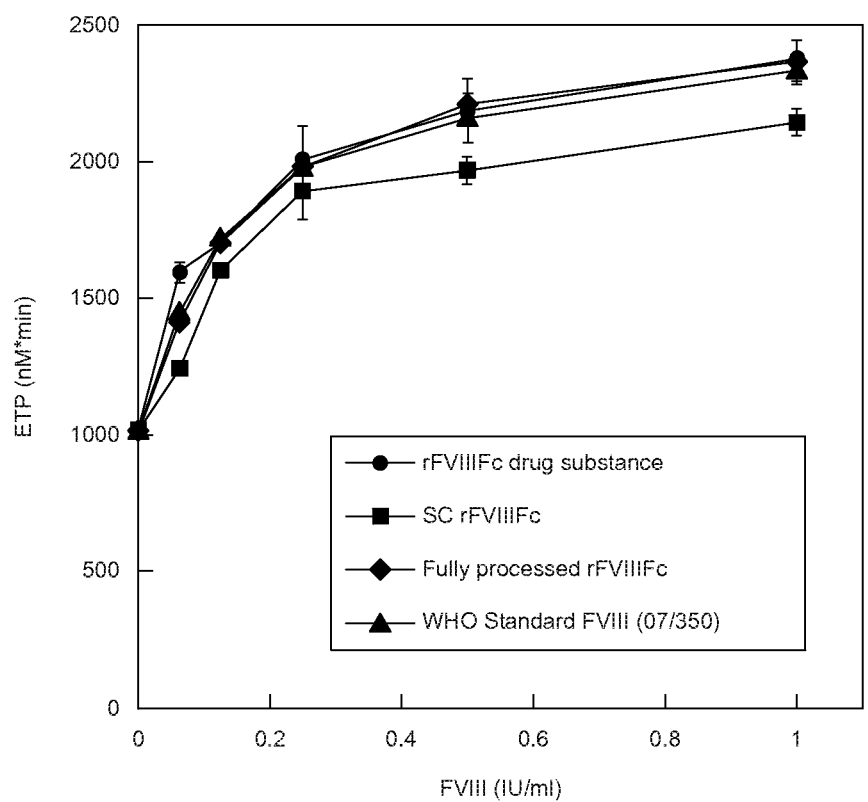

Binding curve, black; 1:1 fit, red
RU, resonance units; SC, single chain

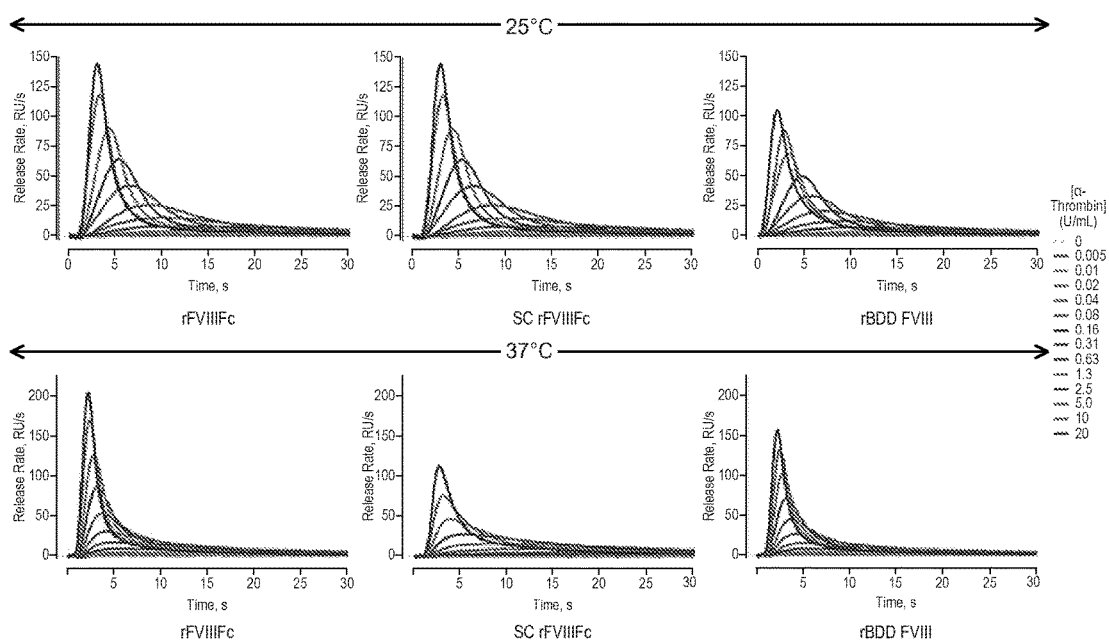

FACTOR VIII CHIMERIC AND HYBRID POLYPEPTIDES, AND METHODS OF USE THEREOF

REFERENCE TO EARLIER FILED APPLICATIONS

This application is the national phase application of International Application No. PCT/US2012/045784, filed Jul. 6, 2012 and published as WO 2013/009627, which claims the benefit of U.S. Provisional Application No. 61/506,015, filed Jul. 8, 2011, U.S. Provisional Application No. 61/522,647, filed Aug. 11, 2011, U.S. Provisional Application No. 61/541,561, filed Sep. 30, 2011, U.S. Provisional Application No. 61/569,158, filed Dec. 9, 2011, U.S. Provisional Application No. 61/586,443, filed Jan. 13, 2012, U.S. Provisional Application No. 61/622,789, filed Apr. 11, 2012, and U.S. Provisional Application No. 61/657,641, filed Jun. 8, 2012, all of which are incorporated herein by reference in their entireties.

REFERENCE TO SEQUENCE LISTING SUBMITTED ELECTRONICALLY VIA EFS-WEB

The content of the electronically submitted sequence listing (Name: 2159_3540007sequencelisting_ascii.txt, Size: 62,540 bytes; and Date of Creation: Jan. 8, 2014) was originally submitted in the International Application No. PCT/US2012/045784 and is incorporated herein by reference in its entirety.

FIELD OF THE INVENTION

The present invention relates generally to the field of therapeutics for hemostatic disorders.

BACKGROUND ART

Hemophilia A is an X-linked bleeding disorder caused by mutations and/or deletions in the factor VIII (FVIII) gene resulting in a deficiency of FVIII activity (Peyvandi, F. et al. *Haemophilia* 12:82-89 (2006). The disease is characterized by spontaneous hemorrhage and excessive bleeding after trauma. Over time, the repeated bleeding into muscles and joints, which often begins in early childhood, results in hemophilic arthropathy and irreversible joint damage. This damage is progressive and can lead to severely limited mobility of joints, muscle atrophy and chronic pain (Rodriguez-Merchan, E. C., *Semin. Thromb. Hemost.* 29:87-96 (2003), which is herein incorporated by reference in its entirety).

The A2 domain is necessary for the procoagulant activity of the factor VIII molecule. Studies show that porcine factor VIII has six-fold greater procoagulant activity than human factor VIII (Lollar, P., and E. T. Parker, *J. Biol. Chem.* 266:12481-12486 (1991)), and that the difference in coagulant activity between human and porcine factor VIII appears to be based on a difference in amino acid sequence between one or more residues in the human and porcine A2 domains (Lollar, P., et al., *J. Biol. Chem.* 267:23652-23657 (1992)), incorporated herein by reference in its entirety.

Treatment of hemophilia A is by replacement therapy targeting restoration of FVIII activity to 1 to 5% of normal levels to prevent spontaneous bleeding (Mannucci, P. M., et al., *N. Engl. J. Med.* 344:1773-1779 (2001), which is herein incorporated by reference in its entirety). There are plasma-derived and recombinant FVIII products available to treat bleeding episodes on-demand or to prevent bleeding episodes from occurring by treating prophylactically. Based on the short half-life of these products, however, e.g., 8-12 hours, treatment regimens require the administration of frequent intravenous injections. Such frequent administration is painful and inconvenient.

Reduced mortality, prevention of joint damage and improved quality of life have been important achievements due to the development of plasma-derived and recombinant FVIII. Prolonged protection from bleeding would represent another key advancement in the treatment of hemophilia A patients. However, to date, no products that allow for prolonged hemostatic protection have been developed. Therefore, there remains a need for improved methods of treating hemophilia due to factor VIII deficiency that are more tolerable, longer lasting, and more effective than current therapies.

BRIEF SUMMARY OF THE INVENTION

The present invention provides methods of administering Factor VIII; methods of administering chimeric polypeptides comprising Factor VIII and hybrids of such chimeric polypeptides; chimeric polypeptides comprising Factor VIII and hybrids of such chimeric polypeptides; polynucleotides encoding such chimeric and hybrid polypeptides; cells comprising such polynucleotides; and methods of producing such chimeric and hybrid polypeptides using such cells.

The present invention provides a method of administering Factor VIII to a subject in need thereof, comprising administering to the subject a therapeutic dose of a chimeric Factor VIII polypeptide, e.g., a chimeric Factor VIII-Fc polypeptide, at a dosing interval at least about one and one-half times longer than the dosing interval required for an equivalent dose of said Factor VIII without the non-Factor VIII portion (a polypeptide consisting of said Factor VIII portion), e.g., without the Fc portion.

The dosing interval may be at least about one and one-half to six times longer, one and one-half to five times longer, one and one-half to four times longer, one and one-half to three times longer, or one and one-half to two times longer, than the dosing interval required for an equivalent dose of said Factor VIII without the non-Factor VIII portion (a polypeptide consisting of said Factor VIII portion), e.g., the Fc portion. The dosing interval may be at least about one and one-half, two, two and one-half, three, three and one-half, four, four and one-half, five, five and one-half or six times longer than the dosing interval required for an equivalent dose of said Factor VIII without the non-Factor VIII portion (a polypeptide consisting of said Factor VIII portion), e.g., the Fc portion. The dosing interval may be about every five, six, seven, eight, nine, ten, eleven, twelve, thirteen, or fourteen days or longer.

The dosing interval may be at least about one and one-half to 5, one and one-half, 2, 3, 4, or 5 days or longer.

The present invention also provides a method of administering Factor VIII to a subject in need thereof, comprising administering to the subject a therapeutic dose of a chimeric Factor VIII polypeptide, e.g., a chimeric Factor VIII-Fc polypeptide, to obtain an area under the plasma concentration versus time curve (AUC) at least about one and one-quarter times greater than the AUC obtained by an equivalent dose of said Factor VIII without the non-Factor VIII portion (a polypeptide consisting of said Factor VIII portion), e.g., without the Fc portion.

The present invention also provides a method of administering Factor VIII to a subject in need thereof, comprising administering to the subject a therapeutic dose of a polypeptide comprising a Factor VIII and an Fc at a dosing interval of about every three, four, five, six, seven, eight, nine, ten, eleven, twelve, thirteen, or fourteen days or longer.

The methods of the invention may be practiced on a subject in need of prophylactic treatment or on-demand treatment.

On-demand treatment includes treatment for a bleeding episode, hemarthrosis, muscle bleed, oral bleed, hemorrhage, hemorrhage into muscles, oral hemorrhage, trauma, trauma capitis (head trauma), gastrointestinal bleeding, intracranial hemorrhage, intra-abdominal hemorrhage, intrathoracic hemorrhage, bone fracture, central nervous system bleeding, bleeding in the retropharyngeal space, bleeding in the retroperitoneal space, or bleeding in the illiopsoas sheath. The subject may be in need of surgical prophylaxis, peri-operative management, or treatment for surgery. Such surgeries include, e.g., minor surgery, major surgery, tooth extraction, tonsillectomy, inguinal herniotomy, synovectomy, total knee replacement, craniotomy, osteosynthesis, trauma surgery, intracranial surgery, intra-abdominal surgery, intrathoracic surgery, or joint replacement surgery.

For on-demand treatment, the dosing interval of said chimeric polypeptide is about once every 24-36, 24-48, 24-72, 24-96, 24-120, 24-144, 24-168, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, or 72 hours or longer.

The therapeutic doses that may be used in the methods of the invention are about 10 to about 100 IU/kg, more specifically, about 10-20, 20-30, 30-40, 40-50, 50-60, 60-70, 70-80, 80-90, or 90-100 IU/kg, and more specifically, about 10, 15, 20, 25, 30, 35, 40, 45, 50, 55, 60, 65, 70, 75, 80, 85, 90, 95, or 100 IU/kg.

The therapeutic doses that may be used in the methods of the invention are about 10 to about 150 IU/kg, more specifically, about 100-110, 110-120, 120-130, 130-140, 140-150 IU/kg, and more specifically, about 110, 115, 120, 125, 130, 135, 140, 145, or 150 IU/kg.

The subject in the methods of the invention is a human subject. The determination of dosing interval and AUC may be carried out in a single subject or in a population of subjects.

The Factor VIII (or Factor VIII portion of a chimeric polypeptide) is a human Factor VIII. The Factor VIII (or Factor VIII portion of a chimeric polypeptide) may have a full or partial deletion of the B domain.

The Factor VIII (or Factor VIII portion of a chimeric polypeptide) may be at least 90% or 95% identical to a Factor VIII amino acid sequence shown in Table 2 without a signal sequence (amino acids 20 to 1457 of SEQ ID NO:2 or amino acids 4 to 2351 of SEQ ID NO:6). The Factor VIII (or Factor VIII portion of a chimeric polypeptide) may be identical to a Factor VIII amino acid sequence shown in Table 2 without a signal sequence (amino acids 20 to 1457 of SEQ ID NO:2 or amino acids 20 to 2351 of SEQ ID NO:6).

The Factor VIII (or Factor VIII portion of a chimeric polypeptide) may be at least 90% or 95% identical to a Factor VIII amino acid sequence shown in Table 2 with a signal sequence (amino acids 1 to 1457 of SEQ ID NO:2 or amino acids 1 to 2351 of SEQ ID NO:6). The Factor VIII (or Factor VIII portion of a chimeric polypeptide) may be identical to a Factor VIII amino acid sequence shown in Table 2 with a signal sequence (amino acids 1 to 1457 of SEQ ID NO:2 or amino acids 1 to 2351 of SEQ ID NO:6).

The Fc portion (or Fc portion of a chimeric polypeptide) may be at least 90% or 95% identical to the Fc amino acid sequence shown in Table 2 (amino acids 1458 to 1684 of SEQ ID NO:2 or amino acids 2352 to 2578 of SEQ ID NO:6). The Fc portion (or Fc portion of a chimeric polypeptide) may be identical to the Fc amino acid sequence shown in Table 2 (amino acids 1458 to 1684 of SEQ ID NO:2 or amino acids 2352 to 2578 of SEQ ID NO:6).

The chimeric polypeptide may comprise a sequence at least 90% or 95% identical to the Factor VIII and Fc amino acid sequence shown in Table 2A(i) without a signal sequence (amino acids 20 to 1684 of SEQ ID NO:2) or at least 90% or 95% identical to the Factor VIII and Fc amino acid sequence shown in Table 2A(i) with a signal sequence (amino acids 1 to 1684 of SEQ ID NO:2). The chimeric polypeptide may comprise a sequence identical to the Factor VIII and Fc amino acid sequence shown in Table 2A(i) without a signal sequence (amino acids 20 to 1684 of SEQ ID NO:2) or identical to the Factor VIII and Fc amino acid sequence shown in Table 2A(i) with a signal sequence (amino acids 1 to 1684 of SEQ ID NO:2).

The chimeric polypeptide may be in the form of a hybrid comprising a second polypeptide in association with said chimeric polypeptide, wherein said second polypeptide comprises or consists essentially of an Fc.

The second polypeptide may comprise or consist essentially of a sequence at least 90% or 95% identical to the amino acid sequence shown in Table 2A(ii) without a signal sequence (amino acids 21 to 247 of SEQ ID NO:4) or at least 90% or 95% identical to the amino acid sequence shown in Table 2A(ii) with a signal sequence (amino acids 1 to 247 of SEQ ID NO:4). The second polypeptide may comprise or consist essentially of a sequence identical to the amino acid sequence shown in Table 2A(ii) without a signal sequence (amino acids 21 to 247 of SEQ ID NO:4) or identical to the amino acid sequence shown in Table 2A(ii) with a signal sequence (amino acids 1 to 247 of SEQ ID NO:4).

The chimeric polypeptide or hybrid may be administered as part of a pharmaceutical composition comprising at least one excipient.

The invention also provides the above-described chimeric and hybrid polypeptides themselves, polynucleotides encoding them, a cultured human embryonic cells comprising the polynucleotides, and methods of producing such chimeric and hybrid polypeptides, and the polypeptides produced by such methods.

The present invention also provide a chimeric polypeptide that has Factor VIII activity comprising a Factor VIII portion and a second portion, wherein the Factor VIII portion is processed Factor VIII comprising two chains, a first chain comprising a heavy chain and a second chain comprising a light chain, wherein said first chain and said second chain are associated by a metal bond. For example, at least about 50%, about 60%, about 70%, about 75%, about 80%, about 85%, about 90%, about 95%, or about 99% of the Factor VIII portion of the chimeric polypeptide is processed Factor VIII.

In addition, the present invention includes a chimeric polypeptide that has Factor VIII activity, wherein the Factor VIII portion is single chain Factor VIII. In one aspect, the single chain Factor VIII can contain an intact intracellular processing site. In one embodiment, at least about 1%, about 5%, about 10%, about 15%, about 20%, or about 25% of the Factor VIII portion of the chimeric polypeptide is single chain Factor VIII. In another embodiment, at least about 30%, about 40%, about 50%, about 60%, about 70%, about 80%, about 90%, about 95%, or about 99% of the Factor VIII portion of the chimeric polypeptide is single chain Factor VIII. In another aspect, the single chain FVIII does not contain an intracellular processing site. For example, the SCFVIII comprises a substitution or mutation at an amino acid position corresponding to Arginine 1645, a substitution or mutation at an amino acid position corresponding to Arginine 1648, or a substitution or mutation at amino acid positions corresponding to Arginine 1645 and Arginine 1648 in full-length Factor VIII. The amino acid substituted at the amino acid position corresponding to Arginine 1645 is a different amino acid from the amino acid substituted at the amino acid position corresponding to Arginine 1648. In certain embodiments, the substitution or mutation is an amino acid other than arginine, e.g., alanine.

In some embodiments, the chimeric polypeptide comprising single chain Factor VIII has Factor VIII activity at a level comparable to a chimeric polypeptide consisting of two Fc portions and processed Factor VIII, which is fused to one of the two Fc portions, when the Factor VIII activity is measured in vitro by a chromogenic assay. In other embodiments, the chimeric polypeptide comprising single chain Factor VIII has Factor VIII activity in vivo comparable to a chimeric polypeptide consisting of two Fc portions and processed Factor VIII, which is fused to one of the two Fc portions. In still other embodiments, the chimeric polypeptide comprising single chain Factor VIII has a Factor Xa generation rate comparable to a chimeric polypeptide consisting of two Fc portions and processed Factor VIII, which is fused to one of the two Fc portions. In certain embodiments, single chain Factor VIII in the chimeric polypeptide is inactivated by activated Protein C at a level comparable to processed Factor VIII in a chimeric polypeptide consisting of two Fc portions and processed Factor VIII. In yet other embodiments, the single chain Factor VIII in the chimeric polypeptide has a Factor IXa interaction rate comparable to processed Factor VIII in a chimeric polypeptide consisting of two Fc portions and processed Factor VIII. In further embodiments, the single chain Factor VIII in the chimeric polypeptide binds to von Willebrand Factor at a level comparable to processed Factor VIII in a chimeric polypeptide consisting of two Fc portions and the processed Factor VIII.

The present invention further includes a composition comprising a chimeric polypeptide having Factor VIII activity, wherein at least about 30%, about 40%, about 50%, about 60%, about 70%, about 80%, about 90%, about 95%, about 96%, about 97%, about 98%, about 99%, or about 100% of said polypeptide comprises a Factor VIII portion, which is single chain Factor VIII, and a second portion, wherein said single chain Factor VIII is at least 90% or 95% identical to a Factor VIII amino acid sequence shown in Table 2 without a signal sequence (amino acids 20 to 1457 of SEQ ID NO:2 or amino acids 20 to 2351 of SEQ ID NO:6). In one embodiment, the second portion can be an Fc. In another embodiment, the polypeptide is in the form of a hybrid comprising a second polypeptide, wherein said second polypeptide consists essentially of an Fc. In other embodiments, the polypeptide has a half-life at least one and one-half to six times longer, one and one-half to five times longer, one and one-half to four times longer, one and one-half to three times longer, or one and one-half to two times longer to a polypeptide consisting of said Factor VIII.

Also provided is a method of treating a bleeding condition comprising administering a therapeutically effective amount of the composition. The treatment can be prophylactic treatment or on-demand treatment or perioperative. The bleeding coagulation disorder can be hemophilia. In one embodiment, the subject that is treated is a pediatric subject.

The present invention is also directed to a method of preventing, decreasing, or treating a bleeding episode in a subject comprising administering to the subject an effective amount of a long-acting Factor VIII (FVIII) protein, wherein the subject expresses a high level of von Willebrand Factor (VWF) in plasma. In one embodiment, the subject has been identified as expressing a high level of VWF in plasma. The present invention is also directed to a method of preventing, decreasing, or treating a bleeding episode in a subject comprising: (a) identifying a subject having high levels of VWF by measuring the level of VWF in the plasma of said subject, wherein a VWF level of at least about 100 IU/dL identifies the subject as having a high level of VWF; and (b) administering to the subject an effective amount of a long-acting FVIII protein.

In one embodiment, the subject is a human. In another embodiment, the subject is a pediatric subject. In another embodiment, the subject has hemophilia A.

In one embodiment, the high level of VWF is at least about 100 IU/dL. In another embodiment, the high level of VWF is between about 100 IU/dL and about 200 IU/dL. In another embodiment, the high level of VWF is about 110 IU/dL, about 120 IU/dL, about 130 IU/dL, about 140 IU/dL, about 150 IU/dL, about 160 IU/dL, about 170 IU/dL, about 180 IU/dL, about 190 IU/dL, or about 200 IU/dL.

In one embodiment the subject has the blood serotype A, B, or AB.

In one embodiment, the long-acting FVIII protein has a half-life in said subject of between about 20 and about 40 hours. In another embodiment, the long-acting FVIII protein has a half-life of about 21 hours, 22 hours, 23 hours, 24 hours, 25 hours, 26 hours, 27 hours, 28 hours, 29 hours, 30 hours, 31 hours, 31 hours, 32 hours, 33 hours, 34 hours, 35 hours, 36 hours, 37 hours, 38 hours, 39 hours, or 40 hours. In another embodiment, the long-acting FVIII protein has a half-life of between about 20 and 27 hours. In another embodiment, the long-acting FVIII protein has a half-life that is at least about 1.2 times greater than the half-life of said said long-acting FVIII protein when administered to an individual having average levels of VWF. In another embodiment, the long-acting FVIII protein has a half-life that is at least about about 1.3, 1.4, 1.5, 1.6, 1.7, 1.8, 1.9, 2.0, 2.1, 2.2, 2.3, 2.4, or 2.5-fold times greater than the half-life of said said long-acting FVIII protein when administered to an individual having average levels of VWF.

In one embodiment, the effective amount of long-acting FVIII protein that is administered is at least about 20 IU/kg, at least about 25 IU/kg, at least about 30 IU/kg, at least about 35 IU/kg, at least about 40 IU/kg, at least about 45 IU/kg, at least about 50 IU/kg, at least about 55 IU/kg, at least about 60 IU/kg, at least about 65 IU/kg, at least about 70 IU/kg, at least about 75 IU/kg, at least about 80 IU/kg, at least about 85 IU/kg, or at least about 90 IU/kg. In another embodiment, the effective amount is at least about 65 IU/kg to at least about 90 IU/kg. In another embodiment, the effective amount is 80 IU/kg.

In one embodiment, the long-acting FVIII protein is administered every 72 hours or longer. In another embodiment, the long-acting FVIII protein is administered about once a week or longer. In another embodiment, the long-acting FVIII protein is administered about once every 10 days, about once every two weeks, about once every 15 days, about once every 20 days, about once every three weeks, about once every 25 days, about once every four weeks, or about once every one month.

In one embodiment, the long-acting FVIII is administered at a dosage of 80 IU/kg once every 72 hours. In a further embodiment the long-acting FVIII is administered at a dosage of 80 IU/kg once every 72 hours to a pediatric subject.

In one embodiment, administration of the long-acting FVIII protein resolves greater than 5-20%, greater than 5-15%, greater than 5-10%, greater than 10-20%, or greater than 10-15% of bleeding episodes. In one embodiment, the trough level of plasma Factor VIII:C in the subjects is maintained above 1-3 or 3-5 IU/dl. In one embodiment, the administration prevents a bleeding episode in the subject. In another embodiment, the bleeding episode is spontaneous. In another embodiment, the administration resolves greater than 80-100%, greater than 80-90%, greater than 85-90%, greater than 90-100%, greater than 90-95%, or greater than 95-100% of bleeding episodes.

In one embodiment, the administration maintains homeostatis in the population of the subjects in need of a surgery. In another embodiment, the long-acting FVIII protein is administered prior to, during, or after the surgery. In another embodiment, the surgery is minor surgery, major surgery, tooth extraction, tonsillectomy, inguinal herniotomy, synovectomy, total knee replacement, craniotomy, osteosynthesis, trauma surgery, intracranial surgery, intra-abdominal surgery, intrathoracic surgery, or joint replacement surgery. In another embodiment, the surgery is an emergency surgery.

In one embodiment, the long-acting FVIII protein has a half-life longer than a polypeptide consisting of FVIII. In another embodiment, the long-acting FVIII protein is pegylated, hesylated, or polysialylated.

In one embodiment, the long-acting FVIII protein is a chimeric protein comprising a FVIII portion and a second portion. In another embodiment, the second portion is an Fc region, albumin, a PAS sequence, transferrin, CTP (28 amino acid C-terminal peptide (CTP) of hCG with its 4 O-glycans), polyethylene glycol (PEG), hydroxyethyl starch (HES), albumin binding polypeptide, albumin-binding small molecules, or two or more combinations thereof. In another embodiment, the second portion is fused to the amino-terminus or the carboxy-terminus of the FVIII portion. In another embodiment, the second portion is inserted between two amino acids in the FVIII portion. In another embodiment, the chimeric protein is a FVIIIFc monomer dimer hybrid. In another embodiment, the FVIII portion is a single chain. In another embodiment, the FVIII portion comprises a heavy chain and a light chain. In another embodiment, the FVIII portion comprises full-length factor VIII, mature factor VIII, or factor VIII with a full or partial deletion of the B domain. In another embodiment, the FVIII portion comprises an amino acid sequence at least 80%, 85%, 90%, 95%, 96%, 97%, 98%, 99%, or 100% identical to amino acids 1 to 1438 of SEQ ID NO: 2 or amino acids 1 to 2332 of SEQ ID NO: 6. In another embodiment, the FVIII portion comprises amino acids 1 to 1438 of SEQ ID NO: 2 or amino acids 1 to 2332 of SEQ ID NO: 6. In another embodiment, the chimeric polypeptide comprises an Fc region which is at least 80%, 85%, 90%, 95%, 96%, 97%, 98%, 99%, or 100% identical to amino acids 1439 to 1665 of SEQ ID NO: 2 or amino acids 2333 to 2559 of SEQ ID NO: 6. In another embodiment, the second portion comprises amino acids 1439 to 1665 of SEQ ID NO: 2 or amino acids 2333 to 2559 of SEQ ID NO: 6. In another embodiment, the long-acting FVIII polypeptide is administered as part of a pharmaceutical composition comprising at least one excipient.

The invention also provides a method of treating a subject diagnosed with bleeding disorder, comprising measuring the half-life of FVIII-Fc in said subject, wherein a half-life that is at least about 1.2 times greater than the half-life of FVIII-Fc in a normal subject indicates the subject is a candidate for long interval dosing, and administering a FVIII-Fc polypeptide in an effective amount and at a dosing interval of at least 3 days.

The invention also provides a method of treating a subject diagnosed with bleeding disorder, comprising administering a FVIII-Fc polypeptide in an effective amount and at a dosing interval of at least 3 days to a subject, wherein the half-life of FVIII-Fc in said subject is at least about 1.2 times greater than the half-life of FVIII-Fc when administered to a subject having average levels of VWF.

In one embodiment, the plasma half-life of FVIII-Fc in said subject is at least about 1.3, 1.4, 1.5, 1.6, 1.7, 1.8, 1.9, 2.0, 2.1, 2.2, 2.3, 2.4, or 2.5-fold times greater than the plasma half-life of FVIII-Fc when administered to a subject having average levels of VWF. In another embodiment, the FVIII-Fc plasma half-life is between 20-40 hours. In another embodiment, the long-acting FVIII protein has a half-life of about 21 hours, 22 hours, 23 hours, 24 hours, 25 hours, 26 hours, 27 hours, 28 hours, 29 hours, 30 hours, 31 hours, 31 hours, 32 hours, 33 hours, 34 hours, 35 hours, 36 hours, 37 hours, 38 hours, 39 hours, or 40 hours. In another embodiment, the long-acting FVIII protein has a half-life of between about 20 and 27 hours.

The invention also provides a method of treating a subject diagnosed with bleeding disorder, comprising measuring the half-life of a short-acting FVIII administered to said subject, wherein a half-life that is at least about 1.2 times greater than the half-life of said short-acting FVIII in a subject having average VWF levels indicates that the subject is a candidate for long interval dosing, and administering a long-acting FVIII-Fc polypeptide in an effective amount and at a dosing interval of at least 3 days. In one embodiment, the half-life of the short-acting FVIII in said subject is at least about 1.3, 1.4, 1.5, 1.6, 1.7, 1.8, 1.9, 2.0, 2.1, 2.2, 2.3, 2.4, or 2.5-fold greater than the half-life of a short-acting FVIII when administered to a subject having average levels of VWF.

In one embodiment, the subject is a human. In another embodiment, the subject is a pediatric subject. In another embodiment, the subject has hemophilia A. In another embodiment, the subject has the blood serotype A, B, or AB.

In one embodiment, the long-acting FVIII-Fc is administered in an effective amount that is at least about 20 IU/kg, at least about 25 IU/kg, at least about 30 IU/kg, at least about 35 IU/kg, at least about 40 IU/kg, at least about 45 IU/kg, at least about 50 IU/kg, at least about 55 IU/kg, at least about 60 IU/kg, at least about 65 IU/kg, at least about 70 IU/kg, at least about 75 IU/kg, at least about 80 IU/kg, at least about 85 IU/kg, or at least about 90 IU/kg. In another embodiment, the effective amount is at least about 65 IU/kg to at least about 90 IU/kg.

In one embodiment, the effective amount of the FVIII-Fc protein is administered about once every week, about once every 10 days, about once every two weeks, about once every 15 days, about once every 20 days, about once every three weeks, about once every 25 days, about once every four weeks, or about once every one month.

In one embodiment, the administration resolves greater than 5-20%, greater than 5-15%, greater than 5-10%, greater than 10-20%, or greater than 10-15% of bleeding episodes.

In one embodiment, the trough level of plasma Factor VIII:C in the subjects is maintained above 1-3 or 3-5 IU/dl.

In one embodiment, the administration prevents a bleeding episode in the subject. In one embodiment, the bleeding episode is spontaneous. In one embodiment, the administration resolves greater than 80-100%, greater than 80-90%, greater than 85-90%, greater than 90-100%, greater than 90-95%, or greater than 95-100% of bleeding episodes. In one embodiment, the administration maintains homeostatis in the population of the subjects in need of a surgery. In one embodiment, the FVIII-Fc protein is administered prior to, during, or after the surgery. In one embodiment, the surgery is minor surgery, major surgery, tooth extraction, tonsillectomy, inguinal herniotomy, synovectomy, total knee replacement, craniotomy, osteosynthesis, trauma surgery, intracranial surgery, intra-abdominal surgery, intrathoracic surgery, or joint replacement surgery. In one embodiment the surgery is an emergency surgery.

In one embodiment, the FVIII-Fc protein has a half-life longer than a polypeptide consisting of FVIII. In one embodiment, the FVIII-Fc protein is pegylated, hesylated, or polysialylated. In one embodiment, the FVIII-Fc protein is a FVIIIFc monomer dimer hybrid. In one embodiment, the FVIII portion is a single chain. In one embodiment, the FVIII portion comprises a heavy chain and a light chain. In one embodiment, the FVIII portion comprises full-length factor VIII, mature factor VIII, or factor VIII with a full or partial deletion of the B domain. In one embodiment, the FVIII portion comprises an amino acid sequence at least 80%, 85%, 90%, 95%, 96%, 97%, 98%, 99%, or 100% identical to amino acids 1 to 1438 of SEQ ID NO: 2 or amino acids 1 to 2332 of SEQ ID NO: 6. In one embodiment, the FVIII portion comprises amino acids 1 to 1438 of SEQ ID NO: 2 or amino acids 1 to 2332 of SEQ ID NO: 6. In one embodiment, the second portion of the chimeric polypeptide comprises an Fc region which is at least 80%, 85%, 90%, 95%, 96%, 97%, 98%, 99%, or 100% identical to amino acids 1439 to 1665 of SEQ ID NO: 2 or amino acids 2333 to 2559 of SEQ ID NO: 6. In one embodiment, the second portion comprises amino acids 1439 to 1665 of SEQ ID NO: 2 or amino acids 2333 to 2559 of SEQ ID NO: 6.

In one embodiment, the FVIII-Fc polypeptide is administered as part of a pharmaceutical composition comprising at least one excipient.

The invention also provides a method for determining whether a subject diagnosed with bleeding disorder is a candidate for long interval dosing with a long-acting FVIII polypeptide, comprising measuring the expression levels of plasma VWF, wherein an VWF expression level of at least 100 IU/dL indicates that the subject is a candidate for long interval dosing using a long-acting FVIII polypeptide. In one embodiment, the VWF expression level is at least about 110 IU/dL, about 120 IU/dL, about 130 IU/dL, about 140 IU/dL, about 150 IU/dL, about 160 IU/dL, about 170 IU/dL, about 180 IU/dL, about 190 IU/dL, or about 200 IU/dL.

The invention also provides a method for determining whether a subject diagnosed with bleeding disorder is a candidate for long interval dosing of a long-acting FVIII polypeptide, comprising measuring the half-life of FVIII-Fc in said subject, wherein a half-life that is at least about 1.2-fold greater than the half-life of FVIII-Fc when administered to a subject having average VWF levels indicates the subject is a candidate for long interval dosing. In one embodiment, the half-life of FVIII-Fc is at least about 1.3, 1.4, 1.5, 1.6, 1.7, 1.8, 1.9, 2.0, 2.1, 2.2, 2.3, 2.4, or 2.5-fold greater than the half-life of FVIII-Fc when administered to a subject having average levels of VWF.

The invention also provides a method for determining whether a subject diagnosed with bleeding disorder is a candidate for long interval dosing of a long-acting FVIII polypeptide, comprising measuring the half-life of short-acting FVIII in said subject, wherein a half-life that is at least about 1.2-fold greater than the half-life of short-acting FVIII when administered to a subject having average VWF levels indicates the subject is a candidate for long interval dosing. In one embodiment, the half-life is at least about 1.3, 1.4, 1.5, 1.6, 1.7, 1.8, 1.9, 2.0, 2.1, 2.2, 2.3, 2.4, or 2.5-fold greater than the half-life of FVIII-Fc when administered to a subject having average levels of VWF.

BRIEF DESCRIPTION OF THE DRAWINGS/FIGURES

FIG. 1. Schematic Representation of rFVIIIFc monomer.

FIGS. 2A-E. A-B. Non-reducing and reducing SDS-PAGE analysis of rFVIIIFc (processed or single chain). C. rFVIIIFc structure analyzed by LC/UV and LC/MS. D. Total Ion Current (TIC) chromatogram (LC/MS map) of rFVIIIFc after thrombin cleavage. Major digestion products are indicated. E. Deconvoluted Mass Spectrum of the A2 domain of rFVIIIFc and rBDDFVIII. Major products and their cognate masses are indicated, corresponding to thrombin-cleaved A2 domain (S373 to R740) and two truncated products, S373 to Y729 and S373 to E720.

FIGS. 3A-C. Biochemical characterization of rFVIII-Fc: A. Activation of Factor X as a function of phospholipid vesicle concentration; B. Activation of Factor X as a function of FX concentration. C. Activation of Factor X as a function of Factor IXa concentration.

FIG. 4. Activation of Factor X following cleavage by activated Protein C.

FIGS. 5A-D. Observed group mean FVIII activity (±SE) versus time profiles, sorted by dose level, grouped by compound (one stage assay, 25 IU/kg (A) or 65 IU/kg (B); and chromogenic assay, 25 IU/kg (C) or 65 IU/kg (D)) versus time.

Figure 6A:
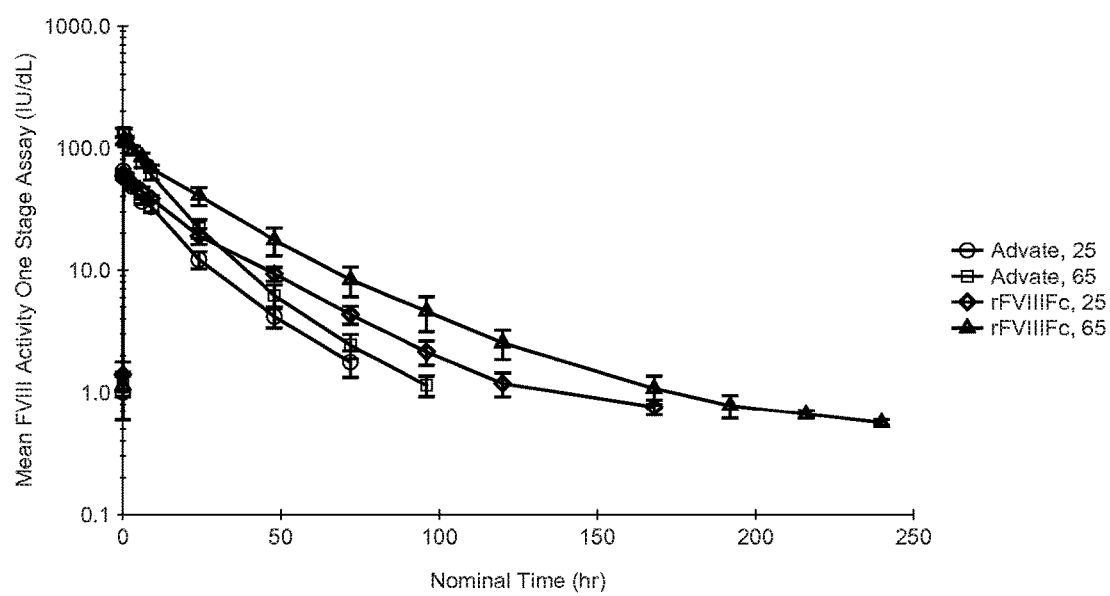
Figure 6B:
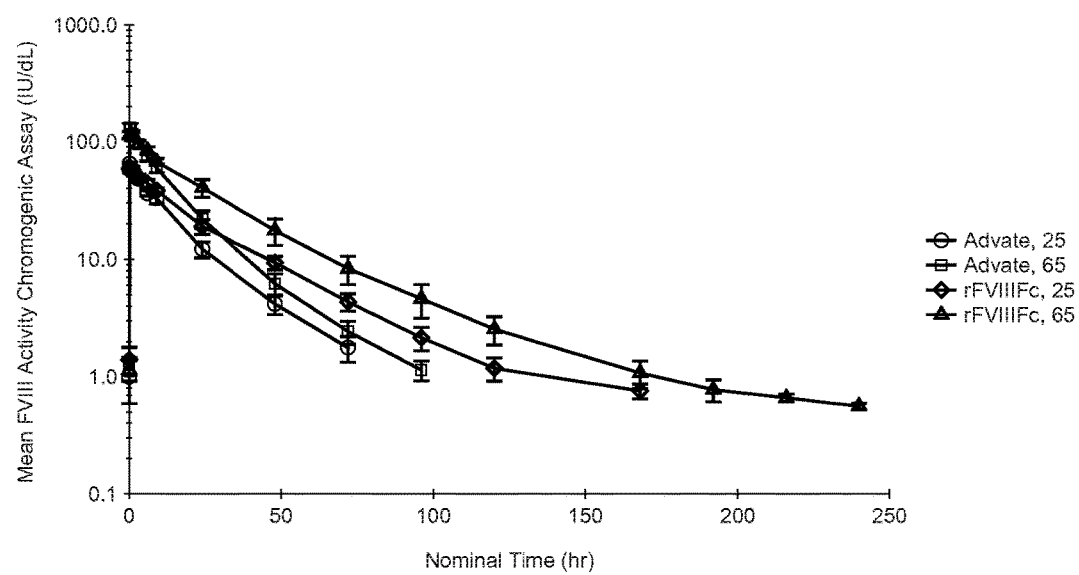

FIGS. 6A-B. Observed group mean FVIII activity (±SE) versus time profiles, grouped by dose level and compound (one stage assay (A) or chromogenic assay (B)) versus time.

Figure 7A:
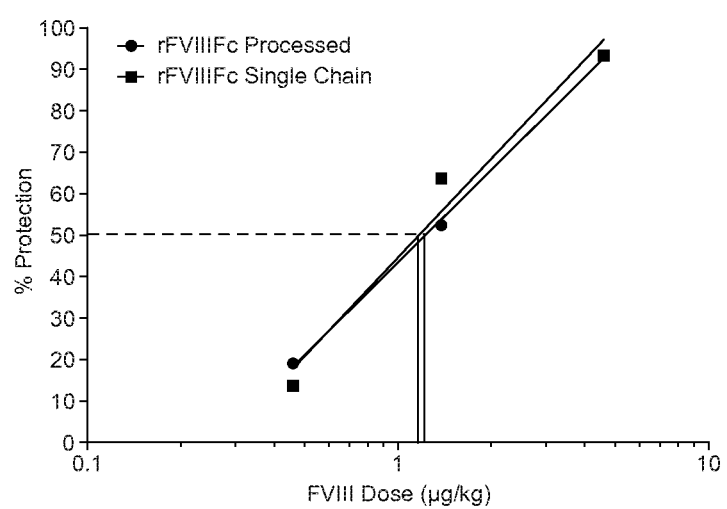

FIGS. 7(A)-(C). In Vivo Efficacy of Single Chain FVIII:Fc in HemA Mouse Tail Vein Transection Model. (A) Single chain rFVIII:Fc doses are shown as squares, and processed rFVIII:Fc doses are shown as circles. (B) Percent survival following tail vein transection of 4.6 µg/kg, 1.38 µg/kg, and 0.46 µg/kg of rFVIIIFc or SC rFVIIIFc. (C) Percent of non-bleeders following tail vein transection of 4.6 µg/kg (black circle or inverted triangle), 1.38 µg/kg (triangle or diamond), and 0.46 µg/kg (square and gray circle) of rFVII-IFc or SC rFVIIIFc, respectively.

FIG. 8. Study Design. FIG. 8 depicts the study design of the phase 1/2a study, which was a dose-escalation, sequential design to evaluate the safety and PK of rFVIIIFc compared with ADVATE® after a single intravenous dose of either 25 IU/kg (low dose Cohort A) or 65 IU/kg (high dose Cohort B).

Figure 9:
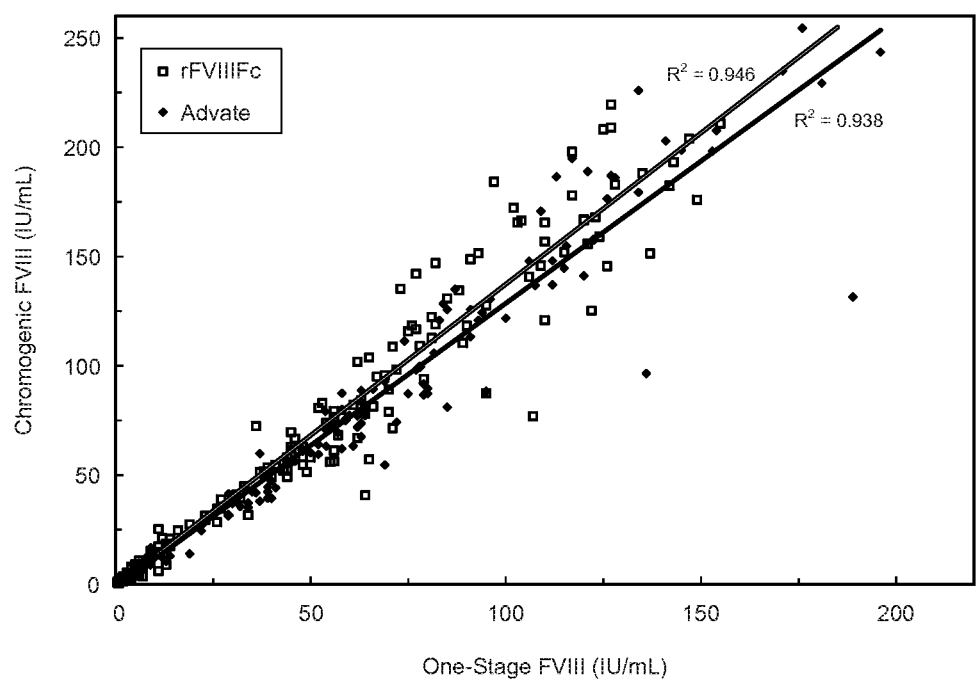

FIG. 9. Correlation of rFVIII Activity by One-Stage (aPTT) and Chromogenic Assays. Correlation between one-stage clotting (aPTT) and chromogenic assay results measuring FVIII activity (IU/mL) following injection of ADVATE® (♦) and rFVIIIFc (□).

FIGS. 10(A)-(B). Group Mean Plasma FVIII Activity Pharmacokinetic Profiles for Low-Dose and High-Dose Cohorts. The plasma FVIII activity (one stage aPTT assay) versus time curve after a single intravenous injection of rFVIIIFc or ADVATE® are shown for (A) 25 IU/kg (low-dose cohort, n=6); and (B) 65 IU/kg (high dose cohort, n=10 [ADVATE®]; n=9 [rFVIIIFc]). Results presented are group mean±standard error of mean (SEM).

Figure 11:
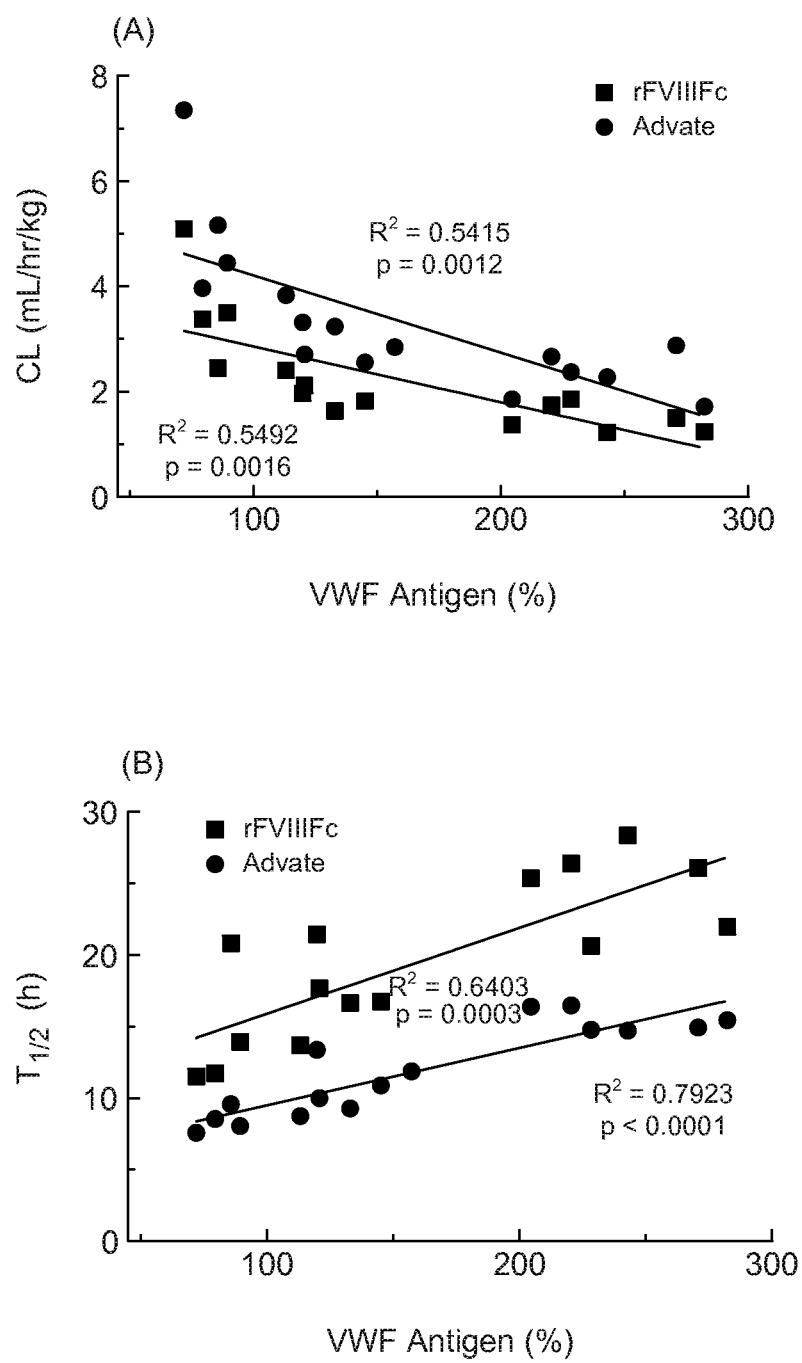

FIGS. 11(A)-(B). Effect of VWF Antigen Levels on Cl and $t_{1/2}$ of FVIII Activity after Injection of ADVATE® or rFVIIIFc. Correlation between VWF antigen levels and (A) the weight-adjusted Cl of ADVATE® ($R^2$=0.5415 and p=0.0012) and rFVIIIFc ($R^2$=0.5492 and p=0.0016); and (B) the $t_{1/2}$ of ADVATE® ($R^2$=0.7923 and p<0.0001) and rFVIIIFc ($R^2$=0.6403 and p=0.0003). Each dot represents an individual subject.

FIGS. 12(A)-(B). Ex Vivo Whole Blood ROTEM® Results for Individual Subjects After Injection of ADVATE® or rFVIIIFc. Blood was sampled from subjects prior to and after treatment at doses of (A) 25 IU/kg ADVATE® and rFVIIIFc; and (B) 65 IU/kg ADVATE® and rFVIIIFc at specified time points. Clotting time was determined by NATEM initiated with Ca++ on a ROTEM® instrument. Results presented are mean±standard error of mean (SEM) from triplicate channel readings for each individual sample.

Figure 13B:
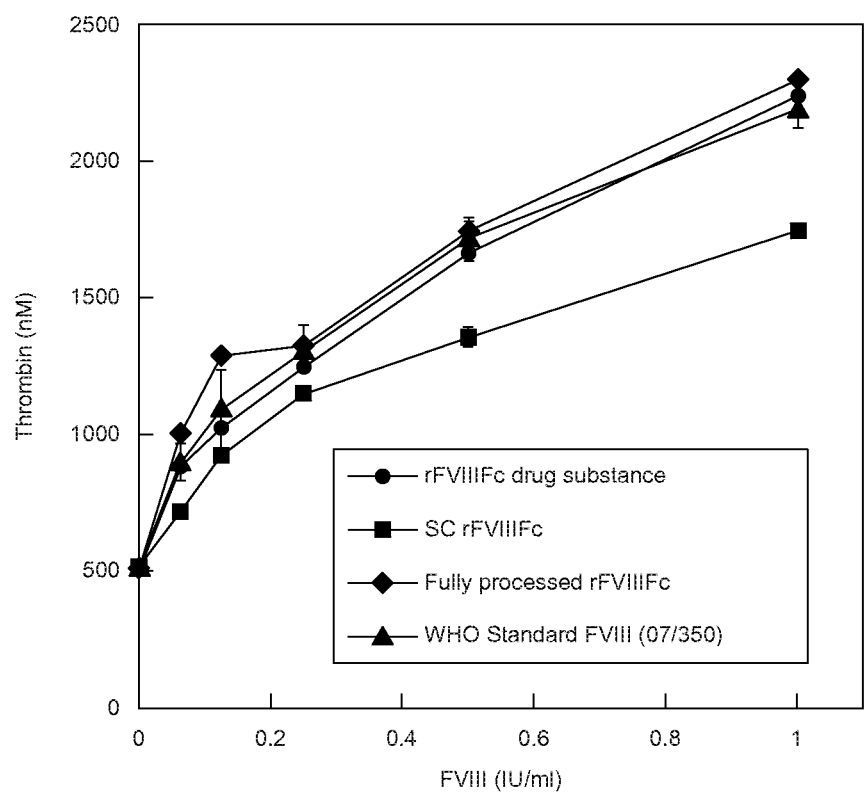

FIGS. 13(A)-(B). Activity comparison in thrombin generation assay (TGA). (A) SC rFVIIIFc showed a reduced endogenous thrombin potential (ETP), and (B) a reduced peak thrombin compared to rFVIIIFc.

FIGS. 14(A)-(C): In vitro ROTEM data. ROTEM (NATEM) results (Mean±SD) for varying concentratios of XYNTHA, ADVATE< and rFVIIIFc spked in pooled whole blood obtained from naïve HemA mice. (A). Average clot time (CT) (FIG. 14A), (B). clot formation time (CFT), and (C). alpha angle.

FIGS. 15(A)-(C). Ex vivo ROTEM data. ROTEM (NATEM) results (Mean±SD) from HemA mice following a single intravenous administration of 50 IU/kg of XYNTHA, ADVATE, or rFVIIIFc at 5 min, 24, 48, 72, and 96 hours after dosing. (A). Average clot time (CT), (B). Clot formation time (CFT), and (C). alpha angle.

FIGS. 16(A)-(E): Real-time evaluation of the interaction of rFVIIIFc and single chain (SC) rFVIIIFc with vWF, and real-time evaluation of thrombin mediated release of rFVIIIFc and SC rFVIIIFc from vWF. (A). Surface plasmon resonance (SPR) analysis of rFVIIIFc and SC rFVIIIFc affinity for vWF. Depicted are the binding curve and the 1:1 fit interaction model. The x-axis shows time in seconds and the y-axis shows response in response units (RU). (B). Reference subtracted sensograms of thrombin-mediated release of activated rFVIIIFc, SC rFVIIIFc, and B-domain deleted rFVIII lacking Fc moieties (rBDD FVIII) at 25° C. (top) and 37° C. (bottom). The x-axis shows time in seconds and the y-axis shows response in response units (RU). Individual lines indicate the response at different α-thrombin concentrations. The uppermost line is the response at 0 U/mL α-thrombin, and each subsequent line runs in order for α-thrombin concentrations of 0.005, 0.01, 0.02, 0.04, 0.08, 0.16, 0.31, 0.63, 1.3, 2.5, 5, 10, and 20 U/mL. (C). Double reference subtracted sensograms of thrombin mediated release phase for rFVIIIFc, SC rFVIIIFc, and rBDD FVIII at 25° C. (top) and 37° C. (bottom). The x-axis shows time in seconds and the y-axis shows response in response units (RU). Individual lines indicate response at different α-thrombin concentrations. The uppermost line is the response at 0 U/mL α-thrombin, and each subsequent line runs in order for α-thrombin concentrations of 0.005, 0.01, 0.02, 0.04, 0.08, 0.16, 0.31, 0.63, 1.3, 2.5, 5.0, 10, and 20 U/mL. (D). Thrombin-mediated release rate as a function of time for rFVIIIFc, SC rFVIIIFc, and rBDD FVIII at 25° C. (top) and 37° C. (bottom). The x-axis shows time in seconds and the y-axis shows response in response units (RU). Individual lines indicate response at different α-thrombin concentrations. The uppermost line is the response at 20 U/mL α-thrombin, and each subsequent line runs in order for α-thrombin concentrations of 10, 5, 2.5, 1.3, 0.63, 0.31, 0.16, 0.08, 0.04, 0.02, 0.01, and 0.005 U/mL. (E). Peak thrombin-mediated release rate as a function of thrombin concentration for rFVIIIFc, SC rFVIIIFc, and rBDD FVIII at 25° C. (top) and 37° C. (bottom). $EC_{50}$ is half maximal effective concentration. The x-axis is α-thrombin concentration in U/mL and the y-axis is maximum release rate in RU/second.

DETAILED DESCRIPTION OF THE INVENTION

The present invention provides a method of treating Hemophilia A with Factor VIII (processed, single chain, or a combination thereof) using a longer dosing interval and/or greater AUC than is possible with currently known Factor VIII products. The present invention also provides improved Factor VIII chimeric polypeptides and methods of production.

Treatment of hemophilia A is by replacement therapy targeting restoration of FVIII activity to 1 to 5% of normal levels to prevent spontaneous bleeding (Mannucci, P. M. et al., N. Engl. J. Med. 344:1773-9 (2001), herein incorporated by reference in its entirety). There are plasma-derived and recombinant FVIII products available to treat bleeding episodes on-demand or to prevent bleeding episodes from occurring by treating prophylactically. Based on the short half-life of these products (8-12 hr) (White G. C., et al., Thromb. Haemost. 77:660-7 (1997); Morfini, M., Haemophilia 9 (suppl 1):94-99; discussion 100 (2003)), treatment regimens require frequent intravenous administration, commonly two to three times weekly for prophylaxis and one to three times daily for on-demand treatment (Manco-Johnson, M. J., et al., N. Engl. J. Med. 357:535-544 (2007)), each of which is incorporated herein by reference in its entirety. Such frequent administration is painful and inconvenient.

The present invention provides a method of administering Factor VIII to a human subject in need thereof (e.g., human patient), comprising administering to the subject a therapeutic dose of a chimeric Factor VIII polypeptide, e.g., a chimeric Factor VIII-Fc polypeptide, or a hybrid of such a polypeptide at a dosing interval at least about one and one-half times longer than the dosing interval required for an equivalent dose of said Factor VIII without the non-Factor VIII portion (a polypeptide consisting of said Factor VIII portion), e.g., without the Fc portion. The present invention is also directed to a method of increasing dosing interval of Factor VIII administration in a human subject in need thereof comprising administering the chimeric Factor VIII polypeptide.

The dosing interval may be at least about one and one-half to six times longer, one and one-half to five times longer, one and one-half to four times longer, one and one-half to three times longer, or one and one-half to two times longer, than the dosing interval required for an equivalent dose of said Factor VIII without the non-Factor VIII portion (a polypeptide consisting of said Factor VIII portion), e.g., without the Fc portion. The dosing interval may be at least about one and one-half, two, two and one-half, three, three and one-half, four, four and one-half, five, five and one-half or six times longer than the dosing interval required for an equivalent dose of said Factor VIII without the non-Factor VIII portion (a polypeptide consisting of said Factor VIII portion), e.g., without the Fc portion. The dosing interval may be about every three, four, five, six, seven, eight, nine, ten, eleven, twelve, thirteen, or fourteen days or longer.

The dosing interval may be at least about one and one-half to 5, one and one-half, 2, 3, 4, or 5 days or longer.

The present invention also provides a method of administering Factor VIII to a human subject in need thereof, comprising administering to the subject a therapeutic dose of a chimeric Factor VIII polypeptide, e.g., a chimeric Factor VIII-Fc polypeptide, or a hybrid of such a polypeptide to obtain an area under the plasma concentration versus time curve (AUC) at least about one and one-quarter times greater than the AUC obtained by an equivalent dose of said Factor VIII without non-Factor VIII portion (a polypeptide consisting of said Factor VIII portion), e.g., without the Fc portion. The present invention thus includes a method of increasing or extending AUC of Factor VIII activity in a human patient in need thereof comprising administering the chimeric Factor VIII polypeptide.

The present invention also provides a method of administering Factor VIII to a subject in need thereof, comprising administering to the subject a therapeutic dose of a polypeptide comprising a Factor VIII and an Fc or a hybrid of such a polypeptide at a dosing interval of about every three, four, five, six, seven, eight, nine, ten, eleven, twelve, thirteen, or fourteen days or longer.

The methods of the invention may be practiced on a subject in need of prophylactic treatment or on-demand treatment.

"Administering," as used herein, means to give a pharmaceutically acceptable Factor VIII polypeptide of the invention to a subject via a pharmaceutically acceptable route. Routes of administration can be intravenous, e.g., intravenous injection and intravenous infusion. Additional routes of administration include, e.g., subcutaneous, intramuscular, oral, nasal, and pulmonary administration. Chimeric polypeptides and hybrid proteins may be administered as part of a pharmaceutical composition comprising at least one excipient.

"Area under the plasma concentration versus time curve (AUC)," as used herein, is the same as the term of art in pharmacology, and is based upon the rate and extent of absorption of Factor VIII following administration. AUC is determined over a specified time period, such as 12, 18, 24, 36, 48, or 72 hours, or for infinity using extrapolation based on the slope of the curve. Unless otherwise specified herein, AUC is determined for infinity. The determination of AUC may be carried out in a single subject, or in a population of subjects for which the average is calculated.

A "B domain" of Factor VIII, as used herein, is the same as the B domain known in the art that is defined by internal amino acid sequence identity and sites of proteolytic cleavage by thrombin, e.g., residues Ser741-Arg1648 of full length human factor VIII. The other human factor VIII domains are defined by the following amino acid residues: A1, residues Ala1-Arg372; A2, residues Ser373-Arg740; A3, residues Ser1690-Ile2032; C1, residues Arg2033-Asn2172; C2, residues Ser2173-Tyr2332. The A3-C1-C2 sequence includes residues Ser1690-Tyr2332. The remaining sequence, residues Glu1649-Arg1689, is usually referred to as the factor VIII light chain activation peptide. The locations of the boundaries for all of the domains, including the B domains, for porcine, mouse and canine factor VIII are also known in the art. In one embodiment, the B domain of Factor VIII is deleted ("B domain deleted factor VIII" or "BDD FVIII"). An example of a BDD FVIII is REFACTO® (recombinant BDD FVIII), which has the same sequence as the Factor VIII portion of the sequence in Table 2A(i) (amino acids 1 to 1457 or 20 to 1457 of SEQ ID NO:2). In another embodiment, the B domain deleted Factor VIII contains an intact intracellular processing site, which corresponds to Arginine at residue 754 of B domain deleted Factor VIII, which corresponds to Arginine residue 773 of SEQ ID NO: 2, or residue 1648 of full-length Factor VIII, which corresponds to Arginine residue 1667 of SEQ ID NO: 6. The sequence residue numbers used herein without referring to any SEQ ID Numbers correspond to the Factor VIII sequence without the signal peptide sequence (19 amino acids) unless otherwise indicated. For example, S743/Q1638 of full-length Factor VIII corresponds to S762/Q1657 of SEQ ID NO: 6 due to the 19 amino acid signal peptide sequence. In other embodiments, the B domain deleted FVIII comprises a substitution or mutation at an amino acid position corresponding to Arginine 1645, a substitution or mutation at an amino acid position corresponding to Arginine 1648, or a substitution or mutation at amino acid positions corresponding to Arginine 1645 and Arginine 1648 in full-length Factor VIII. In some embodiments, the amino acid substituted at the amino acid position corresponding to Arginine 1645 is a different amino acid from the amino acid substituted at the amino acid position corresponding to Arginine 1648. In certain embodiments, the substitution or mutation is an amino acid other than arginine, e.g., alanine.

A "B domain deleted factor VIII" may have the full or partial deletions disclosed in U.S. Pat. Nos. 6,316,226, 6,346,513, 7,041,635, 5,789,203, 6,060,447, 5,595,886, 6,228,620, 5,972,885, 6,048,720, 5,543,502, 5,610,278, 5,171,844, 5,112,950, 4,868,112, and 6,458,563, each of which is incorporated herein by reference in its entirety. In some embodiments, a B domain deleted factor VIII sequence of the present invention comprises any one of the deletions disclosed at col. 4, line 4 to col. 5, line 28 and examples 1-5 of U.S. Pat. No. 6,316,226 (also in U.S. Pat. No. 6,346,513). In some embodiments, a B domain deleted factor VIII of the present invention has a deletion disclosed at col. 2, lines 26-51 and examples 5-8 of U.S. Pat. No. 5,789,203 (also U.S. Pat. No. 6,060,447, U.S. Pat. No. 5,595,886, and U.S. Pat. No. 6,228,620). In some embodiments, a B domain deleted factor VIII has a deletion described in col. 1, lines 25 to col. 2, line 40 of U.S. Pat. No. 5,972,885; col. 6, lines 1-22 and example 1 of U.S. Pat. No. 6,048,720; col. 2, lines 17-46 of U.S. Pat. No. 5,543,502; col. 4, line 22 to col. 5, line 36 of U.S. Pat. No. 5,171,844; col. 2, lines 55-68, FIG. 2, and example 1 of U.S. Pat. No. 5,112,950; col. 2, line 2 to col. 19, line 21 and table 2 of U.S. Pat. No. 4,868,112; col. 2, line 1 to col. 3, line 19, col. 3, line 40 to col. 4, line 67, col. 7, line 43 to col. 8, line 26, and col. 11, line 5 to col. 13, line 39 of U.S. Pat. No. 7,041,635; or col. 4, lines 25-53, of U.S. Pat. No. 6,458,563. In some embodiments, a B domain deleted factor VIII has a deletion of most of the B domain, but still contains amino-terminal sequences of the B domain that are essential for in vivo proteolytic processing of the primary translation product into two polypeptide chain (i.e., intracellular processing site), as disclosed in WO 91/09122, which is incorporated herein by reference in its entirety. In some embodiments, a B domain deleted factor VIII is constructed with a deletion of amino acids 747-1638, i.e., virtually a complete deletion of the B domain. Hoeben R. C., et al. *J. Biol. Chem.* 265 (13): 7318-7323 (1990), incorporated herein by reference in its entirety. A B domain deleted factor VIII may also contain a deletion of amino acids 771-1666 or amino acids 868-1562 of factor VIII. Meulien P., et al. *Protein Eng.* 2(4): 301-6

(1988), incorporated herein by reference in its entirety. Additional B domain deletions that are part of the invention include, e.g.: deletion of amino acids 982 through 1562 or 760 through 1639 (Toole et al., *Proc. Natl. Acad. Sci. U.S.A.* 83:5939-5942 (1986)), 797 through 1562 (Eaton et al., *Biochemistry* 25:8343-8347 (1986)), 741 through 1646 (Kaufman (PCT published application No. WO 87/04187)), 747-1560 (Sarver et al., *DNA* 6:553-564 (1987)), 741 through 1648 (Pasek (PCT application No. 88/00831)), 816 through 1598 or 741 through 1689 (Lagner (Behring Inst. Mitt. (1988) No. 82:16-25, EP 295597)), each of which is incorporated herein by reference in its entirety. Each of the foregoing deletions may be made in any Factor VIII sequence.

In one embodiment, the B domain deleted Factor VIII portion in the chimeric polypeptide is processed into two chains connected (or associated) by a metal bond, the first chain comprising a heavy chain (A1-A2-partial B) and a second chain comprising a light chain (A3-C1-C2). In another embodiment, the B domain deleted Factor VIII portion is a single chain Factor VIII. The single chain Factor VIII can comprise an intracellular processing site, which corresponds to Arginine at residue 754 of B domain deleted Factor VIII (residue 773 of SEQ ID NO: 2) or at residue 1648 of full-length Factor VIII (residue 1657 of SEQ ID NO: 6).

The metal bond between the heavy chain and the light chain can be any metal known in the art. For example, the metals useful for the invention can be a divalent metal ion. The metals that can be used to associate the heavy chain and light chain include, but not limited to, $Ca^{2+}$, $Mn^{2+}$, or $Cu^{2+}$. Fatouros et al., *Intern. J. Pharm.* 155(1): 121-131 (1997); Wakabayashi et al., *JBC.* 279(13): 12677-12684 (2004).

"Chimeric polypeptide," as used herein, means a polypeptide that includes within it at least two polypeptides (or subsequences or peptides) from different sources. Chimeric polypeptides may include, e.g., two, three, four, five, six, seven, or more polypeptides from different sources, such as different genes, different cDNAs, or different animal or other species. Chimeric polypeptides may include, e.g., one or more linkers joining the different subsequences. Thus, the subsequences may be joined directly or they may be joined indirectly, via linkers, or both, within a single chimeric polypeptide. Chimeric polypeptides may include, e.g., additional peptides such as signal sequences and sequences such as 6His and FLAG that aid in protein purification or detection. In addition, chimeric polypeptides may have amino acid or peptide additions to the N- and/or C-termini.

In some embodiments, the chimeric polypeptide comprises a Factor VIII portion and a non-Factor VIII portion. Exemplary non-Factor VIII portions include, e.g., Fc, XTEN, albumin, a PAS sequence, transferrin, CTP (28 amino acid C-terminal peptide (CTP) of human chorionic gonadotropin (hCG) with its 4 O-glycans), polyethylene glycol (PEG), hydroxyethyl starch (HES), albumin binding polypeptide, and albumin-binding small molecules. Exemplary chimeric polypeptides of the invention include, e.g., chimeric Factor VIII-Fc polypeptides, chimeric Factor VIII-XTEN polypeptides, chimeric Factor VIII-albumin polypeptides, chimeric Factor VIII-PAS polypeptides, chimeric Factor VIII-transferrin polypeptides, chimeric Factor VIII-CTP polypeptides, chimeric Factor VIII-PEG polypeptides, chimeric Factor VIII-HES polypeptides, chimeric Factor VIII-albumin binding polypeptide polypeptides, and chimeric Factor VIII.-albumin-binding small molecule polypeptides.

Exemplary chimeric Factor VIII-Fc polypeptides include, e.g., SEQ ID NO:2 or 6 (Table 2), with or without their signal sequences and the chimeric Fc polypeptide of SEQ ID NO:4 (Table 2).

The chimeric polypeptide may comprise a sequence at least 90% or 95% identical to the Factor VIII and Fc amino acid sequence shown in Table 2A(i) without a signal sequence (amino acids 20 to 1684 of SEQ ID NO:2) or at least 90% or 95% identical to the Factor VIII and Fc amino acid sequence shown in Table 2A(i) with a signal sequence (amino acids 1 to 1684 of SEQ ID NO:2), wherein the sequence has Factor VIII activity. The Factor VIII activity can be measured by activated Partial Thromboplastin Time (aPPT) assay, chromogenic assay, or other known methods. The chimeric polypeptide may comprise a sequence identical to the Factor VIII and Fc amino acid sequence shown in Table 2A(i) without a signal sequence (amino acids 20 to 1684 of SEQ ID NO:2) or identical to the Factor VIII and Fc amino acid sequence shown in Table 2A(i) with a signal sequence (amino acids 1 to 1684 of SEQ ID NO:2).

As discussed above, exemplary chimeric polypeptides include Factor VIII fused to one or more XTEN polypeptides. Schellenburger et al., *Nat. Biotech.* 27:1186-90 (2009), which is incorporated herein by reference in its entirety. The XTEN polypeptide can be fused to either the N-terminal end of FVIII or to the C-terminal end of FVIII. A protease site may be included between the XTEN portion and the Factor VIII portion to allow such processing. XTEN polypeptides include, e.g., those disclosed in WO 2009/023270, WO 2010/091122, WO 2007/103515, US 2010/0189682, and US 2009/0092582, each of which is incorporated herein by reference in its entirety.

As discussed above, exemplary chimeric polypeptides also include Factor VIII fused to one or more albumin polypeptides, albumin binding polypeptides, or albumin-binding small molecules. In one embodiment, the albumin is human albumin. The albumin or albumin binding protein can be fused to either the N-terminal end of FVIII or to the C-terminal end of FVIII or inserted between two amino acids in FVIII. Examples of albumin, e.g., fragments thereof, that may be used in the present invention are known. e.g., U.S. Pat. No. 7,592,010; U.S. Pat. No. 6,686,179; and Schulte, *Thrombosis Res.* 124 Suppl. 2:S6-S8 (2009), each of which is incorporated herein by reference in its entirety.

The albumin binding polypeptides can compromise, without limitation, bacterial albumin-binding domains, albumin-binding peptides, or albumin-binding antibody fragments that can bind to albumin. Domain 3 from streptococcal protein G, as disclosed by Kraulis et al., *FEBS Lett.* 378: 190-194 (1996) and Linhult et al., *Protein Sci.* 11:206-213 (2002) is an example of a bacterial albumin-binding domain. Examples of albumin-binding peptides include a series of peptides having the core sequence DICLPRWGCLW (SEQ ID NO: 7). See, e.g., Dennis et al., *J. Biol. Chem.* 2002, 277: 35035-35043 (2002). Examples of albumin-binding antibody fragments are disclosed in Muller and Kontermann, *Curr. Opin. Mol. Ther.* 9:319-326 (2007); Rooverset et al., *Cancer Immunol. Immunother.* 56:303-317 (2007), and Holt et al., *Prot. Eng. Design Sci.,* 21:283-288 (2008), which are incorporated herein by reference in their entireties.

In certain aspects, a recombinant FVIII polypeptide of the invention comprises at least one attachment site for a non-polypeptide small molecule, variant, or derivative that can bind to albumin thereof. An example of such albumin binding moieties is 2-(3-maleimidopropanamido)-6-(4-(4- iodophenyl)butanamido)hexanoate ("Albu" tag) as disclosed by Trusselet et al., *Bioconjugate Chem.* 20:2286-2292 (2009).

As discussed above, exemplary chimeric polypeptides also include Factor VIII fused to at least one β subunit of the C-terminal peptide (CTP) of human chorionic gonadotropin or fragment, variant, or derivative thereof. The CTP can be fused to Factor VIII either the N-terminal end of FVIII or to the C-terminal end of FVIII or inserted between two amino acids in FVIII. One or more CTP peptides fused to or inserted into a recombinant protein is known to increase the in vivo half-life of that protein. See, e.g., U.S. Pat. No. 5,712,122, incorporated by reference herein in its entirety. Exemplary CTP peptides include DPRFQDSSSSKAPPPSLPSPSRLPGPSDTPIL (SEQ ID NO: 8) or SSSSKAPPPSLPSPSRLPGPSDTPILPQ. (SEQ ID NO: 9). See, e.g., U.S. Patent Application Publication No. US 2009/0087411 A1, incorporated by reference.

As discussed above, exemplary chimeric polypeptides also include Factor VIII fused to at least one PAS sequence or fragment, variant, or derivative thereof. The PAS sequence can be fused to either the N-terminal end of FVIII or to the C-terminal end of FVIII or inserted between two amino acids in FVIII. A PAS peptide or PAS sequence, as used herein, means an amino acid sequence comprising mainly alanine and serine residues or comprising mainly alanine, serine, and proline residues, the amino acid sequence forming random coil conformation under physiological conditions. Accordingly, the PAS sequence is a building block, an amino acid polymer, or a sequence cassette comprising, consisting essentially of, or consisting of alanine, serine, and proline which can be used as a part of the heterologous moiety in the chimeric protein. An amino acid polymer also can form random coil conformation when residues other than alanine, serine, and proline are added as a minor constituent in the PAS sequence. By "minor constituent" is meant that that amino acids other than alanine, serine, and proline can be added in the PAS sequence to a certain degree, e.g., up to about 12%, i.e., about 12 of 100 amino acids of the PAS sequence, up to about 10%, up to about 9%, up to about 8%, about 6%, about 5%, about 4%, about 3%, i.e. about 2%, or about 1%, of the amino acids. The amino acids different from alanine, serine and proline cab be selected from the group consisting of Arg, Asn, Asp, Cys, Gln, Glu, Gly, His, Ile, Leu, Lys, Met, Phe, Thr, Trp, Tyr, and Val. Under physiological conditions, a PAS peptide forms a random coil conformation and thereby can mediate an increased in vivo and/or in vitro stability to a recombinant protein of the invention, and has procoagulant activity.

Non-limiting examples of the PAS peptides include ASPAAPAPASPAAPAPSAPA (SEQ ID NO: 10), AAPASPAPAAPSAPAPAAPS (SEQ ID NO: 11), APSSPSPSAPSSPSPASPSS (SEQ ID NO: 12), APSSPSPSAPSSPSPASPS (SEQ ID NO: 13), SSPSAPSPSSPASPSPSSPA (SEQ ID NO: 14), AASPAAPSAPPAAASPAAPSAPPA (SEQ ID NO: 15), ASAAAPAAASAAASAPSAAA (SEQ ID NO: 16) or any variants, derivatives, fragments, or combinations thereof. Additional examples of PAS sequences are known from, e.g., US Pat. Publ. No. 2010/0292130 A1 and PCT Appl. Publ. No. WO 2008/155134 A1. European issued patent EP2173890.

As discussed above, exemplary chimeric polypeptides also include Factor VIII fused to at least one transferrin peptide or fragment, variant, or derivative thereof. At least one transferrin peptide can be fused to either the N-terminal end of FVIII or to the C-terminal end of FVIII or inserted between two amino acids in FVIII. Any transferrin can be fused to or inserted into a recombinant FVIII protein of the invention. As an example, wild-type human Tf (Tf) is a 679 amino acid protein, of approximately 75 KDa (not accounting for glycosylation), with two main domains, N (about 330 amino acids) and C (about 340 amino acids), which appear to originate from a gene duplication. See GenBank accession numbers NM001063, XM002793, M12530, XM039845, XM 039847 and S95936 (www.ncbi.nlm.nih.gov), all of which are herein incorporated by reference in their entirety.

Transferrin transports iron through transferrin receptor (TfR)-mediated endocytosis. After the iron is released into an endosomal compartment and Tf-TfR complex is recycled to cell surface, the Tf is released back extracellular space for next cycle of iron transporting. Tf possesses a long half-life that is in excess of 14-17 days (Li et al., *Trends Pharmacol. Sci.* 23:206-209 (2002)). Transferrin fusion proteins have been studied for half-life extension, targeted deliver for cancer therapies, oral delivery and sustained activation of proinsulin (Brandsma et al., *Biotechnol. Adv.*, 29: 230-238 (2011); Bai et al., *Proc. Natl. Acad. Sci. USA* 102:7292-7296 (2005); Kim et al., *J. Pharmacol. Exp. Ther.*, 334:682-692 (2010); Wang et al., *J. Controlled Release* 155:386-392 (2011)).

As discussed above, exemplary chimeric polypeptides also include Factor VIII fused to at least one polyethylene glycol (PEG) moieties.

PEGylated FVIII can refer to a conjugate formed between FVIII and at least one polyethylene glycol (PEG) molecule. PEG is commercially available in a large variety of molecular weights and average molecular weight ranges. Typical examples of PEG average molecular weight ranges include, but are not limited to, about 200, about 300, about 400, about 600, about 1000, about 1300-1600, about 1450, about 2000, about 3000, about 3000-3750, about 3350, about 3000-7000, about 3500-4500, about 5000-7000, about 7000-9000, about 8000, about 10000, about 8500-11500, about 16000-24000, about 35000, about 40000, about 60000, and about 80000 daltons. These average molecular weights are provided merely as examples and are not meant to be limiting in any way.

A recombinant FVIII protein of the invention can be PEGylated to include mono- or poly- (e.g., 2-4) PEG moieties. PEGylation can be carried out by any of the PEGylation reactions known in the art. Methods for preparing a PEGylated protein product will generally include (i) reacting a polypeptide with polyethylene glycol (such as a reactive ester or aldehyde derivative of PEG) under conditions whereby the peptide of the invention becomes attached to one or more PEG groups; and (ii) obtaining the reaction product(s). In general, the optimal reaction conditions for the reactions will be determined case by case based on known parameters and the desired result.

There are a number of PEG attachment methods available to those skilled in the art, for example Malik F et al., *Exp. Hematol.* 20:1028-35 (1992); Francis, *Focus on Growth Factors* 3(2):4-10 (1992); European Pat. Pub. Nos. EP0401384, EP0154316, and EP0401384; and International Pat. Appl. Pub. Nos. WO92/16221 and WO95/34326. As a non-limiting example, FVIII variants can contain cysteine substitutions in one or more insertion sites in FVIII, and the cysteines can be further conjugated to PEG polymer. See Mei et al., *Blood* 116:270-279 (2010) and U.S. Pat. No. 7,632,921, which are incorporated herein by reference in their entireties.

As discussed above, exemplary chimeric polypeptides also include Factor VIII fused to at least one hydroxyethyl starch (HES) polymer. HES is a derivative of naturally occurring amylopectin and is degraded by alpha-amylase in the body. HES exhibits advantageous biological properties and is used as a blood volume replacement agent and in hemodilution therapy in the clinics. See, e.g., Sommermeyer et al., *Krankenhauspharmazie* 8:271-278 (1987); and Weidler et al., *Arzneim.-Forschung/Drug Res.* 41: 494-498 (1991).

HES is mainly characterized by the molecular weight distribution and the degree of substitution. HES has a mean molecular weight (weight mean) of from 1 to 300 kD, from 2 to 200 kD, from 3 to 100 kD, or from 4 to 70 kD. Hydroxyethyl starch can further exhibit a molar degree of substitution of from 0.1 to 3, from 0.1 to 2, from 0.1 to 0.9, or from 0.1 to 0.8, and a ratio between C2:C6 substitution in the range of from 2 to 20 with respect to the hydroxyethyl groups. HES with a mean molecular weight of about 130 kD is Voluven® from Fresenius. Voluven® is an artificial colloid, employed, e.g., for volume replacement used in the therapeutic indication for therapy and prophylaxis of hypovolaemia. There are a number of HES attachment methods available to those skilled in the art, e.g., the same PEG attachment methods described above.

In some embodiments, a chimeric polypeptide comprising a Factor VIII portion has an increased half-life (t1/2) over a polypeptide consisting of the same Factor VIII portion without the non Factor VIII portion. A chimeric Factor VIII polypeptide with an increased t1/2 may be referred to herein as a long-acting Factor VIII. Long-acting chimeric Factor VIII polypeptides include, e.g., Factor VIII fused to Fc (including, e.g., chimeric Factor VIII polypeptides in the form of a hybrid such as a FVIIIFc monomer dimer hybrid; see Example 1, FIG. 1, and Table 2A; and U.S. Pat. Nos. 7,404,956 and 7,348,004), Factor VIII fused to XTEN, and Factor VIII fused to albumin.

"Culture," "to culture" and "culturing," as used herein, means to incubate cells under in vitro conditions that allow for cell growth or division or to maintain cells in a living state. "Cultured cells," as used herein, means cells that are propagated in vitro.

"Factor VIII," as used herein, means functional factor VIII polypeptide in its normal role in coagulation, unless otherwise specified. Thus, the term Factor VIII includes variant polypeptides that are functional. Factor VIII proteins can be the human, porcine, canine, and murine factor VIII proteins. As described in the Background Art section, the full length polypeptide and polynucleotide sequences are known, as are many functional fragments, mutants and modified versions. Examples of human factor VIII sequences are shown as subsequences in SEQ ID NOs:2 or 6 (Table 2). Factor VIII polypeptides include, e.g., full-length factor VIII, full-length factor VIII minus Met at the N-terminus, mature factor VIII (minus the signal sequence), mature factor VIII with an additional Met at the N-terminus, and/or factor VIII with a full or partial deletion of the B domain. Factor VIII variants include B domain deletions, whether partial or full deletions.

A great many functional factor VIII variants are known, as is discussed above and below. In addition, hundreds of nonfunctional mutations in factor VIII have been identified in hemophilia patients, and it has been determined that the effect of these mutations on factor VIII function is due more to where they lie within the 3-dimensional structure of factor VIII than on the nature of the substitution (Cutler et al., *Hum. Mutat.* 19:274-8 (2002)), incorporated herein by reference in its entirety. In addition, comparisons between factor VIII from humans and other species have identified conserved residues that are likely to be required for function (Cameron et al., Thromb. Haemost. 79:317-22 (1998); U.S. Pat. No. 6,251,632), incorporated herein by reference in its entirety.

The human factor VIII gene was isolated and expressed in mammalian cells (Toole, J. J., et al., *Nature* 312:342-347 (1984); Gitschier, J., et al., *Nature* 312:326-330 (1984); Wood, W. I., et al., *Nature* 312:330-337 (1984); Vehar, G. A., et al., *Nature* 312:337-342 (1984); WO 87/04187; WO 88/08035; WO 88/03558; U.S. Pat. No. 4,757,006), each of which is incorporated herein by reference in its entirety, and the amino acid sequence was deduced from cDNA. Capon et al., U.S. Pat. No. 4,965,199, incorporated herein by reference in its entirety, discloses a recombinant DNA method for producing factor VIII in mammalian host cells and purification of human factor VIII. Human factor VIII expression in CHO (Chinese hamster ovary) cells and BHKC (baby hamster kidney cells) has been reported. Human factor VIII has been modified to delete part or all of the B domain (U.S. Pat. Nos. 4,994,371 and 4,868,112, each of which is incorporated herein by reference in its entirety), and replacement of the human factor VIII B domain with the human factor V B domain has been performed (U.S. Pat. No. 5,004,803, incorporated herein by reference in its entirety). The cDNA sequence encoding human factor VIII and predicted amino acid sequence are shown in SEQ ID NOs:1 and 2, respectively, of US Application Publ. No. 2005/0100990, incorporated herein by reference in its entirety.

U.S. Pat. No. 5,859,204, Lollar, J. S., incorporated herein by reference in its entirety, reports functional mutants of factor VIII having reduced antigenicity and reduced immunoreactivity. U.S. Pat. No. 6,376,463, Lollar, J. S., incorporated herein by reference in its entirety, also reports mutants of factor VIII having reduced immunoreactivity. US Application Publ. No. 2005/0100990, Saenko et al., incorporated herein by reference in its entirety, reports functional mutations in the A2 domain of factor VIII.

A number of functional factor VIII molecules, including B-domain deletions, are disclosed in the following patents U.S. Pat. No. 6,316,226 and U.S. Pat. No. 6,346,513, both assigned to Baxter; U.S. Pat. No. 7,041,635 assigned to In2Gen; U.S. Pat. No. 5,789,203, U.S. Pat. No. 6,060,447, U.S. Pat. No. 5,595,886, and U.S. Pat. No. 6,228,620 assigned to Chiron; U.S. Pat. No. 5,972,885 and U.S. Pat. No. 6,048,720 assigned to Biovitrum, U.S. Pat. No. 5,543, 502 and U.S. Pat. No. 5,610,278 assigned to Novo Nordisk; U.S. Pat. No. 5,171,844 assigned to Immuno Ag; U.S. Pat. No. 5,112,950 assigned to Transgene S.A.; U.S. Pat. No. 4,868,112 assigned to Genetics Institute, each of which is incorporated herein by reference in its entirety.

The porcine factor VIII sequence is published, (Toole, J. J., et al., *Proc. Natl. Acad. Sci. USA* 83:5939-5942 (1986)), incorporated herein by reference in its entirety, and the complete porcine cDNA sequence obtained from PCR amplification of factor VIII sequences from a pig spleen cDNA library has been reported (Healey, J. F. et al., *Blood* 88:4209-4214 (1996), incorporated herein by reference in its entirety). Hybrid human/porcine factor VIII having substitutions of all domains, all subunits, and specific amino acid sequences were disclosed in U.S. Pat. No. 5,364,771 by Lollar and Runge, and in WO 93/20093, incorporated herein by reference in its entirety. More recently, the nucleotide and corresponding amino acid sequences of the A1 and A2 domains of porcine factor VIII and a chimeric factor VIII with porcine A1 and/or A2 domains substituted for the corresponding human domains were reported in WO 94/11503, incorporated herein by reference in its entirety. U.S. Pat. No. 5,859,204, Lollar, J. S., also discloses the porcine cDNA and deduced amino acid sequences. U.S. Pat. No. 6,458,563, incorporated herein by reference in its entirety assigned to Emory discloses a B-domain deleted porcine Factor VIII.

The Factor VIII (or Factor VIII portion of a chimeric polypeptide) may be at least 90% or 95% identical to a Factor VIII amino acid sequence shown in Table 2 without a signal sequence (amino acids 20 to 1457 of SEQ ID NO:2; and amino acids 20 to 2351 of SEQ ID NO:6), wherein said Factor VIII portion has Factor VIII activity. The Factor VIII (or Factor VIII portion of a chimeric polypeptide) may be identical to a Factor VIII amino acid sequence shown in Table 2 without a signal sequence (amino acids 20 to 1457 of SEQ ID NO:2; and amino acids 20 to 2351 of SEQ ID NO:6).

The Factor VIII (or Factor VIII portion of a chimeric polypeptide) may be at least 90% or 95% identical to a Factor VIII amino acid sequence shown in Table 2 with a signal sequence (amino acids 1 to 1457 of SEQ ID NO:2 and amino acids 1 to 2351 of SEQ ID NO:6), wherein said Factor VIII portion has Factor VIII activity. The Factor VIII (or Factor VIII portion of a chimeric polypeptide) may be identical to a Factor VIII amino acid sequence shown in Table 2 with a signal sequence (amino acids 1 to 1457 of SEQ ID NO:2 and amino acids 1 to 2351 of SEQ ID NO:6).

"Equivalent dose," as used herein, means the same dose of Factor VIII activity as expressed in International Units, which is independent of molecular weight of the polypeptide in question. One International Unit (IU) of factor VIII activity corresponds approximately to the quantity of factor VIII in one milliliter of normal human plasma. Several assays are available for measuring Factor VIII activity, including the European Pharmacopoeia chromogenic substrate assay and a one stage clotting assay.

"Fc," as used herein, means functional neonatal Fc receptor (FcRn) binding partners, unless otherwise specified. An FcRn binding partner is any molecule that can be specifically bound by the FcRn receptor with consequent active transport by the FcRn receptor of the FcRn binding partner. Thus, the term Fc includes any variants of IgG Fc that are functional. The region of the Fc portion of IgG that binds to the FcRn receptor has been described based on X-ray crystallography (Burmeister et al., Nature 372:379 (1994), incorporated herein by reference in its entirety). The major contact area of the Fc with the FcRn is near the junction of the CH2 and CH3 domains. Fc-FcRn contacts are all within a single Ig heavy chain. The FcRn binding partners include, e.g., whole IgG, the Fc fragment of IgG, and other fragments of IgG that include the complete binding region of FcRn. The major contact sites include amino acid residues 248, 250-257, 272, 285, 288, 290-291, 308-311, and 314 of the CH2 domain and amino acid residues 385-387, 428, and 433-436 of the CH3 domain. References made to amino acid numbering of immunoglobulins or immunoglobulin fragments, or regions, are all based on Kabat et al. 1991, Sequences of Proteins of Immunological Interest, U. S. Department of Public Health, Bethesda; MD, incorporated herein by reference in its entirety. (The FcRn receptor has been isolated from several mammalian species including humans. The sequences of the human FcRn, rat FcRn, and mouse FcRn are known (Story et al., J. Exp. Med. 180: 2377 (1994), incorporated herein by reference in its entirety.) An Fc may comprise the CH2 and CH3 domains of an immunoglobulin with or without the hinge region of the immunoglobulin. Exemplary Fc variants are provided in WO 2004/101740 and WO 2006/074199, incorporated herein by reference in its entirety.

Fc (or Fc portion of a chimeric polypeptide) may contain one or more mutations, and combinations of mutations.

Fc (or Fc portion of a chimeric polypeptide) may contain mutations conferring increased half-life such as M252Y, S254T, T256E, and combinations thereof, as disclosed in Oganesyan et al., Mol. Immunol. 46:1750 (2009), which is incorporated herein by reference in its entirety; H433K, N434F, and combinations thereof, as disclosed in Vaccaro et al., Nat. Biotechnol. 23:1283 (2005), which is incorporated herein by reference in its entirety; the mutants disclosed at pages 1-2, paragraph [0012], and Examples 9 and 10 of US 2009/0264627 A1, which is incorporated herein by reference in its entirety; and the mutants disclosed at page 2, paragraphs [0014] to [0021] of US 20090163699 A1, which is incorporated herein by reference in its entirety.

Fc (or Fc portion of a chimeric polypeptide) may also include, e.g., the following mutations: The Fc region of IgG can be modified according to well recognized procedures such as site directed mutagenesis and the like to yield modified IgG or Fc fragments or portions thereof that will be bound by FcRn. Such modifications include, e.g., modifications remote from the FcRn contact sites as well as modifications within the contact sites that preserve or even enhance binding to the FcRn. For example the following single amino acid residues in human IgG1 Fc (Fcγ1) can be substituted without significant loss of Fc binding affinity for FcRn: P238A, S239A, K246A, K248A, D249A, M252A, T256A, E258A, T260A, D265A, S267A, H268A, E269A, D270A, E272A, L274A, N276A, Y278A, D280A, V282A, E283A, H285A, N286A, T289A, K290A, R292A, E293A, E294A, Q295A, Y296F, N297A, S298A, Y300F, R301A, V303A, V305A, T307A, L309A, Q311A, D312A, N315A, K317A, E318A, K320A, K322A, S324A, K326A, A327Q, P329A, A330Q, A330S, P331A, P331S, E333A, K334A, T335A, S337A, K338A, K340A, Q342A, R344A, E345A, Q347A, R355A, E356A, M358A, T359A, K360A, N361A, Q362A, Y373A, S375A D376A, A378Q, E380A, E382A, S383A, N384A, Q386A, E388A, N389A, N390A, Y391F, K392A, L398A, S400A, D401A, D413A, K414A, R416A, Q418A, Q419A, N421A, V422A, S424A, E430A, N434A, T437A, Q438A, K439A, S440A, S444A, and K447A, where for example P238A represents wildtype proline substituted by alanine at position number 238. In addition to alanine other amino acids may be substituted for the wildtype amino acids at the positions specified above. Mutations may be introduced singly into Fc giving rise to more than one hundred FcRn binding partners distinct from native Fc. Additionally, combinations of two, three, or more of these individual mutations may be introduced together, giving rise to hundreds more FcRn binding partners. Certain of these mutations may confer new functionality upon the FcRn binding partner. For example, one embodiment incorporates N297A, removing a highly conserved N-glycosylation site. The effect of this mutation is to reduce immunogenicity, thereby enhancing circulating half-life of the FcRn binding partner, and to render the FcRn binding partner incapable of binding to FcγRI, FcγRIIA, FcγRIIB, and FcγRIIIA, without compromising affinity for FcRn (Routledge et al. 1995, Transplantation 60:847, which is incorporated herein by reference in its entirety; Friend et al. 1999, Transplantation 68:1632, which is incorporated herein by reference in its entirety; Shields et al. 1995, J. Biol. Chem. 276:6591, which is incorporated herein by reference in its entirety). Additionally, at least three human Fc gamma receptors appear to recognize a binding site on IgG within the lower hinge region, generally amino acids 234-237. Therefore, another example of new functionality and potential decreased immunogenicity may arise from mutations of this region, as for example by replacing amino acids 233-236 of human IgG1 "ELLG" to the corresponding sequence from IgG2 "PVA" (with one amino acid deletion). It has been shown that FcyRI, FcyRII, and FcyRIII which mediate various effector functions will not bind to IgG1 when such mutations have been introduced (Ward and Ghetie, *Therapeutic Immunology* 2:77 (1995), which is incorporated herein by reference in its entirety; and Armour et al., *Eur. J. Immunol.* 29:2613 (1999), which is incorporated herein by reference in its entirety). As a further example of new functionality arising from mutations described above affinity for FcRn may be increased beyond that of wild type in some instances. This increased affinity may reflect an increased "on" rate, a decreased "off" rate or both an increased "on" rate and a decreased "off" rate. Mutations believed to impart an increased affinity for FcRn include, e.g., T256A, T307A, E380A, and N434A (Shields et al., *J. Biol. Chem.* 276:6591 (2001), which is incorporated herein by reference in its entirety).

The Fc (or Fc portion of a chimeric polypeptide) may be at least 90% or 95% identical to the Fc amino acid sequence shown in Table 2 (amino acids 1458 to 1684 of SEQ ID NO:2 or amino acids 2352 to 2578 of SEQ ID NO:6). The Fc (or Fc portion of a chimeric polypeptide) may be identical to the Fc amino acid sequence shown in Table 2 (amino acids 1458 to 1684 of SEQ ID NO:2 and amino acids 2352 to 2578 of SEQ ID NO:6).

"Hybrid" polypeptides and proteins, as used herein, means a combination of a chimeric polypeptide with a second polypeptide. The chimeric polypeptide and the second polypeptide in a hybrid may be associated with each other via protein-protein interactions, such as charge-charge or hydrophobic interactions. The chimeric polypeptide and the second polypeptide in a hybrid may be associated with each other via disulfide or other covalent bond(s). Hybrids are described in WO 2004/101740 and WO 2006/074199, each of which is incorporated herein by reference in its entirety. See also U.S. Pat. Nos. 7,404,956 and 7,348,004, each of which is incorporated herein by reference in its entirety. The second polypeptide may be a second copy of the same chimeric polypeptide or it may be a non-identical chimeric polypeptide. See, e.g., FIG. 1, Example 1, and Table 2. In one embodiment, the second polypeptide is a polypeptide comprising an Fc. In another embodiment, the chimeric polypeptide is a chimeric Factor VIII-Fc polypeptide and the second polypeptide consists essentially of Fc, e.g., the hybrid polypeptide of Example 1, which is a rFVIIIFc recombinant fusion protein consisting of a single molecule of recombinant B-domain deleted human FVIII (BDD-rFVIII) fused to the dimeric Fc domain of the human IgG1, with no intervening linker sequence. This hybrid polypeptide is referred to herein as FVIIIFc monomeric Fc fusion protein, FVIIIFc monomer hybrid, monomeric FVIIIFc hybrid, and FVIIIFc monomer-dimer See Example 1, FIG. 1, and Table 2A. The Examples provide preclinical and clinical data for this hybrid polypeptide.

The second polypeptide in a hybrid may comprise or consist essentially of a sequence at least 90% or 95% identical to the amino acid sequence shown in Table 2A(ii) without a signal sequence (amino acids 21 to 247 of SEQ ID NO:4) or at least 90% or 95% identical to the amino acid sequence shown in Table 2A(ii) with a signal sequence (amino acids 1 to 247 of SEQ ID NO:4). The second polypeptide may comprise or consist essentially of a sequence identical to the amino acid sequence shown in Table 2A(ii) without a signal sequence (amino acids 21 to 247 of SEQ ID NO:4) or identical to the amino acid sequence shown in Table 2A(ii) with a signal sequence (amino acids 1 to 247 of SEQ ID NO:4).

FIG. 1 is a schematic showing the structure of a B domain deleted factor VIII-Fc chimeric polypeptide, and its association with a second polypeptide that is an Fc polypeptide. To obtain this hybrid, the coding sequence of human recombinant B-domain deleted FVIII was obtained by reverse transcription-polymerase chain reaction (RT-PCR) from human liver poly A RNA (Clontech) using FVIII-specific primers. The FVIII sequence includes the native signal sequence for FVIII. The B-domain deletion was from serine 743 (S743; 2287 bp) to glutamine 1638 (Q1638; 4969 bp) for a total deletion of 2682 bp. Then, the coding sequence for human recombinant Fc was obtained by RT-PCR from a human leukocyte cDNA library (Clontech) using Fc specific primers. Primers were designed such that the B-domain deleted FVIII sequence was fused directly to the N-terminus of the Fc sequence with no intervening linker. The FVIIIFc DNA sequence was cloned into the mammalian dual expression vector pBUDCE4.1 (Invitrogen) under control of the CMV promoter. A second identical Fc sequence including the mouse Igk signal sequence was obtained by RT-PCR and cloned downstream of the second promoter, EF1α, in the expression vector pBUDCE4.1.

The rFVIIIFc expression vector was transfected into human embryonic kidney 293 cells (HEK293H; Invitrogen) using Lipofectamine 2000 transfection reagent (Invitrogen). Stable clonal cell lines were generated by selection with Zeocin (Invitrogen). One clonal cell line, 3C4-22 was used to generate FVIIIFc for characterization in vivo. Recombinant FVIIIFc was produced and purified (McCue et al. 2009) at Biogen Idec (Cambridge, Mass.). The transfection strategy described above was expected to yield three products, i.e., monomeric rFVIIIFc hybrids, dimeric rFVIIIFc hybrids and dimeric Fc. However, there was essentially no dimeric rFVIIIFc detected in the conditioned medium from these cells. Rather, the conditioned medium contained Fc and monomeric rFVIIIFc. It is possible that the size of dimeric rFVIIIFc was too great and prevented efficient secretion from the cell. This result was beneficial since it rendered the purification of the monomer less complicated than if all three proteins had been present. The material used in these studies had a specific activity of approximately 9000 IU/mg.

In one embodiment, the polypeptides of the invention are administered to a patient who expresses high level of von Willebrand factor (VWF). "Subject" or "patient" as used herein means a human individual. A subject can be a patient who is currently suffering from a bleeding disorder or is expected to be in need of such a treatment. "Subject" can include an adult or a pediatric subject. The pediatric subject can be a pediatric patient under the age of 12. The term "pediatrics" as used herein is the branch of medicine that deals with the care of infants and children and the treatment of their diseases. In one embodiment, the subject is a pediatric patient who has a diagnosis of severe hemophilia A. In certain embodiments, pediatric subjects are treated with a long-acting Factor VIII polypeptide of the invention.

VWF is a plasma protein having a multimer structure in which the molecular weight of the various forms varies between approximately 230 kDa for each monomer subunit and up to more than 20 million Da in the multimer forms of greater molecular weight, thus forming the largest known soluble protein. Its plasma concentration is approximately around 5-10 μg/ml (Siedlecki et al., Blood, vol 88: 2939-2950 (1996)) and the plasma form of smaller size is that corresponding to the dimer, with an approximate size of 500 kDa.

VWF has an essential role to play in primary haemostasis, being responsible for the adhesion of platelets to damaged vascular surfaces and therefore formation of the platelet plug on which the mechanisms for formation of the fibrin coagulate develop. It is suggested that the higher molecular weight multimers support platelet adhesion mechanisms to the sub-endothelium with greater efficiency and the clinical efficacy of VWF concentrates has been related to the concentration of these multimers of higher molecular weight (Metzner et al., Haemophilia 4:25-32 (1998).

Therefore, subjects expressing high levels of VWF would require less frequent dosing of FVIII compared to a subject who expresses lower or normal levels of VWF. The average range of VWF in plasma is between about 50 IU/dL and about 200 IU/dL. In one embodiment, the average level of VWF in plasma is about 50 IU/dL. In another embodiment, a VWF level in plasma of at least about 100 IU/dL is considered a high VWF level. In another embodiment, a high level of VWF in plasma is between about 100 IU/dL and about 200 IU/dL. In another embodiment a high level of VWF in plasma is at least about 110 IU/dL, about 120 IU/dL, about 130 IU/dL, about 140 IU/dL, about 150 IU/dL, about 160 IU/dL, about 170 IU/dL, about 180 IU/dL, about 190 IU/dL, or about 200 IU/dL.

Therefore, in one embodiment, subjects expressing at least about 100 IU/dL of plasma VWF are administered a long-acting FVIII polypeptide of the invention at a long interval dosing regimen. In one embodiment, the long-acting FVIII polypeptide is administered at a dosing interval of at least about 3 days. In another embodiment, the long-acting FVIII polypeptide is administered at a dosing interval of at least about once every week, about once every two weeks, about once every 15 days, about once every 20 days, about once every three weeks, about once every 25 days, about once every four weeks, or about once every one month.

In one embodiment, the subjects were previously identified as having high levels of VWF. In certain embodiments, subjects having a blood serotype other than O (i.e., A, B, or AB) require less frequent dosing of long-acting FVIII because the long-acting FVIII has a longer half-life in these subjects. In these subjects, the increased half-life is due to their elevated VWF levels.

Moreover, pharmacokinetic data, defined as the study of the time course of drug absorption, distribution, metabolism, and excretion, can be used as an identifier of subjects eligible for longer or shorter dosing intervals using a long-acting FVIII polypeptide of the invention. Cinical pharmacokinetics is the application of pharmacokinetic principles to the safe and effective therapeutic management of drugs in an individual patient. The primary goals of clinical pharmacokinetics include enhancing efficacy and decreasing toxicity of a patient's drug therapy. The development of strong correlations between drug concentrations and their pharmacologic responses has enabled clinicians to apply pharmacokinetic principles to actual patient situations.

Thus, in one embodiment, the half-life of a FVIII-Fc polypeptide of the invention is used to identify patients who express high levels of VWF. The range of half-life of FVIII-Fc is between about 10 and about 40 hours, depending at least in part on the levels of VWF also present. On average however, the half-life of FVIII-Fc is about 18 hours. Generally, FVIII-Fc exhibits an increased half-life of at least about 1.2-fold in patients having high levels of VWF compared to the half-life of FVIII-Fc when administered to individuals having average levels of VWF. In one embodiment, FVIII-Fc exhibits an increased half-life of at least about 1.3, 1.4, 1.5, 1.6, 1.7, 1.8, 1.9, 2.0, 2.1, 2.2, 2.3, 2.4, or 2.5-fold compared to the half-life of FVIII-Fc when administered to individuals having average levels of VWF. In one embodiment, in subjects expressing high levels of VWF, the half-life of FVIII-Fc is between at least about 20 hours and about 40 hours. In another embodiment, the half-life of FVIII-Fc is at least about 21 hours, 22 hours, 23 hours, 24 hours, 25 hours, 26 hours, 27 hours, 28 hours, 29 hours, 30 hours, 31 hours, 32 hours, 33 hours, 34 hours, 35 hours, 36 hours, 37 hours, 38 hours, 39 hours, or 40 hours. In one embodiment the half-life of FVIII-Fc is between about 20 and about 27 hours in subjects having high levels of VWF. Thus, in one embodiment, an increased half-life of FVIII-Fc compared to average values is indicative of a subject that is eligible for a longer dosing interval with a long-acting FVIII polypeptide of the invention.

In another embodiment, the half-life of a short-acting FVIII polypeptide is used to identify patients who express high levels of VWF. As used herein, the term "short-acting FVIII" refers to a FVIII polypeptide in which no extenders of half-life have been added. In one embodiment, short-acting FVIII polypeptides consist of full-length or B domain-deleted FVIII. Examples of short-acting FVIII polypeptides are Advate® and ReFacto®.

Since the half-life of short-acting FVIII also varies depending at least in part on VWF levels, short-acting FVIII polypeptides can also be used to identify patients that are eligible for a longer dosing interval of a long-acting FVIII polypeptide of the invention. In one embodiment, the short-acting FVIII exhibits an increased half-life of at least about 1.2-fold in individuals expressing high levels of VWF compared to the half-life of the short-acting FVIII when administered to individuals having average levels of VWF. In another embodiment, the short-acting FVIII exhibits an increased half-life of at least about 1.3, 1.4, 1.5, 1.6, 1.7, 1.8, 1.9, 2.0, 2.1, 2.2, 2.3, 2.4, or 2.5-fold in individuals expressing high levels of VWF compared to the half-life of the short-acting FVIII when administered to individuals having average levels of VWF. Thus, individuals that demonstrate an increased half-life of at least about 1.2-fold when they are administered a short-acting FVIII are eligible for a longer dosing interval with a long-acting FVIII polypeptide of the invention.

"Dosing interval," as used herein, means the dose of time that elapses between multiple doses being administered to a subject. The comparison of dosing interval may be carried out in a single subject or in a population of subjects and then the average obtained in the population may be calculated.

The dosing interval when administering a chimeric Factor VIII polypeptide, e.g., a chimeric Factor VIII-Fc polypeptide (a polypeptide comprising a Factor VIII or a hybrid) of the invention may be at least about one and one-half times longer than the dosing interval required for an equivalent dose of said Factor VIII without the non-Factor VIII portion, e.g., without the Fc portion (a polypeptide consisting of said Factor VIII). The dosing interval may be at least about one and one-half to six times longer, one and one-half to five times longer, one and one-half to four times longer, one and one-half to three times longer, or one and one-half to two times longer, than the dosing interval required for an equivalent dose of said Factor VIII without the non-Factor VIII portion, e.g., without the Fc portion (a polypeptide consisting of said Factor VIII). The dosing interval may be at least about one and one-half, two, two and one-half, three, three and one-half, four, four and one-half, five, five and one-half or six times longer than the dosing interval required for an equivalent dose of said Factor VIII without the non-Factor VIII portion, e.g., without the Fc portion (a polypeptide consisting of said Factor VIII). The dosing interval may be about every three, four, five, six, seven, eight, nine, ten, eleven, twelve, thirteen, or fourteen days or longer. The dosing interval may be at least about one and one-half to 5, one and one-half, 2, 3, 4, or 5 days or longer. For on-demand treatment, the dosing interval of said chimeric polypeptide or hybrid is about once every 24-36, 24-48, 24-72, 24-96, 24-120, 24-144, 24-168, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, or 72 hours or longer.

In one embodiment, the effective dose is 25-80 IU/kg (25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 62, 64, 65, 66, 67, 68, 69, 70, 71, 72, 73, 74, 75, 76, 77, 78, 79, or 80 IU/kg) and the dosing interval is once every 3-5, 3-6, 3-7, 3, 4, 5, 6, 7, or 8 or more days, or three times per week, or no more than three times per week. In one embodiment, the effective dose is 80 IU/kg and the dosing interval is once every 3 days. In a further embodiment, the effective dose of 80 IU/kg given at a dosing interval of every 3 days is administered to a pediatric subject. In another embodiment, the effective dose is 65 IU/kg and the dosing interval is once weekly, or once every 6-7 days. The doses can be administered repeatedly as long as they are necessary (e.g., at least 10, 20, 28, 30, 40, 50, 52, or 57 weeks, at least 1, 2, 3, 4, 5, 6, 7, 8, 9, or 10 years).

In certain embodiments, the effective dose for on-demand treatment is 20-50 IU/Kg (20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 IU/kg). The on-demand treatment can be one time dosing or repeated dosing. For repeated dosing, the dosing interval can be every 12-24 hours, every 24-36 hours, every 24-48 hours, every 36-48 hours, or every 48-72 hours.

"Long-acting Factor VIII" is a Factor VIII having an increased half-life (also referred to herein as t1/2, t1/2 beta, elimination half-life and HL) over a reference Factor VIII. The increased half-life of a long-acting Factor VIII may be due to fusion to one or more non-Factor VIII polypeptides such as, e.g., Fc, XTEN, albumin, a PAS sequence, transferrin, CTP (28 amino acid C-terminal peptide (CTP) of hCG with its 4 O-glycans), polyethylene glycol (PEG), hydroxyethyl starch (HES), albumin binding polypeptide, albumin-binding small molecules, or two or more combinations thereof. The increased half-life may be due to one or more modification, such as, e.g., pegylation. Exemplary long-acting Factor VIII polypeptides include, e.g., chimeric Factor VIII polypeptides comprising Fc, chimeric Factor VIII polypeptides comprising XTEN and chimeric Factor VIII polypeptides comprising albumin. Additional exemplary long-acting Factor VIII polypeptides include, e.g., pegylated Factor VIII.

The "reference" polypeptide, in the case of a long-acting chimeric Factor VIII polypeptide, is a polypeptide consisting essentially of the Factor VIII portion of the chimeric polypeptide, e.g., the same Factor VIII portion without the Fc portion, without the XTEN portion, or without the albumin portion. Likewise, the reference polypeptide in the case of a modified Factor VIII is the same Factor VIII without the modification, e.g., a Factor VIII without the pegylation.

In some embodiments, the long-acting Factor VIII has one or more of the following properties when administered to a subject:

a mean residence time (MRT) (activity) in said subject of about 14-41.3 hours;

a clearance (CL) (activity) in said subject of about 1.22-5.19 mL/hour/kg or less;

a t1/2beta (activity) in said subject of about 11-26.4 hours;

an incremental recovery (K value) (activity; observed) in said subject of about 1.38-2.88 IU/dL per IU/kg;

a Vss (activity) in said subject of about 37.7-79.4 mL/kg; and an AUC/dose in said subject of about 19.2-81.7 IU*h/dL per IU/kg.

In some embodiments, the long-acting Factor VIII has one or more of the following properties when administered to a patient population:

a mean incremental recovery (K-Value) (activity; observed) greater that 1.38 IU/dL per IU/kg;

a mean incremental recovery (K-Value) (activity; observed) of at least about 1.5, at least about 1.85, or at least about 2.46 IU/dL per IU/kg.

a mean clearance (CL) (activity) in said patient population of about 2.33±1.08 mL/hour/kg or less;

a mean clearance (CL) (activity) in said patient population of about 1.8-2.69 mL/hour/kg;

a mean clearance (CL) (activity) in said patient population that is about 65% of the clearance of a polypeptide comprising said Factor VIII without modification;

a mean mean residence time (MRT) (activity) in said patient population of at least about 26.3±8.33 hours;

a mean MRT (activity) in said patient population of about 25.9-26.5 hours;

a mean MRT (activity) in said patent population that is about 1.5 fold longer than the mean MRT of a polypeptide comprising said Factor VIII without modification;

a mean t1/2beta (activity) in said patient population of about 18.3±5.79 hours;

a mean t1/2beta (activity) in said patient population that is about 18-18.4 hours;

a mean t1/2beta (activity) in said patient population that is about 1.5 fold longer than the mean t1/2beta of a polypeptide comprising said Factor VIII without modification;

a mean incremental recovery (K value) (activity; observed) in said patient population of about 2.01±0.44 IU/dL per IU/kg;

a mean incremental recovery (K value) (activity; observed) in said patient population of about 1.85-2.46 IU/dL per IU/kg;

a mean incremental recovery (K value) (activity; observed) in said patient population that is about 90% of the mean incremental recovery of a polypeptide comprising said Factor VIII without modification;

a mean Vss (activity) in said patient population of about 55.1±12 3 mL/kg;

a mean Vss (activity) in said patient population of about 45.3-56.1 mL/kg;

a mean AUC/dose (activity) in said patient population of about 49.9±18.2 IU*h/dL per IU/kg;

a mean AUC/dose (activity) in said patient population of about 44.8-57.6 IU*h/dL per IU/kg.

In other embodiments, the long-acting Factor VIII has one or more of the following properties when administered to a patient population:

a $C_{max\_}$OBS in said subject administered with the chimeric polypeptide is comparable to the $C_{max\_}$OBS in a subject administered with the same amount of a polypeptide consisting of the full-length, mature Factor VIII when measured by a one stage (aPTT) assay or a two stage (chromogenic) assay;

a $C_{max}$_OBS in said subject of about 60.5 IU/dL, about 60.5±1 IU/dL, about 60.5±2 IU/dL, about 60.5±3 IU/dL, about 60.5±4 IU/dL, about 60.5±5 IU/dL, about 60.5±6 IU/dL, about 60.5±7 IU/dL, about 60.5±8 IU/dL, about 60.5±9 IU/dL, or about 60.5±10 IU/dL as measured by a one stage (aPTT) assay when about 25 IU/kg of the chimeric polypeptide is administered;

a $C_{max}$_OBS in said subject of about 53.1-69 IU/dL as measured by a one stage (aPTT) assay when about 25 IU/kg of the chimeric polypeptide is administered;

a $C_{max}$_OBS in said subject of about 119 IU/dL, about 119±1 IU/dL, about 119±2 IU/dL, about 119±3 IU/dL, about 119±4 IU/dL, about 119±5 IU/dL, about 119±6 IU/dL, about 119±7 IU/dL, about 119±8 IU/dL, about 119±9 IU/dL, about 119±10 IU/dL, about 119±11 IU/dL, about 119±12 IU/dL, about 119±13 IU/dL, about 119±14 IU/dL, about 119±15 IU/dL, about 119±16 IU/dL, about 119±17 IU/dL, or about 119±18 IU/dL, as measured by a one stage (aPTT) assay when about 65 IU/kg of the chimeric polypeptide is administered;

a $C_{max}$_OBS in said subject of about 103-136 IU/dL as measured by a one stage (aPTT) assay when about 65 IU/kg of the chimeric polypeptide is administered;

a $C_{max}$_OBS in said subject of about 76.5 IU/dL, about 76.5±1 IU/dL, about 76.5±2 IU/dL, about 76.5±3 IU/dL, about 76.5±4 IU/dL, about 76.5±5 IU/dL, about 76.5±6 IU/dL, about 76.5±7 IU/dL, about 76.5±8 IU/dL, about 76.5±9 IU/dL, about 76.5±10 IU/dL, about 76.5±11 IU/dL, about 76.5±12 IU/dL, about 76.5±13 IU/dL, about 76.5±14 IU/dL, or about 76.5±15 IU/dL, as measured by a two stage (chromogenic) assay when about 25 IU/kg of the chimeric polypeptide is administered;

a $C_{max}$_OBS in said subject of about 64.9-90.1 IU/dL as measured by a two stage (chromogenic) assay when about 25 IU/kg of the chimeric polypeptide is administered;

a $C_{max}$_OBS in said subject of about 182 IU/dL, about 182±2 IU/dL, about 182±4 IU/dL, about 182±6 IU/dL, about 182±8 IU/dL, about 182±10 IU/dL, about 182±12 IU/dL, about 182±14 IU/dL, about 182±16 IU/dL, about 182±18 IU/dL, or about 182±20 IU/dL as measured by a two stage (chromogenic) assay when about 65 IU/kg of the chimeric polypeptide is administered; or a $C_{max}$_OBS in said subject of about 146-227 IU/dL, about 146±5 IU/dL, about 146±10 IU/dL, about 227±5 IU/dL, or about 146±10 IU/dL as measured by a two stage (chromogenic) assay when about 65 IU/kg of the chimeric polypeptide is administered.

In certain embodiments, the long-acting Factor VIII has one or more of the following properties when administered to a patient population:

a t1/2beta (activity) in said subject that is at least 1.48, 1.49, 1.50, 1.51, 1.52, 1.53, 1.54, 1.55, 1.56, 1.57, 1.58, 1.59, 1.60, 1.61, 1.62, 1.63, 1.64, 1.65, 1.66, 1.67, 1.68, 1.69, 1.70, 1.71, 1.72, 1.73, 1.74, 1.75, 1.76, 1.77, 1.78, 1.79, 1.80, 1.81, 1.82, 1.83, 1.84, 1.85, 1.86, 1.87, 1.88, 1.89, or 1.90 times higher than the t1/2beta (activity) in a subject administered with the same amount of a polypeptide consisting of the full-length, mature Factor VIII when measured by a one stage (aPTT) assay or a two stage (chromogenic) assay;

a t1/2beta (activity) in said subject of about 18.8 hours, 18.8±1 hours, 18.8±2 hours, 18.8±3 hours, 18.8±4 hours, 18.8±5 hours, 18.8±6 hours, 18.8±7 hours, 18.8±8 hours, 18.8±9 hours, 18.8±10 hours, or 18.8±11 hours as measured by a one stage (aPTT) assay;

a t1/2beta (activity) in said subject of about 14.3-24.5 hours as measured by a one stage (aPTT) assay;

a t1/2beta (activity) in said subject of about 16.7 hours, 16.7±1 hours, 16.7±2 hours, 16.7±3 hours, 16.7±4 hours, 16.7±5 hours, 16.7±6 hours, 16.7±7 hours, 16.7±8 hours, 16.7±9 hours, 16.7±10 hours, or 16.7±11 hours as measured by a two stage (chromogenic) assay;

a t1/2beta (activity) in said subject of about 13.8-20.1 hours as measured by a two stage (chromogenic) assay;

a t1/2beta (activity) in said subject of about 19.8 hours, 19.8±1 hours, 19.8±2 hours, 19.8±3 hours, 19.8±4 hours, 19.8±5 hours, 19.8±6 hours, 19.8±7 hours, 19.8±8 hours, 19.8±9 hours, 19.8±10 hours, or 19.8±11 hours as measured by a two stage (chromogenic) assay; or a t1/2beta (activity) in said subject of about 14.3-27.5 hours as measured by a two stage (chromogenic) assay.

In certain embodiments, the long-acting Factor VIII has one or more of the following properties when administered to a patient population:

a clearance (CL) (activity) in said subject is 0.51, 0.52, 0.53, 0.54, 0.55, 0.56, 0.57, 0.58, 0.59, 0.60, 0.61, 0.62, 0.63, 0.64, 0.65, 0.66, 0.67, 0.68, 0.69, or 0.70 times lower than the clearance in a subject administered with the same amount of a polypeptide consisting of the full-length, mature Factor VIII when measured by a one stage (aPTT) assay or a two stage (chromogenic) assay;

a clearance (CL) (activity) in said subject of about 1.68 mL/hour/kg, 1.68±0.1 mL/hour/kg, 1.68±0.2 mL/hour/kg, 1.68±0.3 mL/hour/kg, 1.68±0.4 mL/hour/kg, 1.68±0.5 mL/hour/kg, 1.68±0.6 mL/hour/kg, or 1.68±0 7 mL/hour/kg, as measured by a one stage (aPTT) assay when about 25 IU/kg of the chimeric polypeptide is administered;

a clearance (CL) (activity) in said subject of about 1.31-2.15 mL/hour/kg as measured by a one stage (aPTT) assay when about 25 IU/kg of the chimeric polypeptide is administered;

a clearance (CL) (activity) in said subject of about 2.32 mL/hour/kg, 2.32±0.1 mL/hour/kg, 2.32±0.2 mL/hour/kg, 2.32±0.3 mL/hour/kg, 2.32±0.4 mL/hour/kg, 2.32±0.5 mL/hour/kg, 2.32±0.6 mL/hour/kg, or 2.32±0 7 mL/hour/kg as measured by a one stage (aPTT) assay when about 65 IU/kg of the chimeric polypeptide is administered;

a clearance (CL) (activity) in said subject of about 1.64-3.29 mL/hour/kg as measured by a one stage (aPTT) assay when about 65 IU/kg of the chimeric polypeptide is administered;

a clearance (CL) (activity) in said subject of about 1.49 mL/hour/kg, 1.49±0.1 mL/hour/kg, 1.49±0.2 mL/hour/kg, 1.49±0.3 mL/hour/kg, 1.49±0.4 mL/hour/kg, 1.49±0.5 mL/hour/kg, 1.49±0.6 mL/hour/kg, or 1.49±0 7 mL/hour/kg as measured by a two stage (chromogenic) assay when about 25 IU/kg of the chimeric polypeptide is administered;

a clearance (CL) (activity) in said subject of about 1.16-1.92 mL/hour/kg as measured by a two stage (chromogenic) assay when about 25 IU/kg of the chimeric polypeptide is administered;

a clearance (CL) (activity) in said subject of about 1.52 mL/hour/kg, 1.52±0.1 mL/hour/kg, 1.52±0.2 mL/hour/kg, 1.52±0.3 mL/hour/kg, 1.52±0.4 mL/hour/kg, 1.52±0.5 mL/hour/kg, 1.52±0.6 mL/hour/kg, or 1.52±0 7 mL/hour/kg as measured by a two stage (chromogenic) assay when about 65 IU/kg of the chimeric polypeptide is administered; or a clearance (CL) (activity) in said subject of about 1.05-2.20 mL/hour/kg as measured by a two stage (chromogenic) assay when about 65 IU/kg of the chimeric polypeptide is administered.

In some embodiments, the long-acting Factor VIII has one or more of the following properties when administered to a patient population:

a MRT in said subject is at least 1.46, 1.47, 1.48, 1.49, 1.50, 1.51, 1.52, 1.53, 1.54, 1.55, 1.56, 1.57, 1.58, 1.59, 1.60, 1.61, 1.62, 1.63, 1.64, 1.65, 1.66, 1.67, 1.68, 1.69, 1.70, 1.71, 1.72, 1.73, 1.74, 1.75, 1.76, 1.77, 1.78, 1.79, 1.80, 1.81, 1.82, 1.83, 1.84, 1.85, 1.86, 1.87, 1.88, 1.89, 1.90, 1.91, 1.92, or 1.93 times higher than the MRT in a subject administered with the same amount of a polypeptide consisting of the full-length, mature Factor VIII when measured by a one stage (aPTT) assay or a two stage (chromogenic) assay;

a MRT (activity) in said subject of about 27 hours, 27±1 hours, 27±2 hours, 27±3 hours, 27±4 hours, 27±5 hours, 27±6 hours, 27±7 hours, 27±8 hours, 27±9 hours, or 27±10 hours as measured by a one stage (aPTT) assay;

a MRT (activity) in said subject of about 20.6-35.3 hours as measured by a one stage (aPTT) assay;

a MRT (activity) in said subject of about 23.9-28.5 hours as measured by a two stage (chromogenic) assay;

a MRT (activity) in said subject of about 19.8-28.9 hours as measured by a two stage (chromogenic) assay; or a MRT (activity) in said subject of about 20.5-39.6 hours as measured by a two stage (chromogenic) assay.

In other embodiments, the long-acting Factor VIII has one or more of the following properties when administered to a patient population:

an incremental recovery in said subject that is comparable to the Incremental Recovery in a subject administered with the same amount of a polypeptide consisting of the full-length, mature Factor VIII when measured by a one stage (aPTT) assay or a two stage (chromogenic) assay;

an incremental recovery in said subject of about 2.44 IU/dL per IU/kg, 2.44±0.1 IU/dL per IU/kg, 2.44±0.2 IU/dL per IU/kg, 2.44±0.3 IU/dL per IU/kg, 2.44±0.4 IU/dL per IU/kg, 2.44±0.5 IU/dL per IU/kg, 2.44±0.6 IU/dL per IU/kg, 2.44±0.7 IU/dL per IU/kg, 2.44±0.8 IU/dL per IU/kg, 2.44±0.9 IU/dL per IU/kg, 2.44±1.0 IU/dL per IU/kg, 2.44±1.1 IU/dL per IU/kg, or 2.44±1.2 IU/dL per IU/kg as measured by a one stage (aPTT) assay when about 25 IU/kg of the chimeric polypeptide is administered;

an incremental recovery in said subject of about 2.12-2.81 IU/dL per IU/kg as measured by a one stage (aPTT) assay when about 25 IU/kg of the chimeric polypeptide is administered;

an incremental recovery in said subject of about 1.83 IU/dL per IU/kg, 1.83±0.1 IU/dL per IU/kg, 1.83±0.2 IU/dL per IU/kg, 1.83±0.3 IU/dL per IU/kg, 1.83±0.4 IU/dL per IU/kg, 1.83±0.5 IU/dL per IU/kg, 1.83±0.6 IU/dL per IU/kg, 1.83±0.7 IU/dL per IU/kg, 1.83±0.8 IU/dL per IU/kg, 1.83±0.9 IU/dL per IU/kg, 1.83±1.0 IU/dL per IU/kg, or 1.83±1.1 IU/dL per IU/kg as measured by a one stage (aPTT) assay when about 65 IU/kg of the chimeric polypeptide is administered;

an incremental recovery in said subject of about 1.59-2.10 IU/dL per IU/kg as measured by a one stage (aPTT) assay when about 65 IU/kg of the chimeric polypeptide is administered;

an incremental recovery in said subject of about 3.09 IU/dL per IU/kg, 3.09±0.1 IU/dL per IU/kg, 3.09±0.2 IU/dL per IU/kg, 3.09±0.3 IU/dL per IU/kg, 3.09±0.4 IU/dL per IU/kg, 3.09±0.5 IU/dL per IU/kg, 3.09±0.6 IU/dL per IU/kg, 3.09±0.7 IU/dL per IU/kg, 3.09±0.8 IU/dL per IU/kg, 3.09±0.9 IU/dL per IU/kg, 3.09±1.0 IU/dL per IU/kg, 3.09±1.1 IU/dL per IU/kg, 3.09±1.2 IU/dL per IU/kg, or 3.09±1.3 IU/dL per IU/kg, as measured by a two stage (chromogenic) assay when about 25 IU/kg of the chimeric polypeptide is administered;

an incremental recovery in said subject of about 2.80 IU/dL per IU/kg, 2.80±0.1 IU/dL per IU/kg, 2.80±0.2 IU/dL per IU/kg, 2.80±0.3 IU/dL per IU/kg, 2.80±0.4 IU/dL per IU/kg, 2.80±0.5 IU/dL per IU/kg, 2.80±0.6 IU/dL per IU/kg, 2.80±0.7 IU/dL per IU/kg, 2.80±0.8 IU/dL per IU/kg, 2.80±0.9 IU/dL per IU/kg, 2.80±1.0 IU/dL per IU/kg, 2.80±1.1 IU/dL per IU/kg, or 2.80±1.2 IU/dL per IU/kg, as measured by a two stage (chromogenic) assay when about 65 IU/kg of the chimeric polypeptide is administered;

an incremental recovery in said subject of about 2.61-3.66 IU/dL per IU/kg as measured by a two stage (chromogenic) assay when about 25 IU/kg of the chimeric polypeptide is administered; or an incremental recovery in said subject of about 2.24-3.50 IU/dL per IU/kg as measured by a two stage (chromogenic) assay when about 65 IU/kg of the chimeric polypeptide is administered.

In still other embodiments, the long-acting Factor VIII has one or more of the following properties when administered to a patient population:

a Vss (activity) in said subject that is comparable to the Vss (activity) in a subject administered with the same amount of a polypeptide consisting of the full-length, mature Factor VIII when measured by a one stage (aPTT) assay or a two stage (chromogenic) assay;

a Vss (activity) in said subject of about 45.5 mL/kg, 45.5±1 mL/kg, 45.5±2 mL/kg, 45.5±3 mL/kg, 45.5±4 mL/kg, 45.5±5 mL/kg, 45.5±6 mL/kg, 45.5±7 mL/kg, 45.5±8 mL/kg, 45.5±9 mL/kg, 45.5±10 mL/kg, or 45.5±11 mL/kg, as measured by a one stage (aPTT) assay when about 25 IU/kg of the chimeric polypeptide is administered;

a Vss (activity) in said subject of about 39.3-52.5 mL/kg as measured by a one stage (aPTT) assay when about 25 IU/kg of the chimeric polypeptide is administered;

a Vss (activity) in said subject of about 62.8 mL/kg, 62.8±1 mL/kg, 62.8±2 mL/kg, 62.8±3 mL/kg, 62.8±4 mL/kg, 62.8±5 mL/kg, 62.8±6 mL/kg, 62.8±7 mL/kg, 62.8±8 mL/kg, 62.8±9 mL/kg, 62.8±10 mL/kg, 62.8±11 mL/kg, 62.8±12 mL/kg, 62.8±13 mL/kg, 62.8±14 mL/kg, 62.8±15 mL/kg, or 62.8±16 mL/kg as measured by a one stage (aPTT) assay when about 65 IU/kg of the chimeric polypeptide is administered;

a Vss (activity) in said subject of about 55.2-71.5 mL/kg as measured by a one stage (aPTT) assay when about 65 IU/kg of the chimeric polypeptide is administered;

a Vss (activity) in said subject of about 35.9 mL/kg, 35.9±1 mL/kg, 35.9±2 mL/kg, 35.9±3 mL/kg, 35.9±4 mL/kg, 35.9±5 mL/kg, 35.9±6 mL/kg, 35.9±7 mL/kg, 35.9±8 mL/kg, 35.9±9 mL/kg, 35.9±10 mL/kg, 35.9±11 mL/kg, 35.9±12 mL/kg, or 35.9±13 mL/kg, as measured by a two stage (chromogenic) assay when about 25 IU/kg of the chimeric polypeptide is administered;

a Vss (activity) in said subject of about 30.4-42.3 mL/kg as measured by a two stage (chromogenic) assay when about 25 IU/kg of the chimeric polypeptide is administered;

a Vss (activity) in said subject of about 43.4 mL/kg, 43.4±1 mL/kg, 43.4±2 mL/kg, 43.4±3 mL/kg, 43.4±4 mL/kg, 43.4±5 mL/kg, 43.4±6 mL/kg, 43.4±7 mL/kg, 43.4±8 mL/kg, 43.4±9 mL/kg, 43.4±10 mL/kg, 43.4±11 mL/kg, 43.4±12 mL/kg, 43.4±13 mL/kg, 43.4±14 mL/kg, 43.4±15 mL/kg, or 43.4±16 mL/kg, as measured by a two stage (chromogenic) assay when about 65 IU/kg of the chimeric polypeptide is administered; or a Vss (activity) in said subject of about 38.2-49.2 mL/kg as measured by a two stage (chromogenic) assay when about 65 IU/kg of the chimeric polypeptide is administered.

In yet other embodiments, the long-acting Factor VIII has one or more of the following properties when administered to a patient population:

an $AUC_{INF}$ in said subject that is at least 1.45, 1.46, 1.47, 1.48, 1.49, 1.50, 1.51, 1.52, 1.53, 1.54, 1.55, 1.56, 1.57, 1.58, 1.59, 1.60, 1.61, 1.62, 1.63, 1.64, 1.65, 1.66, 1.67, 1.68, 1.69, 1.70, 1.71, 1.72, 1.73, 1.74, 1.75, 1.76, 1.77, 1.78, 1.79, 1.80, 1.81, 1.82, 1.83, 1.84, 1.85, 1.86, 1.87, 1.88, 1.89, 1.90 times higher than the $AUC_{INF}$ in a subject administered with the same amount of a polypeptide consisting of the full-length, mature Factor VIII when measured by a one stage (aPTT) assay or a two stage (chromogenic) assay;

an $AUC_{INF}$ in said subject of about 1440±316 hr*IU/dL per IU/kg as measured by a one stage (aPTT) assay when about 25 IU/kg of the chimeric polypeptide is administered;

an $AUC_{INF}$ in said subject of about 1160-1880 hr*IU/dL per IU/kg as measured by a one stage (aPTT) assay when about 25 IU/kg of the chimeric polypeptide is administered;

an $AUC_{INF}$ in said subject of about 1480 hr*IU/dL per IU/kg, 1480±100 hr*IU/dL per IU/kg, 1480±200 hr*IU/dL per IU/kg, 1480±300 hr*IU/dL per IU/kg, 1480±400 hr*IU/dL per IU/kg, 1480±500 hr*IU/dL per IU/kg, 1480±600 hr*IU/dL per IU/kg, 1480±700 hr*IU/dL per IU/kg, 1480±800 hr*IU/dL per IU/kg, 1480±900 hr*IU/dL per IU/kg, or 1480±1000 hr*IU/dL per IU/kg, as measured by a one stage (aPTT) assay when about 25 IU/kg of the chimeric polypeptide is administered;

an $AUC_{INF}$ in said subject of about 2910±1320 hr*IU/dL per IU/kg as measured by a one stage (aPTT) assay when about 65 IU/kg of the chimeric polypeptide is administered;

an $AUC_{INF}$ in said subject of about 1980-3970 hr*IU/dL per IU/kg as measured by a one stage (aPTT) assay when about 65 IU/kg of the chimeric polypeptide is administered;

an $AUC_{INF}$ in said subject of about 2800 hr*IU/dL per IU/kg, 2800±100 hr*IU/dL per IU/kg, 2800±200 hr*IU/dL per IU/kg, 2800±300 hr*IU/dL per IU/kg, 2800±400 hr*IU/dL per IU/kg, 2800±500 hr*IU/dL per IU/kg, 2800±600 hr*IU/dL per IU/kg, 2800±700 hr*IU/dL per IU/kg, 2800±800 hr*IU/dL per IU/kg, 2800±900 hr*IU/dL per IU/kg, or 2800±1000 hr*IU/dL per IU/kg as measured by a one stage (aPTT) assay when about 65 IU/kg of the chimeric polypeptide is administered;

an $AUC_{INF}$ in said subject of about 1660 hr*IU/dL per IU/kg, 1660±100 hr*IU/dL per IU/kg, 1660±200 hr*IU/dL per IU/kg, 1660±300 hr*IU/dL per IU/kg, 1660±400 hr*IU/dL per IU/kg, 1660±500 hr*IU/dL per IU/kg, 1660±600 hr*IU/dL per IU/kg, 1660±700 hr*IU/dL per IU/kg, 1660±800 hr*IU/dL per IU/kg, 1660±900 hr*IU/dL per IU/kg, or 1660±1000 hr*IU/dL per IU/kg as measured by a two stage (chromogenic) assay when about 25 IU/kg of the chimeric polypeptide is administered;

an $AUC_{INF}$ in said subject of about 1300-2120 hr*IU/dL per IU/kg as measured by a two stage (chromogenic) assay when about 25 IU/kg of the chimeric polypeptide is administered;

an $AUC_{INF}$ in said subject of about 4280 hr*IU/dL per IU/kg, 4280±100 hr*IU/dL per IU/kg, 4280±200 hr*IU/dL per IU/kg, 4280±300 hr*IU/dL per IU/kg, 4280±400 hr*IU/dL per IU/kg, 4280±500 hr*IU/dL per IU/kg, 4280±600 hr*IU/dL per IU/kg, 4280±700 hr*IU/dL per IU/kg, 4280±800 hr*IU/dL per IU/kg, 4280±900 hr*IU/dL per IU/kg, 4280±1000 hr*IU/dL per IU/kg, 4280±1100 hr*IU/dL per IU/kg, 4280±1200 hr*IU/dL per IU/kg, 4280±1300 hr*IU/dL per IU/kg, 4280±1400 hr*IU/dL per IU/kg, 4280±1500 hr*IU/dL per IU/kg, or 4280±1600 hr*IU/dL per IU/kg as measured by a two stage (chromogenic) assay when about 65 IU/kg of the chimeric polypeptide is administered; or an $AUC_{INF}$ in said subject of about 2960-6190 hr*IU/dL per IU/kg as measured by a two stage (chromogenic) assay when about 65 IU/kg of the chimeric polypeptide is administered.

"On-demand treatment," as used herein, means treatment that is intended to take place over a short course of time and is in response to an existing condition, such as a bleeding episode, or a perceived need such as planned surgery. Conditions that may require on-demand treatment include, e.g., a bleeding episode, hemarthrosis, muscle bleed, oral bleed, hemorrhage, hemorrhage into muscles, oral hemorrhage, trauma, trauma capitis, gastrointestinal bleeding, intracranial hemorrhage, intra-abdominal hemorrhage, intrathoracic hemorrhage, bone fracture, central nervous system bleeding, bleeding in the retropharyngeal space, bleeding in the retroperitoneal space, or bleeding in the illiopsoas sheath. The subject may be in need of surgical prophylaxis, peri-operative management, or treatment for surgery. Such surgeries include, e.g., minor surgery, major surgery, tooth extraction, tonsillectomy, inguinal herniotomy, synovectomy, total knee replacement, craniotomy, osteosynthesis, trauma surgery, intracranial surgery, intra-abdominal surgery, intrathoracic surgery, or joint replacement surgery.

In one embodiment, on-demand treatment resolves greater than 80% (greater than 80%, greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98%, greater than 99%, or 100%) or 80-100%, 80-90%, 85-90%, 90-100%, 90-95%, or 95-100% of bleeds (e.g., spontaneous bleeds) in a single dose. In another embodiment, greater than 80% (greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98%, or 100%) or 80-100%, 80-90%, 85-90%, 90-100%, 90-95%, or 95-100% of bleeding episodes are rated excellent or good by physicians after on-demand treatment. In other embodiments, greater than 5%, (greater than 6%, greater than 7%, greater than 8%, greater than 9%, greater than 10%, greater than 11%, greater than 12%, greater than 13%, greater than 14%, greater than 15%, greater than 16%, greater than 17%, greater than 18%, greater than 19%, greater than 20%), or 5-20%, 5-15%, 5-10%, 10-20%, or 10-15% of bleeding episodes are rated as fair by physicians after on-demand treatment.

"Polypeptide," "peptide" and "protein" are used interchangeably and refer to a polymeric compound comprised of covalently linked amino acid residues.

"Polynucleotide" and "nucleic acid" are used interchangeably and refer to a polymeric compound comprised of covalently linked nucleotide residues. Polynucleotides may be DNA, cDNA, RNA, single stranded, or double stranded, vectors, plasmids, phage, or viruses. Polynucleotides include, e.g., those in Table 1, which encode the polypeptides of Table 2 (see Table 1). Polynucleotides also include, e.g., fragments of the polynucleotides of Table 1, e.g., those that encode fragments of the polypeptides of Table 2, such as the Factor VIII, Fc, signal sequence, 6His and other fragments of the polypeptides of Table 2.

"Prophylactic treatment," as used herein, means administering a Factor VIII polypeptide in multiple doses to a subject over a course of time to increase the level of Factor VIII activity in a subject's plasma. The increased level can be sufficient to decrease the incidence of spontaneous bleeding or to prevent bleeding, e.g., in the event of an unforeseen injury. During prophylactic treatment, the plasma protein level in the subject may not fall below the baseline level for that subject, or below the level of Factor VIII that characterizes severe hemophilia (<1 IU/dl [1%]).

In one embodiment, the prophylaxis regimen is "tailored" to the individual patient, for example, by determining PK data for each patient and administering Factor VIII of the invention at a dosing interval that maintains a trough level of 1-3% FVIII activity. Adjustments may be made when a subject experiences unacceptable bleeding episodes defined as ≥2 spontaneous bleeding episodes over a rolling two-month period. In this case, adjustment will target trough levels of 3-5%. In another embodiment, prophylactic treatment results in prevention and control of bleeding, sustained control of bleeding, sustained protection from bleeding, and/or sustained benefit. Prophylaxis, e.g., sustained protection can be demonstrated by an increased AUC to last measured time point (AUC-LAST) and reduced clearance, resulting in increased terminal t1/2 compared to short acting FVIII. Prophylaxis can be demonstrated by better Cmax, better Tmax, and/or greater mean residence time versus short-acting FVIII. In some embodiments, prophylaxis results in no spontaneous bleeding episodes within about 24, 36, 48, 72, or 96 hours (e.g., 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 96, 87, 88, 89, 90, 91, 92, 93, 94, 95, or 96 hours), after injection (e.g., the last injection). In certain embodiments, prophylaxis results in greater than 30% (e.g., greater than 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 96, 87, 88, 89, or 90%, for example, greater than 50%), mean reduction in annualized bleeding episodes with once weekly dosing (e.g., at 65 IU/kg). "Therapeutic dose," as used herein, means a dose that achieves a therapeutic goal, as described herein. The calculation of the required dosage of factor VIII is based upon the empirical finding that, on average, 1 IU of factor VIII per kg body weight raises the plasma factor VIII activity by approximately 2 IU/dL. The required dosage is determined using the following formula:

Required units=body weight (kg)×desired factor VIII rise (IU/dL or % of normal)×0.5 (IU/kg per IU/dL)

The therapeutic doses that may be used in the methods of the invention are about 10-100 IU/kg, more specifically, 10-20, 20-30, 30-40, 40-50, 50-60, 60-70, 70-80, 80-90, or 90-100 IU/kg, and more specifically, 10, 15, 20, 25, 30, 35, 40, 45, 50, 55, 60, 65, 70, 75, 80, 85, 90, 95, or 100 IU/kg.

Additional therapeutic doses that may be used in the methods of the invention are about 10 to about 150 IU/kg, more specifically, about 100-110, 110-120, 120-130, 130-140, 140-150 IU/kg, and more specifically, about 110, 115, 120, 125, 130, 135, 140, 145, or 150 IU/kg.

"Variant," as used herein, refers to a polynucleotide or polypeptide differing from the original polynucleotide or polypeptide, but retaining essential properties thereof, e.g., factor VIII coagulant activity or Fc (FcRn binding) activity. Generally, variants are overall closely similar, and, in many regions, identical to the original polynucleotide or polypeptide. Variants include, e.g., polypeptide and polynucleotide fragments, deletions, insertions, and modified versions of original polypeptides.

Variant polynucleotides may comprise, or alternatively consist of, a nucleotide sequence which is at least 85%, 90%, 95%, 96%, 97%, 98% or 99% identical to, for example, the nucleotide coding sequence in SEQ ID NO:1, 3, or 5 (the factor VIII portion, the Fc portion, individually or together) or the complementary strand thereto, the nucleotide coding sequence of known mutant and recombinant factor VIII or Fc such as those disclosed in the publications and patents cited herein or the complementary strand thereto, a nucleotide sequence encoding the polypeptide of SEQ ID NO:2, 4, or 6 (the factor VIII portion, the Fc portion, individually or together), and/or polynucleotide fragments of any of these nucleic acid molecules (e.g., those fragments described herein). Polynucleotides which hybridize to these nucleic acid molecules under stringent hybridization conditions or lower stringency conditions are also included as variants, as are polypeptides encoded by these polynucleotides as long as they are functional.

Variant polypeptides may comprise, or alternatively consist of, an amino acid sequence which is at least 85%, 90%, 95%, 96%, 97%, 98%, 99% identical to, for example, the polypeptide sequence shown in SEQ ID NOS:2, 4, or 6 (the factor VIII portion, the Fc portion, individually or together), and/or polypeptide fragments of any of these polypeptides (e.g., those fragments described herein).

By a nucleic acid having a nucleotide sequence at least, for example, 95% "identical" to a reference nucleotide sequence, it is intended that the nucleotide sequence of the nucleic acid is identical to the reference sequence except that the nucleotide sequence may include up to five point mutations per each 100 nucleotides of the reference nucleotide sequence. In other words, to obtain a nucleic acid having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. The query sequence may be, for example, the entire sequence shown in SEQ ID NO:1 or 3, the ORF (open reading frame), or any fragment specified as described herein.

As a practical matter, whether any particular nucleic acid molecule or polypeptide is at least 85%, 90%, 95%, 96%, 97%, 98% or 99% identical to a nucleotide sequence or polypeptide of the present invention can be determined conventionally using known computer programs. In one embodiment, a method for determining the best overall match between a query sequence (reference or original sequence) and a subject sequence, also referred to as a global sequence alignment, can be determined using the FASTDB computer program based on the algorithm of Brutlag et al., Comp. App. Biosci. 6:237-245 (1990), which is herein incorporated by reference in its entirety In a sequence alignment the query and subject sequences are both DNA sequences. An RNA sequence can be compared by converting U's to T's. The result of said global sequence alignment is in percent identity. In another embodiment, parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the length of the subject nucleotide sequence, whichever is shorter.

If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of the present invention. Only bases outside the 5' and 3' bases of the subject sequence, as displayed by the FASTDB alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the FASTDB alignment does not show a matched/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are to made for the purposes of the present invention.

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted, deleted, (indels) or substituted with another amino acid. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 85%, 90%, 95%, 96%, 97%, 98% or 99% identical to, for instance, the amino acid sequences of SEQ ID NO:2 (the factor VIII portion, the Fc portion, individually or together) or 4, or a known factor VIII or Fc polypeptide sequence, can be determined conventionally using known computer programs. In one embodiment, a method for determining the best overall match between a query sequence (reference or original sequence) and a subject sequence, also referred to as a global sequence alignment, can be determined using the FASTDB computer program based on the algorithm of Brutlag et al., Comp. App. Biosci. 6:237-245 (1990), incorporated herein by reference in its entirety. In a sequence alignment the query and subject sequences are either both nucleotide sequences or both amino acid sequences. The result of said global sequence alignment is in percent identity. In another embodiment, parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter.

If the subject sequence is shorter than the query sequence due to N- or C-terminal deletions, not because of internal deletions, a manual correction must be made to the results. This is because the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence.

For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. No other manual corrections are to made for the purposes of the present invention.

The polynucleotide variants may contain alterations in the coding regions, non-coding regions, or both. In one embodiment, the polynucleotide variants contain alterations which produce silent substitutions, additions, or deletions, but do not alter the properties or activities of the encoded polypeptide. In another embodiment, nucleotide variants are produced by silent substitutions due to the degeneracy of the genetic code. In other embodiments, variants in which 5-10, 1-5, or 1-2 amino acids are substituted, deleted, or added in any combination. Polynucleotide variants can be produced for a variety of reasons, e.g., to optimize codon expression for a particular host (change codons in the human mRNA to others, e.g., a bacterial host such as *E. coli*).

Naturally occurring variants are called "allelic variants," and refer to one of several alternate forms of a gene occupying a given locus on a chromosome of an organism (Genes II, Lewin, B., ed., John Wiley & Sons, New York (1985)). These allelic variants can vary at either the polynucleotide and/or polypeptide level and are included in the present invention. Alternatively, non-naturally occurring variants may be produced by mutagenesis techniques or by direct synthesis.

Using known methods of protein engineering and recombinant DNA technology, variants may be generated to improve or alter the characteristics of the polypeptides. For instance, one or more amino acids can be deleted from the N-terminus or C-terminus of the secreted protein without substantial loss of biological function. Ron et al., *J. Biol. Chem.* 268: 2984-2988 (1993), incorporated herein by reference in its entirety, reported variant KGF proteins having heparin binding activity even after deleting 3, 8, or 27 amino-terminal amino acid residues. Similarly, Interferon gamma exhibited up to ten times higher activity after deleting 8-10 amino acid residues from the carboxy terminus of this protein. (Dobeli et al., *J. Biotechnology* 7:199-216 (1988), incorporated herein by reference in its entirety.)

Moreover, ample evidence demonstrates that variants often retain a biological activity similar to that of the naturally occurring protein. For example, Gayle and coworkers (*J. Biol. Chem* 268:22105-22111 (1993), incorporated herein by reference in its entirety) conducted extensive mutational analysis of human cytokine IL-1a. They used random mutagenesis to generate over 3,500 individual IL-1a mutants that averaged 2.5 amino acid changes per variant over the entire length of the molecule. Multiple mutations were examined at every possible amino acid position. The investigators found that "[m]ost of the molecule could be altered with little effect on either [binding or biological activity]." (See Abstract.) In fact, only 23 unique amino acid sequences, out of more than 3,500 nucleotide sequences examined, produced a protein that significantly differed in activity from wild-type.

As stated above, polypeptide variants include, e.g., modified polypeptides. Modifications include, e.g., acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation (Mei et al., *Blood* 116:270-79 (2010), which is incorporated herein by reference in its entirety), proteolytic processing, phosphorylation, prenylation, racemization, selenoylation, sulfation, transfer-RNA mediated addition of amino acids to proteins such as arginylation, and ubiquitination. In some embodiments, Factor VIII is modified, e.g., pegylated, at any convenient location. In some embodiments, Factor VIII is pegylated at a surface exposed amino acid of Factor VIII, e.g., a surface exposed cysteine, which may be an engineered cysteine. Id. In some embodiments, modified Factor VIII, e.g., pegylated Factor VIII, is a long-acting Factor VIII.

"Volume of distribution at steady state (Vss)," as used herein, has the same meaning as the term used in pharmacology, which is the apparent space (volume) into which a drug distributes. Vss=the amount of drug in the body divided by the plasma concentration at steady state.

"About" as used herein for a range, modifies both ends of the range. Thus, "about 10-20" means "about 10 to about 20."

The chimeric polypeptide used herein can comprise processed Factor VIII or single chain Factor VIII or a combination thereof "Processed Factor VIII," as used herein means Factor VIII that has been cleaved at Arginine 1648 (for full-length Factor VIII) or Arginine 754 (for B-domain deleted Factor VIII), i.e., intracellular processing site. Due to the cleavage at the intracellular processing site, processed Factor VIII comprises two polypeptide chains, the first chain being a heavy chain and the second chain being a light chain. For example, the processed Factor VIII-Fc fusion protein (i.e., Heavy chain and Light chain fused to Fc) run at approximately 90 kDa and 130 kDa on a non-reducing SDS-PAGE, respectively, and 90 kDa and 105 kDa on a reducing SDS-PAGE, respectively. Therefore, in one embodiment, at least about 50%, about 60%, about 70%, about 75%, about 80%, about 85%, about 90%, about 95%, about 96%, about 97%, about 98%, about 99%, or about 100% of the Factor VIII portion in the chimeric polypeptide is processed Factor VIII. In another embodiment, about 50%, about 60%, about 70%, about 75%, about 80%, about 85%, about 90%, about 95%, about 96%, about 97%, about 98%, about 99%, or about 100% of the Factor VIII portion in the chimeric polypeptide is processed Factor VIII. In a particular embodiment, the chimeric polypeptide comprising processed Factor VIII is purified (or isolated) from the chimeric polypeptide comprising single chain Factor VIII, and at least about 90%, about 95%, about 96%, about 97%, about 98%, about 99%, or about 100% of the Factor VIII portion in the chimeric polypeptide is processed Factor VIII.

"Single chain Factor VIII," "SC Factor VIII," or "SCFVIII" as used herein means Factor VIII that has not been cleaved at the Arginine site (residue 1648 for full-length Factor VIII (i.e., residue 1667 of SEQ ID NO: 6) or residue 754 for B-domain deleted Factor VIII (i.e., residue 773 of SEQ ID NO: 2). Therefore, single chain Factor VIII in the chimeric polypeptide used herein comprises a single chain. In one embodiment, the single chain Factor VIII contains an intact intracellular processing site. In another embodiment, the single chain Factor VIII of the invention comprises a substitution or mutation at an amino acid position corresponding to Arginine 1645, a substitution or mutation at an amino acid position corresponding to Arginine 1648, or a substitution or mutation at amino acid positions corresponding to Arginine 1645 and Arginine 1648 in full-length Factor VIII. In other embodiments, the amino acid substituted at the amino acid position corresponding to Arginine 1645 is a different amino acid from the amino acid substituted at the amino acid position corresponding to Arginine 1648. In certain embodiments, the substitution or mutation is an amino acid other than arginine, e.g., isoleucine, leucine, lysine, methionine, phenylalanine, threonine, tryptophan, valine, alanine, asparagine, aspartic acid, cysteine, glutamic acid, glutamine, glycine, proline, selenocysteine, serine, tyrosine, histidine, ornithine, pyrrolysine, or taurine. The single chain Factor VIII-Fc fusion protein can run at approximately 220 kDa on a non reducing SDS-PAGE and at approximately 195 kDa on a reducing SDS-PAGE.

In one embodiment, the chimeric polypeptide comprising single chain Factor VIII is purified (or isolated) from the chimeric polypeptide comprising processed Factor VIII, and at least about 30%, about 40%, about 50%, about 60%, about 70%, about 75%, about 80%, about 85%, about 90%, about 95%, about 99%, or about 100% of the Factor VIII portion of the chimeric polypeptide used herein is single chain Factor VIII. In another embodiment, at least about 1%, about 5%, about 10%, about 15%, about 20%, about 25%, about 30%, or about 35% of the Factor VIII portion of the chimeric polypeptide is single chain Factor VIII. In other embodiments, about 1%-about 10%, about 5%-about 15%, about 10%-about 20%, about 15%-about 25%, about 20%-about 30%, about 25%-about 35%, about 30%-about 40% of the Factor VIII portion of the chimeric polypeptide used herein is single chain Factor VIII. In a particular embodiment, about 1%, about 5%, about 10%, about 15%, about 20% about 25%, about 30%, about 35% of the Factor VIII portion of the chimeric polypeptide used herein is single chain Factor VIII. In other embodiments, about 30%, about 40%, about 50%, about 60%, about 70%, about 80%, about 90%, about 95%, about 96%, about 97%, about 98%, about 99%, or about 100% of the Factor VIII portion of the chimeric polypeptide used herein is single chain Factor VIII. In some embodiments, the ratio of the single chain Factor VIII to the processed Factor VIII of the chimeric polypeptide is (a) about 25% of single chain Factor VIII and about 75% of processed Factor VIII; (b) about 20% of single chain Factor VIII and about 80% of processed Factor VIII; (c) about 15% of single chain Factor VIII and about 85% of processed Factor VIII; (d) about 10% of single chain Factor VIII and about 90% of processed Factor VIII; (e) about 5% of single chain Factor VIII and about 95% of processed Factor VIII; (f) about 1% of single chain Factor VIII and about 99% of processed Factor VIII; (g) about 100% of processed Factor VIII, (h) about 30% of single chain Factor VIII and about 70% of processed Factor VIII, (i) about 35% of single chain Factor VIII and about 65% of processed Factor VIII, or (j) about 40% of single chain Factor VIII and about 60% of processed Factor VIII. In other embodiments, the ratio of the single chain Factor VIII to the processed Factor VIII of the chimeric polypeptide is (a) about 30% of single chain Factor VIII and about 70% of processed Factor VIII; (b) about 40% of single chain Factor VIII and about 60% of processed Factor VIII; (c) about 50% of single chain Factor VIII and about 50% of processed Factor VIII; (d) about 60% of single chain Factor VIII and about 40% of processed Factor VIII; (e) about 70% of single chain Factor VIII and about 30% of processed Factor VIII; (f) about 80% of single chain Factor VIII and about 20% of processed Factor VIII; (g) about 90% of single chain Factor VIII and about 10% of processed Factor VIII; (h) about 95% of single chain Factor VIII and about 5% of processed Factor VIII; (i) about 99% of single chain Factor VIII and about 1% of processed Factor VIII; or (j) about 100% of single chain Factor VIII.

The Factor VIII portion in the chimeric polypeptide used herein has Factor VIII activity. Factor VIII activity can be measured by any known methods in the art. For example, one of those methods can be a chromogenic assay. The chromogenic assay mechanism is based on the principles of the blood coagulation cascade, where activated Factor VIII accelerates the conversion of Factor X into Factor Xa in the presence of activated Factor IX, phospholipids and calcium ions. The Factor Xa activity is assessed by hydrolysis of a p-nitroanilide (pNA) substrate specific to Factor Xa. The initial rate of release of p-nitroaniline measured at 405 nM is directly proportional to the Factor Xa activity and thus to the Factor VIII activity in the sample. The chromogenic assay is recommended by the Factor VIII and Factor IX Subcommittee of the Scientific and Standardization Committee (SSC) of the International Society on Thrombosis and Hemostatsis (ISTH). Since 1994, the chromogenic assay has also been the reference method of the European Pharmacopoeia for the assignment of FVIII concentrate potency. Thus, in one embodiment, the chimeric polypeptide comprising single chain Factor VIII has Factor VIII activity comparable to a chimeric polypeptide comprising processed Factor VIII (e.g., a chimeric polypeptide consisting essentially of or consisting of two Fc portions and processed Factor VIII, wherein said processed Factor VIII is fused to one of the two Fc portions), when the Factor VIII activity is measured in vitro by a chromogenic assay.

In another embodiment, the chimeric polypeptide comprising single chain Factor VIII of this invention has a Factor Xa generation rate comparable to a chimeric polypeptide comprising processed Factor VIII (e.g., a chimeric polypeptide consisting essentially of or consisting of two Fc portions and processed Factor VIII, wherein the processed Factor VIII is fused to one Fc of the two Fc portions).

In order to activate Factor X to Factor Xa, activated Factor IX (Factor IXa) hydrolyses one arginine-isoleucine bond in Factor X to form Factor Xa in the presence of Ca2+, membrane phospholipids, and a Factor VIII cofactor. Therefore, the interaction of Factor VIII with Factor IX is critical in coagulation pathway. In certain embodiments, the chimeric polypeptide comprising single chain factor VIII can interact with Factor IXa at a rate comparable to a chimeric polypeptide comprising processed Factor VIII (e.g., a chimeric polypeptide consisting essentially of or consisting of two Fc portions and processed Factor VIII, wherein the processed Factor VIII is fused to one Fc of the two Fc portions).

In addition, Factor VIII is bound to von Willebrand Factor while inactive in circulation. Factor VIII degrades rapidly when not bound to vWF and is released from vWF by the action of thrombin. In some embodiments, the chimeric polypeptide comprising single chain Factor VIII binds to von Willebrand Factor at a level comparable to a chimeric polypeptide comprising processed Factor VIII (e.g., a chimeric polypeptide consisting essentially of or consisting of two Fc portions and processed Factor VIII, wherein the processed Factor VIII is fused to one Fc of the two Fc portions).

Factor VIII can be inactivated by activated protein C in the presence of calcium and phospholipids. Activated protein C cleaves Factor VIII heavy chain after Arginine 336 in the A1 domain, which disrupts a Factor X substrate interaction site, and cleaves after Arginine 562 in the A2 domain, which enhances the dissociation of the A2 domain as well as disrupts an interaction site with the Factor IXa. This cleavage also bisects the A2 domain (43 kDa) and generates A2-N (18 kDa) and A2-C (25 kDa) domains. Thus, activated protein C can catalyze multiple cleavage sites in the heavy chain. In one embodiment, the chimeric polypeptide comprising single chain Factor VIII is inactivated by activated Protein C at a level comparable to a chimeric polypeptide comprising processed Factor VIII (e.g., a chimeric polypeptide consisting essentially of or consisting of two Fc portions and processed Factor VIII, wherein the processed Factor VIII is fused to one Fc of the two Fc portions).

In other embodiments, the chimeric polypeptide comprising single chain Factor VIII has Factor VIII activity in vivo comparable to a chimeric polypeptide comprising processed Factor VIII (e.g., a chimeric polypeptide consisting essentially of or consisting of two Fc portions and processed Factor VIII, wherein the processed Factor VIII is fused to one Fc of the two Fc portions). In a particular embodiment, the chimeric polypeptide comprising single chain Factor VIII is capable of protecting a HemA mouse at a level comparable to a chimeric polypeptide comprising processed Factor VIII (e.g., a chimeric polypeptide consisting essentially of or consisting of two Fc portions and processed Factor VIII, wherein said processed Factor VIII is fused to one Fc of the two Fc portions) in a HemA mouse tail vein transection model.

The term "comparable" as used herein means a compared rate or level resulted from using the chimeric polypeptide is equal to, substantially equal to, or similar to the reference rate or level. The term "similar" as used herein means a compared rate or level has a difference of no more than 10% or no more than 15% from the reference rate or level (e.g., FXa generation rate by a chimeric polypeptide consisting essentially of or consisting of two Fc portions and processed Factor VIII, wherein said processed Factor VIII is fused to one Fc of the two Fc portions). The term "substantially equal" means a compared rate or level has a difference of no more than 0.01%, 0.5% or 1% from the reference rate or level.

The present invention further includes a composition comprising a chimeric polypeptide having Factor VIII activity, wherein at least about 30%, about 40%, about 50%, about 60%, about 70%, about 80%, about 85%, about 90%, about 95%, or about 99% of the chimeric polypeptide comprises a Factor VIII portion, which is single chain Factor VIII and a second portion. In another embodiment, about 30%, about 40%, about 50%, about 60%, about 70%, about 80%, about 85%, about 90%, about 95%, about 96%, about 97%, about 98%, or about 99% of the chimeric polypeptide in the composition is single chain Factor VIII. In other embodiments, the second portion is an Fc, XTEN, albumin, a PAS sequence, transferrin, CTP (28 amino acid C-terminal peptide (CTP) of hCG with its 4 O-glycans), polyethylene glycol (PEG), hydroxyethyl starch (HES), albumin binding polypeptide, albumin-binding small molecules, or two or more combinations thereof. In still other embodiments, the composition of the present invention comprises a combination of a chimeric polypeptide comprising processed Factor VIII and a chimeric polypeptide comprising single chain Factor VIII, (a) wherein about 30% of the Factor VIII portion of the chimeric polypeptide is single chain Factor VIII, and about 70% of the Factor VIII portion of the chimeric polypeptide is processed Factor VIII; (b) wherein about 40% of the Factor VIII portion of the chimeric polypeptide is single chain Factor VIII, and about 60% of the Factor VIII portion of the chimeric polypeptide is processed Factor VIII; (c) wherein about 50% of the Factor VIII portion of the chimeric polypeptide is single chain Factor VIII, and about 50% of the Factor VIII portion of the chimeric polypeptide is processed Factor VIII; (d) wherein about 60% of the Factor VIII portion of the chimeric polypeptide is single chain Factor VIII and about 40% of the Factor VIII portion of the chimeric polypeptide being processed Factor VIII; (e) wherein about 70% of the Factor VIII portion of the chimeric polypeptide is single chain Factor VIII and about 30% of the Factor VIII portion of the chimeric polypeptide is processed Factor VIII; (f) wherein about 80% of the Factor VIII portion of the chimeric polypeptide is single chain Factor VIII and about 20% of the Factor VIII portion of the chimeric polypeptide is processed Factor VIII; (g) wherein about 90% of the Factor VIII portion of the chimeric polypeptide is single chain Factor VIII and about 10% of the Factor VIII portion of the chimeric polypeptide is processed Factor VIII; (h) wherein about 95% of the Factor VIII portion of the chimeric polypeptide is single chain Factor VIII and about 5% of the Factor VIII portion of the chimeric polypeptide is processed Factor VIII; (i) wherein about 99% of the Factor VIII portion of the chimeric polypeptide is single chain Factor VIII and about 1% of the Factor VIII portion of the chimeric polypeptide is processed Factor VIII; or (j) wherein about 100% of the Factor VIII portion of the chimeric polypeptide is single chain Factor VIII.

In certain embodiments, the composition of the present invention has Factor VIII activity comparable to the composition comprising processed Factor VIII (e.g., a composition comprising a chimeric polypeptide, which consists essentially of or consists of two Fc portions and processed Factor VIII, wherein said processed Factor VIII is fused to one of the two Fc portions), when the Factor VIII activity is measured in vitro by a chromogenic assay.

In other embodiments, the composition of the invention has a Factor Xa generation rate comparable to a composition comprising processed Factor VIII (e.g., a composition comprising a chimeric polypeptide, which consists essentially of or consists of two Fc portions and processed Factor VIII, wherein the processed Factor VIII is fused to one Fc of the two Fc portions). In still other embodiments, the composition comprising single chain factor VIII can interact with Factor IXa at a rate comparable to a composition comprising processed Factor VIII (e.g., a composition comprising a chimeric polypeptide, which consists essentially of or consists of two Fc portions and processed Factor VIII, wherein the processed Factor VIII is fused to one Fc). In further embodiments, the single chain Factor VIII in the chimeric polypeptide of the present composition is inactivated by activated Protein C at a level comparable to processed Factor VIII in a chimeric polypeptide of a composition (e.g., a composition comprising a chimeric polypeptide, which consists essentially of or consists of two Fc portions and processed Factor VIII, wherein the processed Factor VIII is fused to one Fc of the two Fc portions). In a particular embodiment, the composition comprising single chain Factor VIII has Factor VIII activity in vivo comparable to the composition comprising processed Factor VIII (e.g., a composition comprising a chimeric polypeptide, which consists essentially of or consists of two Fc portions and processed Factor VIII, wherein the processed Factor VIII is fused to one Fc of the two Fc portions). In some embodiments, the composition comprising single chain Factor VIII of the invention is capable of protecting HemA mouse at a level comparable to the composition comprising processed Factor VIII (e.g., a composition comprising a chimeric polypeptide, which consists essentially of or consists of two Fc portions and processed Factor VIII, wherein said processed Factor VIII is fused to one Fc of the two Fc portions) in HemA mouse tail vein transection model.

The present invention further provides a method for treating a bleeding condition in a human subject using the composition of the invention. An exemplary method comprises administering to the subject in need thereof a therapeutically effective amount of a pharmaceutical composition/formulation comprising a chimeric polypeptide having Factor VIII activity, wherein at least about 30%, about 40%, about 50%, about 60%, about 70%, about 80%, about 85%, about 90%, about 95%, or about 99% of the chimeric polypeptide comprises a Factor VIII portion, which is single chain Factor VIII, and a second portion.

The bleeding condition can be caused by a blood coagulation disorder. A blood coagulation disorder can also be referred to as a coagulopathy. In one example, the blood coagulation disorder, which can be treated with a pharmaceutical composition of the current disclosure, is hemophilia or von Willebrand disease (vWD). In another example, the blood coagulation disorder, which can be treated with a pharmaceutical composition of the present disclosure is hemophilia A.

In some embodiments, the type of bleeding associated with the bleeding condition is selected from hemarthrosis, muscle bleed, oral bleed, hemorrhage, hemorrhage into muscles, oral hemorrhage, trauma, trauma capitis, gastrointestinal bleeding, intracranial hemorrhage, intra-abdominal hemorrhage, intrathoracic hemorrhage, bone fracture, central nervous system bleeding, bleeding in the retropharyngeal space, bleeding in the retroperitoneal space, and bleeding in the illiopsoas sheath.

In other embodiments, the subject suffering from bleeding condition is in need of treatment for surgery, including, e.g., surgical prophylaxis or peri-operative management. In one example, the surgery is selected from minor surgery and major surgery. Exemplary surgical procedures include tooth extraction, tonsillectomy, inguinal herniotomy, synovectomy, craniotomy, osteosynthesis, trauma surgery, intracranial surgery, intra-abdominal surgery, intrathoracic surgery, joint replacement surgery (e.g., total knee replacement, hip replacement, and the like), heart surgery, and caesarean section.

In another example, the subject is concomitantly treated with FIX. Because the compounds of the invention are capable of activating FIXa, they could be used to pre-activate the FIXa polypeptide before administration of the FIXa to the subject.

The methods of the invention may be practiced on a subject in need of prophylactic treatment or on-demand treatment.

The pharmaceutical compositions comprising at least 30% of single chain Factor VIII may be formulated for any appropriate manner of administration, including, for example, topical (e.g., transdermal or ocular), oral, buccal, nasal, vaginal, rectal or parenteral administration.

The term parenteral as used herein includes subcutaneous, intradermal, intravascular (e.g., intravenous), intramuscular, spinal, intracranial, intrathecal, intraocular, periocular, intraorbital, intrasynovial and intraperitoneal injection, as well as any similar injection or infusion technique The composition can be also for example a suspension, emulsion, sustained release formulation, cream, gel or powder. The composition can be formulated as a suppository, with traditional binders and carriers such as triglycerides.

In one example, the pharmaceutical formulation is a liquid formulation, e.g., a buffered, isotonic, aqueous solution. In another example, the pharmaceutical composition has a pH that is physiologic, or close to physiologic. In other examples, the aqueous formulation has a physiologic or close to physiologic osmolarity and salinity. It can contain sodium chloride and/or sodium acetate. In some examples, the composition of the present invention is lyophilized.

Having now described the present invention in detail, the same will be more clearly understood by reference to the following examples, which are included herewith for purposes of illustration only and are not intended to be limiting of the invention. All patents and publications referred to herein are expressly incorporated by reference.

EXAMPLES

Example 1

Cloning, Expression and Purification of rFVIIIFc

All molecular biology procedures were performed following standard techniques. The coding sequence of human FVIII (Genbank accession number NM_000132), including its native signal sequence, was obtained by reverse transcription-polymerase chain reactions (RT-PCR) from human liver polyA RNA. Due to the large size of FVIII, the coding sequence was obtained in several sections from separate RT-PCR reactions, and assembled through a series of PCR reactions, restriction digests and ligations into an intermediate cloning vector containing a B domain deleted (BDD) FVIII coding region with a fusion of serine 743 (S743) to glutamine 1638 (Q1638), eliminating 2682 bp from the B domain of full length FVIII. The human IgG1 Fc sequence (e.g., GenBank accession number Y14735) was obtained by PCR from a leukocyte cDNA library, and the final expression cassette was made in such a way that the BDD FVIII sequence was fused directly to the N-terminus of the Fc sequence (hinge, CH2 and CH3 domains, beginning at D221 of the IgG1 sequence, EU numbering) with no intervening linker. For expression of the Fc chain alone, the mouse Igκ (kappa) light chain signal sequence was created with synthetic oligonucleotides and added to the Fc coding sequence using PCR to enable secretion of this protein product. The FVIIIFc and Fc chain coding sequences were cloned into a dual expression vector, pBudCE4.1 (Invitrogen, Carlsbad, Calif.).

HEK 293H cells (Invitrogen, Carlsbad, Calif.) were transfected with the pSYN-FVIII-013 plasmid using Lipofectamine transfection reagent (Invitrogen, Carlsbad, Calif.)), and a stable cell line was selected with zeocin. Cells were grown in serum free suspension culture, and rFVIIIFc protein purified from clarified harvest media using a four column purification process, including a FVIII-specific affinity purification step (McCue J. et al., *J. Chromatogr. A.*, 1216(45): 7824-30 (2009)), followed by a combination of anion exchange columns and a hydrophobic interaction column.

Example 2

Biochemical Characterization

Processed recombinant FVIII-Fc (rFVIIIFc) is synthesized as two polypeptide chains, one chain consisting of BDD-FVIII (S743-Q1638 fusion, 1438 amino acids) fused to the Fc domain (hinge, CH2 and CH3 domains) of IgG1 (226 amino acids, extending from D221 to G456, EU numbering), for a total chain length of 1664 amino acids, the other chain consisting of the same Fc region alone (226 amino acids). Though cells transfected with the FVIIIFc/Fc dual expression plasmid were expected to secrete three products (FVIIIFc dimer, FVIIIFc monomer, and Fc dimer), only the FVIIIFc monomer and Fc dimer were detected in conditioned media. Purified FVIIIFc was analyzed by non-reducing and reducing SDS-PAGE analysis (FIGS. 2A and, B). For the nonreduced SDS-PAGE, bands were found migrating at approximately 90 kDa and 130 kDa, consistent with the predicted molecular weights of the FVIIIFc heavy chain (HC) and light chain-dimeric Fc fusion (LCFc2) (FIG. 2A, lane 3). A third band was also detected at approximately 220 kDa, consistent with the predicted molecular weight for single chain FVIIIFc (SC FVIIIFc; HC+LCFc2), in which the arginine residue at position 754 (1648 with respect to the full length sequence) is not cleaved during secretion. For the reduced SDS-PAGE analysis, major bands were seen migrating at approximately 25 kDa, 90 kDa, 105 kDa, and 195 kDa, consistent with the predicted molecular weights for the single chain Fc, HC, LCFc, and SC FVIIIFc (FIG. 2B, lane 3). Cotransfection with human PC5, a member of the proprotein convertase subtlisin/kexin (PCSK) type proteases, resulted in full processing of the rFVIIIFc product (FIG. 2A, B, lane 2).

Densitometry analysis of several batches of rFVIIIFc after SDS-PAGE indicated greater than 98% purity of the expected bands. Size exclusion chromatography (SEC) was also used to assess the degree of aggregation present, and all batches were found to have aggregate levels at 0.5% or less.

rFVIIIFc structure was further analyzed by thrombin cleavage, reduction, and analysis by LC/UV and LC/MS. The four Factor VIII fragments generated by thrombin (by cleavages at three arginine residues, at positions 372, 740 and 795 (795 corresponds to 1689 with respect to the full length FVIII sequence), can be detected by UV absorbance (FIG. 2C), corresponding to the following segments of the protein: Fc (peak 1), light-chain-Fc (peak 2); the A1 domain from the heavy chain (peak 3) and the A2 domain from the heavy chain (peak 4). The 14 amino acid B domain linker and ~6 kDa a3-related peptides are not detected by UV absorbance due to their small size.

Analysis of the thrombin digestion of rFVIIIFc by HPLC/MS provided further detailed information of the four main domains as well as the ~6 kDa a3 related peptides, and was compared to REFACTO®, a CHO-derived recombinant BDD-FVIII protein (rBDD FVIII), using the same methods. FVIII samples were passed through Detergent-OUTDTG-100X columns (GBioscience, Maryland Heights, Mo.) for the removal of Tween, fully digested with thrombin, reduced and analyzed either by RP-HPLC-UV (POROS R1/10, Applied Biosystems) or RP-HPLC-MS (Agilent 1200 coupled to an Agilent 6210TOF mass spectrometer) using gradients of acetonitrile in water+0.1% formic acid. Peptide sequence was also confirmed with LysC peptide mapping, analyzed by RP-HPLC/MS (Thermo Finnigan LTQ-XL-ETD).

Figure 2D:
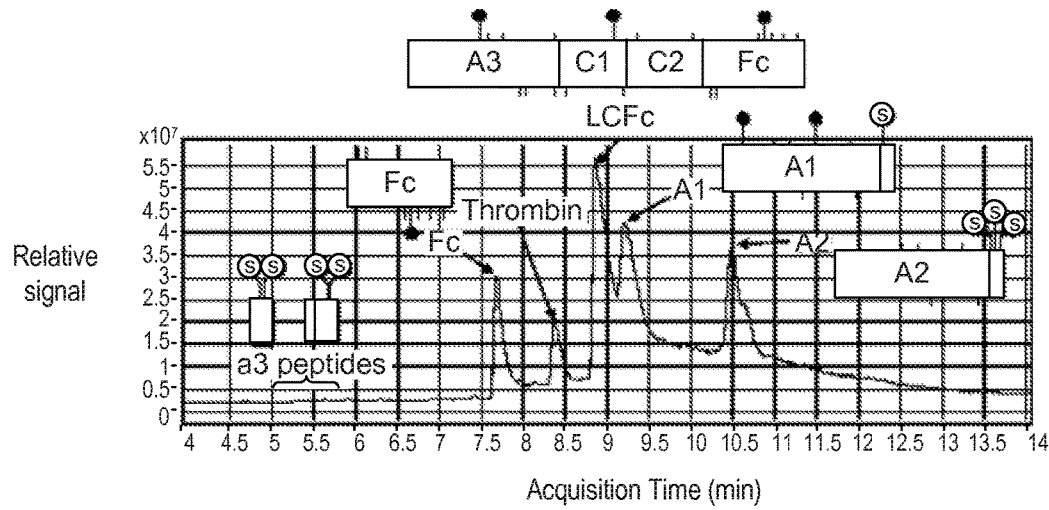

As expected, the total ion current (TIC) chromatogram of rFVIIIFc (FIG. 2D) appears similar to the UV chromatogram (FIG. 2C). Five of the expected six products can be detected by LC/MS, including two forms of the a3 acidic region generated from the processed and single chain isoforms, as well as the thrombin used for the digestion. An additional truncated form of the a3 acidic region was also observed, and is described more fully below. rBDD FVIII yielded a similar TIC chromatogram, but without the free Fc chain and having a different mass for the LC compared to the rFVIIIFc LC-Fc, consistent with the lack of an Fc region (data not shown).

Due to the heterogeneity of glycosylation over much of the protein, the deconvoluted mass spectra for the A1, LC-Fc, and Fc regions are complex and therefore the identity of all of the molecular ions have not been established. However, the observed mass for the three major peaks from the Fc region were found to match the G0, G1, and G2 isoforms found on IgG molecules, corresponding to biantennary oligosaccharides terminating in 0, 1 or 2 galactose residues. The deconvoluted mass spectra of the a3-related peptides and the A2 domain provide the most definitive data, as there are no heterogeneity in the posttranslational modifications in these regions, allowing the expected masses to be identified unambiguously.

The 6 kDa N-terminal peptide released from the LC after cleavage of R1689 is predicted to comprise the a3 acidic region (amino acids E1649 to R1689) if derived from the processed isoform, and the 14 amino acid truncated B domain fused to the a3 acidic region if derived from the single chain isoform. Both rFVIIIFc and rBDD FVIII were found to contain both forms of the a3 region, proportional to the expected levels based on SDS-PAGE analysis. In addition, both proteins contained a truncated form of the a3 region corresponding to amino acids D1658-R1689, as has been reported for other FVIII products, though this was found in greater abundance in rBDD FVIII than in rFVIIIFc.

Figure 2E:
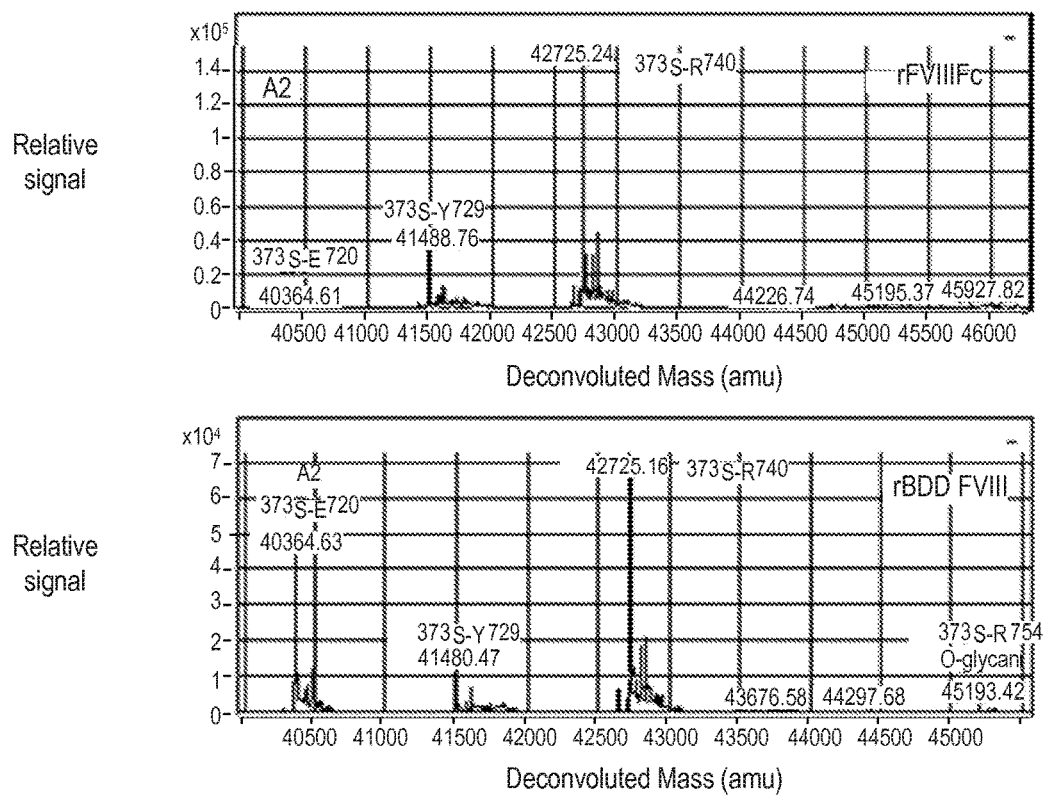
Figure 5A:
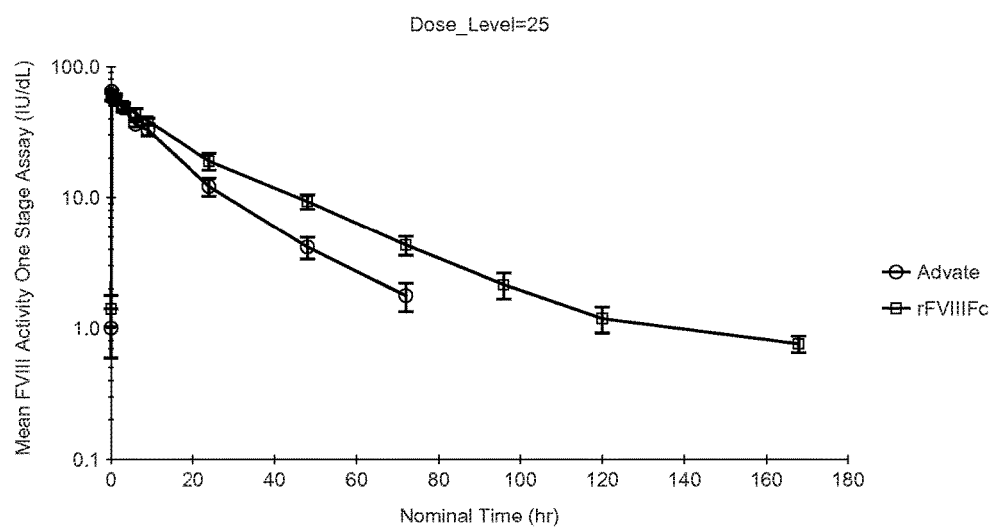
Figure 5C:
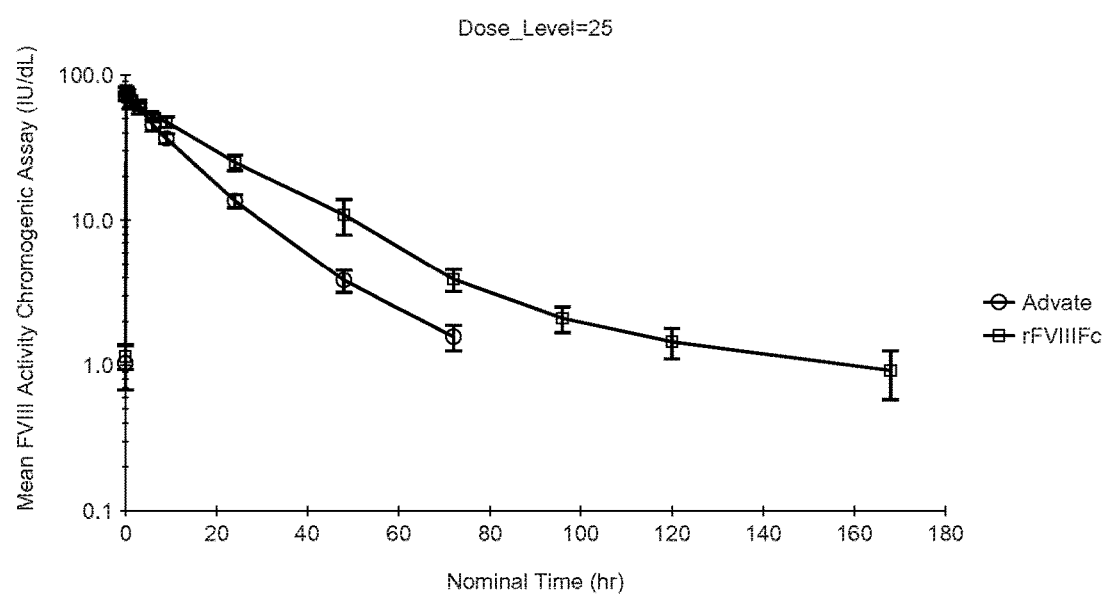

The A2 domain contains three potential tyrosine sulfation sites, but no glycosylation sites that could result in complex heterogeneity, and therefore the exact masses of this region can be calculated. In addition to the primary expected peak in the deconvoluted mass spectrum of rFVIIIFc correlating to the mass of the S373 to R740 sequence (FIG. 2E), two additional forms were identified corresponding to known truncations of the FVIII HC, correlating with an A2 domain truncated at E720 and Y729. These reported truncated forms were also observed directly in the deconvoluted spectrum of rBDD FVIII A2 (FIG. 2E). Both rFVIIIFc and rBDD FVIII A2 contained similar relative amounts of the form truncated at Y729 while the rBDD FVIII A2 domain contained a notably greater level of the form truncated at E720 as compared to the same form in rFVIIIFc (FIG. 2E).

The primary sequence of rFVIIIFc was confirmed by peptide mapping with lysyl endopeptidase (Lys-C) digests followed by UV and mass spectrometric detection. Of the 99 theoretical peptides produced from rFVIIIFc, 81 were detected, corresponding to 98% of the total sequence. The posttranslational modifications of rFVIIIFc were also characterized by this method. FVIII contains 6 potential tyrosine sulfation sites, corresponding to positions 346, 718, 719, 723, 1664, and 1680. Fully sulfated peptides corresponding to these six sites were found, with trace amounts of non-sulfated peptide corresponding to position 1680 as assessed by integration of the total ion chromatogram in the mass spectra, and no detectable non-sulfated peptides corresponding to the other positions. BDD FVIII also contains 6 potential N-glycosylation sites, four of which have been reported to be glycosylated in recombinant FVIII products. Consistent with this, rFVIIIFc was found to have the same 4 sites glycosylated; N239 and N2118 were found to contain high mannose structures, while N41 and N1810 were found to contain more complex carbohydrates, similar to those found on rBDD FVIII. The Fc region N-linked glycosylation was found to match the G0, G1, and G2 isoforms found with the thrombin map by LC/MS. FVIII has been reported to have 0-glycosylation sites at Ser 741 and 743 that are partially occupied, and this was found to be the case with rFVIIIFc as well.

The rFVIIIFc polypeptide produced without cotransfected processing enzymes exhibited 15-25% single chain FVIIIFc (SC FVIIIFc), which differs from processed rFVIIIFc by a single peptide bond between R754 and E755 (R1648/E1649 with respect to the full length FVIII). This isoform was purified and characterized in all of the biochemical assays described above, and found to be comparable to rFVIIIFc as shown below. The activity of purified single chain FVIIIFc was found to be similar to rFVIIIFc in a chromogenic assay as well as by the various functional assays described below.

Measurement of FVIII Activity by Chromogenic and One-Stage aPTT Assays

FVIII activity was measured by a FVIII chromogenic assay. The average specific activity from four separate batches of rFVIIIFc was found to be 9762±449 IU/mg by the chromogenic assay, corresponding to 2148±99 IU/nmol. The average specific activity from fourteen separate batches of rFVIIIFc was found to be 8460±699 IU/mg by the aPTT assay, and 9348±1353 IU/mg by the chromogenic assay, corresponding to 1861±154 and 2057±298 IU/nmol, respectively. FVIII activity of single chain FVIII:Fc was also measured by the chromogenic assay and compared to the completely processed rFVIII:Fc or rFVIII:Fc DS (containing about 25% single chain rFVIII:Fc). As Table 3A shows, single chain rFVIIIFc showed no significant difference in FVIII activity compared to the Factor VIII activity of completely processed FVIIIFc or rFVIIIFc DS by the chromogenic assay, both in the presence and the absence of von Willebrand Factor (VWF). Table 3B shows that full activity of SCrFVIIIFc, as measured by one-stage activated partial thromboplastin time (aPTT) assay, was observed in the absence of VWF.

TABLE_3A_FVIII

Activity by Chromogenic Assay

| Matrix | Sample | Chromogenic Specific Activity(IU/mg) | % CV* |
|---|---|---|---|
| FVIII depleted plasma | rFVIIIFcDS (25% NP) (RECD-19189-09-013) | 9066 | 2.49 |
| | Single chain rFVIIIFc (purified from RECD 19189-09-013) | 8194 | 2.72 |
| | Completely Processed rFVIIIFc (purified from an engineered cell line) | 9577 | 8.34 |
| FVIII and vWF depleted plasma | rFVIIIFcDS (25% NP) (RECD-19189-09-013) | 10801 | 8.92 |
| | Single chain rFVIIIFc (purified from RECD 19189-09-013) | 9498 | 4.70 |
| | Completely Processed rFVIIIFc (purified from an engineered cell line) | 9569 | 4.54 |
| FVIII/VWF-depleted plasma supplemented with human VWF | rFVIIIFc | 9982 | 4.3 |
| | SC rFVIIIFc | 8984 | 4.6 |
| | Completely-processed rFVIIIFc | 8275 | 8.2 |

*CV = coefficient of variation

TABLE_3B_FVIII

Activity by aPTT assay

| Matrix | Sample | Coagulation (aPTT) Specific Activity (IU/mg) | % CV |
|---|---|---|---|
| FVIII-depleted plasma | rFVIIIFcDS (25% NP) (RECD-19189-09-013) | 8210 | 5.88 |
| | Single chain rFVIIIFc (purified from RECD 19189-09-013) | 3108 | 6.57 |
| | Completely Processed rFVIIIFc (purified from an engineered cell line) | 8683 | 3.57 |
| FVIII and vWF depleted plasma | rFVIIIFcDS (25% NP) (RECD-19189-09-013) | 15621 | 6.47 |
| | Single chain rFVIIIFc (purified from RECD 19189-09-013) | 13572 | 2.41 |
| | Completely Processed rFVIIIFc (purified from an engineered cell line) | 15170 | 10.42 |
| FVIII/VWF-depleted plasma supplemented with human VWF | rFVIIIFc | 7742 | 7.4 |
| | SC rFVIIIFc | 3133 | 4.9 |
| | Completely-processed rFVIIIFc | 8495 | 4.0 |

In one-stage clotting assay (APTT), SC rFVIIIFc demonstrated a 60% decrease in activity when the plasma has normal VWF level, suggesting the potential role of VWF in the activation of SC rFVIIIFc. This observation was further confirmed by addition of human VWF back to the FVIII/VWF-depleted plasma (Table 3), where the coagulant activity of SC rFVIIIFc was reduced to the same level as in congenital FVIII-deficient plasma.

Activity in Xase Complex

FVIII activity was also measured in the context of the Xase complex, by incubating activated FIX and thrombin-activated REFACTO® or rFVIIIFc protein on a phospholipid surface in the presence of calcium, and monitoring the conversion of FX to FXa as measured by cleavage of a chromogenic or fluorogenic substrate, from which FXa generation rates were determined. This assay was then modified by varying one component of the assay while keeping the others constant in order to examine the interactions with each individual component.

The FXa generation rate was determined as a function of varying phospholipid concentrations for rFVIIIFc DS, rBDD FVIII, and single chain rFVIIIFc (FIG. 3A), using synthetic phospholipid vesicles (25% phosphotadyl serine/75% phosphotadyl choline). Both proteins were found to have a similar activity profile, with peak activity at approximately 156 µM phospholipids.

The FXa generation rate was then determined as a function of varying FX concentrations, and Km and Vmax values calculated (FIG. 3B). The activity profiles for rFVIIIFc DS, rBDD FVIII, and single chain rFVIIIFc were found to be similar, with similar Km and Vmax (Table 4). Finally, the FXa generation rate was determined as a function of varying FIX concentrations (FIG. 3C). The activity profiles appeared similar, with similar Kd and Vmax (Table 4). Similar results were obtained using platelets as a phospholipid source (unpublished data, June 2009).

TABLE 4

FXa Generation Parameters for FVIII Proteins on Phospholipids

| Lipid Source | Molecule | Km (nM) | Vmax (nM/min) |
|---|---|---|---|
| 25% PS-75% PC | rFVIIIFc DS | 55.0 ± 5.9 | 65.6 ± 8.6 |
|  | rBDD FVIII | 51.0 ± 8.7 | 73.5 ± 10.1 |
|  | NP rFVIIIFc | 53.2 ± 7.5 | 56.0 ± 13.8 |

TABLE 5

FIXa Interactions with FVIII Proteins

| Lipid Source | Molecule | Km (nM) | Vmax (nM/min) |
|---|---|---|---|
| 25% PS-75% PC | rFVIIIFc DS | 2.8 ± 0.4 | 4.5 ± 0.3 |
|  | rBDD FVIII | 2.5 ± 0.3 | 4.0 ± 1.0 |
|  | NP rFVIIIFc | 2.3 ± 0.2 | 3.8 ± 0.4 |

Inactivation by APC

Once active, FVIII is inactivated by cleavage by activated protein C (APC), as well as by dissociation of the A2 domain. rFVIIIFc and rBDD FVIII were both activated by thrombin, then incubated with APC for different times and activity determined in a FXa generation assay (FIG. 4). In the absence of thrombin activation, little FXa generation was detected, and this was increased significantly with thrombin digestion. Treatment with APC for 90 min led to a significant decrease in FXa generation rates, similar to non-activated samples, and these results were similar for rFVIIIFc DS, rBDD FVIII, and single chain rFVIIIFc.

Affinity for vWF

FVIII interactions with von Willebrand factor (vWF) were measured by real-time biomolecular interaction analysis (BIAcore), based on surface Plasmon resonance (SPR) technology, to determine the kinetics of binding of rFVIIIFc and rBDD FVIII towards vWF (Table 6). Kinetic rate parameters of Ka (on-rate) and Kd (off-rate), and the affinity KD (Kd/Ka), were determined for each FVIII interaction under identical conditions. Both rFVIIIFc and rBDD FVIII were found to have a low nM binding affinity (KD) for vWF, of 1.64±0.37 and 0.846±0.181 nM, respectively. The proteins had similar off-rates, with a two fold difference in on-rate resulting in a two fold difference in the affinity.

As shown in Table 6, the affinity of rFVIII:Fc DS or single chain rFVIIIFc with vWF was found to be in the low nM range, approximately two fold greater than that of BDD FVIII alone. At physiological concentrations, this would result in a slight decrease in the percentage of rFVIIIFc (processed or single chain) complexed with vWF as compared to free FVIII, however in vivo studies have indicated that the half life of rFVIIIFc is significantly prolonged over full length or BDD FVIII despite this slightly lower affinity, and therefore this does not appear to compromise the half life of the molecule. It may be possible that the free rFVIIIFc is more efficiently recycled through the FcRn pathway and therefore this may contribute to a greater prolongation of half life.

Affinity for vWF and Thrombin-Mediated Release from vWF

Recombinant B-domain deleted Factor VIIIFc (rFVIIIFc) was expressed in HEK293 cells. During biosynthesis in HEK293 cells, most of the rFVIIIFc is processed by limited proteolysis to generate a FVIII heavy chain (HC) and a FVIII light chain (LC) to which the Fc moiety is attached. Spontaneous disassociation of the HC and LC in plasma, and during storage of FVIII drug products, is thought to contribute to a loss of FVIII activity. The remaining portion of the biosynthesized rFVIIIFc, which is not processed, forms a single chain isoform of rFVIIIFc (SC rFVIIIFc), which may provide enhanced manufacturability and stability compared to the processed rFVIIIFc.

This example describes an assay comparing the interaction of SC rFVIIIFc with von Willebrand factor (vWF) in relation to the interaction of rFVIIIFc with vWF. Interactions with vWF were measured by real-time biomolecular interaction analysis (BIAcore), based on surface Plasmon resonance (SPR) technology, to determine the kinetics of binding of rFVIIIFc and SC rFVIIIFc towards vWF (Table 11 and FIG. 16A). FVIII-free human plasma derived vWF was immobilized by amine coupling on the surface of a biosensor at levels low enough to prevent mass transport limitation. rFVIIIFc and SC rFVIIIFc were sequentially injected in single-cycle kinetics mode at concentrations ranging from 0.13 to 5.0 nM. Sensorgram data was fit to a 1:1 interaction model.

Kinetic rate parameters of Ka (on-rate) and Kd (off-rate), and the affinity KD (Kd/Ka), were determined for each FVIII interaction under identical conditions. Both rFVIIIFc and SC rFVIIIFc were found to have a low nM binding affinity (KD) for vWF, of 0.34±0.1 and 0.31±0.1 nM, respectively. Both isoforms also had similar on-rates and off-rates.

TABLE 6

Biocore Binding Analysis of FVIII Proteins to vWF

| | | | Kinetic rate parameters | | Off-rate/On-rate |
|---|---|---|---|---|---|
| Analyte | Ligand | N | On-rate (M − 1 s − 1) | Off-rate (s − 1) | KD(M) |
| rFVIIIFc DS | hvWf | 5 | 7.92 ± 1.51 × $10^5$ | 1.25 ± 1.12 × $10^{-3}$ | 1.64 ± 0.37 × $10^{-9}$ |
| NP rFVIIIFc | hvWf | 5 | 8.66 ± 1.10 × $10^5$ | 1.09 ± 0.09 × $10^{-3}$ | 1.28 ± 0.22 × $10^{-9}$ |
| rBDD FVIII | hvWf | 5 | 13.7 ± 1.50 × $10^5$ | 1.14 ± 0.12 × $10^{-3}$ | 0.846 ± 0.181 × $10^{-9}$ |

TABLE 11

Biocore Binding Analysis of FVIII Proteins to vWF

| Analyte | Ligand | N | Kinetic rate parameters On-rate (M − 1 s − 1) | Off-rate (s − 1) | Off-rate/ On-rate KD(M) |
|---|---|---|---|---|---|
| rFVIIIFc | hvWf | 6 | $2.6 \pm 0.4 \times 10^5$ | $8.9 \pm 1.3 \times 10^{-4}$ | $3.4 \pm 0.1 \times 10^{-10}$ |
| SC rFVIIIFc | hvWf | 6 | $2.7 \pm 0.1 \times 10^5$ | $8.4 \pm 0.4 \times 10^{-4}$ | $3.1 \pm 0.1 \times 10^{-10}$ |

Figure 16A:
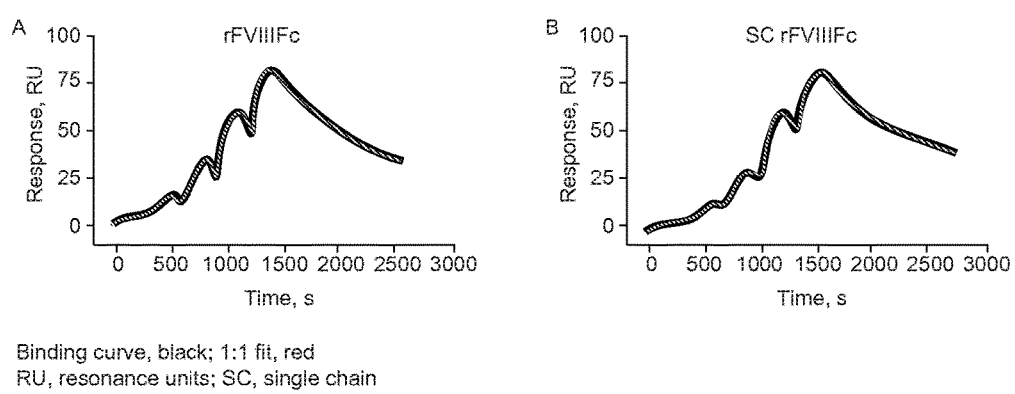
Figure 16B:
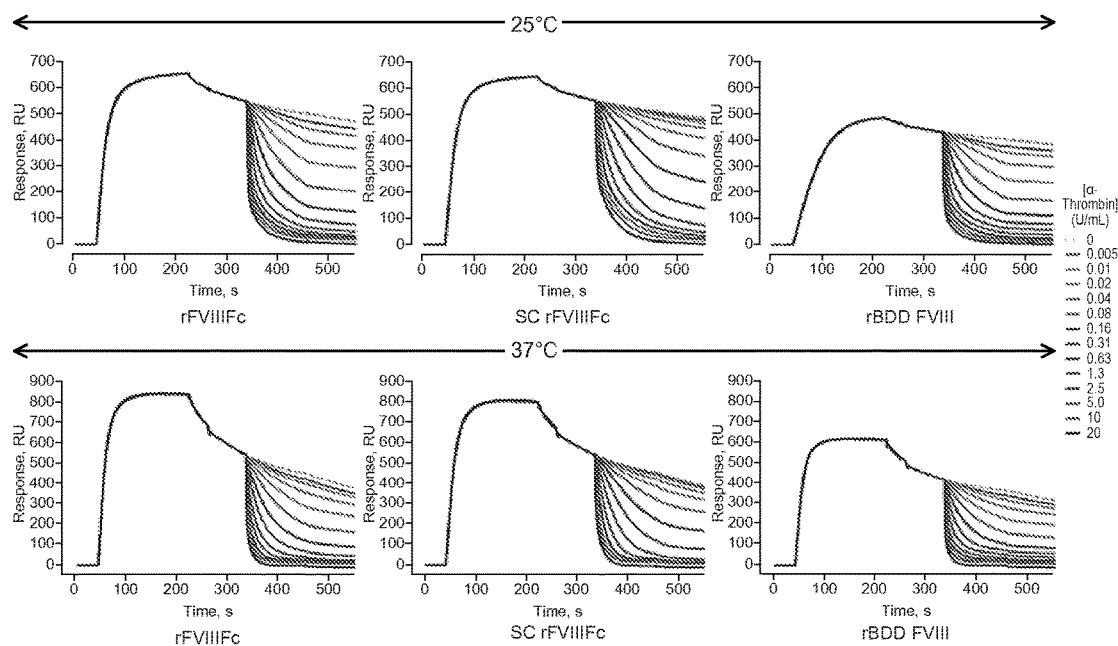
Figure 16C:
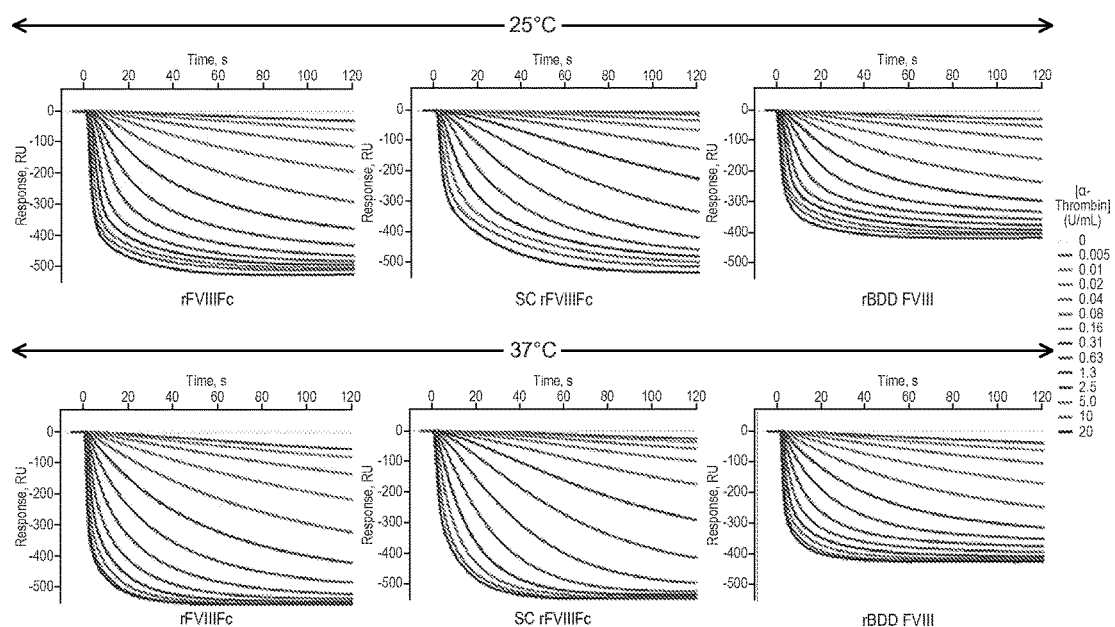
Figure 16E:
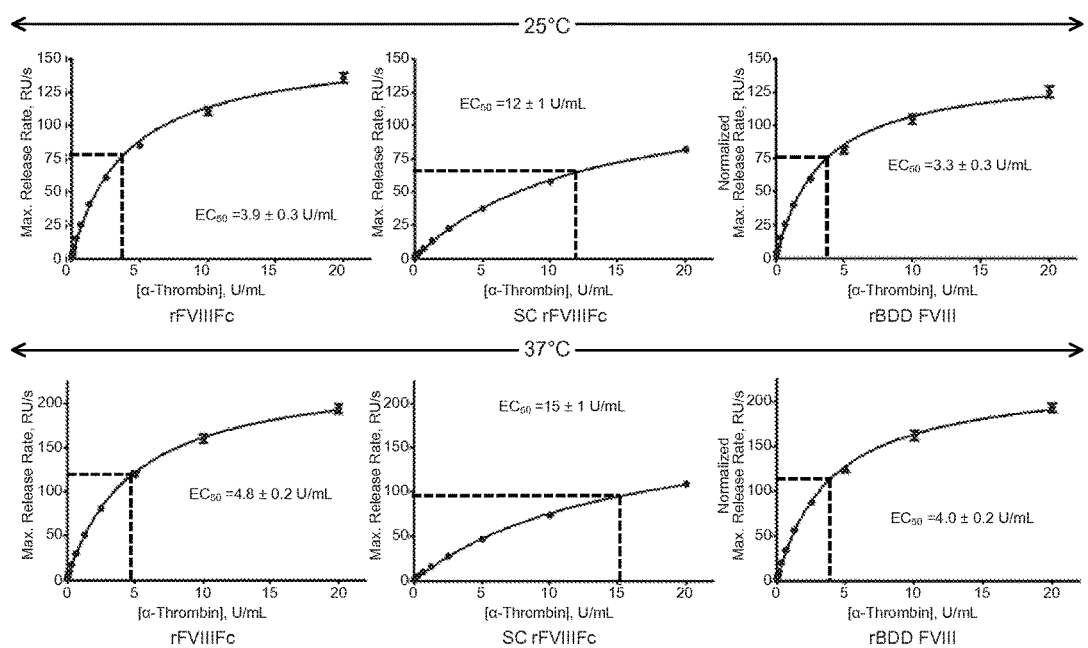

Next, thrombin-mediated release of rFVIIIFc, SC rFVIIIFc, and B-domain deleted FVIII lacking Fc moieties (rBDD FVIII) was measured at both 25° C. and 37° C. Human vWF was immobilized by amine coupling at similar levels on three flow cells on the biosensor surface. The remaining flow cell served as a blank for reference purposes. The rFVIIIFc and SC rFVIIIFc proteins were captured by vWF and allowed to slowly disassociate, and the concentrations of rFVIIIFc and SC rFVIIIFc were adjusted to obtain equimolar capture levels by the end of the dissociation phase. Human α-thrombin solutions were prepared by 2-fold serial dilution and applied at concentrations that ranged from 0.005 to 20 U/mL, resulting in proteolytic release of FVIIIa species from vWF. Thrombin mediated release of activated rFVIIIFc, SC rFVIIIFc, and rBDD FVIII from vWF was monitored in real-time using an SPR-based optical biosensor (FIG. 16B). Following blank reference subtraction (FIG. 16C), the release rate as a function of α-thrombin concentration was determined (FIG. 16D). The thrombin half maximal effective concentration ($EC_{50}$) for SC rFVIIIFc was 12±1 U/mL compared to 3.9±0.3 U/mL for rFVIIIFc at 25° C. and was 15±1 U/mL for SC rFVIIIFc compared to 4.8±0.2 U/mL for rFVIIIFc at 37° C. (FIG. 16E). rFVIIIFc had a similar thrombin $EC_{50}$ value compared to rBDD FVIII, having values of 3.9±0.3 U/mL and 3.3±0.3 U/mL, respectively at 25° C. and values of 4.8±0.2 U/mL and 4.0±0.2 U/mL, respectively at 37° C. SC rFVIIIFc had a thrombin $EC_{50}$ value that was approximately 3-fold higher than rFVIIIFc. This impairment of thrombin mediated release from vWF may underlie the specific reduction in specific activity for SC rFVIIIFc observed in the aPTT assay in which vWF was present (Table 3B).

Example 3

A Phase I/IIa, open-label, crossover, dose-escalation, multi-center, and first-in-human study was designed to evaluate the safety, tolerability, and pharmacokinetics of a single dose of rFVIIIFc in subjects with severe (defined as <1 IU/dL [1%] endogenous factor VIII [FVIII]) hemophilia A. A total of approximately 12 previously treated patients were enrolled and dosed with rFVIIIFc at 25 or 65 IU/kg. After the screening (scheduled within 28 days prior to the first dose of the ADVATE® [rFVIII], the reference comparator agent) and a minimum of 4-days (96 hours) elapsing with no FVIII treatment prior to the first injection, approximately 6 subjects received a single 25 IU/kg dose of ADVATE® followed by a 3-day (72 hours) pharmacokinetic (PK) profile then crossover and receive a 25 IU/kg single, open-label dose of rFVIIIFc for a 7-day (168 hours) PK profiling. The first 3 subjects were dosed sequentially. For the first three (3) subjects dosed with 25 IU/kg of rFVIIIFc, each subject underwent an inhibitor assessment at 14-days (336 hours) post-injection of rFVIIIFc. Dosing of the next subject (for the first three subjects only) occurred once the inhibitor testing is completed. After the 3rd subject completed the 14 day inhibitor assessment, the remaining three subjects at 25 IU/kg and the six subjects at 65 IU/kg began enrollment sequentially at least 1 day apart within each dose group.

One week after the last subject received the 25 IU/kg dose of the rFVIIIFc, approximately 6 unique subjects were recruited for the 65 IU/kg cohort. Each subject in the 65 IU/kg cohort received a single 65 IU/kg dose of ADVATE® followed by a 4-day (96 hours) PK profiling then crossover and receive a 65 IU/kg single, open-label dose of rFVIIIFc for a 10-day (240 hours) profiling. If a bleeding episode occurred before the first injection of rFVIIIFc in any cohort, subject's pre-study FVIII product was used for treatment and an interval of at least 4 days had to pass before receiving the first injection of rFVIIIFc for the PK profile.

All subjects were followed for a 14-day (336 hours) and 28 day safety evaluation period after administration of rFVIIIFc 25 IU/kg or 65 IU/kg for safety. All subjects underwent pharmacokinetic sampling pre- and post-dosing along with blood samples for analysis of FVIII activity at designated time points.

The pharmacokinetic data for the Phase I/IIa clinical trial demonstrated the following results for FVIIIFc. FVIIIFc had about a 50% increase in systemic exposure ($AUC_{INF}$), about 50% reduction in clearance (Cl), and about 50-70% increase in elimination half-life and MRT compared to ADVATE® (full length rFVIII). In addition, FVIIIFc showed increased C168, TBLP1, TBLP3, and TBLP5 values compared to ADVATE®.

| | |
|---|---|
| $AUC_{INF}$ | Area under the concentration-time curve from zero to infinity |
| Beta HL | Elimination phase half-life; also referred to as $t_{1/2\beta}$ |
| C168 | Estimated FVIIIFc activity above baseline at approximately 168 h after dose |
| Cl | Clearance |
| MRT | Mean residence time |
| TBLP1 | Model-predicted time after dose when FVIIIFc activity has declined to approximately 1 IU/dL above baseline |
| TBLP3 | Model-predicted time after dose when FVIIIFc activity has declined to approximately 3 IU/dL above baseline |
| TBLP5 | Model-predicted time after dose when FVIIIFc activity has declined to approximately 5 IU/dL above baseline |

Example 4

A recombinant B-domain-deleted factor VIII-Fc (rFVIIIFc) fusion protein has been created as an approach to extend the half-life of FVIII. The pharmacokinetics (PK) of rFVIIIFc were compared to rFVIII in hemophilia A mice. We found that the terminal half-life was twice as long for rFVIIIFc compared to rFVIII. In order to confirm that the underlying mechanism for the extension of half-life was due to the protection of rFVIIIFc by FcRn, the PK were evaluated in FcRn knockout and human FcRn transgenic mice. A single intravenous dose (125 IU/kg) was administered and the plasma concentration measured using a chromogenic activity assay. The Cmax was similar between rFVIIIFc and rFVIII (XYNTHA®) in both mouse strains. However, while the half-life for rFVIIIFc was comparable to that of rFVIII in the FcRn knockout mice, the half-life for rFVIIIFc was extended to approximately twice longer than that for rFVIII in the hFcRn transgenic mice. These results confirm that FcRn mediates or is responsible for the prolonged half-life of rFVIIIFc compared to rFVIII. Since hemostasis in whole blood measured by rotation thromboelastometry (ROTEM®) has been shown to correlate with the efficacy of coagulation factors in bleeding models of hemophilia mice as well as in clinical applications, we sought to evaluate the ex vivo efficacy of rFVIIIFc in the hemophilia A mice using ROTEM®. Hemophilia A mice were administered a single intravenous dose of 50 IU/kg rFVIIIFc, XYNTHA® (FVIII) or ADVATE® (FVIII). At 5 minutes post dose, clot formation was similar with respect to clotting time (CT), clot formation time (CFT) and α-angle. However, rFVIIIFc showed significantly improved CT at 72 and 96 hr post dose, and CFT and α-angle were also improved at 96 hrs compared to both XYNTHA® (FVIII) and ADVATE® (FVIII), consistent with prolonged PK of rFVIIIFc. Therefore construction of an Fc fusion of FVIII produces a molecule with a defined mechanism of action that has an increased half-life and the potential to provide prolonged protection from bleeding.

Example 5

This Example presents final analysis results for FVIII activity from 16 patients treated with 25 and 65 IU/kg FVIII products. See Example 3.

In this Example, rFVIIIFc is a recombinant fusion protein comprised of a single molecule of recombinant B-domain deleted human FVIII (BDD-rFVIII) fused to the dimeric Fc domain of the human IgG1, with no intervening linker sequence. This protein construct is also referred to herein as rFVIIIFc heterodimeric hybrid protein, FVIIIFc monomeric Fc fusion protein, FVIIIFc monomer hybrid, monomeric FVIIIFc hybrid, and FVIIIFc monomer-dimer. See Example 1, FIG. 1, and Table 2A.

Preclinical studies with rFVIIIFc have shown an approximately 2-fold prolongation of the half-life of rFVIII activity compared to commercially available rFVIII products. The rationale for this study was to evaluate the safety and tolerability of a single dose of rFVIIIFc in frozen liquid formulation and provide data on the PK in severe hemophilia A subjects. For this study, 16 evaluable subjects were available for PK evaluation. Single administration of two doses of both rFVIIIFc and ADVATE® at a nominal dose of 25 (n=6) and 65 IU/kg of body weight (n=10) were infused intravenously over approximately 10 minutes. Blood samples for plasma PK assessments were obtained before infusion, as well as up to 10 days after dosing. The PK of FVIII activity for both ADVATE® and rFVIIIFc were characterized in this study using a model-dependent method.

Objectives

The primary objective of this study was to assess the safety and tolerability of single administration of two doses of rFVIIIFc (25 and 65 IU/kg) in previously treated patients (PTPs) aged 12 and above with severe hemophilia A.

The secondary objectives were to determine the pharmacokinetics (PK) parameters determined by pharmacodynamic (PD) activity of FVIII over time after a single administration of 25 or 65 IU/kg of rFVIIIFc compared to ADVATE® in one-stage clotting and chromogenic assays.

Study Design (See Example 3)

Blood samples were collected for FVIII activity PK evaluations at the screening visit (within 28 days prior to dosing ADVATE®); on Day 0 (injection of ADVATE®) pre-injection and at 10 and 30 minutes and 1, 3, 6, and 9 hours post-injection; on Day 1 at 24 hours post-injection of ADVATE®; on Day 2 at 48 hours post-injection of ADVATE®; on Day 3 at 72 hours post-injection of ADVATE®; and on Day 4 at 96 hours post-injection of high dose of ADVATE® (Cohort B only).

Blood samples were collected for FVIII activity PK evaluations on the day of rFVIIIFc injection just prior to the administration of rFVIIIFc, at 10 and 30 minutes and 1, 3, 6, and 9 hours post-injection of rFVIIIFc; on Day 1 at 24 hours post-injection of rFVIIIFc; on Days 2 through 5 at 48, 72, 96, and 120 hours post-injection of rFVIIIFc; on Day 7 at 168 hours post-injection of rFVIIIFc; on Days 8, 9, and 10 at 192, 216, and 240 hours post-injection of high dose of rFVIIIFc (Cohort B only). FVIII activity was also measured at the final study visit (28 days post-injection of rFVIIIFc) at 672 hours post-injection of rFVIIIFc.

Pharmacokinetic Modeling and Calculations
Abbreviations
  TBLP1=Model-predicted time after dose when FVIII activity has declined to approximately 1 IU/dL above baseline.
  TBLP3=Model-predicted time after dose when FVIII activity has declined to approximately 3 IU/dL above baseline
  KV_M=Cmax_M/Actual Dose (IU/kg)
  KV_OB=Cmax_OB/Actual Dose (IU/kg)
  IVR_M=100×Cmax_M×Plasma Volume (dL)/Total Dose in IU; where plasma volume in mL=(23.7×Ht in cm)+(9.0×Wt in kg)−1709.
  IVR_OB=100×Cmax_OB×Plasma Volume (dL)/Total Dose in IU; where plasma volume in mL=(23.7×Ht in cm)+(9.0×Wt in kg)−1709.

Results
Single-Dose Pharmacokinetics (One-Stage Assay)

Observed FVIII activity increased sharply after the short IV infusion of either ADVATE® or rFVIIIFc, with mean (±SD) model-predicted Cmax values of 56.6±4.74 and 121±28.2 IU/dL for ADVATE® and 55.6±8.18 and 108±16.9 IU/dL for rFVIIIFc for the 25 and 65 IU/kg dose groups, respectively. All ADVATE®- and rFVIIIFc-treated patients had dose-related increases in FVIII activity. The observed increase in both Cmax and $AUC_{INF}$ was slightly less than proportional to dose over the dose range evaluated.

After the end of the infusion, the decline of the observed FVIII activity exhibited monoexponential decay characteristics until the baseline level was reached. The rate of decline in FVIII activity was slower for rFVIIIFc than for ADVATE® with mean (±SD) model-predicted elimination half-life values of 11.9±2.98 and 10.4±3.03 hr for ADVATE® and 18.0±3.88 and 18.4±6.99 hr for rFVIIIFc for the 25 and 65 IU/kg dose groups, respectively. Elimination half-life values appeared to be dose-independent over the dose range evaluated for both FVIII products.

Total systemic FVIII exposure (assessed by $AUC_{INF}$) was ~48% and 61% greater following rFVIIIFc administration than ADVATE® at 25 and 65 IU/kg dose levels, respectively. Mean (±SD) model-predicted $AUC_{INF}$ values were 974±259 and 1810±606 hr*IU/dL for ADVATE® and 1440±316 and 2910±1320 hr*IU/dL for rFVIIIFc for the 25 and 65 IU/kg dose groups, respectively.

Similar to elimination half-life, the MRT was prolonged for rFVIIIFc relative to ADVATE®. Mean (±SD) model-predicted MRT values were 17.1±4.29 and 14.9±4.38 hr for ADVATE® and 25.9±5.60 and 26.5±10.1 hr for rFVIIIFc for the 25 and 65 IU/kg dose groups, respectively. MRT values appeared to be dose-independent over the dose range evaluated for both FVIII products.

In addition, primary PK parameter values for CL and V were determined CL values for rFVIIIFc only accounted for ~66% of those observed for ADVATE® at equivalent doses. Mean (±SD) model-predicted CL values were 2.70±0.729 and 4.08±1.69 mL/hr/kg for ADVATE® and 1.80±0.409 and 2.69±1.25 mL/hr/kg for rFVIIIFc for the 25 and 65 IU/kg dose groups, respectively. V values were comparable between ADVATE® and rFVIIIFc with mean (±SD) model-predicted V values of 43.9±4.27 and 56.1±13.4 mL/kg for ADVATE® and 45.3±7.23 and 61.6±10.6 mL/kg for rFVIIIFc for the 25 and 65 IU/kg dose groups, respectively. Slight increases in mean CL and V values were noted with increasing dose of ADVATE® and rFVIIIFc; however, the increase in standard deviations at the 65 IU/kg dose coupled with limited dose levels confounded an assessment of the dose-dependency of these parameters. For example, the CV % geometric mean CL value for the rFVIIIFc treatment group increased from 23.0% (25 IU/kg) to 48.6% (65 IU/kg).

In addition to the primary PK parameters, secondary PK parameters (e.g. K-values, IVR, etc.) were determined to evaluate FVIII duration of effect. Evidence of PK difference was also observed with rFVIIIFc demonstrating increased TBLP1 and TBLP3 values compared to ADVATE® at equivalent doses. IVR and K-values for ADVATE® and rFVIIIFc appeared to be comparable. A slight increase in TBLP1 and TBLP3 values were observed with increasing dose of ADVATE® and rFVIIIFc. In contrast, slight decreases in mean IVR and K-values were noted with increasing dose of ADVATE® and rFVIIIFc. As previously indicated, an assessment of the dose dependency of these parameters is confounded by limited dose levels.

Mean (±SD) observed TBLP1 were 2.88±0.733 and 2.93±0.848 IU/dL per IU/kg for ADVATE® and 4.28±0.873 and 5.16±2.02 IU/dL per IU/kg for rFVIIIFc for the 25 and 65 IU/kg dose groups, respectively. Mean (±SD) observed TBLP3 were 2.06±0.527 and 2.26±0.666 IU/dL per IU/kg for ADVATE® and 3.09±0.623 and 3.93±1.59 IU/dL per IU/kg for rFVIIIFc for the 25 and 65 IU/kg dose groups, respectively.

Mean IVR and K-values calculated using observed Cmax values (subtracted with baseline and residual drug within the model) were generally greater than values determined using model-predicted Cmax values; consistent with slight under-estimation of the observed peak activity using the one-compartment model. Mean (±SD) observed K-values were 2.57±0.198 and 2.13±0.598 IU/dL per IU/kg for ADVATE® and 2.46±0.330 and 1.85±0.332 IU/dL per IU/kg for rFVIIIFc for the 25 and 65 IU/kg dose groups, respectively. Mean (±SD) observed IVR values were 94.1±15.6 and 85.8±16.5% for ADVATE® and 89.5±11.9 and 74.8±6.72% for rFVIIIFc for the 25 and 65 IU/kg dose groups, respectively.

Single-Dose Pharmacokinetics (Chromogenic Assay)

Observed FVIII activity increased sharply after the short IV infusion of either ADVATE® or rFVIIIFc, with mean (±SD) model-predicted Cmax values of 70.2±9.60 and 157±38.6 IU/dL for ADVATE® and 70.3±10.0 and 158±34.7 IU/dL for rFVIIIFc for the 25 and 65 IU/kg dose groups, respectively.

All ADVATE®- and rFVIIIFc-treated patients had dose-related increases in FVIII activity. The observed increase in both Cmax and $AUC_{INF}$ was slightly less than proportional to dose over the dose range evaluated.

After the end of the infusion, the decline of the observed FVIII activity exhibited monoexponential decay character-istics until the baseline level was reached. The rate of decline in FVIII activity was slower for rFVIIIFc than for ADVATE® with mean (±SD) model-predicted elimination half-life values of 10.7±1.98 and 10.3±3.27 hr for ADVATE® and 16.2±2.92 and 19.0±7.94 hr for rFVIIIFc for the 25 and 65 IU/kg dose groups, respectively. Elimination half-life values appeared to be dose-independent over the dose range evaluated for both FVIII products.

Total systemic FVIII exposure (assessed by $AUC_{INF}$) was ~53% and 84% greater following rFVIIIFc administration than ADVATE® at 25 and 65 IU/kg dose levels, respectively. Mean (±SD) model-predicted $AUC_{INF}$ values were 1080±236 and 2320±784 hr*IU/dL for ADVATE® and 1650±408 and 4280±1860 hr*IU/dL for rFVIIIFc for the 25 and 65 IU/kg dose groups, respectively.

Similar to elimination half-life, the MRT was prolonged for rFVIIIFc relative to ADVATE®. Mean (±SD) model-predicted MRT values were 15.3±2.86 and 14.8±4.72 hr for ADVATE® and 23.4±4.22 and 27.3±11.4 hr for rFVIIIFc for the 25 and 65 IU/kg dose groups, respectively. MRT values appeared to be dose-independent over the dose range evaluated for both FVIII products.

In addition, primary PK parameter values for CL and V were determined CL values for rFVIIIFc only accounted for ~58-66% of those observed for ADVATE® at equivalent doses. Mean (±SD) model-predicted CL values were 2.39±0.527 and 3.21±1.40 mL/hr/kg for ADVATE® and 1.57±0.349 and 1.86±0.970 mL/hr/kg for rFVIIIFc for the 25 and 65 IU/kg dose groups, respectively. V values were comparable between ADVATE® and rFVIIIFc with mean (±SD) model-predicted V values of 35.8±5.52 and 43.6±11.2 mL/kg for ADVATE® and 35.9±6.65 and 42.7±8.91 mL/kg for rFVIIIFc for the 25 and 65 IU/kg dose groups, respectively. Increases in mean CL and V values were noted with increasing dose of ADVATE® and rFVIIIFc; however, the increase in standard deviations at 65 IU/kg coupled with limited dose levels confounded an assessment of the dose-dependency of these parameters.

In addition to the primary PK parameters, secondary PK parameters (e.g. K-values, IVR, etc.) were determined to evaluate FVIII duration of effect. Evidence of PK difference was also observed with rFVIIIFc demonstrating increased TBLP1 and TBLP3 values compared to ADVATE® at equivalent doses. IVR and K-values for ADVATE® and rFVIIIFc appeared to be comparable.

A slight increase in TBLP1 and TBLP3 values were observed with increasing dose of ADVATE® and rFVIIIFc. In contrast, slight decreases in mean IVR and K-values were noted with increasing dose of ADVATE® and rFVIIIFc. As previously indicated, an assessment of the dose dependency of these parameters is confounded by limited dose levels.

Mean (±SD) observed TBLP1 were 2.70±0.511 and 3.09±0.978 IU/dL per IU/kg for ADVATE® and 4.06±0.798 and 5.66±2.38 IU/dL per IU/kg for rFVIIIFc for the 25 and 65 IU/kg dose groups, respectively. Mean (±SD) observed TBLP3 were 1.98±0.377 and 2.39±0.718 IU/dL per IU/kg for ADVATE® and 3.04±0.598 and 4.44±1.84 IU/dL per IU/kg for rFVIIIFc for the 25 and 65 IU/kg dose groups, respectively.

Mean IVR and K-values calculated using observed Cmax values (subtracted with baseline and residual drug within the model) were generally greater than values determined using model-predicted Cmax values; consistent with slight under-estimation of the observed peak activity using the one-compartment model. Mean (±SD) observed K-values were 3.08±0.429 and 2.85±0.721 IU/dL per IU/kg for ADVATE® and 3.12±0.451 and 2.92±0.985 IU/dL per IU/kg for rFVIIIFc for the 25 and 65 IU/kg dose groups, respectively. Mean (±SD) observed IVR values were 112±14.5 and 116±26.9% for ADVATE® and 113±16.3 and 117±33.6% for rFVIIIFc for the 25 and 65 IU/kg dose groups, respectively.

CONCLUSIONS

All ADVATE®- and rFVIIIFc-treated patients had comparable dose-related increases in Cmax and AUCINF over the dose range evaluated. Peak plasma levels of ADVATE® and rFVIIIFc activity were generally observed within the first hour after the end of the infusion and remained detectable for several days after dosing. After the end of infusion, the decline in baseline corrected FVIII activity exhibited monoexponential decay until the baseline was reached for both products. Parameter values for elimination half-life and MRT appeared to be dose-independent over the dose range evaluated for both FVIII products. Slight increases in mean CL and V values were noted with increasing dose of ADVATE® and rFVIIIFc; however, increased intersubject variability at the 65 IU/kg coupled with limited dose levels confounded an assessment of the dose-dependency of these parameters.

Comparison of rFVIIIFc and ADVATE® activity PK revealed an approximate 48-61% (One-Stage Assay) or 53-84% (Chromogenic Assay) increase in systemic exposure, approximate 30-40% reduction in clearance, and an approximate 50-80% increase in both elimination half-life and MRT for rFVIIIFc relative to ADVATE® at comparable doses. Evidence of PK difference was also observed with rFVIIIFc demonstrating increased TBLP1 and TBLP3 values compared to ADVATE® at equivalent doses. IVR and K-values for ADVATE® and rFVIIIFc appeared to be comparable.

The PK parameters obtained from the Chromogenic Assay results generally agreed with those from the One-Stage Assay, except that the Chomogenic Assay yielded a higher estimation of exposure parameters (e.g., Cmax, AUCINF, etc.).

With the observed improvements in PK, rFVIIIFc may provide a prolonged protection from bleeding, allowing less frequent injections for individuals with Hemophilia A.

Example 6

On the basis of the interim PK analysis from the first in-human study of rFVIII:Fc (Example 3), the A-LONG study was designed. A-LONG is an open label, multi-center evaluation of the safety, pharmacokinetics, and efficacy of recombinant Factor VIII Fc fusion (FVIII:Fc) in the prevention and treatment of bleeding in previously treated subjects with severe hemophilia A (defined as <1 IU/dL [<1%] endogenous FVIII).

Approximately 106 subjects will be enrolled into one of three regimens: a tailored prophylaxis regimen (arm 1), a weekly dosing regimen (arm 2), and an on-demand regimen (arm 3).

Arm 1: Tailored Prophylaxis Regimen

Arm 1 will include an overall group and a PK subgroup. Approximately 66 subjects will be enrolled. The initial regimen will be twice weekly at 25 IU/kg on the first day, followed by 50 IU/kg on the fourth day of the week. Subjects will administer rFVIIIFc on this weekly prophylaxis regimen until PK results for rFVIIIFc are available. Based on these results, a tailored prophylaxis regimen will be established for each individual, in which the dose and interval will be determined to maintain a trough level of 1-3% FVIII activity. Each subject will then administer his individually tailored prophylaxis regimen throughout the study.

Subjects will be monitored throughout the study and ongoing dose and interval adjustments will be made. Adjustments will only be made when a subject experiences unacceptable bleeding episodes defined as ≥2 spontaneous bleeding episodes over a rolling two-month period. In this case, adjustment will target trough levels of 3-5%.

Arm 2: Weekly Dosing Regimen

Approximately 20 subjects will be enrolled/randomized and undergo abbreviated rFVIIIFc PK profiling as follows: Washout of at least 96 hours; a single dose of rFVIIIFc 65 IU/kg; Abbreviated sampling beginning on rFVIIIFc Day 0, including pre-injection and 10 (±2) minutes, 3 hours (±15 minutes), 72 (±2) hours [Day 3], and 96 (±2) hours [Day 4] from the start of injection. Following the abbreviated PK profiling, subjects will then administer a fixed dose of 65 IU/kg rFVIIIFc every 7 days at least for 28 weeks and up to 52 weeks.

Arm 3: On-Demand Regimen

A minimum of 10 major surgeries in at least 5 subjects will be evaluated in the study. Major surgery is defined as any surgical procedure (elective or emergent) that involves general anesthesia and/or respiratory assistance in which a major body cavity is penetrated and exposed, or for which a substantial impairment of physical or physiological functions is produced (e.g., laparotomy, thoracotomy, craniotomy, joint replacement, and limb amputation).

For prophylaxis during surgery, subjects will be treated with 20 to 50 IU/kg rFVIIIFc every 12 to 24 hours. Prior to surgery, the physician will review the subject's rFVIIIFc PK profile and assess the dose regimen of Factor VIII replacement generally required for the type of planned surgery and the clinical status of the subject. Recommendation for the appropriate dosing of rFVIIIFc in the surgical treatment period, including any rehabilitation time, will take these factors into consideration.

The primary objectives of this study are (a) to evaluate the safety and tolerability of rFVIIIFc administered as prophylaxis, on-demand, and surgical treatment regimens; and (b) to evaluate the efficacy of rFVIIIFc administered as prophylaxis, on-demand, and surgical treatment regimens. The secondary objectives of this study are (a) to characterize the PK profile of rFVIIIFc and compare the PK of FVIIIFc with the currently marketed product, ADVATE®; (b) to evaluate individual responses with FVIIIFc; and (c) to evaluate FVIIIFc consumption.

Primary Objectives
   To evaluate safety and tolerability of rFVIIIFc administered as prophylaxis, weekly, on-demand, and surgical treatment regimens
   To evaluate the efficacy of rFVIIIFc administered as tailored prophylaxis, on-demand, and surgical treatment regimens
Secondary Objectives
   To characterize the PK profile of rFVIIIFc and compare the PK of rFVIIIFc with the currently marketed product, ADVATE®
   To evaluate individual responses with rFVIIIFc
   To characterize the range of dose and schedules required to adequately prevent bleeding in a prophylaxis regimen; maintain homeostasis in a surgical setting; or to treat bleeding episodes in an on-demand, weekly treatment, or prophylaxis setting
   To evaluate rFVIIIFc consumption (e.g., total annualized rFVIIIFc consumption per subject)

Example 7

Clinical ROTEM® Assessment

In the study in Example 7, in addition to the measurement of plasma FVIII activity by one-stage activated partial thromboplastin time (aPTT) assay, whole blood rotational thromboelastometry (ROTEM®) has also been explored to assess the improvement in global hemostasis by rFVIIIFc and ADVATE® in 2 subjects, specifically, 1 in the low dose cohort and 1 in the high dose cohort.

rFVIIIFc and ADVATE® appear to be comparably active in clot formation when spiked into subjects' blood prior to rFVIIIFc treatment. The clotting time (CT) was linear with respect to the dose of rFVIIIFc and ADVATE® in the range of approximately 1% of 100% of normal, and the dose response was comparable between rFVIIIFc and ADVATE® in the same subject.

Following dosing with ADVATE® and subsequently rFVIIIFc, citrated whole blood was sampled at various time points and the clot formation following recalcification was monitored by ROTEM®. Despite the variable baseline CT due to residue FVIII levels prior to ADVATE® or rFVIIIFc dosing, both products effectively corrected the CT to comparable levels 30 minutes post-injection. In addition, the improvement in CT was better sustained at and after 3 hours post-injection of 25 IU/kg of rFVIIIFc relative to ADVATE® in the subject dosed at this low dose. However, the differential improvement of rFVIIIFc versus ADVATE® was much less appreciable at the 65 IU/kg dose.

Example 8

HemA mice were used for tail clip studies. The mice were first anesthetized and then injected with 4.6 µg/kg, 1.38 µg/kg, or 0.46 µg/kg of either processed rFVIIIFc (Drug Substance, which contain about 75%-85% processed rFVIIIFc) and purified single chain rFVIIIFc. After the injection, the tail was cut from the tip and immediately placed into a tube to collect blood. Percentage of protection on survival was measured for rFVIIIFc processed (drug substance) and single chain FVIIIFc as shown in Table 7 and FIG. 7.

TABLE 7

In Vivo Efficacy of rFVIII: Fc DS and Single chain rFVIIIFc

| | | Dose (µg/kg) | | |
|---|---|---|---|---|
| | | 4.6 | 1.38 | 0.46 |
| % of Protection on Survival | FVIIIFc DS | 93 | 52 | 19 |
| | Single chain rFVIIIFc | 93 | 64 | 14 |

As shown in Table 7 and FIG. 7, the protection on survival by single chain rFVIIIFc is comparable to processed rFVIIIFc (DS).

Clotting Activity by In Vitro ROTEM

Figure 14:
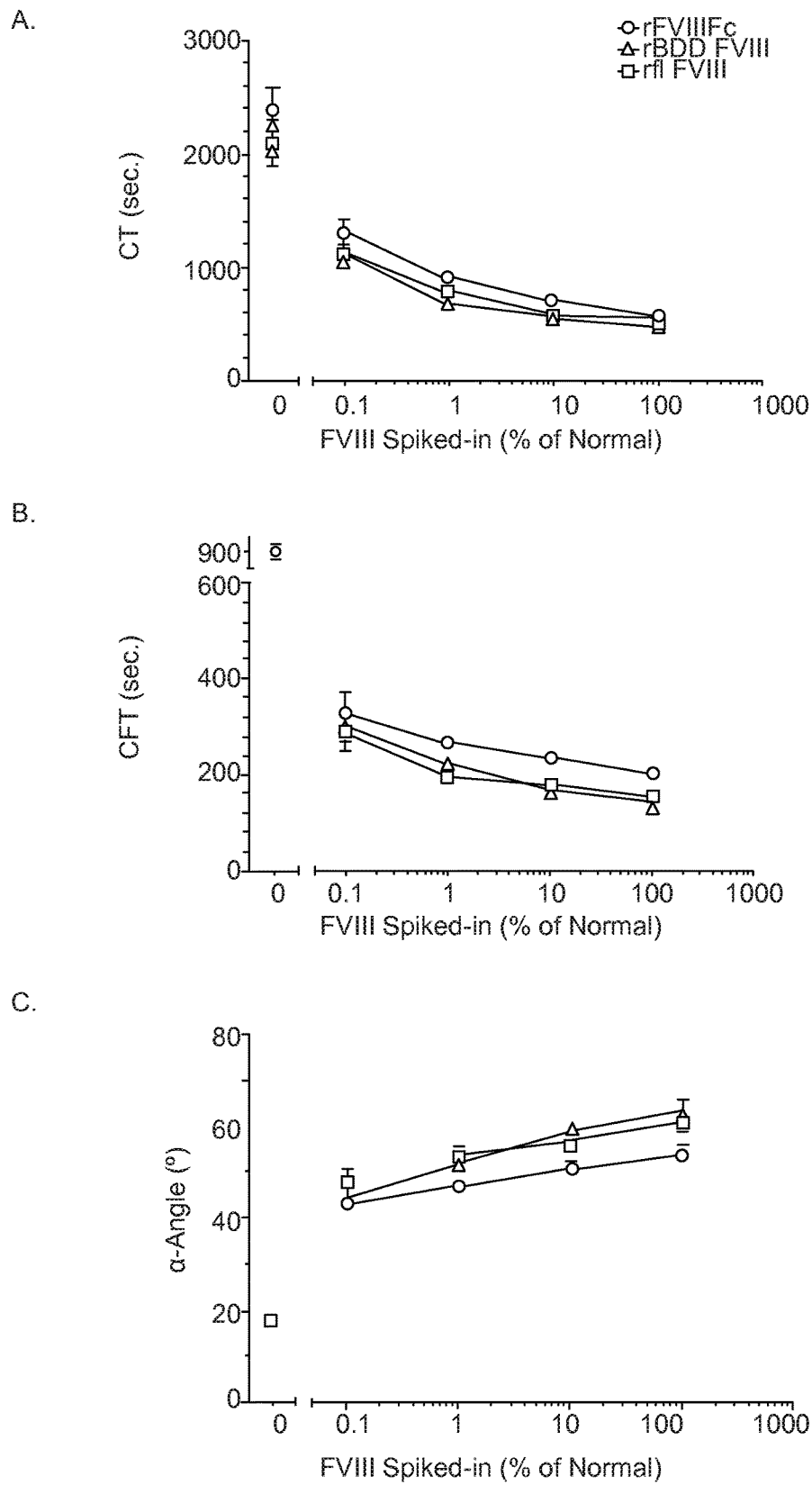

The clotting potency of rFVIIIFc was further explored in whole blood Rotational Thromboelastometry (ROTEM) over a range of concentrations, and compared to both rBDD FVIII (Xyntha) and recombinant full length FVIII (rflFVIII; Advate). For in vitro ROTEM, rFVIII proteins were spiked in triplicate into citrated pooled blood collected from the vena cava of 5-6 male HemA mice to the final concentration of 0, 0.1, 1, 10, and 100% of normal plasma FVIII level. The clot was initiated by the addition of $CaCl_2$ (NATEM) and clotting time (CT), clot formation time (CFT), alpha-angle and maximum clot firmness (MCF) were recorded on the ROTEM system (Pentapharm GmbH, Munich, Germany). The clotting time (CT), clot formation time (CFT), and alpha angle for the three proteins spiked in HemA mouse blood at escalating doses from 0.1-100% of normal FVIII levels are shown in FIG. 14. In the wide range of 0.1 to 100% of normal, the CT and CFT are comparable among rFVIIIFc, rBDD FVIII and rflFVIII. The alpha angle is only significantly different ($p<0.05$) between rFVIIIFc and rBDD FVIII at 10%.

Clotting Activity by Ex Vivo ROTEM

Figure 15:
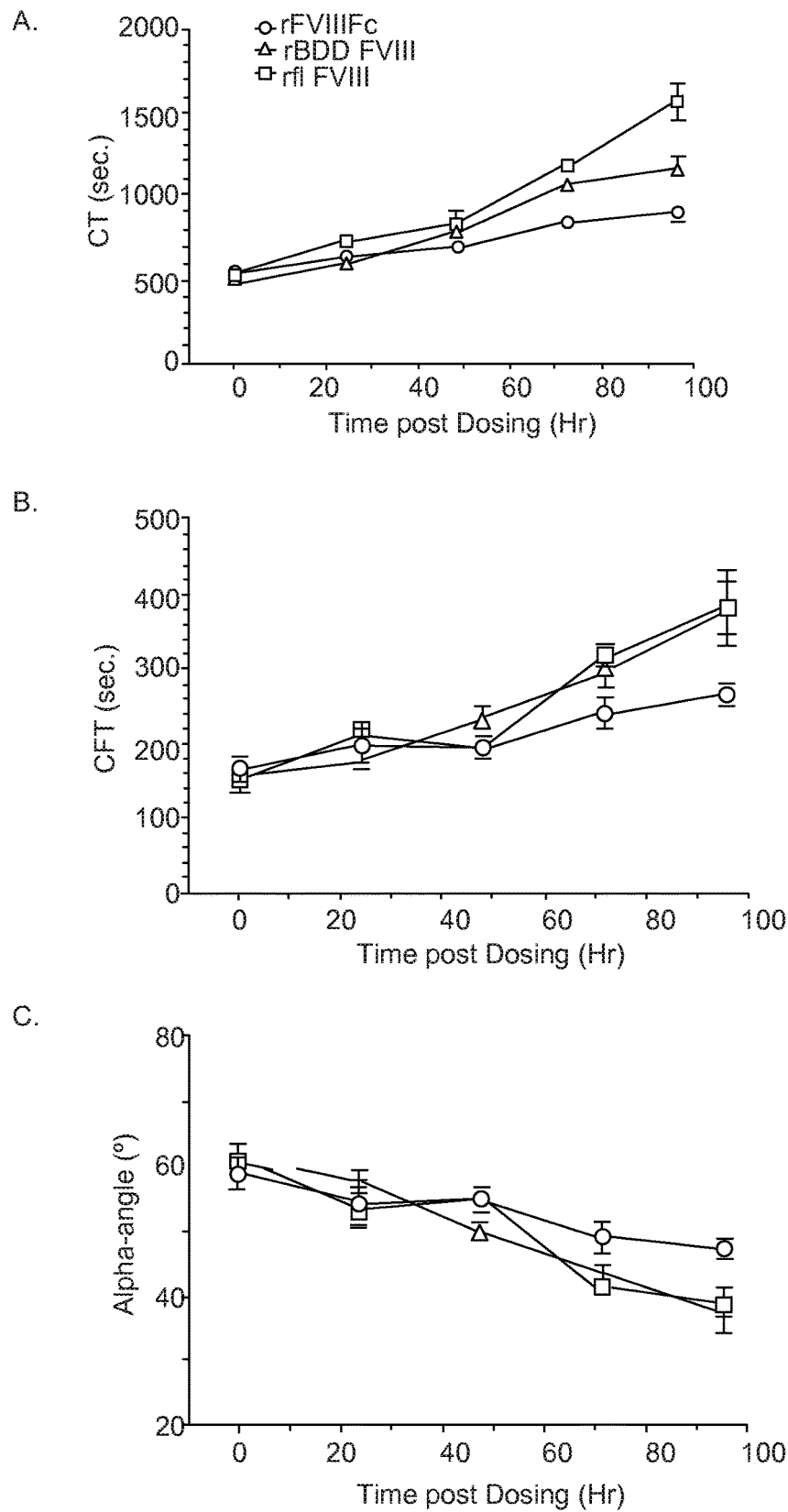

The pharmacodynamics of rFVIIIFc, as measured by ROTEM, was compared to rBDD FVIII and rflFVIII after a single intravenous injection into Hemophilia A mice. For ex vivo ROTEM, male HemA mice were injected intravenously with a single dose of 50 IU/kg rFVIIIFc, ADVATE®, or XYNTHA®, and 5 mice sacrificed at each time point (5 minutes, 24, 48, 72 and 96 hours post dosing). Individual citrated whole blood collected from the vena cava was immediately analyzed by NATEM on the ROTEM system and parameters measured as above. The CT, CFT, and alpha angle were determined for samples taken from 5 min to 96 hours after dosing, and shown in FIG. 15. At 5 min, all are comparably effective resulting in similar CT, CFT and alpha angle (FIG. 15A-C). However, rFVIIIFc demonstrated a significantly improved ($p<0.05$) CT at 72 and 96 hrs, CFT and alpha angle at 96 hrs (FIGS. 15A-C) relative to rBDD FVIII and rflFVIII.

Example 9

Recombinant factor VIIIFc (rFVIIIFc) is comprised of a B domain deleted (BDD) rFVIII protein genetically fused to the Fc domain of human immunoglobulin G1 (IgG1). Prior to secretion from HEK 293 cells, most of the rFVIIIFc is processed into a FVIII heavy chain (HC) and light chain (LC+Fc). In circulation, rFVIIIFc is complexed with von Willebrand factor (VWF) and released upon activation in a manner that is indistinguishable from native FVIII. Spontaneous dissociation of the HC and LC is thought to contribute to the loss of FVIII activity in plasma and during storage of FVIII drug products. Here we describe a single chain non-processed isoform of rFVIIIFc (SC rFVIIIFc), which may provide superior manufacturability and enhanced stability compared to native FVIII.

SC rFVIIIFc was purified from rFVIIIFc, which contains a fraction of the non-processed isoform. Compared to rFVIIIFc, SC rFVIIIFc showed equivalent chromogenic activity but approximately 60% reduced activity by the one stage (aPTT) assay, (Table 3A-B). Thrombin generation assay (TGA) was performed using calibrated automated thrombogram (from Thrombinoscope®). In a thrombin generation assay (TGA), SC rFVIIIFc also showed a reduced thrombin potential (FIG. 13A), and peak thrombin (FIG. 13B) compared to rFVIIIFc. However, as shown in Table 3B, full activity of SC rFVIIIFc by aPTT was observed in the absence of vWF, suggesting release from vWF may be delayed due to covalent linkage of the a3 acidic region to the HC after Arg 1680 cleavage in SC rFVIIIFc, in contrast to a3 release and dissociation from fully processed FVIII. Delayed dissociation from vWF may explain the reduced activity observed in the aPTT assay and TGA, while full activity was observed in the two-stage chromogenic assay. A reduced rate of activation in the presence of vWF was confirmed in a modified chromogenic substrate assay with limiting thrombin as FVIII activator.

In vivo function of SC rFVIIIFc was assessed in the HemA mouse tail vein transection (TVT) model. HemA male mice were treated with indicated doses of either rFVIIIFc drug product or SC rFVIIIFc 48 hours prior to TVT. Tail re-bleeding and survival were monitored hourly up to 12 hours post TVT with final observation performed at 24-hour post TVT. SC rFVIIIFc and the rFVIIIFc demonstrated equivalent in vivo efficacy in this model, with an ED50 of 1.17 µg/kg and 1.23 µg/kg respectively when TVT was performed at 48 hours post infusion (FIG. 7(A)). Comparable 24 hour post TVT survival curves (p≥0.65) (FIG. 7(B)) and re-bleed rates (FIG. 7(C)) in HemA mice were observed for the SC rFVIIIFc and rFVIIIFc at each tested dose level, indicating that SC rFVIIIFc was equally effective as rFVIIIFc despite its lower apparent aPTT activity. The delayed in vitro activation of SC rFVIIIFc in the presence of vWF therefore appears to have no significant impact on its in vivo efficacy. Thus, SC rFVIIIFc represents a novel and efficacious isoform of rFVIIIFc with potential clinical applications. Further studies will be required to demonstrate enhanced product stability in the context of this Fc fusion protein.

Example 10

Current factor VIII (FVIII) products display a half-life ($t_{1/2}$) of approximately 8-12 hours, requiring frequent intravenous injections for prophylaxis and treatment of hemophilia A patients. rFVIIIFc is a recombinant fusion protein composed of a single molecule of FVIII covalently linked to the Fc domain of human $IgG_1$ to extend circulating rFVIII half-life. This first-in-human study in previously-treated male subjects with severe hemophilia A investigated safety and pharmacokinetics of rFVIIIFc. Sixteen subjects received a single dose of ADVATE® at 25 or 65 IU/kg followed by an equal dose of rFVIIIFc. Most adverse events were unrelated to study drug. None of the study subjects developed anti-FVIIIFc antibodies or inhibitors. Across dose levels, as compared with ADVATE®, rFVIIIFc showed 1.54 to 1.71-fold longer elimination $T_{1/2}$ and mean residence time, 1.49 to 1.56-fold lower clearance, and 1.48 to 1.56-fold higher total systemic exposure. ADVATE® and rFVIIIFc had comparable dose-dependent peak plasma concentrations and recoveries. Time to 1% FVIII activity above baseline was approximately 1.53 to 1.68-fold longer than ADVATE® across dose levels. Thus, rFVIIIFc may offer a viable therapeutic approach to achieve prolonged hemostatic protection and less frequent dosing in patients with hemophilia A.

Hemophilia A is an inherited bleeding disorder that results in frequent spontaneous and traumatic bleeding into the joints and soft tissues. Mannucci P M, Tuddenham E G D, *N Engl J Med*, 344:1773-1779 (2001). When inadequately treated, this bleeding leads to chronic arthropathy, disability, and increased risk of death. Soucie J M et al., *Blood*. 96(2):437-442 (2000).

Plasma-derived FVIII (pdFVIII) and recombinant human FVIII (rFVIII) products are utilized for treatment (on-demand therapy) and prevention (prophylaxis therapy) of bleeding episodes. rFVIII was developed to reduce the risk of blood-borne pathogen transmission following the widespread contamination of plasma products with HIV and hepatitis viruses, and to secure an adequate supply of FVIII product. However, hemostatic protection with current FVIII products is temporally limited due to a short half-life ($t_{1/2}$) of approximately 8-12 hours, requiring prophylactic injections three times per week or every other day for most patients in order to maintain FVIII levels above 1%, a level that has been established as protective against most spontaneous bleeding episodes. Manco-Johnson et al., *New Engl J Med*. 357(6):535-44 (2007).

Many studies have shown that, even at high doses, on-demand therapy is not effective in preventing arthropathy. Aledort L. et al., *J Intern Med*. 236:391-399 (1994); Petrini P. et al., *Am J Pediatr Hematol Oncol*. 13:280-287 (1991). The benefits of prophylactic therapy have been demonstrated in numerous clinical studies[4, 6-15] and Manco-Johnson et al., supra, established that children started on primary prophylaxis after their first joint bleed had significantly fewer bleeds and less joint damage than children treated on-demand.

Compared to on-demand treatment, prophylactic therapy also decreases disability, hospitalization rate, and time lost from school or work;[6,16] and improves quality of life for patients and their families.[17] However, prophylactic therapy often requires use of central venous access devices in children, and their attendant risks of infection, sepsis, and thrombosis. In addition, despite the benefits, acceptance of and compliance with prophylaxis decreases with age, in part because of inconvenience and invasiveness.[18,19] Thus, a rFVIII product with a prolonged plasma $t_{1/2}$ would potentially be of benefit. Lillicrap D., *Current Opinion in Hematology* 17:393-397 (2010).

rFVIIIFc is a recombinant fusion protein composed of a single molecule of B-domain deleted rFVIII covalently linked to the human $IgG_1$ Fc domain. Potential advantages of Fc-fusion proteins include better tolerability and prolonged hemostatic protection, and the Fc domain represents a natural molecule with no known inherent toxicity.[21,22] Attachment to the $IgG_1$ Fc domain permits binding to the neonatal Fc receptor (FcRn), which is expressed in many cell types, including endothelial cells. FcRn expression remains stable throughout life and is responsible for protecting $IgG_1$ and Fc-fusion proteins from lysosomal degradation, thus prolonging the $t_{1/2}$ of the protein.[21,23] Numerous proteins within the circulation are internalized into the cells lining the vasculature via nonspecific pinocytosis and are trafficked to endosomal and lysosomal degradation pathways.

Fc proteins interact with FcRn, resident within endosomes. Endosomes containing FcRn direct the Fc fusion proteins back to the plasma membrane, releasing them into circulation in a pH-dependent manner,[24] thereby avoiding lysosomal degradation. This recycling approach has been used successfully to extend the $t_{1/2}$ of therapeutic biologics; a number of Fc fusion-based drugs have been approved for clinical use (eg etanercept, romiplostim) and others are in development.[25,26]

Preclinical data for rFVIIIFc indicate that FVIII can be rescued from degradation by a natural protective pathway mediated by FcRn, thus extending $t_{1/2}$. In Hemophilia A mice and dogs, terminal plasma $t_{1/2}$ for rFVIIIFc was approximately 2 times longer than with rFVIII.[27,28] Based on these data, we conducted a first-in-human clinical study to investigate the safety and PK of a long-lasting rFVIIIFc fusion protein in subjects with hemophilia A.

Study Design: This open-label, dose-escalation, multicenter Phase 1/2a study in previously treated patients with severe hemophilia A investigated the safety of rFVIIIFc and its pharmacokinetics (PK) compared with ADVATE® (anti-hemophilic factor [recombinant], plasma/albumin-free method, octocog alfa, Baxter Healthcare). This study was performed in accordance with the US CFR and ICH Guidelines on Good Clinical Practices. Prior to any testing, approval from participating Institutional Review Boards and written informed consents from all subjects were obtained. The study design was sequential; a single dose of ADVATE® was administered at 25 or 65 IU/kg followed by an equal dose of rFVIIIFc (FIG. 8). Both drugs were injected intravenously over approximately 10 minutes. The two dose levels were expected to bracket the typical therapeutic dose ranges. Subjects were followed for 28 days after receiving rFVIIIFc for safety analyses, including testing for anti-FVIII antibodies and inhibitors at 14 and 28 days post-injection. Plasma FVIII activity was measured in subjects before injection, 10 and 30 minutes, 1, 3, 6, 9, 24, 48, 72, 96, 120, and 168 hours (7 days) after rFVIIIFc injection, with additional samples at 192, 216, and 240 hours (10 days) for subjects dosed at 65 IU/kg of rFVIIIFc. Plasma FVIII activity was measured at the same time points after ADVATE® treatment, through 72 hours for the 25 IU/kg group and 96 hours for the 65 IU/kg group.

Subjects: Male subjects were at least 12 years of age with severe hemophilia A (defined as FVIII activity level <1%) and had at least 100 documented prior exposure days to FVIII concentrates (pdFVIII or rFVIII). Subjects with known hypersensitivity to mouse or hamster protein, history of inhibitor or detectable inhibitor titer at screening, or who were taking any medications that could affect hemostasis or systemic immunosuppressive drugs, or who experienced an active bacterial or viral infection (other than hepatitis or HIV) within 30 days of screening were excluded. Subject's genotype was recorded at study entry, when known.

Treatment Product: The human rFVIIIFc and Fc transgenes were stably transfected into HEK293 cells and the cell line was extensively tested for stability, sterility, and viral contamination to ensure safety. The purified drug product is composed of a monomeric B-domain-deleted FVIII covalently linked through its carboxy-terminus to the N-terminus of an Fc monomer, which forms a disulfide bond with a second Fc monomer during synthesis and secretion from the cells. rFVIIIFc was purified by chromatography and nanofiltration, and was fully active in one-stage and chromogenic clotting assays relative to commercially available rFVIII preparations. It was supplied as a frozen liquid containing 1000 IU per 2 mL of solution and formulated with L-histidine (pH 7), sodium chloride, calcium chloride, sucrose, mannitol, and Polysorbate 20. For injection, the product was diluted with saline solution (0.9% NaCl).

Outcome Measures: The primary objective of the study was safety, evaluated through physical examination, reporting of treatment-emergent adverse events (AEs), development of antibodies, and laboratory monitoring over time. The secondary objectives included parameters derived from PK analyses. Laboratory assessments included prothrombin time, activated partial thromboplastin time (aPTT), international normalized ratio, levels of D-dimer, von Willebrand factor (vWF) antigen, standard hematology and blood chemistry tests, and urinalysis.

FVIII activity was measured by the one-stage clotting (aPTT) assay on a Siemens BCS-XP analyzer using commercial reagents (Dade Actin FSL) with calibration against a normal reference plasma (Precision Biologics CRYOcheck™) traceable to the World Health Organization (WHO) $5^{th}$ International Standard (IS) for human plasma. In addition to the aPTT assay, FVIII activity was measured by a chromogenic substrate assay[29] using a commercially available kit (Aniara BIOPHEN FVIII:C) that complies with European Pharmacopoeia recommendations. The chromogenic assay was calibrated against normal human reference plasma (Instrumentation Laboratories ORKE45), which also had a potency assigned against the WHO 5th IS human plasma standard.

The lower limit of quantification (LLOQ) for the one-stage and chromogenic assays was 0.5 IU/dL and 0.4 IU/dL, respectively. FVIII inhibitors were measured by the Nijmegen-modified Bethesda assay and less than 0.6 BU/mL was considered negative. Anti-rFVIIIFc antibodies were assessed using a specific bridging electrochemiluminescent immunoassay which uses biotin and sulfo-tagged rFVIIIFc. Assay sensitivity was determined to be 89 ng/mL using an anti-human FVIII monoclonal antibody as a surrogate control. Exploratory whole blood rotation thromboelastometry (ROTEM®) was performed in two subjects, one from each dose level, at various time points to assess the improvement in global hemostasis following injection with ADVATE® and rFVIIIFc.

Pharmacokinetic Analyses: A user-defined one-compartment disposition model, which automatically estimates the endogenous FVIII level and subsequent residual decay, was utilized in WinNonLin for analysis of the individual subject plasma FVIII activity-versus-time data following a single administration of ADVATE® or rFVIIIFc. Actual sampling times, doses, and duration of injection were used for calculations of parameters including maximum activity (Cmax), $t_{1/2}$, clearance (CL), volume of distribution at steady-state ($V_{ss}$), area under the curve (time zero extrapolated to infinity [$AUC_{INF}$]), mean residence time (MRT), and incremental recovery.

Monte Carlo Simulation of rFVIIIFc Activity-Versus-Time Profile—To construct FVIII activity-time profiles following dosing regimens of 25 IU/kg or 65 IU/kg, a Monte Carlo simulation was conducted using the population PK model of ADVATE® and rFVIIIFc. The mean estimates of model parameters (CL, volume of distribution) in the tested population, the inter-individual variance, and the residual variability were estimated based on the one-stage (aPTT) clotting assay activity data of ADVATE® and rFVIIIFc from 16 subjects in this Phase1/2a study. Five hundred subjects were simulated with 15 sampling points for each subject for each dosing regimen. The percentage of the population with FVIII activity above or equal to 1% and 3% at different times following different dosing regimens of ADVATE® or rFVIIIFc was estimated.

Statistical Analyses—Selected PK parameters for rFVIIIFc and ADVATE® were compared using an analysis of variance model. PK parameters were log-transformed for these analyses and estimated means, mean differences, and confidence intervals on the log-scale were transformed to obtain estimates for geometric means, geometric mean ratios (GMR), and confidence intervals, respectively, on the original scale. The GMR is the geometric mean of the intra-subject ratio of the rFVIIIFc PK parameter value to the ADVATE® PK parameter value.

Results

Subject Disposition—Nineteen subjects were enrolled in the study; 16 underwent PK evaluation for both ADVATE® and rFVIIIFc. One subject self-administered his previous product prior to completing the wash-out period following the dose with ADVATE® and was thus excluded from the PK analysis, but was included in the safety analysis. Three subjects were discontinued from the study before receiving either study drug: one voluntarily withdrew; a second was withdrawn by the Investigator for non-compliance; and one was withdrawn at the Sponsor's request due to completion of study enrollment. Of the subjects dosed, six subjects received 25 IU/kg and 10 subjects received 65 IU/kg of both ADVATE® and rFVIIIFc. Mean age was 40.3 years (23 to 61 years). Genotypic identification was collected for seven subjects; inversion of intron 22 was reported in six subjects; and a frame-shift defect was reported in one subject. The genotype was unknown for nine subjects. Thirteen subjects had hepatitis C antibodies, four of whom were also positive for HIV.

Safety—Forty-four treatment-emergent AEs were reported by 11 (69%) subjects during the treatment and follow-up periods. This included the day of dosing with Advate or rFVIIIFc through a 28-day post-dosing observation period. The majority of events were considered mild and none led to withdrawal from the study. One event, dysgeusia, occurred transiently in one subject while receiving a 65 IU/kg dose of rFVIIIFc and was considered related to rFVIIIFc.

One subject experienced an anxiety attack after receiving 65 IU/kg of rFVIIIFc which resulted in 21 AEs, 19 of which were graded as mild, and two of which (headache and photophobia) were rated as moderate. Neither was deemed related to rFVIIIFc by the Investigator.

No serious bleeding episodes were reported. No evidence of allergic reactions to injection was detected. All plasma samples tested negative for FVIII inhibitors and anti-rFVIIIFc antibodies. No signs of injection site reactions were observed. No clinically meaningful changes in abnormal laboratory values were reported.

Pharmacokinetics: Correlation Between aPTT and Chromogenic Activity for rFVIIIFc in Plasma—ADVATE® and rFVIIIFc activities were determined in the same assays using commercially available reagents and calibration against normal human plasma standards. There was a strong correlation between the results obtained by the one-stage clotting assay and the chromogenic assay in samples that had an activity above the LLOQ. Correlation coefficients (Pearson $R^2$) of 0.94 and 0.95 were observed between the two assay results for 151 samples following ADVATE® dosing and 185 samples following rFVIIIFc dosing, respectively. Compared to the aPTT results, the chromogenic FVIII activities were, on average, 21% higher for ADVATE® and 32% higher for rFVIIIFc, not statistically significant (FIG. 9). This observation led to a slightly higher estimation of exposure parameters by the chromogenic assessment for both drugs. The apparent higher FVIII recoveries by the chromogenic assay are typical for recombinant FVIII products tested in clinical assays, and are in agreement with most other marketed FVIII products.[30-32]

Figure 10:
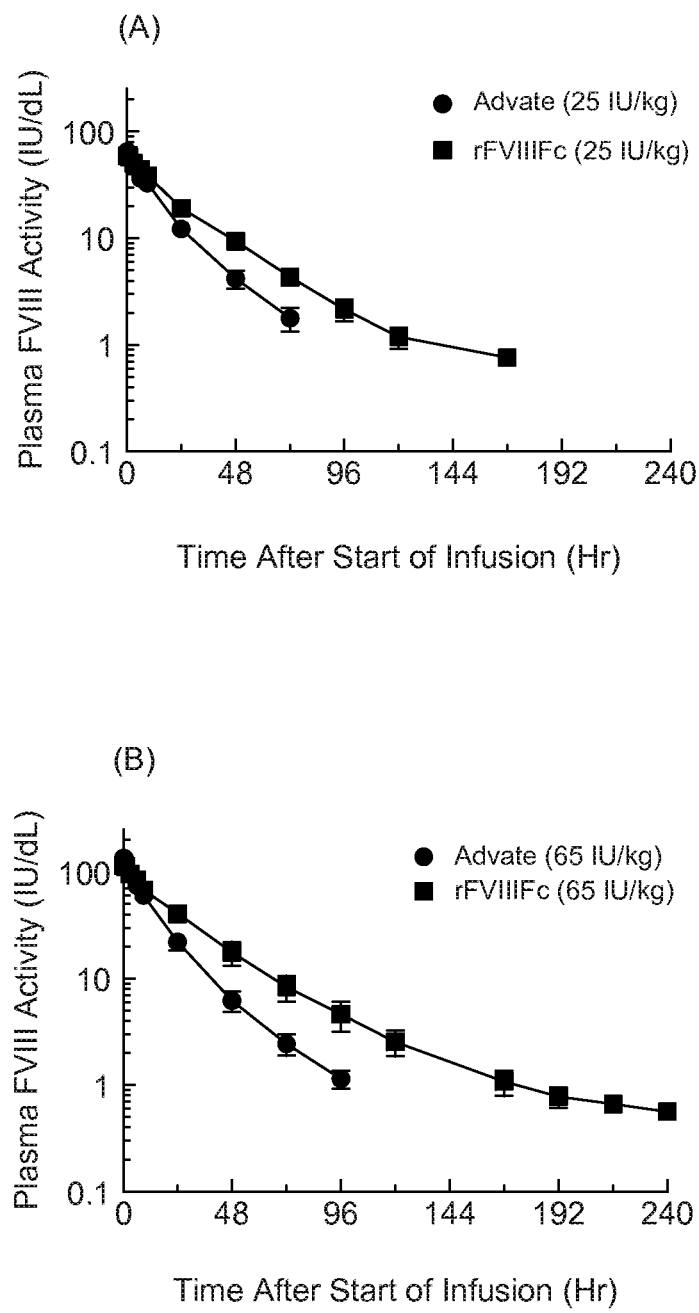

Improved Pharmacokinetics for rFVIIIFc—The primary PK estimates were derived from one-stage (aPTT) clotting assay activity data. In subjects who received 25 or 65 IU/kg of ADVATE® followed by an equal dose of rFVIIIFc, the plasma FVIII activity rose sharply and reached $C_{max}$ within the first hour following dosing. The subsequent decline of the observed FVIII activity exhibited monoexponential decay characteristics until the baseline FVIII activity was reached (FIG. 10). The $C_{max}$ increased proportionally to the dose, but was comparable between equal doses of ADVATE® and rFVIIIFc (Table 8) The total exposure ($AUC_{INF}$) also increased proportionally to the dose. However, the $AUC_{INF}$ of rFVIIIFc was 1.48 and 1.56-fold greater than that of ADVATE® at 25 IU/kg (p=0.002) and 65 IU/kg (p<0.001), respectively (Table 8).

TABLE 8

PK Parameters by One-Stage (aPTT) Assay for rFVIIIFc and ADVATE ® Per Dose Group

| Parameter | Dose: 25 IU/kg (N = 6) | | | Dose: 65 IU/kg (N = 9) | | |
|---|---|---|---|---|---|---|
| | ADVATE ® Geom. Mean [95% CI] | rFVIIIFc Geom. Mean [95% CI] | Geom. Mean Ratio [95% CI] (p-value) | ADVATE ® Geom. Mean [95% CI] | rFVIIIFc Geom. Mean [95% CI] | Geom. Mean Ratio [95% CI] (p-value) |
| $C_{max}$_OBS (IU/dL) | 63.6 [59.1, 68.3] | 60.5 [53.1, 69.0] | 0.952 [0.819, 1.11] (p = 0.440) | 133 [105, 168] | 119 [103, 136] | 0.895 [0.795, 1.01] (p = 0.061) |
| $AUC_{INF}$ (hr*IU/dL) | 994 [723, 1370] | 1480 [1160, 1880] | 1.48 [1.26, 1.76] (p = 0.002) | 1800 [1350, 2400] | 2800 [1980, 3970] | 1.56 [1.33, 1.83] (p < 0.001) |
| $t_{1/2}$ (hr) | 12.2 [9.14, 16.3] | 18.8 [14.8, 23.8] | 1.54 [1.40, 1.69] (p < 0.001) | 11.0 [8.76, 13.9] | 18.8 [14.3, 24.5] | 1.70 [1.54, 1.89] (p < 0.001) |
| MRT (hr) | 17.5 [13.1, 23.4] | 27.0 [21.3, 34.2] | 1.54 [1.40, 1.69] (p < 0.001) | 15.8 [12.6, 19.9] | 27.0 [20.6, 35.3] | 1.71 [1.54, 1.89] (p < 0.001) |
| CL (mL/hour/kg) | 2.49 [1.80, 3.45] | 1.68 [1.31, 2.15] | 0.673 [0.569, 0.796] (p = 0.002) | 3.61 [2.71, 4.83] | 2.32 [1.64, 3.29] | 0.642 [0.547, 0.753] (p < 0.001) |
| $V_{ss}$ (mL/kg) | 43.9 [39.3, 49.0] | 45.4 [39.3, 52.5] | 1.04 [0.947, 1.13] (p = 0.357) | 57.4 [48.3, 68.3] | 62.8 [55.2, 71.5] | 1.09 [0.976, 1.22] (p = 0.107) |
| Incremental Recovery (IU/dL per IU/kg) | 2.56 [2.36, 2.78] | 2.44 [2.12, 2.81] | 0.952 [0.819, 1.11] (p = 0.444) | 2.04 [1.61, 2.59] | 1.83 [1.59, 2.10] | 0.894 [0.795, 1.01] (p = 0.060) |

CI = Confidence Interval;
Geom. Mean = Geometric Mean;
OBS = observed.
Estimated means, 95% CI for means, and mean differences were transformed to obtain estimated geometric means, 95% CI for geometric means, and geometric mean ratios, respectively.

The $t_{1/2}$, MRT, CL, and $V_{ss}$ appeared to be independent of dose (Table 8). The geometric mean $t_{1/2}$ of rFVIIIFc was 18.8 hours for both the 25 IU/kg and 65 IU/kg dose groups. This represents a 1.54 and 1.70-fold improvement over that of ADVATE® (12.2 hours and 11.0 hours) at equivalent doses (p<0.001), respectively (Table 8). The same intra-subject improvement was observed in the MRT of rFVIIIFc (27.0 hours for both dose groups) compared with ADVATE® (17.5 hours for the 25 IU/kg and 15.8 hours for the 65 IU/kg) (p<0.001). Consistent with improvement in the $t_{1/2}$ and MRT was a corresponding 1.49 and 1.56-fold reduction in intra-subject CL at doses of 25 IU/kg (p=0.002) and 65 IU/kg (p<0.001), respectively. There were no significant differences in $V_{ss}$ and incremental recovery between ADVATE® and rFVIIIFc. Therefore, within each subject, rFVIIIFc demonstrated an improved PK profile compared with ADVATE®. It was also observed that the patients with shorter half-life on ADVATE® had shorter half-life on rFVIIIFc, and patients with longer half-life on ADVATE® had longer half-life on rFVIIIFc.

The improved PK profile of rFVIIIFc resulted in increased time post-dosing to 1% FVIII activity which was 1.53 and 1.68-fold longer respectively, than with ADVATE® at 25 IU/kg (p<0.001) and 65 IU/kg (p<0.001) (data not shown), suggesting a potentially longer therapeutic duration for rFVIIIFc.

The favorable PK profile of rFVIIIFc relative to ADVATE® was also demonstrated by FVIII activity measured in the chromogenic assay (Table 9), which was comparable to data derived from aPTT assays. The estimation of exposure, ie, $C_{max}$ and $AUC_{INF}$, was slightly higher, however, based on the chromogenic assay than on the one-stage (aPTT) clotting assay for both ADVATE® and rFVIIIFc.

Effects of Prolonged PK of rFVIIIFc on Whole Blood ROTEM®—Prior to administration of study drug, blood from one subject in each dose group was spiked with an equal dose of rFVIIIFc or ADVATE® and analyzed by whole blood ROTEM®. Clotting time (CT) was linear with respect to the dose in the range of approximately 1% to 100% of normal, and the dose response was comparable between rFVIIIFc and ADVATE® in the same subject (data not shown), indicating comparable potency of rFVIIIFc and ADVATE® in clot formation.

Despite the variable baseline CT due to residual FVIII levels prior to the administration of ADVATE® or rFVIIIFc, both products effectively corrected the CT to comparable levels 30 minutes post-dosing (FIG. 12). The improvement in CT was better sustained by rFVIIIFc than ADVATE® after 3 hours following a dose of 25 IU/kg (FIG. 12A), and after 24 hours following a dose of 65 IU/kg (FIG. 12B).

TABLE 9

PK Parameters by Two-Stage (Chromogenic) Assay for rFVIIIFc and ADVATE ® Per Dose Group

| | Dose: 25 IU/kg (N = 6) | | | Dose: 65 IU/kg (N = 9) | | |
| --- | --- | --- | --- | --- | --- | --- |
| Parameter | ADVATE ® Geom. Mean [95% CI] | rFVIIIFc Geom. Mean [95% CI] | Geom. Mean Ratio [95% CI] (p-value) | ADVATE ® Geom. Mean [95% CI] | rFVIIIFc Geom. Mean [95% CI] | Geom. Mean Ratio [95% CI] (p-value) |
| $C_{max\_}$OBS (IU/dL) | 75.5 [65.5, 87.1] | 76.5 [64.9, 90.1] | 1.01 [0.940, 1.09] (p = 0.686) | 175 [143, 215] | 182 [146, 227] | 1.04 [0.900, 1.20] (p = 0.571) |
| $AUC_{INF}$ (hr*IU/dL) | 1060 [822, 1360] | 1660 [1300, 2120] | 1.57 [1.38, 1.80] (p < 0.001) | 2270 [1670, 3070] | 4280 [2960, 6190] | 1.89 [1.61, 2.21] (p < 0.001) |
| $t_{1/2}$ (hr) | 10.5 [8.49, 12.9] | 16.7 [13.8, 20.1] | 1.59 [1.35, 1.87] (p < 0.001) | 10.8 [8.16, 14.2] | 19.8 [14.3, 27.5] | 1.84 [1.60, 2.12] (p < 0.001) |
| MRT (hr) | 15.0 [12.2, 18.6] | 23.9 [19.8, 28.9] | 1.59 [1.35, 1.87] (p < 0.001) | 15.4 [11.7, 20.4] | 28.5 [20.5, 39.6] | 1.85 [1.61, 2.12] (p < 0.001) |
| CL (mL/hour/kg) | 2.35 [1.80, 3.06] | 1.49 [1.16, 1.92] | 0.636 [0.557, 0.727] (p < 0.001) | 2.87 [2.12, 3.89] | 1.52 [1.05, 2.20] | 0.530 [0.453, 0.620] (p < 0.001) |
| Vss (mL/kg) | 35.5 [30.5, 41.3] | 35.9 [30.4, 42.3] | 1.01 [0.898, 1.14] (p = 0.822) | 44.5 [36.7, 54.1] | 43.4 [38.2, 49.4] | 0.975 [0.863, 1.10] (p = 0.653) |
| Incremental Recovery (IU/dL per IU/kg) | 3.05 [2.62, 3.54] | 3.09 [2.61, 3.66] | 1.01 [0.940, 1.09] (p = 0.679) | 2.70 [2.20, 3.31] | 2.80 [2.24, 3.50] | 1.04 [0.900, 1.20] (p = 0.571) |

CI = Confidence Interval;
Geom. Mean = Geometric Mean;
OBS = observed.
Estimated means, 95% CI for means, and mean differences were transformed to obtain estimated geometric means, 95% CI for geometric means, and geometric mean ratios, respectively.

Correlation Between von Willebrand Factor and Disposition of rFVIIIFc—

Because the majority of FVIII in circulation is in complex with VWF[33] and because the genome-wide association study has identified that the genetic determinants of FVIII levels are primarily dependent on VWF levels,[34] we examined the association between VWF and rFVIIIFc. A strong correlation was observed between VWF levels and CL and $t_{1/2}$ for both rFVIIIFc and ADVATE®. As shown in FIG. 10, as the level of VWF increased, the CL of rFVIIIFc (p=0.0016) and of ADVATE® (p=0.0012) decreased.

The opposite relationship was observed between the level of VWF and $t_{1/2}$. As the level of VWF increased, the $t_{1/2}$ of rFVIIIFc (p=0.0003) and of ADVATE® (p<0.0001) increased. This correlation suggests that the Fc moiety of rFVIIIFc does not alter the role of VWF in protecting FVIII from clearance.

rFVIIIFc was well tolerated by subjects at both doses. There were no clinically significant changes observed in hematology, blood chemistry, or urinalysis parameters. The majority of AEs were mild, unrelated to rFVIIIFc, and resolved without sequelae. No serious AEs or deaths occurred during the study, and no subjects at either dose developed neutralizing or binding antibodies to rFVIIIFc.

rFVIIIFc demonstrated a significantly improved FVIII activity PK profile relative to ADVATE®, with $t_{1/2}$ and MRT across dose levels being 1.54 to 1.71-fold longer, as measured by the one-stage (aPTT) clotting assay and 1.59 to 1.84-fold longer by the two-stage chromogenic assay. The prolonged activity of rFVIIIFc predicts possible prolonged efficacy, allowing for a less frequent dosing regimen in the prophylactic treatment of patients with Hemophilia A.

Adopting the PK parameters derived from this study, the Monte Carlo simulation predicts that a higher percentage of patients receiving rFVIIIFc will sustain FVIII levels above 1% or 3% as compared with patients receiving equal doses of ADVATE® (Table 10). For example, at a dose of 25 IU/kg, 12.2% of ADVATE® patients versus 71.2% of rFVIIIFc patients are predicted to have FVIII trough levels above 1% on Day 4; at a dose of 65 IU/kg, 11.0% of ADVATE® patients versus 66.4% of rFVIIIFc patients are predicted to have FVIII levels above 3% on Day 4. Clinical trials in larger numbers of patients are planned to confirm results from this Phase 1/2a study and from the Monte Carlo simulation predictions.

TABLE 10

Predicted Percentage of Subjects Achieving FVIII Trough Levels Above 1% and 3% of Normal at a Specified Dose Regimen of ADVATE ® or rFVIIIFc

| Timepoint following dosing (Day) | ADVATE ® | | rFVIIIFc | |
|---|---|---|---|---|
| | 25 IU/kg | 65 IU/kg | 25 IU/kg | 65 IU/kg |
| Percent of Subjects with FVIII Trough Levels above 1% | | | | |
| 3 | 40.0 | 67.8 | 92.6 | 99.0 |
| 4 | 12.2 | 31.0 | 71.2 | 90.0 |
| 5 | 4.20 | 13.6 | 39.4 | 71.6 |
| 7 | 0.200 | 1.40 | 7.80 | 26.4 |
| Percent of Subjects with FVIII Trough Levels above 3% | | | | |
| 3 | 10.6 | 34.6 | 62.2 | 91.0 |
| 4 | 1.60 | 11.0 | 25.4 | 66.4 |
| 5 | 0.200 | 3.20 | 7.00 | 36.2 |
| 7 | 0 | 0.200 | 0.400 | 6.60 |

Despite the success of Fc fusion technology in prolonging circulating $t_{1/2}$ for a variety of protein therapeutics, rFVIII was considered too large to successfully produce dimeric Fc fusions. We thus created a monomeric Fc fusion protein whereby a single effector molecule was covalent linked to a dimeric Fc, enabling binding to intracellular FcRn and subsequent recycling.[21,22] In vitro coagulation assays demonstrate no loss of specific activity for rFVIIIFc, compared to B-domain deleted or native FVIII, by either clotting or chromogenic assays, using commercially available reagents and commonly used FVIII reference standards (JAD, TL, SCL, et al., manuscript submitted August, 2011). In addition, these results indicate that rFVIIIFc can be reliably assayed in a clinic setting by either the one-stage assay or the chromogenic method.

In summary, this Phase 1/2a clinical trial is the first trial to demonstrate the safety and prolonged $t_{1/2}$ of rFVIIIFc in patients with severe hemophilia A. A pivotal Phase 3 study is ongoing with rFVIIIFc to establish effective prophylaxis dosing regimens for individuals with hemophilia A.

Example 11

A novel single-chain (SC) isoform of factor VIII (FVIII), resulting from incomplete proteolysis at residue R1648 during biosynthesis, may provide superior manufacturability and stability relative to native FVIII. A single recombinant B domain deleted factor VIII molecule fused to an immunoglobulin Fc domain (rFVIIIFc) and its purified SC counterpart (SC-rFVIIIFc) exhibited similar specific activity in one stage clotting assays using plasma depleted of von Willebrand factor (VWF), but SC-rFVIIIFc exhibited lower specific activity in the presence of VWF. This study was undertaken to determine if VWF-bound rFVIIIFc, SC-rFVIIIFc and rBDD-FVIII (XYNTHA®, REFACTO AF®) differ with respect to thrombin-mediated proteolytic release from VWF.

Equimolar amounts of rFVIIIFc, SC-rFVIIIFc, and rBDD-FVIII were captured on an optical biosensor chip on which human VWF had been immobilized by amine coupling. Human α-thrombin at a range of concentrations was infused over the chip surface, and the rates of FVIII release from immobilized VWF were monitored in real time. The half maximal effective concentration ($EC_{50}$) of α-thrombin was determined for each FVIII species.

α-thrombin $EC_{50}$ values for rFVIIIFc and rBDD-FVIII were comparable (3.7±0.2 U/mL and 3.2±0.3 U/mL, respectively), whereas the $EC_{50}$ value for SC-rFVIIIFc was greater than 3-fold higher (11.7±0.9 U/mL). This finding that SC-rFVIIIFc is released more slowly from VWF than are either rFVIIIFc or rBDD-FVIII is consistent with a previously observed finding regarding the activities of rFVIIIFc and SC-rFVIIIFc in a one-stage clotting assay (aPTT) in which SC-FVIIIFc had a lower apparent activity only when VWF was present in the assay plasma sample. However, all samples possessed equivalent activities in a mouse bleeding model, indicating that responsiveness of FVIII preparations to thrombin in the release of FVIII from VWF does not correlate with efficacy in vivo.

TABLE 1

Polynucleotide Sequences

A. B-Domain Deleted FVIIIFc (i) B-Domain Deleted FVIIIFc Chain DNA Sequence (FVIII signal peptide underlined, Fc region in bold) (SEQ ID NO: 1, which encodes SEQ ID NO: 2)

```
 661                     A TGCAAATAGA GCTCTCCACC TGCTTCTTTC
 721 TGTGCCTTTT GCGATTCTGC TTTAGTGCCA CCAGAAGATA CTACCTGGGT GCAGTGGAAC
 781 TGTCATGGGA CTATATGCAA AGTGATCTCG GTGAGCTGCC TGTGGACGCA AGATTTCCTC
 841 CTAGAGTGCC AAAATCTTTT CCATTCAACA CCTCAGTCGT GTACAAAAAG ACTCTGTTTG
 901 TAGAATTCAC GGATCACCTT TTCAACATCG CTAAGCCAAG GCCACCCTGG ATGGGTCTGC
 961 TAGGTCCTAC CATCCAGGCT GAGGTTTATG ATACAGTGGT CATTACACTT AAGAACATGG
1021 CTTCCCATCC TGTCAGTCTT CATGCTGTTG GTGTATCCTA CTGGAAAGCT TCTGAGGGAG
1081 CTGAATATGA TGATCAGACC AGTCAAAGGG AGAAAGAAGA TGATAAAGTC TTCCCTGGTG
1141 GAAGCCATAC ATATGTCTGG CAGGTCCTGA AAGAGAATGG TCCAATGGCC TCTGACCCAC
1201 TGTGCCTTAC CTACTCATAT CTTTCTCATG TGGACCTGGT AAAAGACTTG AATTCAGGCC
1261 TCATTGGAGC CCTACTAGTA TGTAGAGAAG GGAGTCTGGC CAAGGAAAAG ACACAGACCT
1321 TGCACAAATT TATACTACTT TTTGCTGTAT TTGATGAAGG GAAAAGTTGG CACTCAGAAA
1381 CAAAGAACTC CTTGATGCAG GATAGGGATG CTGCATCTGC TCGGGCCTGG CCTAAAATGC
1441 ACACAGTCAA TGGTTATGTA AACAGGTCTC TGCCAGGTCT GATTGGATGC CACAGGAAAT
```

TABLE 1-continued

Polynucleotide Sequences

```
1501 CAGTCTATTG GCATGTGATT GGAATGGGCA CCACTCCTGA AGTGCACTCA ATATTCCTCG
1561 AAGGTCACAC ATTTCTTGTG AGGAACCATC GCCAGGCGTC CTTGGAAATC TCGCCAATAA
1621 CTTTCCTTAC TGCTCAAACA CTCTTGATGG ACCTTGGACA GTTTCTACTG TTTTGTCATA
1681 TCTCTTCCCA CCAACATGAT GGCATGGAAG CTTATGTCAA AGTAGACAGC TGTCCAGAGG
1741 AACCCCAACT ACGAATGAAA AATAATGAAG AAGCGGAAGA CTATGATGAT GATCTTACTG
1801 ATTCTGAAAT GGATGTGGTC AGGTTTGATG ATGACAACTC TCCTTCCTTT ATCCAAATTC
1861 GCTCAGTTGC CAAGAAGCAT CCTAAAACTT GGGTACATTA CATTGCTGCT GAAGAGGAGG
1921 ACTGGGACTA TGCTCCCTTA GTCCTCGCCC CCGATGACAG AAGTTATAAA AGTCAATATT
1981 TGAACAATGG CCCTCAGCGG ATTGGTAGGA AGTACAAAAA AGTCCGATTT ATGGCATACA
2041 CAGATGAAAC CTTTAAGACT CGTGAAGCTA TTCAGCATGA ATCAGGAATC TTGGGACCTT
2101 TACTTTATGG GGAAGTTGGA GACACACTGT TGATTATATT TAAGAATCAA GCAAGCAGAC
2161 CATATAACAT CTACCCTCAC GGAATCACTG ATGTCCGTCC TTTGTATTCA AGGAGATTAC
2221 CAAAAGGTGT AAAACATTTG AAGGATTTTC CAATTCTGCC AGGAGAAATA TTCAAATATA
2281 AATGGACAGT GACTGTAGAA GATGGGCCAA CTAAATCAGA TCCTCGGTGC CTGACCCGCT
2341 ATTACTCTAG TTTCGTTAAT ATGGAGAGAG ATCTAGCTTC AGGACTCATT GGCCCTCTCC
2401 TCATCTGCTA CAAAGAATCT GTAGATCAAA GAGGAAACCA GATAATGTCA GACAAGAGGA
2461 ATGTCATCCT GTTTTCTGTA TTTGATGAGA ACCGAAGCTG GTACCTCACA GAGAATATAC
2521 AACGCTTTCT CCCCAATCCA GCTGGAGTGC AGCTTGAGGA TCCAGAGTTC CAAGCCTCCA
2581 ACATCATGCA CAGCATCAAT GGCTATGTTT TTGATAGTTT GCAGTTGTCA GTTTGTTTGC
2641 ATGAGGTGGC ATACTGGTAC ATTCTAAGCA TTGGAGCACA GACTGACTTC CTTTCTGTCT
2701 TCTTCTCTGG ATATACCTTC AAACACAAAA TGGTCTATGA AGACACACTC ACCCTATTCC
2761 CATTCTCAGG AGAAACTGTC TTCATGTCGA TGGAAACCCA AGGTCTATGG ATTCTGGGGT
2821 GCCACAACTC AGACTTTCGG AACAGAGGCA TGACCGCCTT ACTGAAGGTT TCTAGTTGTG
2881 ACAAGAACAC TGGTGATTAT TACGAGGACA GTTATGAAGA TATTTCAGCA TACTTGCTGA
2941 GTAAAAACAA TGCCATTGAA CCAAGAAGCT CTCTCAAAA CCCACCAGTC TTGAAACGCC
3001 ATCAACGGGA ATAACTCGT ACTACTCTTC AGTCAGATCA AGAGGAAATT GACTATGATG
3061 ATACCATATC AGTTGAAATG AAGAAGGAAG ATTTTGACAT TTATGATGAG GATGAAAATC
3121 AGAGCCCCCG CAGCTTTCAA AAGAAAACAC GACACTATTT TATTGCTGCA GTGGAGAGGC
3181 TCTGGGATTA TGGGATGAGT AGCTCCCCAC ATGTTCTAAG AAACAGGGCT CAGAGTGGCA
3241 GTGTCCCTCA GTTCAAGAAA GTTGTTTTCC AGGAATTTAC TGATGGCTCC TTTACTCAGC
3301 CCTTATACCG TGGAGAACTA AATGAACATT TGGGACTCCT GGGGCATAT ATAAGAGCAG
3361 AAGTTGAAGA TAATATCATG GTAACTTTCA GAAATCAGGC CTCTCGTCCC TATTCCTTCT
3421 ATTCTAGCCT TATTTCTTAT GAGGAAGATC AGAGGCAAGG AGCAGAACCT AGAAAAAACT
3481 TTGTCAAGCC TAATGAAACC AAAACTTACT TTTGGAAAGT GCAACATCAT ATGGCACCCA
3541 CTAAAGATGA GTTTGACTGC AAAGCCTGGG CTTATTTCTC TGATGTTGAC CTGGAAAAAG
3601 ATGTGCACTC AGGCCTGATT GGACCCCTTC TGGTCTGCCA CACTAACACA GTGAACCCTG
3661 CTCATGGGAG ACAAGTGACA GTACAGGAAT TTGCTCTGTT TTTCACCATC TTTGATGAGA
3721 CCAAAAGCTG GTACTTCACT GAAAATATGG AAAGAAACTG CAGGGCTCCC TGCAATATCC
3781 AGATGGAAGA TCCCACTTTT AAAGAGAATT ATCGCTTCCA TGCAATCAAT GGCTACATAA
3841 TGGATACACT ACCTGGCTTA GTAATGGCTC AGGATCAAAG GATTCGATGG TATCTGCTCA
3901 GCATGGGCAG CAATGAAAAC ATCCATTCTA TTCATTTCAG TGGACATGTG TTCACTGTAC
3961 GAAAAAAAGA GGAGTATAAA ATGGCACTGT ACAATCTCTA TCCAGGTGTT TTTGAGACAG
4021 TGGAAATGTT ACCATCCAAA GCTGGAATTT GGCGGGTGGA ATGCCTTATT GGCGAGCATC
4081 TACATGCTGG GATGAGCACA CTTTTTCTGG TGTACAGCAA TAAGTGTCAG ACTCCCCTGG
4141 GAATGGCTTC TGGACACATT AGAGATTTTC AGATTACAGC TTCAGGACAA TATGACAGT
4201 GGGCCCCAAA GCTGGCCAGA CTTCATTATT CCGGATCAAT CAATGCCTGG AGCACCAAGG
4261 AGCCCTTTTC TTTGGATCAA GGTGGATCTGT TGGCACCAAT GATTATTCAC GGCATCAAGA
4321 CCCAGGGTGC CCGTCAGAAG TTCTCCAGCC TCTACATCTC TCAGTTTATC ATCATGTATA
4381 GTCTTGATGG GAAGAAGTGG CAGACTTATC GAGGAAATTC CACTGGAACC TTAATGGTCT
4441 TCTTTGGCAA TGTGGATTCA TCTGGGATAA AACACAATAT TTTTAACCCT CCAATTATTG
4501 CTCGATACAT CCGTTTGCAC CCAACTCATT ATAGCATTCG CAGCACTCTT CGCATGGAGT
4561 TGATGGGCTG TGATTTAAAT AGTTGCAGCA TGCCATTGGG AATGGAGAGT AAAGCAATAT
4621 CAGATGCACA GATTACTGCT TCATCCTACT TTACCAATAT GTTTGCCACC TGGTCTCCTT
4681 CAAAAGCTCG ACTTCACCTC AAGGGAGGA GTAATGCCTG GAGACCTCAG GTGAATAATC
4741 CAAAAGAGTG GCTGCAAGTG GACTTCCAGA AGACAATGAA AGTCACAGGA GTAACTACTC
4801 AGGGAGTAAA ATCTCTGCTT ACCAGCATGT ATGTGAAGGA GTTCCTCATC TCCAGCAGTC
4861 AAGATGGCCA TCAGTGGACT CTCTTTTTTC AGAATGGCAA AGTAAAGGTT TTTCAGGGAA
4921 ATCAAGACTC CTTCACACCT GTGGTGAACT CTCTAGACCC ACCGTTACTG ACTCGCTACC
4981 TTCGAATTCA CCCCCAGAGT TGGGTGCACC AGATTGCCCT GAGGATGGAG GTTCTGGGCT
5041 GCGAGGCACA GGACCTCTAC GACAAAACTC ACACATGCCC ACCGTGCCCA GCTCCAGAAC
5101 TCCTGGGCGG ACCGTCAGTC TTCCTCTTCC CCCCAAAACC CAAGGACACC CTCATGATCT
5161 CCCGGACCCC TGAGGTCACA TGCGTGGTGG TGGACGTGAG CCACGAAGAC CCTGAGGTCA
5221 AGTTCAACTG GTACGTGGAC GGCGTGGAGG TGCATAATGC CAAGACAAAG CCGCGGGAGG
5281 AGCAGTACAA CAGCACGTAC CGTGTGGTCA GCGTCCTCAC CGTCCTGCAC CAGGACTGGC
5341 TGAATGGCAA GGAGTACAAG TGCAAGGTCT CCAACAAAGC CCTCCCAGCC CCCATCGAGA
5401 AAACCATCTC CAAAGCCAAA GGGCAGCCCC GAGAACCACA GGTGTACACC CTGCCCCCAT
5461 CCCGGGATGA GCTGACCAAG AACCAGGTCA GCCTGACCTG CCTGGTCAAA GGCTTCTATC
5521 CCAGCGACAT CGCCGTGGAG TGGGAGAGCA ATGGGCAGCC GGAGAACAAC TACAAGACCA
5581 CGCCTCCCGT GTTGGACTCC GACGGCTCCT TCTTCCTCTA CAGCAAGCTC ACCGTGGACA
5641 AGAGCAGGTG GCAGCAGGGG AACGTCTTCT CATGCTCCGT GATGCATGAG GCTCTGCACA
5701 ACCACTACAC GCAGAAGAGC CTCTCCCTGT CTCCGGGTAA A
```

(ii) Fc DNA sequence (mouse Igκ signal peptide underlined) (SEQ ID NO: 3, which encodes SEQ ID NO: 4)

```
7981                                              ATGGA GACAGACACA
8041 CTCCTGCTAT GGGTACTGCT GCTCTGGGTT CCAGGTTCCA CTGGTGACAA AACTCACACA
8101 TGCCCACCGT GCCCAGCACC TGAACTCCTG GGAGGACCGT CAGTCTTCCT CTTCCCCCCA
8161 AAACCCAAGG ACACCCTCAT GATCTCCCGG ACCCCTGAGG TCACATGCGT GGTGGTGGAC
```

TABLE 1-continued

Polynucleotide Sequences

```
8221 GTGAGCCACG AAGACCCTGA GGTCAAGTTC AACTGGTACG TGGACGGCGT GGAGGTGCAT
8281 AATGCCAAGA CAAAGCCGCG GGAGGAGCAG TACAACAGCA CGTACCGTGT GGTCAGCGTC
8341 CTCACCGTCC TGCACCAGGA CTGGCTGAAT GGCAAGGAGT ACAAGTGCAA GGTCTCCAAC
8401 AAAGCCCTCC CAGCCCCCAT CGAGAAAACC ATCTCCAAAG CCAAAGGGCA GCCCCGAGAA
8461 CCACAGGTGT ACACCCTGCC CCCATCCCGC GATGAGCTGA CCAAGAACCA GGTCAGCCTG
8521 ACCTGCCTGG TCAAAGGCTT CTATCCCAGC GACATCGCCG TGGAGTGGGA GAGCAATGGG
8581 CAGCCGGAGA ACAACTACAA GACCACGCCT CCCGTGTTGG ACTCCGACGG CTCCTTCTTC
8641 CTCTACAGCA AGCTCACCGT GGACAAGAGC AGGTGGCAGC AGGGGAACGT CTTCTCATGC
8701 TCCGTGATGC ATGAGGCTCT GCACAACCAC TACACGCAGA AGAGCCTCTC CCTGTCTCCG
8761 GGTAAA
```

B. Full Length FVIIIFc (i) Full Length FVIIIFc DNA Sequence (FVIII signal peptide underlined, Fc region in bold) (SEQ ID NO: 5, which encodes SEQ ID NO: 6)

```
 661                                          ATG CAAATAGAGC TCTCCACCTG
 721 CTTCTTTCTG TGCCTTTTGC GATTCTGCTT TAGTGCCACC AGAAGATACT ACCTGGGTGC
 781 AGTGGAACTG TCATGGGACT ATATGCAAAG TGATCTCGGT GAGCTGCCTG TGGACGCAAG
 841 ATTTCCTCCT AGAGTGCCAA AATCTTTTCC ATTCAACACC AGTCGTGT ACAAAAAGAC
 901 TCTGTTTGTA GAATTCACGG ATCACCTTTT CAACATCGCT AAGCCAAGGC CACCCTGGAT
 961 GGGTCTGCTA GGTCCTACCA TCCAGGCTGA GGTTTATGAT ACAGTGGTCA TTACACTTAA
1021 GAACATGGCT TCCCATCCTG TCAGTCTTCA TGCTGTTGGT GTATCCTACT GGAAAGCTTC
1081 TGAGGGAGCT GAATATGATG ATCAGACCAG TCAAAGGGAG AAAGAAGATG ATAAAGTCTT
1141 CCCTGGTGGA AGCCATACAT ATGTCTGGCA GGTCCTGAAA GAGAATGGTC CAATGGCCTC
1201 TGACCCACTG TGCCTTACCT ACTCATATCT TTCTCATGTG GACCTGGTAA AAGACTTGAA
1261 TTCAGGCCTC ATTGGAGCCC TACTAGTATG TAGAGAAGGG AGTCTGGCCA AGGAAAAGAC
1321 ACAGACCTTG CACAAATTTA TACTACTTTT TGCTGTATTT GATGAAGGGA AAAGTTGGCA
1381 CTCAGAAACA AAGAACTCCT TGATGCAGGA TAGGGATGCT GCATCTGCTC GGGCCTGGCC
1441 TAAAATGCAC ACAGTCAATG GTTATGTAAA CAGGTCTCTG CCAGGTCTGA TTGGATGCCA
1501 CAGGAAATCA GTCTATTGGC ATGTGATTGG AATGGGCACC ACTCCTGAAG TGCACTCAAT
1561 ATTCCTCGAA GGTCACACAT TTCTTGTGAG GAACCATCGC CAGGCGTCTT TGGAAATCTC-
1621 GCCAATAACT TTCCTTACTG CTCAAACACT CTTGATGGAC CTTGGACAGT TTCTACTGTT
1681 TTGTCATATC TCTTCCCACC AACATGATGG CATGGAAGCT TATGTCAAAG TAGACAGCTG
1741 TCCAGAGGAA CCCCAACTAC GAATGAAAAA TAATGAAGAA GCGGAAGACT ATGATGATGA
1801 TCTTACTGAT TCTGAAATGG ATGTGGTCAG GTTTGATGAT GACAACTCTC CTTCCTTTAT
1861 CCAAATTCGC TCAGTTGCCA AGAAGCATCC TAAAACTTGG GTACATTACA TTGCTGCTGA
1921 AGAGGAGGAC TGGGACTATG CTCCCTTAGT CCTCGCCCCC GATGACAGAA GTTATAAAAG
1981 TCAATATTTG AACAATGGCC CTCAGCGGAT TGGTAGGAAG TACAAAAAAG TCCGATTTAT
2041 GGCATACACA GATGAAACCT TTAAGACTCG TGAAGCTATT CAGCATGAAT CAGGAATCTT
2101 GGGACCTTTA CTTTATGGGG AAGTTGGAGA CACACTGTTG ATTATATTTA AGAATCAAGC
2161 AAGCAGACCA TATAACATCT ACCCTCACGG AATCACTGAT GTCCGTCCTT TGTATTCAAG
2221 GAGATTACCA AAAGGTGTAA AACATTTGAA GGATTTTCCA ATTCTGCCAG GAGAAATATT
2281 CAAATATAAA TGGACAGTGA CTGTAGAAGA TGGGCCAACT AAATCAGATC CTCGGTGCCT
2341 GACCCGCTAT TACTCTAGTT TCGTTAATAT GGAGAGATAT CTAGCTTCAG GACTCATTGG
2401 CCCTCTCCTC ATCTGCTACA AGGAATCTGT AGATCAAAGA GGAAACCAGA TAATGTCAGA
2461 CAAGAGGAAT GTCATCCTGT TTTCTGTATT TGATGAGAAC CGAAGCTGGT ACCTCACAGA
2521 GAATATACAA CGCTTTCTCC CCAATCCAGC TGGAGTGCAG CTTGAGGATC CAGAGTTCCA
2581 AGCCTCCAAC ATCATGCACA GCATCAATGG CTATGTTTTT GATAGTTTGC AGTTGTCAGT
2641 TTGTTTGCAT GAGGTGGCAT ACTGGTACAT TCTAAGCATT GGAGCACAGA CTGACTTCCT
2701 TTCTGTCTTC TTCTCTGGAT ATACCTTCAA ACACAAAATG GTCTATGAAG ACACACTCAC
2761 CCTATTCCCA TTCTCAGGAG AAACTGTCTT CATGTCGATG GAAAACCCAG GTCTATGGAT
2821 TCTGGGGTGC CACAACTCAG ACTTTCGGAA CAGAGGCATG ACCGCCTTAC TGAAGGTTTC
2881 TAGTTGTGAC AAGAACACTG GTGATTATTA CGAGGACAGT TATGAAGATA TTTCAGCATA
2941 CTTGCTGAGT AAAAACAATG CCATTGAACC AAGAAGCTTC TCCCAGAATT CAAGACACCC
3001 TAGCACTAGG CAAAAGCAAT TTAATGCCAC CACAATTCCA GAAAATGACA TAGAGAAGAC
3061 TGACCCTTGG TTTGCACACA GAACACCTAT GCCTAAAATA CAAAATGTCT CCTCTAGTGA
3121 TTTGTTGATG CTCTTGCGAC AGAGTCCTAC TCCACATGGG CTATCCTTAT CTGATCTCCA
3181 AGAAGCCAAA TATGAGACTT TTTCTGATGA TCCATCACCT GGAGCAATAG ACAGTAATAA
3241 CAGCCTGTCT GAAATGACAC ACTTCAGGCC ACAGCTCCAT CACAGTGGGG ACATGGTATT
3301 TACCCCTGAG TCAGGCCTCC AATTAAGATT AAATGAGAAA CTGGGGACAA CTGCAGCAAC
3361 AGAGTTGAAG AAACTTGATT TCAAAGTTTC TAGTACATCA AATAATCTGA TTTCAACAAT
3421 TCCATCAGAC AATTTGGCAG CAGGTACTGA TAATACAAGT TCCTTAGGAC CCCCAAGTAT
3481 GCCAGTTCAT TATGATAGTC AATTAGATAC CACTCTATTT GGCAAAAAGT CATCTCCCCT
3541 TACTGAGTCT GGTGGACCTC TGAGCTTGAG TGAAGAAAAT AATGATTCAA AGTTGTTAGA
3601 ATCAGGTTTA ATGAATAGCC AAGAAAGTTC ATGGGGAAAA AATGTATCGT CAACAGAGAG
3661 TGGTAGGTTA TTTAAAGGGA AAAGAGCTCA TGGACCTGCT TGTTGACTA AGATAATGC
3721 CTTATTCAAA GTTAGCATCT CTTTGTTAAA GACAAACAAA ACTTCCAATA ATTCAGCAAC
3781 TAATAGAAAG ACTCACATTG ATGGCCCATC ATTATTAATT GAGAATAGTC CATCAGTCTG
3841 GCAAAATATA TTAGAAAGTG ACACTGAGTT TAAAAAAGTG ACACCTTTGA TTCATGACAG
3901 AATGCTTATG GACAAAAATG CTACAGCTTT GAGGCTAAAT CATATGTCAA TAAAAACTAC
3961 TTCATCAAAA AACATGGAAA TGGTCCAACA GAAAAAAGAG GCCCCATTC ACCAGATGC
4021 ACAAAATCCA GATATGTCGT TCTTTAAGAT GCTATTCTTG CCAGAATCAG CAAGGTGGAT
4081 ACAAAGGACT CATGGAAAGA ACTCTCTGAA CTCTGGGCAA GGCCCCAGTC CAAAGCAATT
4141 AGTATCCTTA GGACCAGAAA ATCTGTGGA AGGTCAGAAT TTCTTGTCTG AGAAAAACAA
4201 AGTGGTAGTA GGAAAGGGTG AATTTACAAA GGACGTAGGA CTCAAAGAGA TGGTTTTTCC
4261 AAGCAGCAGA AACCTATTTC TTACTAACTT GGATAATTTA CATGAAAATA ATACACACAA
4321 TCAAGAAAAA AAAATTCAGG AAGAAATAGA AAAGAAGGAA ACATTAATCC AAGAGAATGT
4381 AGTTTTGCCT CAGATACATA CAGTGACTGG CACTAAGAAT TTCATGAAGA ACCTTTTCTT
```

TABLE 1-continued

Polynucleotide Sequences

```
4441 ACTGAGCACT AGGCAAAATG TAGAAGGTTC ATATGACGGG GCATATGCTC CAGTACTTCA
4501 AGATTTTAGG TCATTAAATG ATTCAACAAA TAGAACAAAG AAACACACAG CTCATTTCTC
4561 AAAAAAAGGG GAGGAAGAAA ACTTGGAAGG CTTGGGAAAT CAAACCAAGC AAATTGTAGA
4621 GAAATATGCA TGCACCACAA GGATATCTCC TAATACAAGC CAGCAGAATT TTGTCACGCA
4681 ACGTAGTAAG AGAGCTTTGA AACAATTCAG ACTCCCACTA GAAGAAACAG AACTTGAAAA
4741 AAGGATAATT GTGGATGACA CCTCAACCCA GTGGTCCAAA AACATGAAAC ATTTGACCCC
4801 GAGCACCCTC ACACAGATAG ACTACAATGA GAAGGAGAAA GGGGCCATTA CTCAGTCTCC
4861 CTTATCAGAT TGCCTTACGA GGAGTCATAG CATCCCTCAA GCAAATAGAT CTCCATTACC
4921 CATTGCAAAG GTATCATCAT TTCCATCTAT TAGACCTATA TATCTGACCA GGGTCCTATT
4981 CCAAGCACAA CTTCTCATC TTCCAGCAGC ATCTTATAGA AAGAAAGATT CTGGGGTCCA
5041 AGAAAGCAGT CATTTCTTAC AAGGAGCCAA AAAAAATAAC CTTTCTTTAG CCATTCTAAC
5101 CTTGGAGATG ACTGGTGATC AAAGAGAGGT TGGCTCCCTG GGGACAAGTG CCACAAATTC
5161 AGTCACATAC AAGAAAGTTG AGAACACTGT TCTCCCGAAA CCAGACTTGC CAAAACATC
5221 TGGCAAAGTT GAATTGCTTC CAAAAGTTCA CATTTATCGA AAGGACCTAT TCCCTACGGA
5281 AACTAGCAAT GGGTCTCCTG GCCATCTGGA TCTCGTGGAA GGGAGCCTTC TTCAGGGAAC
5341 AGAGGGAGCG ATTAAGTGGA ATGAAGCAAA CAGACCTGGA AAAGTTCCCT TTCTGAGAGT
5401 AGCAACAGAA AGCTCTGCAA AGACTCCCTC CAAGCTATTG GATCCTCTTG CTTGGGATAA
5461 CCACTATGGT ACTCAGATAC CAAAAGAAGA GTGGAAATCC CAAGAGAAGT CACCAGAAAA
5521 AACAGCTTTT AAGAAAAAGG ATACCATTTT GTCCCTGAAC GCTTGTGAAA GCAATCATGC
5581 AATAGCAGCA ATAAATGAGG GACAAAATAA GCCCGAAATA GAAGTCACCT GGGCAAAGCA
5641 AGGTAGGACT GAAAGGCTGT GCTCTCAAAA CCCACCAGTC TTGAAACGCC ATCAACGGGA
5701 AATAACTCGT ACTACTCTTC AGTCAGATCA AGAGGAAATT GACTATGATG ATACCATATC
5761 AGTTGAAATG AAGAAGGAAG ATTTTGACAT TTATGATGAG GATGAAAATC AGAGCCCCCG
5821 CAGCTTTCAA AAGAAAACAC GACACTATTT TATTGCTGAG TCTGGAGAGGG TCTGGGATTA
5881 TGGGATGAGT AGCTCCCCAC ATGTTCTAAG AAAACAGGGCT CAGAGTGGCA GTGTCCCTCA
5941 GTTCAAGAAA GTTGTTTTCC AGGAATTTAC TGATGGCTCC TTTACTCAGC CCTTATACCG
6001 TGGAGAACTA AATGAACATT TGGGACTCCT GGGGCCATAT ATAAGAGCAG AAGTTGAAGA
6061 TAATATCATG GTAACTTTCA GAAATCAGGC CTCTCGTCCC TATTCCTTCT ATTCTAGCCT
6121 TATTTCTTAT GAGGAAGATC AGAGGCAAGG AGCAGAACCT AGAAAAAACT TTGTCAAGCC
6181 TAATGAAACC AAAACTTACT TTTGGAAAGT GCAACATCAT ATGGCACCCA CTAAAGATGA
6241 GTTTGACTGC AAAGCCTGGG CTTATTTCTC TGATGTTGAC CTGGAAAAAG ATGTGCACTC
6301 AGGCCTGATT GGACCCCTTC TGGTCTGCCA CACTAACACA CTGAACCCTG CTCATGGGAG
6361 ACAAGTGACA GTACAGGAAT TTGCTCTGTT TTTCACCATC TTTGATGAGA CCAAAAGCTG
6421 GTACTTCACT GAAAATATGG AAAGAAACTG CAGGGCTCCC TGCAATATCC AGATGGAAGA
6481 TCCCACTTTT AAAGAGAATT ATCGCTTCCA TGCAATCAAT GGCTACATAA TGGATACACT
6541 ACCTGGCTTA GTAATGGCTC AGGATCAAAG GATTCGATGG TATCTGCTCA GCATGGGCAG
6601 CAATGAAAAC ATCCATTCTA TTCATTTCAG TGGACATGTG TTCACTGTAC GAAAAAAAGA
6661 GGAGTATAAA ATGGCACTGT ACAATCTCTA TCCAGGTGTT TTTGAGACAG TGGAAATGTT
6721 ACCATCCAAA GCTGGAATTT GGCGGGTGGA ATGCCTTATT GGCGAGCATC TACATGCTGG
6781 GATGAGCACA CTTTTTCTGG TGTACAGCAA TAAGTGTCAG ACTCCCCTGG GAATGGCTTC
6841 TGGACACATT AGAGATTTTC AGATTACAGC TTCAGGACAA TATGGACAGT GGGCCCCAAA
6901 GCTGGCCAGA CTTCATTATT CCGGATCAAT CAATGCCTGG AGCACCAAGG AGCCCTTTTC
6961 TTGGATCAAG GTGGATCTGT TGGCACCAAT GATTATTCAC GGCATCAAGA CCCAGGGTGC
7021 CCGTCAGAAG TTCTCCAGCC TCTACATCTC TCAGTTTATC ATCATGTATA GTCTTGATGG
7081 GAAGAAGTGG CAGACTTATC GAGGAAATTC CACTGGAACC TTAATGGTCT TCTTTGGCAA
7141 TGTGGATTCA TCTGGGATAA AACACAATAT TTTTAACCCT CCAATTATTG CTCGATACAT
7201 CCGTTTGCAC CCAACTCATT ATAGCATTCG CAGCACTCTT CGCATGGAGT TGATGGGCTG
7261 TGATTTAAAT AGTTGCAGCA TGCCATTGGG AATGGAGAGT AAAGCAATAT CAGATGCACA
7321 GATTACTGCT TCATCCTACT TTACCAATAT GTTTGCCACC TGGTCTCCTT CAAAAGCTCG
7381 ACTTCACCTC AAGGGAGGA GTAATGCCTG GAGACCTCAG GTGAATAATC CAAAAGAGTG
7441 GCTGCAAGTG GACTTCCAGA AGACAATGAA AGTCACAGGA GTAACTACTC AGGGAGTAAA
7501 ATCTCTGCTT ACCAGCATGT ATGTGAAGGA GTTCCTCATC TCCAGCAGTC AAGATGGCCA
7561 TCAGTGGACT CTCTTTTTTC AGAATGGCAA AGTAAAGGTT TTTCAGGGAA ATCAAGACTC
7621 CTTCACACCT GTGGTGAACT CTCTAGACCC ACCGTTACTG ACTCGCTACC TTCGAATTCA
7681 CCCCCAGAGT TGGGTGCACC AGATTGCCCT GAGGATGGAG GTTCTGGGCT GCGAGGCACA
7741 GGACCTCTAC GACAAAACTC ACACATGCCC ACCGTGCCCA GCTCCAGAAC TCCTGGGCGG
7801 ACCGTCAGTC TTCCTCTTCC CCCCAAAACC CAAGGACACC CTCATGATCT CCCGGACCCC
7861 TGAGGTCACA TGCGTGGTGG TGGACGTGAG CCACGAAGAC CCTGAGGTCA AGTTCAACTG
7921 GTACGTGGAC GGCGTGGAGG TGCATAATGC CAAGACAAAG CCGCGGGAGG AGCAGTACAA
7981 CAGCACGTAC CGTGTGGTCA GCGTCCTCAC CGTCCTGCAC CAGGACTGGC TGAATGGCAA
8041 GGAGTACAAG TGCAAGGTCT CCAACAAAGC CCTCCCAGCC CCCATCGAGA AAACCATCTC
8101 CAAAGCCAAA GGGCAGCCCC GAGAACCACA GGTGTACACC CTGCCCCCAT CCCGGGATGA
8161 GCTGACCAAG AACCAGGTCA GCCTGACCTG CCTGGTCAAA GGCTTCTATC CAGCGACAT
8221 CGCCGTGGAG TGGGAGAGCA ATGGGCAGCC GGAGAACAAC TACAAGACCA CGCCTCCCGT
8281 GTTGGACTCC GACGGCTCCT TCTTCCTCTA CAGCAAGCTC ACCGTGGACA AGAGCAGGTG
8341 GCAGCAGGGG AACGTCTTCT CATGCTCCGT GATGCATGAG GCTCTGCACA ACCACTACAC
8401 GCAGAAGAGC CTCTCCCTGT CTCCGGGTAA A
```

(ii) Fc (same sequence as A(ii)(SEQ ID NO: 3))]

TABLE 2

Polypeptide Sequences

A. B-Domain Deleted FVIII-Fc Monomer Hybrid (BDD FVIIIFc monomer dimer):
created by coexpressing BDD FVIIIFc and Fc chains.
Construct = HC-LC-Fc fusion. An Fc expression cassette is cotransfected
with BDDFVIII-Fc to generate the BDD FVIIIFc monomer-. For the BDD FVIIIFc
chain, the Fc sequence is shown in bold; HC sequence is shown in double
underline; remaining B domain sequence is shown in italics. Signal peptides
are underlined.

i) B domain deleted FVIII-Fc chain (19 amino acid signal sequence underlined)
(SEQ ID NO: 2)
<u>MQIELSTCFFLCLLRFCFS</u>
<u>ATRRYYLGAVELSWDYMQSDLGELPVDARFPPRVPKSFPFNTSVVYKKTLFVEFTDHLFNIAKPRPPWMGL</u>
<u>LGPTIQAEVYDTVVITLKNMASHPVSLHAVGVSYWKASEGAEYDDQTSQREKEDDKVFPGGSHTYVWQVLK</u>
<u>ENGPMASDPLCLTYSYLSHVDLVKDLNSGLIGALLVCREGSLAKEKTQTLHKFILLFAVFDEGKSWHSETK</u>
<u>NSLMQDRDAASARAWPKMHTVNGYVNRSLPGLIGCHRKSVYWHVIGMTTPEVHSIFLEGHTFLVRNHRQA</u>
<u>SLEISPITFLTAQTLLMDLGQFLLFCHISSHQHDGMEAYVKVDSCPEEPQLRMKNNEEAEDYDDDLTDSEM</u>
<u>DVVRFDDDNSPSFIQIRSVAKKHPKTWVHYIAAEEEDWDYAPLVLAPDDRSYKSQYLNNGPQRIGRKYKKV</u>
<u>RFMAYTDETFKTREAIQHESGILGPLLYGEVGDTLLIIFKNQASRPYNIYPHGITDVRPLYSRRLPKGVKH</u>
<u>LKDFPILPGEIFKYKWTVTVEDGPTKSDPRCLTRYYSSFVNMERDLASGLIGPLLICYKESVDQRGNQIMS</u>
<u>DKRNVILFSVFDENRSWYLTENIQRFLPNPAGVQLEDPEFQASNIMHSINGYVFDSLQLSVCLHEVAYWYI</u>
<u>LSIGAQTDFLSVFFSGYTFKHKMVYEDTLTLFPFSGETVFMSMENPGLWILGCHNSDFRNRGMTALLKVSS</u>
<u>CDKNTGDYYEDSYEDISAYLLSKNNAIEPR</u>*SFSQNPPVLKRHQR*EITRTTLQSDQEEIDYDDTISVEMKKE
DFDIYDEDENQSPRSFQKKTRHYFIAAVERLWDYGMSSSPHVLRNRAQSGSVPQFKKVVFQEFTDGSFTQP
LYRGELNEHLGLLGPYIRAEVEDNIMVTFRNQASRPYSFYSSLISYEEDQRQGAEPRKNFVKPNETKTYFW
KVQHHMAPTKDEFDCKAWAYFSDVDLEKDVHSGLIGPLLVCHTNTLNPAHGRQVTVQEFALFFTIFDETKS
WYFTENMERNCRAPCNIQMEDPTFKENYRFHAINGYIMDTLPGLVMAQDQRIRWYLLSMGSNENIHSIHFS
GHVFTVRKKEEYKMALYNLYPGVFETVEMLPSKAGIWRVECLIGEHLHAGMSTLFLVYSNKCQTPLGMASG
HIRDFQITASGQYGQWAPKLARLHYSGSINAWSTKEPFSWIKVDLLAPMIIHGIKTQGARQKFSSLYISQF
IIMYSLDGKKWQTYRGNSTGTLMVFFGNVDSSGIKHNIFNPPIIARYIRLHPTHYSIRSTLRMELMGCDLN
SCSMPLGMESKAISDAQITASSYFTNMFATWSPSKARLHLQGRSNAWRPQVNNPKEWLQVDFQKTMKVTGV
TTQGVKSLLTSMYVKEFLISSSQDGHQWTLFFQNGKVHVFQGNQDSFTPVVNSLDPPLLTRYLRIHPQSWV
HQIALRMEVLGCEAQDLY<b>DKTHTCPPCPAPELLGGPSVFLFPPKPKDTLMISRTPEVTCVVVDVSHEDPEV</b>
<b>KFNWYVDGVEVHNAKTKPREEQYNSTYRVVSVLTVLHQDWLNGKEYKCKVSNKALPAPIEKTISKAKGQPR</b>
<b>EPQVYTLPPSRDELTKNQVSLTCLVKGFYPSDIAVEWESNGQPENNYKTTPPVLDSDGSFFLYSKLTVDKS</b>
<b>RWQQGNVFSCSVMHEALHNHYTQKSLSLSPGK</b> ii) Fc chain (20 amino acid heterologous signal peptide from mouse Igκ
chain underlined)(SEQ ID NO: 4)
<u>METDTLLLWVLLLWVPGSTG</u>
DKTHTCPPCPAPELLGGPSVFLFPPKPKDTLMISRTPEVTCVVVDVSHEDPEVKFNWYVDGVEVHNAKTKP
REEQYNSTYRVVSVLTVLHQDWLNGKEYKCKVSNKALPAPIEKTISKAKGQPREPQVYTLPPSRDELTKNQ
VSLTCLVKGFYPSDIAVEWESNGQPENNYKTTPPVLDSDGSFFLYSKLTVDKSRWQQGNVFSCSVMHEALH
NHYTQKSLSLSPGK B. Full length FVIIIFc monomer hybrid (Full length FVIIIFc monomer dimer):
created by coexpressing FVIIIFc and Fc chains.
Construct = HC-B-LC-Fc fusion. An Fc expression cassette is cotransfected
with FVIII-Fc to generate the full length FVIIIFc monomer. For
the FVIIIFc chain, the Fc sequence is shown in bold; HC sequence is shown in
double underline; B domain sequence is shown in italics. Signal peptides are
underlined.

i) Full length FVIIIFc chain (FVIII signal peptide underlined (SEQ ID NO: 6)
<u>MQIELSTCFFLCLLRFCFS</u>
<u>ATRRYYLGAVELSWDYMQSDLGELPVDARFPPRVPKSFPFNTSVVYKKTLFVEFTDHLFNIAKPRPPWMGL</u>
<u>LGPTIQAEVYDTVVITLKNMASHPVSLHAVGVSYWKASEGAEYDDQTSQREKEDDKVFPGGSHTYVWQVLK</u>
<u>ENGPMASDPLCLTYSYLSHVDLVKDLNSGLIGALLVCREGSLAKEKTQTLHKFILLFAVFDEGKSWHSETK</u>
<u>NSLMQDRDAASARAWPKMHTVNGYVNRSLPGLIGCHRKSVYWHVIGMTTPEVHSIFLEGHTFLVRNHRQA</u>
<u>SLEISPITFLTAQTLLMDLGQFLLFCHISSHQHDGMEAYVKVDSCPEEPQLRMKNNEEAEDYDDDLTDSEM</u>
<u>DVVRFDDDNSPSFIQIRSVAKKHPKTWVHYIAAEEEDWDYAPLVLAPDDRSYKSQYLNNGPQRIGRKYKKV</u>
<u>RFMAYTDETFKTREAIQHESGILGPLLYGEVGDTLLIIFKNQASRPYNIYPHGITDVRPLYSRRLPKGVKH</u>
<u>LKDFPILPGEIFKYKWTVTVEDGPTKSDPRCLTRYYSSFVNMERDLASGLIGPLLICYKESVDQRGNQIMS</u>
<u>DKRNVILFSVFDENRSWYLTENIQRFLPNPAGVQLEDPEFQASNIMHSINGYVFDSLQLSVCLHEVAYWYI</u>
<u>LSIGAQTDFLSVFFSGYTFKHKMVYEDTLTLFPFSGETVFMSMENPGLWILGCHNSDFRNRGMTALLKVSS</u>
<u>CDKNTGDYYEDSYEDISAYLLSKNNAIEPR</u>*SFSQNSRHPSTRQKQFNATTIPENDIEKTDPWFAHRTPMPK*
*IQNVSSSDLLMLLRQSPTPHGLSLSDLQEAKYETFSDDPSPGAIDSNNSLSEMTHFRPQLHHSGDMVFTPE*
*SGLQLRLNEKLGTTAATELKKLDFKVSSTSNNLISTIPSDNLAAGTDNTSSLGPPSMPVHYDSQLDTTLFG*
*KKSSPLTESGGPLSLSEENNDSKLLESGLMNSQESSWGKNVSSTESGRLFKGKRAHGPALLTKDNALFKVS*
*ISLLKTNKTSNNSATNRKTHIDGPSLLIENSPSVWQNILESDTEFKKVTPLIHDRMLMDKNATALRLNHMS*
*NKTTSSKNMEMVQQKKEGPIPPDAQNPDMSFFKMLFLPESARWIQRTHGKNSLNSGQGPSPKQLVSLGPEK*
*SVEGQNFLSEKNKVVVGKGEFTKDVGLKEMVFPSSRNLFLTNLDNLHENNTHNQEKKIQEEIEKKETLIQE*
*NVVLPQIHTVTGTKNFMKNLFLLSTRQNVEGSYDGAYAPVLQDFRSLNDSTNRTKKHTAHFSKKGEEENLE*
*GLGNQTKQIVEKYACTTRISPNTSQQNFVTQRSKRALQFRLPLEETELEKRIIVDDTSTQSWKNMKHLTP*
*STLTQIDYNEKEKGAITQSPLSDCLTRSHSIPQANRSPLPIAKVSSFPSIRPIYLTRVLFQDNSSHLPAAS*
*YRKKDSGVQESSHFLQGAKKNNLSLAILTLEMTGDQREVGSLGTSATNSVTYKKVENTVLPKPDLPKTSGK*
*VELLPKVHIYQKDLFPTETSNGSPGHLDLVEGSLLQGTEGAIKWNEANRPGKVPFLRVATESSAKTPSKLL*
*DPLAWDNHYGTQIPKEEWKSQEKSPEKTAFKKKDTILSLNACESNHAIAAINEGQNKPEIEVTWAKQGRTE*
*RLCSQNPPVLKRHQREITRTTLQSDQEEIDYDDTISVEMKKEDFDIYDEDENQSPRSFQKKTRHYFIAAVE*

TABLE 2-continued

Polypeptide Sequences

```
RLWDYGMSSSPHVLRNRAQSGSVPQFKKVVFQEFTDGSFTQPLYRGELNEHLGLLGPYIRAEVEDNIMVTF
RNQASRPYSFYSSLISYEEDQRQGAEPRKNFVKPNETKTYFWKVQHHMAPTKDEFDCKAWAYFSDVDLEKD
VHSGLIGPLLVCHTNTLNPAHGRQVTVQEFALFFTIFDETKSWYFTENMERNCRAPCNIQMEDPTFKENYR
FHAINGYIMDTLPGLVMAQDQRIRWYLLSMGSNENIHSIHFSGHVFTVRKKEEYKMALYNLYPGVFETVEM
LPSKAGIWRVECLIGEHLHAGMSTLFLVYSNKCQTPLGMASGHIRDFQITASGQYGQWAPKLARLHYSGSI
NAWSTKEPFSWIKVDLLAPMIIHGIKTQGARQKFSSLYISQFIIMYSLDGKKWQTYRGNSTGTLMVFFGNV
DSSGIKHNIFNPPIIARYIRLHPTHYSIRSTLRMELMGCDLNSCSMPLGMESKAISDAQITASSYFTNMFA
TWSPSKARLHLQGRSNAWRPQVNNPKEWLQVDFQKTMKVTGVTTQGVKSLLTSMYVKEFLISSSQDGHQWT
LFFQNGKVKVFQGNQDSFTPVVNSLDPPLLTRYLRIHPQSWVHQIALRMEVLGCEAQDLYDKTHTCPPCPA
PELLGGPSVFLFPPKPKDTLMISRTPEVTCVVVDVSHEDPEVKFNWYVDGVEVHNAKTKPREEQYNSTYRV
VSVLTVLHQDWLNGKEYKCKVSNKALPAPIEKTISKAKGQPREPQVYTLPPSRDELTKNQVSLTCLVKGFY
PSDIAVEWESNGQPENNYKTTPPVLDSDGSFFLYSKLTVDKSRWQQGNVFSCSVMHEALHNHYTQKSLSLS
PGK
``` ii) Fc chain (20 amino acid heterologous signal peptide from mouse Igκ chain underlined) (SEQ ID NO: 4)

```
METDTLLLWVLLLWVPGSTG
DKTHTCPPCPAPELLGGPSVFLFPPKPKDTLMISRTPEVTCVVVDVSHEDPEVKFNWYVDGVEVHNAKTKP
REEQYNSTYRVVSVLTVLHQDWLNGKEYKCKVSNKALPAPIEKTISKAKGQPREPQVYTLPPSRDELTKNQ
VSLTCLVKGFYPSDIAVEWESNGQPENNYKTTPPVLDSDGSFFLYSKLTVDKSRWQQGNVFSCSVMHEALH
NHYTQKSLSLSPGK
```

CITED REFERENCES

4. Aledort L. et al., *J Intern Med.*: 236:391-399 (1994)
5. Petrini P. et al., *Am J Pediatr Hematol Oncol.* 13:280-287 (1991).
6. Aznar J. et al., *Haemophilia* 6(3):170-176 (2000).
7. Feldman B. et al., *J Thromb Haemost.* 4:1228-1236 (2006).
8. Kreuz W. et al., *Haemophilia* 4:413-417 (1998).
9. Liesner R. et al., *B J Haem.* 92:973-978 (1996).
10. Ljung R., *Haemophilia.* 4(4):409-412 (1998).
11. Löfquist T, et al., *J Intern Med* 241:395-400 (1997).
12. Nilsson I, et al., *B. J Int Med* 232:25-32 (1992).
13. Risebrough N. et al., *Haemophilia.* 14:743-752 (2008).
14. Van Den Berg H. et al., *Haemophilia* 9 (Suppl. 1):27-31 (2003).
15. Van Den Berg H. et al., *Haematologica* 89(6):645-650 (2004).
16. Molho P. et al., *Haemophilia* 6(1):23-32 (2000).
17. Coppola A. et al., *Blood Transfus.* 6(2): 4-11 (2008).
18. Geraghty S. et al., *Haemophilia* 12:75-81 (2006).
19. Hacker M. et al., *Haemophilia* 7(4):392-396 (2001).
20. Lillicrap D., *Current Opinion in Hematology* 17:393-397 (2010).
21. Dumont J. A. et al., *BioDrugs* 20(3):151-60 (2006).
22. Dumont J. A. et al., "Monomeric Fc fusion technology: an approach to create long lasting clotting factors," in: Kontermann R., ed., *Therapeutic Proteins—Strategies to Modulate Half-Life*, Chapter 11, Wiley VCH publisher; in press.
23. Roopenian D. C. et al., *Nat Rev Immunol.* 7(9):715-25 (Epub 2007 Aug. 17).
24. Lencer W. I. and Blumberg R. S., *Trends Cell Biol.* 15(1):5-9 (2005).
25. Huang C., *Curr Opin Biotechnol.* 20(6):692-9. (Epub 2009 Nov. 4).
26. Schmidt S. R., *Curr Opin Drug Discov Devel.* 12(2): 284-295 (2009).
27. Dumont J. et al., *Blood.* 116(21) Abstract 545 (2009).
28. Liu T. et al., *J Thromb Haemost.* 9(52):561 (2011).
29. Rosen S., *Scand J Haematol Suppl.* 33(Suppl 40):139-45 (1984).
30. Lee C. A. et al., *Thromb Haemost.* 82(6):1644-7 (December 1999).
31. Mikaelsson M. and Oswaldsson U., *Semin Thromb Hemost.* 28(3):257-64 (June 2002).
32. Stroobants A. K. et al., *J Thromb Haemost.* 9 (Suppl 2) (2011).
33. Lenting P. J. et al., *J Thromb Haemost.* 5: 1353-60 (2007).
34. Smith N. L. et al., *Circulation* 121:1382-1392 (2010).

What is claimed is:

1. A pharmaceutical composition comprising (i) a chimeric polypeptide, which comprises Factor VIII (FVIII) and a second portion, and (ii) at least one pharmaceutically acceptable excipient, wherein 15% to 25% of the FVIII of the chimeric polypeptide is single chain FVIII and 75% to 85% of the FVIII of the chimeric polypeptide is processed FVIII, wherein the single chain FVIII comprises a FVIII heavy chain and a FVIII light chain on a single polypeptide chain and the processed FVIII comprises a FVIII heavy chain and a FVIII light chain on two polypeptide chains.

2. The pharmaceutical composition of claim 1, wherein (a) 25% of the FVIII of the chimeric polypeptide is single chain FVIII and 75% of the FVIII of the chimeric polypeptide is processed FVIII, (b) 20% of the FVIII of the chimeric polypeptide is single chain FVIII and 80% of the FVIII of the chimeric polypeptide is processed FVIII, or (c) 15% of the FVIII of the chimeric polypeptide is single chain FVIII and 85% of the FVIII of the chimeric polypeptide is processed FVIII.

3. The pharmaceutical composition of claim 1, wherein the single chain FVIII in the chimeric polypeptide has FVIII activity comparable to processed FVIII.

4. The pharmaceutical composition of claim 1, wherein the chimeric polypeptide is a long-acting FVIII polypeptide.

5. The pharmaceutical composition of claim 1, wherein the second portion is selected from the group consisting of an Fc region, albumin, a PAS sequence, transferrin, CTP (28 amino acid C-terminal peptide (CTP) of hCG with its 4 O-glycans), polyethylene glycol (PEG), hydroxyethyl starch (HES), albumin binding polypeptide, albumin-binding small molecules, and two or more combinations thereof.

6. The pharmaceutical composition of claim 5, wherein the chimeric polypeptide is a FVIIIFc monomer dimer hybrid.

7. The pharmaceutical composition of claim 1, wherein the FVIII comprises B-domain deleted FVIII.

8. The pharmaceutical composition of claim 7, wherein residue 1645 corresponding to full-length, mature FVIII, residue 1648 corresponding to full-length, mature FVIII, or both residues in the single chain FVIII is arginine.

9. The pharmaceutical composition of claim 4, wherein the chimeric polypeptide has a half-life longer than a polypeptide consisting of the FVIII.

10. The pharmaceutical composition of claim 1, which is suitable for subcutaneous, intradermal, intravascular, intravenous, intramuscular, spinal, intracranial, intrathecal, intraocular, periocular, intraorbital, intrasynovial or intraperitoneal injection to a human.

11. The pharmaceutical composition of claim 1, which is lyophilized.

12. The pharmaceutical composition of claim 2, which is lyophilized.

13. The pharmaceutical composition of claim 3, which is lyophilized.

14. The pharmaceutical composition of claim 4, which is lyophilized.

15. The pharmaceutical composition of claim 5, which is lyophilized.

16. The pharmaceutical composition of claim 6, which is lyophilized.

17. The pharmaceutical composition of claim 7, which is lyophilized.

18. The pharmaceutical composition of claim 8, which is lyophilized.

19. The pharmaceutical composition of claim 10, which is lyophilized.

20. The pharmaceutical composition of claim 11, wherein 25% of the FVIII of the chimeric polypeptide is single chain FVIII and 75% of the FVIII of the chimeric polypeptide is processed FVIII.

21. The pharmaceutical composition of claim 11, wherein 20% of the FVIII of the chimeric polypeptide is single chain FVIII and 80% of the FVIII of the chimeric polypeptide is processed FVIII.

22. The pharmaceutical composition of claim 11, wherein 15% of the FVIII of the chimeric polypeptide is single chain FVIII and 85% of the FVIII of the chimeric polypeptide is processed FVIII.

* * * * *

SEQUENCE LISTING

```
<160> NUMBER OF SEQ ID NOS: 16

<210> SEQ ID NO 1
<211> LENGTH: 5052
<212> TYPE: DNA
<213> ORGANISM: Artificial Sequence
<220> FEATURE:
<223> OTHER INFORMATION: B-Domain Deleted FVIIIFc Chain
<220> FEATURE:
<221> NAME/KEY: misc_feature
<222> LOCATION: (1)..(57)
<223> OTHER INFORMATION: FVIII signal
<220> FEATURE:
<221> NAME/KEY: misc_feature
<222> LOCATION: (4372)..(5052)
<223> OTHER INFORMATION: Fc region
```

<400> SEQUENCE: 1

```
atgcaaatag agctctccac ctgcttcttt ctgtgccttt tgcgattctg ctttagtgcc      60
accagaagat actacctggg tgcagtggaa ctgtcatggg actatatgca aagtgatctc     120
ggtgagctgc ctgtggacgc aagatttcct cctagagtgc caaaatcttt tccattcaac     180
acctcagtcg tgtacaaaaa gactctgttt gtagaattca cggatcacct tttcaacatc     240
gctaagccaa ggccaccctg gatgggtctg ctaggtccta ccatccaggc tgaggtttat     300
gatacagtgg tcattacact taagaacatg gcttcccatc ctgtcagtct tcatgctgtt     360
ggtgtatcct actggaaagc ttctgaggga gctgaatatg atgatcagac cagtcaaagg     420
gagaaagaag atgataaagt cttccctggt ggaagccata catatgtctg gcaggtcctg     480
aaagagaatg gtccaatggc ctctgaccca ctgtgcctta cctactcata tctttctcat     540
gtggacctgg taaaagactt gaattcaggc ctcattggag ccctactagt atgtagagaa     600
gggagtctgg ccaaggaaaa gacacagacc ttgcacaaat ttatactact ttttgctgta     660
tttgatgaag ggaaaagttg gcactcagaa acaaagaact ccttgatgca ggatagggat     720
gctgcatctg ctcgggcctg gcctaaaatg cacacagtca atggttatgt aaacaggtct     780
ctgccaggtc tgattggatg ccacaggaaa tcagtctatt ggcatgtgat tggaatgggc     840
accactcctg aagtgcactc aatattcctc gaaggtcaca catttcttgt gaggaaccat     900
cgccaggcgt ccttggaaat ctcgccaata actttcctta ctgctcaaac actcttgatg     960
gaccttggac agtttctact gttttgtcat atctcttccc accaacatga tggcatggaa    1020
gcttatgtca agtagacag ctgtccagag gaacccaac tacgaatgaa aaataatgaa    1080
gaagcggaag actatgatga tgatcttact gattctgaaa tggatgtggt caggtttgat    1140
gatgacaact ctccttcctt tatccaaatt cgctcagttg ccaagaagca tcctaaaact    1200
tgggtacatt acattgctgc tgaagaggag gactgggact atgctcccttt agtcctcgcc    1260
cccgatgaca gaagttataa aagtcaatat ttgaacaatg ccctcagcg gattggtagg    1320
aagtacaaaa aagtccgatt tatggcatac acagatgaaa cctttaagac tcgtgaagct    1380
attcagcatg aatcaggaat cttgggacct ttactttatg gggaagttgg agacacactg    1440
ttgattatat ttaagaatca agcaagcaga ccatataaca tctaccctca cggaatcact    1500
gatgtccgtc ctttgtattc aaggagatta ccaaaaggtg taaaacattt gaaggatttt    1560
ccaattctgc caggagaaat attcaaatat aaatggacag tgactgtaga agatgggcca    1620
actaaatcag atcctcggtg cctgacccgc tattactcta gtttcgttaa tatggagaga    1680
gatctagctt caggactcat tggccctctc ctcatctgct acaaagaatc tgtagatcaa    1740
agaggaaacc agataatgtc agacaagagg aatgtcatcc tgttttctgt atttgatgag    1800
aaccgaagct ggtacctcac agagaatata caacgctttc tccccaatcc agctggagtg    1860
cagcttgagg atccagagtt ccaagcctcc aacatcatgc acagcatcaa tggctatgtt    1920
tttgatagtt tgcagttgtc agtttgtttg catgaggtgg catactggta cattctaagc    1980
attggagcac agactgactt cctttctgtc ttcttctctg gatataccctt caaacacaaa    2040
atggtctatg aagacacact caccctattc ccattctcag gagaaactgt cttcatgtcg    2100
atggaaaacc caggtctatg gattctgggg tgccacaact cagactttcg aacagaggc    2160
atgaccgcct tactgaaggt ttctagttgt gacaagaaca ctggtgatta ttacgaggac    2220
agttatgaag atatttcagc atacttgctg agtaaaaaca atgccattga accaagaagc    2280
ttctctcaaa acccaccagt cttgaaacgc catcaacggg aaataactcg tactactctt    2340
```

```
cagtcagatc aagaggaaat tgactatgat gataccatat cagttgaaat gaagaaggaa    2400
gattttgaca tttatgatga ggatgaaaat cagagccccc gcagctttca aaagaaaaca    2460
cgacactatt ttattgctgc agtggagagg ctctgggatt atgggatgag tagctcccca    2520
catgttctaa gaaacagggc tcagagtggc agtgtccctc agttcaagaa agttgttttc    2580
caggaattta ctgatggctc ctttactcag cccttatacc gtggagaact aaatgaacat    2640
ttgggactcc tggggccata taagagcag aagttgaag ataatatcat ggtaactttc      2700
agaaatcagg cctctcgtcc ctattccttc tattctagcc ttatttctta tgaggaagat    2760
cagaggcaag gagcagaacc tagaaaaaac tttgtcaagc ctaatgaaac caaaacttac    2820
ttttggaaag tgcaacatca tatggcaccc actaaagatg agtttgactg caaagcctgg    2880
gcttatttct ctgatgttga cctggaaaaa gatgtgcact caggcctgat tggacccctt    2940
ctggtctgcc acactaacac actgaaccct gctcatggga gacaagtgac agtacaggaa    3000
tttgctctgt ttttcaccat ctttgatgag accaaaagct ggtacttcac tgaaaatatg    3060
gaaagaaact gcagggctcc ctgcaatatc cagatggaag atcccacttt taaagagaat    3120
tatcgcttcc atgcaatcaa tggctacata atggatacac tacctggctt agtaatggct    3180
caggatcaaa ggattcgatg gtatctgctc agcatgggca gcaatgaaaa catccattct    3240
attcatttca gtggacatgt gttcactgta cgaaaaaaag aggagtataa aatggcactg    3300
tacaatctct atccaggtgt ttttgagaca gtggaaatgt taccatccaa agctggaatt    3360
tggcgggtgg aatgccttat tggcgagcat ctacatgctg ggatgagcac acttttctg     3420
gtgtacagca ataagtgtca gactccctg ggaatggctt ctggacacat tagagatttt    3480
cagattacag cttcaggaca atatggacag tgggccccaa agctggccag acttcattat    3540
tccggatcaa tcaatgcctg gagcaccaag gagccctttt cttggatcaa ggtggatctg    3600
ttggcaccaa tgattattca cggcatcaag acccagggtg cccgtcagaa gttctccagc    3660
ctctacatct ctcagtttat catcatgtat agtcttgatg gaagaagtg gcagacttat    3720
cgaggaaatt ccactggaac cttaatggtc ttctttggca atgtggattc atctgggata    3780
aaacacaata tttttaaccc tccaattatt gctcgataca tccgtttgca cccaactcat    3840
tatagcattc gcagcactct tcgcatggga ttgatgggct gtgatttaaa tagttgcagc    3900
atgccattgg gaatggagag taagcaata tcagatgcac agattactgc ttcatcctac    3960
tttaccaata tgtttgccac ctggtctcct tcaaaagctc gacttcacct ccaagggagg    4020
agtaatgcct ggagacctca ggtgaataat ccaaaagagt ggctgcaagt ggacttccag    4080
aagacaatga agtcacagg agtaactact cagggagtaa aatctctgct taccagcatg    4140
tatgtgaagg agttcctcat ctccagcagt caagatggcc atcagtggac tctcttttt    4200
cagaatggca agtaaaggt ttttcaggga atcaagact ccttcacacc tgtggtgaac    4260
tctctagacc caccgttact gactcgctac cttcgaattc accccagag ttgggtgcac    4320
cagattgccc tgaggatgga ggttctgggc tgcgaggcac aggacctcta cgacaaaact    4380
cacacatgcc caccgtgccc agctccagaa ctcctgggcg gaccgtcagt cttcctcttc    4440
ccccaaaac ccaaggacac cctcatgatc tcccggaccc ctgaggtcac atgcgtggtg    4500
gtggacgtga gccacgaaga ccctgaggtc aagttcaact ggtacgtgga cggcgtggag    4560
gtgcataatg ccaagacaaa gccgcgggag gagcagtaca acagcacgta ccgtgtggtc    4620
agcgtcctca ccgtcctgca ccaggactgg ctgaatggca aggagtacaa gtgcaaggtc    4680
```

```
tccaacaaag ccctcccagc ccccatcgag aaaaccatct ccaaagccaa agggcagccc     4740
cgagaaccac aggtgtacac cctgccccca tcccgggatg agctgaccaa gaaccaggtc     4800
agcctgacct gcctggtcaa aggcttctat cccagcgaca tcgccgtgga gtgggagagc     4860
aatgggcagc cggagaacaa ctacaagacc acgcctcccg tgttggactc cgacggctcc     4920
ttcttcctct acagcaagct caccgtggac aagagcaggt ggcagcaggg gaacgtcttc     4980
tcatgctccg tgatgcatga ggctctgcac aaccactaca cgcagaagag cctctccctg     5040
tctccgggta aa                                                        5052
```

<210> SEQ ID NO 2
<211> LENGTH: 1684
<212> TYPE: PRT
<213> ORGANISM: Artificial Sequence
<220> FEATURE:
<223> OTHER INFORMATION: B domain deleted FVIII-Fc chain
<220> FEATURE:
<221> NAME/KEY: MISC_FEATURE
<222> LOCATION: (1)..(19)
<223> OTHER INFORMATION: Signal
<220> FEATURE:
<221> NAME/KEY: MISC_FEATURE
<222> LOCATION: (20)..(753)
<223> OTHER INFORMATION: Heavy chain (HC)
<220> FEATURE:
<221> NAME/KEY: MISC_FEATURE
<222> LOCATION: (760)..(773)
<223> OTHER INFORMATION: B domain
<220> FEATURE:
<221> NAME/KEY: MISC_FEATURE
<222> LOCATION: (1457)..(1684)
<223> OTHER INFORMATION: Fc region

<400> SEQUENCE: 2

```
Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
                20                  25                  30

Trp Asp Tyr Met Gln Ser Asp Leu Gly Glu Leu Pro Val Asp Ala Arg
            35                  40                  45

Phe Pro Pro Arg Val Pro Lys Ser Phe Pro Phe Asn Thr Ser Val Val
        50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205
```

```
Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asn Ser
    370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
    530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
        595                 600                 605

Asn Ile Gln Arg Phe Leu Pro Asn Pro Ala Gly Val Gln Leu Glu Asp
    610                 615                 620

Pro Glu Phe Gln Ala Ser Asn Ile Met His Ser Ile Asn Gly Tyr Val
```

```
                625                 630                 635                 640
            Phe Asp Ser Leu Gln Leu Ser Val Cys Leu His Glu Val Ala Tyr Trp
                            645                 650                 655
            Tyr Ile Leu Ser Ile Gly Ala Gln Thr Asp Phe Leu Ser Val Phe Phe
                            660                 665                 670
            Ser Gly Tyr Thr Phe Lys His Lys Met Val Tyr Glu Asp Thr Leu Thr
                            675                 680                 685
            Leu Phe Pro Phe Ser Gly Glu Thr Val Phe Met Ser Met Glu Asn Pro
                690                 695                 700
            Gly Leu Trp Ile Leu Gly Cys His Asn Ser Asp Phe Arg Asn Arg Gly
            705                 710                 715                 720
            Met Thr Ala Leu Leu Lys Val Ser Ser Cys Asp Lys Asn Thr Gly Asp
                            725                 730                 735
            Tyr Tyr Glu Asp Ser Tyr Glu Asp Ile Ser Ala Tyr Leu Leu Ser Lys
                            740                 745                 750
            Asn Asn Ala Ile Glu Pro Arg Ser Phe Ser Gln Asn Pro Pro Val Leu
                            755                 760                 765
            Lys Arg His Gln Arg Glu Ile Thr Arg Thr Thr Leu Gln Ser Asp Gln
                770                 775                 780
            Glu Glu Ile Asp Tyr Asp Asp Thr Ile Ser Val Glu Met Lys Lys Glu
            785                 790                 795                 800
            Asp Phe Asp Ile Tyr Asp Glu Asp Glu Asn Gln Ser Pro Arg Ser Phe
                            805                 810                 815
            Gln Lys Lys Thr Arg His Tyr Phe Ile Ala Ala Val Glu Arg Leu Trp
                            820                 825                 830
            Asp Tyr Gly Met Ser Ser Ser Pro His Val Leu Arg Asn Arg Ala Gln
                            835                 840                 845
            Ser Gly Ser Val Pro Gln Phe Lys Lys Val Val Phe Gln Glu Phe Thr
                850                 855                 860
            Asp Gly Ser Phe Thr Gln Pro Leu Tyr Arg Gly Glu Leu Asn Glu His
            865                 870                 875                 880
            Leu Gly Leu Leu Gly Pro Tyr Ile Arg Ala Glu Val Glu Asp Asn Ile
                            885                 890                 895
            Met Val Thr Phe Arg Asn Gln Ala Ser Arg Pro Tyr Ser Phe Tyr Ser
                            900                 905                 910
            Ser Leu Ile Ser Tyr Glu Glu Asp Gln Arg Gln Gly Ala Glu Pro Arg
                            915                 920                 925
            Lys Asn Phe Val Lys Pro Asn Glu Thr Lys Thr Tyr Phe Trp Lys Val
                930                 935                 940
            Gln His His Met Ala Pro Thr Lys Asp Glu Phe Asp Cys Lys Ala Trp
            945                 950                 955                 960
            Ala Tyr Phe Ser Asp Val Asp Leu Glu Lys Asp Val His Ser Gly Leu
                            965                 970                 975
            Ile Gly Pro Leu Leu Val Cys His Thr Asn Thr Leu Asn Pro Ala His
                            980                 985                 990
            Gly Arg Gln Val Thr Val Gln Glu Phe Ala Leu Phe Phe Thr Ile Phe
                            995                 1000                1005
            Asp Glu Thr Lys Ser Trp Tyr Phe Thr Glu Asn Met Glu Arg Asn
                1010                1015                1020
            Cys Arg Ala Pro Cys Asn Ile Gln Met Glu Asp Pro Thr Phe Lys
                1025                1030                1035
            Glu Asn Tyr Arg Phe His Ala Ile Asn Gly Tyr Ile Met Asp Thr
                1040                1045                1050
```

Leu Pro Gly Leu Val Met Ala Gln Asp Gln Arg Ile Arg Trp Tyr
    1055            1060                1065

Leu Leu Ser Met Gly Ser Asn Glu Asn Ile His Ser Ile His Phe
    1070            1075                1080

Ser Gly His Val Phe Thr Val Arg Lys Lys Glu Glu Tyr Lys Met
    1085            1090                1095

Ala Leu Tyr Asn Leu Tyr Pro Gly Val Phe Glu Thr Val Glu Met
    1100            1105                1110

Leu Pro Ser Lys Ala Gly Ile Trp Arg Val Glu Cys Leu Ile Gly
    1115            1120                1125

Glu His Leu His Ala Gly Met Ser Thr Leu Phe Leu Val Tyr Ser
    1130            1135                1140

Asn Lys Cys Gln Thr Pro Leu Gly Met Ala Ser Gly His Ile Arg
    1145            1150                1155

Asp Phe Gln Ile Thr Ala Ser Gly Gln Tyr Gly Gln Trp Ala Pro
    1160            1165                1170

Lys Leu Ala Arg Leu His Tyr Ser Gly Ser Ile Asn Ala Trp Ser
    1175            1180                1185

Thr Lys Glu Pro Phe Ser Trp Ile Lys Val Asp Leu Leu Ala Pro
    1190            1195                1200

Met Ile Ile His Gly Ile Lys Thr Gln Gly Ala Arg Gln Lys Phe
    1205            1210                1215

Ser Ser Leu Tyr Ile Ser Gln Phe Ile Ile Met Tyr Ser Leu Asp
    1220            1225                1230

Gly Lys Lys Trp Gln Thr Tyr Arg Gly Asn Ser Thr Gly Thr Leu
    1235            1240                1245

Met Val Phe Phe Gly Asn Val Asp Ser Ser Gly Ile Lys His Asn
    1250            1255                1260

Ile Phe Asn Pro Pro Ile Ile Ala Arg Tyr Ile Arg Leu His Pro
    1265            1270                1275

Thr His Tyr Ser Ile Arg Ser Thr Leu Arg Met Glu Leu Met Gly
    1280            1285                1290

Cys Asp Leu Asn Ser Cys Ser Met Pro Leu Gly Met Glu Ser Lys
    1295            1300                1305

Ala Ile Ser Asp Ala Gln Ile Thr Ala Ser Ser Tyr Phe Thr Asn
    1310            1315                1320

Met Phe Ala Thr Trp Ser Pro Ser Lys Ala Arg Leu His Leu Gln
    1325            1330                1335

Gly Arg Ser Asn Ala Trp Arg Pro Gln Val Asn Asn Pro Lys Glu
    1340            1345                1350

Trp Leu Gln Val Asp Phe Gln Lys Thr Met Lys Val Thr Gly Val
    1355            1360                1365

Thr Thr Gln Gly Val Lys Ser Leu Leu Thr Ser Met Tyr Val Lys
    1370            1375                1380

Glu Phe Leu Ile Ser Ser Ser Gln Asp Gly His Gln Trp Thr Leu
    1385            1390                1395

Phe Phe Gln Asn Gly Lys Val Lys Val Phe Gln Gly Asn Gln Asp
    1400            1405                1410

Ser Phe Thr Pro Val Val Asn Ser Leu Asp Pro Pro Leu Leu Thr
    1415            1420                1425

Arg Tyr Leu Arg Ile His Pro Gln Ser Trp Val His Gln Ile Ala
    1430            1435                1440

Leu Arg Met Glu Val Leu Gly Cys Glu Ala Gln Asp Leu Tyr Asp
1445                1450                1455

Lys Thr His Thr Cys Pro Pro Cys Pro Ala Pro Glu Leu Leu Gly
1460                1465                1470

Gly Pro Ser Val Phe Leu Phe Pro Pro Lys Pro Lys Asp Thr Leu
1475                1480                1485

Met Ile Ser Arg Thr Pro Glu Val Thr Cys Val Val Val Asp Val
1490                1495                1500

Ser His Glu Asp Pro Glu Val Lys Phe Asn Trp Tyr Val Asp Gly
1505                1510                1515

Val Glu Val His Asn Ala Lys Thr Lys Pro Arg Glu Glu Gln Tyr
1520                1525                1530

Asn Ser Thr Tyr Arg Val Val Ser Val Leu Thr Val Leu His Gln
1535                1540                1545

Asp Trp Leu Asn Gly Lys Glu Tyr Lys Cys Lys Val Ser Asn Lys
1550                1555                1560

Ala Leu Pro Ala Pro Ile Glu Lys Thr Ile Ser Lys Ala Lys Gly
1565                1570                1575

Gln Pro Arg Glu Pro Gln Val Tyr Thr Leu Pro Pro Ser Arg Asp
1580                1585                1590

Glu Leu Thr Lys Asn Gln Val Ser Leu Thr Cys Leu Val Lys Gly
1595                1600                1605

Phe Tyr Pro Ser Asp Ile Ala Val Glu Trp Glu Ser Asn Gly Gln
1610                1615                1620

Pro Glu Asn Asn Tyr Lys Thr Thr Pro Pro Val Leu Asp Ser Asp
1625                1630                1635

Gly Ser Phe Phe Leu Tyr Ser Lys Leu Thr Val Asp Lys Ser Arg
1640                1645                1650

Trp Gln Gln Gly Asn Val Phe Ser Cys Ser Val Met His Glu Ala
1655                1660                1665

Leu His Asn His Tyr Thr Gln Lys Ser Leu Ser Leu Ser Pro Gly
1670                1675                1680

Lys

<210> SEQ ID NO 3
<211> LENGTH: 741
<212> TYPE: DNA
<213> ORGANISM: Artificial Sequence
<220> FEATURE:
<223> OTHER INFORMATION: Fc region
<220> FEATURE:
<221> NAME/KEY: misc_signal
<222> LOCATION: (1)..(60)
<223> OTHER INFORMATION: Mouse Ig kappa signal

<400> SEQUENCE: 3
atggagacag acacactcct gctatgggta ctgctgctct ggttccagg ttccactggt      60 gacaaaactc acacatgccc accgtgccca gcacctgaac tcctgggagg accgtcagtc   120
ttcctcttcc cccaaaaacc caaggacacc ctcatgatct cccggacccc tgaggtcaca   180
tgcgtggtgg tggacgtgag ccacgaagac cctgaggtca agttcaactg gtacgtggac   240
ggcgtggagg tgcataatgc aagacaaag ccgcgggagg agcagtacaa cagcacgtac   300
cgtgtggtca gcgtcctcac cgtcctgcac caggactggc tgaatggcaa ggagtacaag   360
tgcaaggtct ccaacaaagc cctcccagcc ccatcgaga aaaccatctc caaagccaaa   420
gggcagcccc gagaaccaca ggtgtacacc ctgcccccat cccgcgatga gctgaccaag   480

```
aaccaggtca gcctgacctg cctggtcaaa ggcttctatc ccagcgacat cgccgtggag        540
tgggagagca atgggcagcc ggagaacaac tacaagacca cgcctcccgt gttggactcc        600
gacggctcct tcttcctcta cagcaagctc accgtggaca agagcaggtg gcagcagggg        660
aacgtcttct catgctccgt gatgcatgag gctctgcaca accactacac gcagaagagc        720
ctctccctgt ctccgggtaa a                                                   741
```

<210> SEQ ID NO 4
<211> LENGTH: 247
<212> TYPE: PRT
<213> ORGANISM: Artificial Sequence
<220> FEATURE:
<223> OTHER INFORMATION: Fc chain
<220> FEATURE:
<221> NAME/KEY: MISC_FEATURE
<222> LOCATION: (1)..(20)
<223> OTHER INFORMATION: heterologous signal from Mouse Ig kappa chain

<400> SEQUENCE: 4

```
Met Glu Thr Asp Thr Leu Leu Leu Trp Val Leu Leu Leu Trp Val Pro
1               5                   10                  15

Gly Ser Thr Gly Asp Lys Thr His Thr Cys Pro Pro Cys Pro Ala Pro
            20                  25                  30

Glu Leu Leu Gly Gly Pro Ser Val Phe Leu Phe Pro Pro Lys Pro Lys
        35                  40                  45

Asp Thr Leu Met Ile Ser Arg Thr Pro Glu Val Thr Cys Val Val Val
    50                  55                  60

Asp Val Ser His Glu Asp Pro Glu Val Lys Phe Asn Trp Tyr Val Asp
65                  70                  75                  80

Gly Val Glu Val His Asn Ala Lys Thr Lys Pro Arg Glu Glu Gln Tyr
                85                  90                  95

Asn Ser Thr Tyr Arg Val Val Ser Val Leu Thr Val Leu His Gln Asp
            100                 105                 110

Trp Leu Asn Gly Lys Glu Tyr Lys Cys Lys Val Ser Asn Lys Ala Leu
        115                 120                 125

Pro Ala Pro Ile Glu Lys Thr Ile Ser Lys Ala Lys Gly Gln Pro Arg
    130                 135                 140

Glu Pro Gln Val Tyr Thr Leu Pro Pro Ser Arg Asp Glu Leu Thr Lys
145                 150                 155                 160

Asn Gln Val Ser Leu Thr Cys Leu Val Lys Gly Phe Tyr Pro Ser Asp
                165                 170                 175

Ile Ala Val Glu Trp Glu Ser Asn Gly Gln Pro Glu Asn Asn Tyr Lys
            180                 185                 190

Thr Thr Pro Pro Val Leu Asp Ser Asp Gly Ser Phe Phe Leu Tyr Ser
        195                 200                 205

Lys Leu Thr Val Asp Lys Ser Arg Trp Gln Gln Gly Asn Val Phe Ser
    210                 215                 220

Cys Ser Val Met His Glu Ala Leu His Asn His Tyr Thr Gln Lys Ser
225                 230                 235                 240

Leu Ser Leu Ser Pro Gly Lys
                245
```

<210> SEQ ID NO 5
<211> LENGTH: 7734
<212> TYPE: DNA
<213> ORGANISM: Artificial Sequence
<220> FEATURE:

<223> OTHER INFORMATION: Full length FVIIIFc
<220> FEATURE:
<221> NAME/KEY: misc_signal
<222> LOCATION: (1)..(57)
<223> OTHER INFORMATION: FVIII signal
<220> FEATURE:
<221> NAME/KEY: misc_feature
<222> LOCATION: (7054)..(7734)
<223> OTHER INFORMATION: Fc region

<400> SEQUENCE: 5

| | | | | | |
|---|---|---|---|---|---|
| atgcaaatag | agctctccac | ctgcttcttt | ctgtgccttt | tgcgattctg | ctttagtgcc | 60 |
| accagaagat | actacctggg | tgcagtggaa | ctgtcatggg | actatatgca | aagtgatctc | 120 |
| ggtgagctgc | ctgtggacgc | aagatttcct | cctagagtgc | aaaatcttt | tccattcaac | 180 |
| acctcagtcg | tgtacaaaaa | gactctgttt | gtagaattca | cggatcacct | tttcaacatc | 240 |
| gctaagccaa | ggccaccctg | gatgggtctg | ctaggtccta | ccatccaggc | tgaggtttat | 300 |
| gatacagtgg | tcattacact | taagaacatg | gcttcccatc | ctgtcagtct | tcatgctgtt | 360 |
| ggtgtatcct | actggaaagc | ttctgaggga | gctgaatatg | atgatcagac | cagtcaaagg | 420 |
| gagaaagaag | atgataaagt | cttccctggt | ggaagccata | catatgtctg | gcaggtcctg | 480 |
| aaagagaatg | gtccaatggc | ctctgaccca | ctgtgcctta | cctactcata | tctttctcat | 540 |
| gtggacctgg | taaaagactt | gaattcaggc | ctcattggag | ccctactagt | atgtagagaa | 600 |
| gggagtctgg | ccaaggaaaa | gacacagacc | ttgcacaaat | ttatactact | ttttgctgta | 660 |
| tttgatgaag | ggaaaagttg | gcactcagaa | acaagaact | ccttgatgca | ggataggga | 720 |
| gctgcatctg | ctcgggcctg | gcctaaaatg | cacacagtca | atggttatgt | aaacaggtct | 780 |
| ctgccaggtc | tgattggatg | ccacaggaaa | tcagtctatt | ggcatgtgat | tggaatgggc | 840 |
| accactcctg | aagtgcactc | aatattcctc | gaaggtcaca | catttcttgt | gaggaaccat | 900 |
| cgccaggcgt | ccttggaaaat | ctcgccaata | actttcctta | ctgctcaaac | actcttgatg | 960 |
| gaccttggac | agtttctact | gttttgtcat | atctcttccc | accaacatga | tggcatggaa | 1020 |
| gcttatgtca | aagtagacag | ctgtccagag | gaaccccaac | tacgaatgaa | aaataatgaa | 1080 |
| gaagcggaag | actatgatga | tgatcttact | gattctgaaa | tggatgtggt | caggtttgat | 1140 |
| gatgacaact | ctccttcctt | tatccaaatt | cgctcagttg | ccaagaagca | tcctaaaact | 1200 |
| tgggtacatt | acattgctgc | tgaagaggag | gactgggact | atgctccctt | agtcctcgcc | 1260 |
| cccgatgaca | gaagttataa | aagtcaatat | ttgaacaatg | gccctcagcg | gattggtagg | 1320 |
| aagtacaaaa | aagtccgatt | tatggcatac | acagatgaaa | cctttaagac | tcgtgaagct | 1380 |
| attcagcatg | aatcaggaat | cttgggacct | ttactttatg | ggaagttgg | agacacactg | 1440 |
| ttgattatat | ttaagaatca | agcaagcaga | ccatataaca | tctaccctca | cggaatcact | 1500 |
| gatgtccgtc | ctttgtattc | aaggagatta | ccaaaaggtg | taaaacattt | gaaggatttt | 1560 |
| ccaattctgc | caggagaaat | attcaaatat | aaatggacag | tgactgtaga | agatgggcca | 1620 |
| actaaatcag | atcctcggtg | cctgacccgc | tattactcta | gtttcgttaa | tatggagaga | 1680 |
| gatctagctt | caggactcat | tggccctctc | ctcatctgct | acaaagaatc | tgtagatcaa | 1740 |
| agaggaaacc | agataatgtc | agacaagagg | aatgtcatcc | tgttttctgt | atttgatgag | 1800 |
| aaccgaagct | ggtacctcac | agagaatata | caacgctttc | tccccaatcc | agctggagtg | 1860 |
| cagcttgagg | atccagagtt | ccaagcctcc | aacatcatgc | acagcatcaa | tggctatgtt | 1920 |
| tttgatagtt | tgcagttgtc | agtttgtttg | catgaggtgg | catactggta | cattctaagc | 1980 |
| attggagcac | agactgactt | cctttctgtc | ttcttctctg | gatataccct | caaacacaaa | 2040 |

```
atggtctatg aagacacact caccctattc ccattctcag gagaaactgt cttcatgtcg    2100
atggaaaacc caggtctatg gattctgggg tgccacaact cagactttcg gaacagaggc    2160
atgaccgcct tactgaaggt ttctagttgt gacaagaaca ctggtgatta ttacgaggac    2220
agttatgaag atatttcagc atacttgctg agtaaaaaca atgccattga accaagaagc    2280
ttctcccaga attcaagaca ccctagcact aggcaaaagc aatttaatgc caccacaatt    2340
ccagaaaatg acatagagaa gactgaccct tggtttgcac acagaacacc tatgcctaaa    2400
atacaaaatg tctcctctag tgatttgttg atgctcttgc gacagagtcc tactccacat    2460
gggctatcct tatctgatct ccaagaagcc aaatatgaga ctttttctga tgatccatca    2520
cctggagcaa tagacagtaa taacagcctg tctgaaatga cacacttcag gccacagctc    2580
catcacagtg gggacatggt atttacccct gagtcaggcc tccaattaag attaaatgag    2640
aaactgggga caactgcagc aacagagttg aagaaacttg atttcaaagt ttctagtaca    2700
tcaaataatc tgatttcaac aattccatca gacaatttgg cagcaggtac tgataataca    2760
agttccttag acccccaag tatgccagtt cattatgata gtcaattaga taccactcta    2820
tttggcaaaa agtcatctcc ccttactgag tctggtggac ctctgagctt gagtgaagaa    2880
aataatgatt caaagttgtt agaatcaggt ttaatgaata gccaagaaag ttcatgggga    2940
aaaaatgtat cgtcaacaga gagtggtagg ttatttaaag ggaaaagagc tcatggacct    3000
gctttgttga ctaaagataa tgccttattc aaagttagca tctctttgtt aaagacaaac    3060
aaaacttcca ataattcagc aactaataga aagactcaca ttgatggccc atcattatta    3120
attgagaata gtccatcagt ctggcaaaat atattagaaa gtgacactga gtttaaaaaa    3180
gtgacacctt tgattcatga cagaatgctt atggacaaaa atgctacagc tttgaggcta    3240
aatcatatgt caaataaaac tacttcatca aaaaacatgg aaatggtcca acagaaaaaa    3300
gagggcccca ttccaccaga tgcacaaaat ccagatatgt cgttctttaa gatgctattc    3360
ttgccagaat cagcaaggtg gatacaaagg actcatggaa agaactctct gaactctggg    3420
caaggcccca gtccaaagca attagtatcc ttaggaccag aaaaatctgt ggaaggtcag    3480
aatttcttgt ctgagaaaaa caaagtggta gtaggaaagg gtgaatttac aaaggacgta    3540
ggactcaaag agatggtttt tccaagcagc agaaacctat ttcttactaa cttggataat    3600
ttacatgaaa ataatacaca caatcaagaa aaaaaaattc aggaagaaat agaaagaag    3660 gaaacattaa tccaagagaa tgtagttttg cctcagatac atacagtgac tggcactaag    3720
aatttcatga agaacctttt cttactgagc actaggcaaa atgtagaagg ttcatatgac    3780
ggggcatatg ctccagtact tcaagatttt aggtcattaa atgattcaac aaatagaaca    3840
aagaaacaca cagctcattt ctcaaaaaaa ggggaggaag aaaacttgga aggcttggga    3900
aatcaaacca agcaaattgt agagaaatat gcatgcacca caaggatatc tcctaataca    3960
agccagcaga tttttgtcac gcaacgtagt aagagagctt tgaaacaatt cagactccca    4020
ctagaagaaa cagaacttga aaaaggata attgtggatg acacctcaac ccagtggtcc    4080
aaaaacatga acatttgac cccgagcacc ctcacacaga tagactacaa tgagaaggag    4140
aaagggccca ttactcagtc tcccttatca gattgcctta cgaggagtca tagcatccct    4200
caagcaaata gatctccatt acccattgca aaggtatcat catttccatc tattagacct    4260
atatatctga ccagggtcct attccaagac aactcttctc atcttccagc agcatcttat    4320
agaaagaaag attctggggt ccaagaaagc agtcatttct tacaaggagc caaaaaaaat    4380
```

```
aacctttctt tagccattct aaccttggag atgactggtg atcaaagaga ggttggctcc    4440
ctggggacaa gtgccacaaa ttcagtcaca tacaagaaag ttgagaacac tgttctcccg    4500
aaaccagact tgcccaaaac atctggcaaa gttgaattgc ttccaaaagt tcacatttat    4560
cagaaggacc tattccctac ggaaactagc aatgggtctc ctggccatct ggatctcgtg    4620
gaagggagcc ttcttcaggg aacagaggga gcgattaagt ggaatgaagc aaacagacct    4680
ggaaaagttc cctttctgag agtagcaaca gaaagctctg caaagactcc ctccaagcta    4740
ttggatcctc ttgcttggga taaccactat ggtactcaga taccaaaaga agagtggaaa    4800
tcccaagaga agtcaccaga aaaaacagct tttaagaaaa aggataccat tttgtccctg    4860
aacgcttgtg aaagcaatca tgcaatagca gcaataaatg agggacaaaa taagcccgaa    4920
atagaagtca cctgggcaaa gcaaggtagg actgaaaggc tgtgctctca aaacccacca    4980
gtcttgaaac gccatcaacg ggaaataact cgtactactc ttcagtcaga tcaagaggaa    5040
attgactatg atgataccat atcagttgaa atgaagaagg aagattttga catttatgat    5100
gaggatgaaa atcagagccc ccgcagcttt caaaagaaaa cacgacacta ttttattgct    5160
gcagtggaga ggctctggga ttatgggatg agtagctccc cacatgttct aagaaacagg    5220
gctcagagtg gcagtgtccc tcagttcaag aaagttgttt tccaggaatt tactgatggc    5280
tcctttactc agcccttata ccgtggagaa ctaaatgaac atttgggact cctggggcca    5340
tatataagag cagaagttga agataatatc atggtaactt tcagaaatca ggcctctcgt    5400
ccctattcct tctattctag ccttatttct tatgaggaag atcagaggca aggagcagaa    5460
cctagaaaaa actttgtcaa gcctaatgaa accaaaactt acttttggaa agtgcaacat    5520
catatggcac ccactaaaga tgagtttgac tgcaaagcct gggcttattt ctctgatgtt    5580
gacctggaaa aagatgtgca ctcaggcctg attggacccc ttctggtctg ccacactaac    5640
acactgaacc ctgctcatgg gagacaagtg acagtacagg aatttgctct gttttttcacc    5700 atctttgatg agaccaaaag ctggtacttc actgaaaata tggaaagaaa ctgcagggct    5760
ccctgcaata tccagatgga agatcccact tttaaagaga attatcgctt ccatgcaatc    5820
aatggctaca taatggatac actacctggc ttagtaatgg ctcaggatca aaggattcga    5880
tggtatctgc tcagcatggg cagcaatgaa acatccatt  ctattcattt cagtggacat    5940
gtgttcactg tacgaaaaaa agaggagtat aaaatggcac tgtacaatct ctatccaggt    6000 gttttttgaga cagtggaaat gttaccatcc aaagctggaa tttggcgggt ggaatgcctt    6060
attggcgagc atctacatgc tgggatgagc acactttttc tggtgtacag caataagtgt    6120
cagactcccc tgggaatggc ttctggacac attagagatt ttcagattac agcttcagga    6180
caatatggac agtgggcccc aaagctggcc agacttcatt attccggatc aatcaatgcc    6240
tggagcacca aggagccctt ttcttggatc aaggtggatc tgttggcacc aatgattatt    6300
cacggcatca agacccaggg tgcccgtcag aagttctcca gcctctacat ctctcagttt    6360
atcatcatgt atagtcttga tgggaagaag tggcagactt atcgaggaaa ttccactgga    6420
accttaatgg tcttctttgg caatgtggat tcatctggga taaaacacaa tattttttaac    6480 cctccaatta ttgctcgata catccgtttg cacccaactc attatagcat cgcagcactt    6540
cttcgcatgg agttgatggg ctgtgattta aatagttgca gcatgccatt gggaatggag    6600
agtaaagcaa tatcagatgc acagattact gcttcatcct actttaccaa tatgtttgcc    6660
acctggtctc cttcaaaagc tcgacttcac ctccaaggga ggagtaatgc ctggagacct    6720
caggtgaata atccaaaaga gtggctgcaa gtggacttcc agaagacaat gaaagtcaca    6780
```

```
ggagtaacta ctcagggagt aaaatctctg cttaccagca tgtatgtgaa ggagttcctc    6840
atctccagca gtcaagatgg ccatcagtgg actctctttt ttcagaatgg caaagtaaag    6900 gttttcagg gaaatcaaga ctccttcaca cctgtggtga actctctaga cccaccgtta    6960
ctgactcgct accttcgaat tcaccccag agttgggtgc accagattgc ctgaggatg    7020 gaggttctgg gctgcgaggc acaggacctc tacgacaaaa ctcacacatg cccaccgtgc    7080
ccagctccag aactcctggg cggaccgtca gtcttcctct tccccccaaa acccaaggac    7140
accctcatga tctcccggac ccctgaggtc acatgcgtgg tggtggacgt gagccacgaa    7200
gaccctgagg tcaagttcaa ctggtacgtg gacggcgtgg aggtgcataa tgccaagaca    7260
aagccgcggg aggagcagta caacagcacg taccgtgtgg tcagcgtcct caccgtcctg    7320
caccaggact ggctgaatgg caaggagtac aagtgcaagg tctccaacaa agccctccca    7380
gcccccatcg agaaaaccat ctccaaagcc aaagggcagc ccgagaacc acaggtgtac    7440 accctgcccc catcccggga tgagctgacc aagaaccagg tcagcctgac ctgcctggtc    7500
aaaggcttct atcccagcga catcgccgtg gagtgggaga gcaatgggca gccggagaac    7560
aactacaaga ccacgcctcc cgtgttggac tccgacggct ccttcttcct ctacagcaag    7620
ctcaccgtgg acaagagcag gtggcagcag gggaacgtct tctcatgctc cgtgatgcat    7680
gaggctctgc acaaccacta cacgcagaag agcctctccc tgtctccggg taaa          7734
```

<210> SEQ ID NO 6
<211> LENGTH: 2578
<212> TYPE: PRT
<213> ORGANISM: Artificial Sequence
<220> FEATURE:
<223> OTHER INFORMATION: Full length FVIIIFc chain
<220> FEATURE:
<221> NAME/KEY: MISC_FEATURE
<222> LOCATION: (1)..(19)
<223> OTHER INFORMATION: FVIII signal
<220> FEATURE:
<221> NAME/KEY: MISC_FEATURE
<222> LOCATION: (20)..(759)
<223> OTHER INFORMATION: HC
<220> FEATURE:
<221> NAME/KEY: MISC_FEATURE
<222> LOCATION: (760)..(1667)
<223> OTHER INFORMATION: B domain
<220> FEATURE:
<221> NAME/KEY: MISC_FEATURE
<222> LOCATION: (2352)..(2578)
<223> OTHER INFORMATION: Fc region

<400> SEQUENCE: 6

```
Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
                20                  25                  30

Trp Asp Tyr Met Gln Ser Asp Leu Gly Glu Leu Pro Val Asp Ala Arg
            35                  40                  45

Phe Pro Pro Arg Val Pro Lys Ser Phe Pro Phe Asn Thr Ser Val Val
        50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110
```

```
His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
                180                 185                 190

Gly Ala Leu Leu Val Cys Arg Glu Gly Ser Leu Ala Lys Glu Lys Thr
                195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
                260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
                340                 345                 350

Gln Leu Arg Met Lys Asn Asn Glu Glu Ala Glu Asp Tyr Asp Asp Asp
    355                 360                 365

Leu Thr Asp Ser Glu Met Asp Val Val Arg Phe Asp Asp Asp Asn Ser
    370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415

Leu Val Leu Ala Pro Asp Asp Arg Ser Tyr Lys Ser Gln Tyr Leu Asn
                420                 425                 430

Asn Gly Pro Gln Arg Ile Gly Arg Lys Tyr Lys Lys Val Arg Phe Met
    435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
                500                 505                 510

Gly Val Lys His Leu Lys Asp Phe Pro Ile Leu Pro Gly Glu Ile Phe
                515                 520                 525
```

```
Lys Tyr Lys Trp Thr Val Thr Val Glu Asp Gly Pro Thr Lys Ser Asp
        530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
        580                 585                 590

Ile Leu Phe Ser Val Phe Asp Glu Asn Arg Ser Trp Tyr Leu Thr Glu
        595                 600                 605

Asn Ile Gln Arg Phe Leu Pro Asn Pro Ala Gly Val Gln Leu Glu Asp
        610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
            675                 680                 685

Leu Phe Pro Phe Ser Gly Glu Thr Val Phe Met Ser Met Glu Asn Pro
690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
            725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Ser Arg His Pro
        755                 760                 765

Ser Thr Arg Gln Lys Gln Phe Asn Ala Thr Thr Ile Pro Glu Asn Asp
        770                 775                 780

Ile Glu Lys Thr Asp Pro Trp Phe Ala His Arg Thr Pro Met Pro Lys
785                 790                 795                 800

Ile Gln Asn Val Ser Ser Ser Asp Leu Leu Met Leu Leu Arg Gln Ser
                805                 810                 815

Pro Thr Pro His Gly Leu Ser Leu Ser Asp Leu Gln Glu Ala Lys Tyr
                820                 825                 830

Glu Thr Phe Ser Asp Asp Pro Ser Pro Gly Ala Ile Asp Ser Asn Asn
            835                 840                 845

Ser Leu Ser Glu Met Thr His Phe Arg Pro Gln Leu His His Ser Gly
        850                 855                 860

Asp Met Val Phe Thr Pro Glu Ser Gly Leu Gln Leu Arg Leu Asn Glu
865                 870                 875                 880

Lys Leu Gly Thr Thr Ala Ala Thr Glu Leu Lys Lys Leu Asp Phe Lys
                885                 890                 895

Val Ser Ser Thr Ser Asn Asn Leu Ile Ser Thr Ile Pro Ser Asp Asn
            900                 905                 910

Leu Ala Ala Gly Thr Asp Asn Thr Ser Ser Leu Gly Pro Pro Ser Met
            915                 920                 925

Pro Val His Tyr Asp Ser Gln Leu Asp Thr Thr Leu Phe Gly Lys Lys
        930                 935                 940

Ser Ser Pro Leu Thr Glu Ser Gly Gly Pro Leu Ser Leu Ser Glu Glu
```

-continued

```
             945                 950                 955                 960
Asn  Asn  Asp  Ser  Lys  Leu  Leu  Glu  Ser  Gly  Leu  Met  Asn  Ser  Gln  Glu
                      965                 970                 975
Ser  Ser  Trp  Gly  Lys  Asn  Val  Ser  Ser  Thr  Glu  Ser  Gly  Arg  Leu  Phe
                      980                 985                 990
Lys  Gly  Lys  Arg  Ala  His  Gly  Pro  Ala  Leu  Leu  Thr  Lys  Asp  Asn  Ala
                      995                1000                1005
Leu  Phe  Lys  Val  Ser  Ile  Ser  Leu  Leu  Lys  Thr  Asn  Lys  Thr  Ser
    1010                1015                1020
Asn  Asn  Ser  Ala  Thr  Asn  Arg  Lys  Thr  His  Ile  Asp  Gly  Pro  Ser
    1025                1030                1035
Leu  Leu  Ile  Glu  Asn  Ser  Pro  Ser  Val  Trp  Gln  Asn  Ile  Leu  Glu
    1040                1045                1050
Ser  Asp  Thr  Glu  Phe  Lys  Lys  Val  Thr  Pro  Leu  Ile  His  Asp  Arg
    1055                1060                1065
Met  Leu  Met  Asp  Lys  Asn  Ala  Thr  Ala  Leu  Arg  Leu  Asn  His  Met
    1070                1075                1080
Ser  Asn  Lys  Thr  Thr  Ser  Ser  Lys  Asn  Met  Glu  Met  Val  Gln  Gln
    1085                1090                1095
Lys  Lys  Glu  Gly  Pro  Ile  Pro  Pro  Asp  Ala  Gln  Asn  Pro  Asp  Met
    1100                1105                1110
Ser  Phe  Phe  Lys  Met  Leu  Phe  Leu  Pro  Glu  Ser  Ala  Arg  Trp  Ile
    1115                1120                1125
Gln  Arg  Thr  His  Gly  Lys  Asn  Ser  Leu  Asn  Ser  Gly  Gln  Gly  Pro
    1130                1135                1140
Ser  Pro  Lys  Gln  Leu  Val  Ser  Leu  Gly  Pro  Glu  Lys  Ser  Val  Glu
    1145                1150                1155
Gly  Gln  Asn  Phe  Leu  Ser  Glu  Lys  Asn  Lys  Val  Val  Val  Gly  Lys
    1160                1165                1170
Gly  Glu  Phe  Thr  Lys  Asp  Val  Gly  Leu  Lys  Glu  Met  Val  Phe  Pro
    1175                1180                1185
Ser  Ser  Arg  Asn  Leu  Phe  Leu  Thr  Asn  Leu  Asp  Asn  Leu  His  Glu
    1190                1195                1200
Asn  Asn  Thr  His  Asn  Gln  Glu  Lys  Lys  Ile  Gln  Glu  Glu  Ile  Glu
    1205                1210                1215
Lys  Lys  Glu  Thr  Leu  Ile  Gln  Glu  Asn  Val  Val  Leu  Pro  Gln  Ile
    1220                1225                1230
His  Thr  Val  Thr  Gly  Thr  Lys  Asn  Phe  Met  Lys  Asn  Leu  Phe  Leu
    1235                1240                1245
Leu  Ser  Thr  Arg  Gln  Asn  Val  Glu  Gly  Ser  Tyr  Asp  Gly  Ala  Tyr
    1250                1255                1260
Ala  Pro  Val  Leu  Gln  Asp  Phe  Arg  Ser  Leu  Asn  Asp  Ser  Thr  Asn
    1265                1270                1275
Arg  Thr  Lys  Lys  His  Thr  Ala  His  Phe  Ser  Lys  Lys  Gly  Glu  Glu
    1280                1285                1290
Glu  Asn  Leu  Glu  Gly  Leu  Gly  Asn  Gln  Thr  Lys  Gln  Ile  Val  Glu
    1295                1300                1305
Lys  Tyr  Ala  Cys  Thr  Thr  Arg  Ile  Ser  Pro  Asn  Thr  Ser  Gln  Gln
    1310                1315                1320
Asn  Phe  Val  Thr  Gln  Arg  Ser  Lys  Arg  Ala  Leu  Lys  Gln  Phe  Arg
    1325                1330                1335
Leu  Pro  Leu  Glu  Glu  Thr  Glu  Leu  Glu  Lys  Arg  Ile  Ile  Val  Asp
    1340                1345                1350
```

```
Asp Thr Ser Thr Gln Trp Ser Lys Asn Met Lys His Leu Thr Pro
    1355                1360                1365

Ser Thr Leu Thr Gln Ile Asp Tyr Asn Glu Lys Glu Lys Gly Ala
    1370                1375                1380

Ile Thr Gln Ser Pro Leu Ser Asp Cys Leu Thr Arg Ser His Ser
    1385                1390                1395

Ile Pro Gln Ala Asn Arg Ser Pro Leu Pro Ile Ala Lys Val Ser
    1400                1405                1410

Ser Phe Pro Ser Ile Arg Pro Ile Tyr Leu Thr Arg Val Leu Phe
    1415                1420                1425

Gln Asp Asn Ser Ser His Leu Pro Ala Ala Ser Tyr Arg Lys Lys
    1430                1435                1440

Asp Ser Gly Val Gln Glu Ser Ser His Phe Leu Gln Gly Ala Lys
    1445                1450                1455

Lys Asn Asn Leu Ser Leu Ala Ile Leu Thr Leu Glu Met Thr Gly
    1460                1465                1470

Asp Gln Arg Glu Val Gly Ser Leu Gly Thr Ser Ala Thr Asn Ser
    1475                1480                1485

Val Thr Tyr Lys Lys Val Glu Asn Thr Val Leu Pro Lys Pro Asp
    1490                1495                1500

Leu Pro Lys Thr Ser Gly Lys Val Glu Leu Leu Pro Lys Val His
    1505                1510                1515

Ile Tyr Gln Lys Asp Leu Phe Pro Thr Glu Thr Ser Asn Gly Ser
    1520                1525                1530

Pro Gly His Leu Asp Leu Val Glu Gly Ser Leu Leu Gln Gly Thr
    1535                1540                1545

Glu Gly Ala Ile Lys Trp Asn Glu Ala Asn Arg Pro Gly Lys Val
    1550                1555                1560

Pro Phe Leu Arg Val Ala Thr Glu Ser Ser Ala Lys Thr Pro Ser
    1565                1570                1575

Lys Leu Leu Asp Pro Leu Ala Trp Asp Asn His Tyr Gly Thr Gln
    1580                1585                1590

Ile Pro Lys Glu Glu Trp Lys Ser Gln Glu Lys Ser Pro Glu Lys
    1595                1600                1605

Thr Ala Phe Lys Lys Lys Asp Thr Ile Leu Ser Leu Asn Ala Cys
    1610                1615                1620

Glu Ser Asn His Ala Ile Ala Ala Ile Asn Glu Gly Gln Asn Lys
    1625                1630                1635

Pro Glu Ile Glu Val Thr Trp Ala Lys Gln Gly Arg Thr Glu Arg
    1640                1645                1650

Leu Cys Ser Gln Asn Pro Pro Val Leu Lys Arg His Gln Arg Glu
    1655                1660                1665

Ile Thr Arg Thr Thr Leu Gln Ser Asp Gln Glu Glu Ile Asp Tyr
    1670                1675                1680

Asp Asp Thr Ile Ser Val Glu Met Lys Lys Glu Asp Phe Asp Ile
    1685                1690                1695

Tyr Asp Glu Asp Glu Asn Gln Ser Pro Arg Ser Phe Gln Lys Lys
    1700                1705                1710

Thr Arg His Tyr Phe Ile Ala Ala Val Glu Arg Leu Trp Asp Tyr
    1715                1720                1725

Gly Met Ser Ser Ser Pro His Val Leu Arg Asn Arg Ala Gln Ser
    1730                1735                1740
```

Gly Ser Val Pro Gln Phe Lys Lys Val Val Phe Gln Glu Phe Thr
1745                1750                1755

Asp Gly Ser Phe Thr Gln Pro Leu Tyr Arg Gly Glu Leu Asn Glu
1760                1765                1770

His Leu Gly Leu Leu Gly Pro Tyr Ile Arg Ala Glu Val Glu Asp
1775                1780                1785

Asn Ile Met Val Thr Phe Arg Asn Gln Ala Ser Arg Pro Tyr Ser
1790                1795                1800

Phe Tyr Ser Ser Leu Ile Ser Tyr Glu Glu Asp Gln Arg Gln Gly
1805                1810                1815

Ala Glu Pro Arg Lys Asn Phe Val Lys Pro Asn Glu Thr Lys Thr
1820                1825                1830

Tyr Phe Trp Lys Val Gln His His Met Ala Pro Thr Lys Asp Glu
1835                1840                1845

Phe Asp Cys Lys Ala Trp Ala Tyr Phe Ser Asp Val Asp Leu Glu
1850                1855                1860

Lys Asp Val His Ser Gly Leu Ile Gly Pro Leu Leu Val Cys His
1865                1870                1875

Thr Asn Thr Leu Asn Pro Ala His Gly Arg Gln Val Thr Val Gln
1880                1885                1890

Glu Phe Ala Leu Phe Phe Thr Ile Phe Asp Glu Thr Lys Ser Trp
1895                1900                1905

Tyr Phe Thr Glu Asn Met Glu Arg Asn Cys Arg Ala Pro Cys Asn
1910                1915                1920

Ile Gln Met Glu Asp Pro Thr Phe Lys Glu Asn Tyr Arg Phe His
1925                1930                1935

Ala Ile Asn Gly Tyr Ile Met Asp Thr Leu Pro Gly Leu Val Met
1940                1945                1950

Ala Gln Asp Gln Arg Ile Arg Trp Tyr Leu Leu Ser Met Gly Ser
1955                1960                1965

Asn Glu Asn Ile His Ser Ile His Phe Ser Gly His Val Phe Thr
1970                1975                1980

Val Arg Lys Lys Glu Glu Tyr Lys Met Ala Leu Tyr Asn Leu Tyr
1985                1990                1995

Pro Gly Val Phe Glu Thr Val Glu Met Leu Pro Ser Lys Ala Gly
2000                2005                2010

Ile Trp Arg Val Glu Cys Leu Ile Gly Glu His Leu His Ala Gly
2015                2020                2025

Met Ser Thr Leu Phe Leu Val Tyr Ser Asn Lys Cys Gln Thr Pro
2030                2035                2040

Leu Gly Met Ala Ser Gly His Ile Arg Asp Phe Gln Ile Thr Ala
2045                2050                2055

Ser Gly Gln Tyr Gly Gln Trp Ala Pro Lys Leu Ala Arg Leu His
2060                2065                2070

Tyr Ser Gly Ser Ile Asn Ala Trp Ser Thr Lys Glu Pro Phe Ser
2075                2080                2085

Trp Ile Lys Val Asp Leu Leu Ala Pro Met Ile Ile His Gly Ile
2090                2095                2100

Lys Thr Gln Gly Ala Arg Gln Lys Phe Ser Ser Leu Tyr Ile Ser
2105                2110                2115

Gln Phe Ile Ile Met Tyr Ser Leu Asp Gly Lys Lys Trp Gln Thr
2120                2125                2130

Tyr Arg Gly Asn Ser Thr Gly Thr Leu Met Val Phe Phe Gly Asn

-continued

```
            2135                2140                2145

Val Asp Ser Ser Gly Ile Lys His Asn Ile Phe Asn Pro Pro Ile
            2150                2155                2160

Ile Ala Arg Tyr Ile Arg Leu His Pro Thr His Tyr Ser Ile Arg
            2165                2170                2175

Ser Thr Leu Arg Met Glu Leu Met Gly Cys Asp Leu Asn Ser Cys
            2180                2185                2190

Ser Met Pro Leu Gly Met Glu Ser Lys Ala Ile Ser Asp Ala Gln
            2195                2200                2205

Ile Thr Ala Ser Ser Tyr Phe Thr Asn Met Phe Ala Thr Trp Ser
            2210                2215                2220

Pro Ser Lys Ala Arg Leu His Leu Gln Gly Arg Ser Asn Ala Trp
            2225                2230                2235

Arg Pro Gln Val Asn Asn Pro Lys Glu Trp Leu Gln Val Asp Phe
            2240                2245                2250

Gln Lys Thr Met Lys Val Thr Gly Val Thr Thr Gln Gly Val Lys
            2255                2260                2265

Ser Leu Leu Thr Ser Met Tyr Val Lys Glu Phe Leu Ile Ser Ser
            2270                2275                2280

Ser Gln Asp Gly His Gln Trp Thr Leu Phe Phe Gln Asn Gly Lys
            2285                2290                2295

Val Lys Val Phe Gln Gly Asn Gln Asp Ser Phe Thr Pro Val Val
            2300                2305                2310

Asn Ser Leu Asp Pro Pro Leu Leu Thr Arg Tyr Leu Arg Ile His
            2315                2320                2325

Pro Gln Ser Trp Val His Gln Ile Ala Leu Arg Met Glu Val Leu
            2330                2335                2340

Gly Cys Glu Ala Gln Asp Leu Tyr Asp Lys Thr His Thr Cys Pro
            2345                2350                2355

Pro Cys Pro Ala Pro Glu Leu Leu Gly Gly Pro Ser Val Phe Leu
            2360                2365                2370

Phe Pro Pro Lys Pro Lys Asp Thr Leu Met Ile Ser Arg Thr Pro
            2375                2380                2385

Glu Val Thr Cys Val Val Val Asp Val Ser His Glu Asp Pro Glu
            2390                2395                2400

Val Lys Phe Asn Trp Tyr Val Asp Gly Val Glu Val His Asn Ala
            2405                2410                2415

Lys Thr Lys Pro Arg Glu Glu Gln Tyr Asn Ser Thr Tyr Arg Val
            2420                2425                2430

Val Ser Val Leu Thr Val Leu His Gln Asp Trp Leu Asn Gly Lys
            2435                2440                2445

Glu Tyr Lys Cys Lys Val Ser Asn Lys Ala Leu Pro Ala Pro Ile
            2450                2455                2460

Glu Lys Thr Ile Ser Lys Ala Lys Gly Gln Pro Arg Glu Pro Gln
            2465                2470                2475

Val Tyr Thr Leu Pro Pro Ser Arg Asp Glu Leu Thr Lys Asn Gln
            2480                2485                2490

Val Ser Leu Thr Cys Leu Val Lys Gly Phe Tyr Pro Ser Asp Ile
            2495                2500                2505

Ala Val Glu Trp Glu Ser Asn Gly Gln Pro Glu Asn Asn Tyr Lys
            2510                2515                2520

Thr Thr Pro Pro Val Leu Asp Ser Asp Gly Ser Phe Phe Leu Tyr
            2525                2530                2535
```

```
Ser Lys Leu Thr Val Asp Lys Ser Arg Trp Gln Gln Gly Asn Val
    2540                2545                2550

Phe Ser Cys Ser Val Met His Glu Ala Leu His Asn His Tyr Thr
    2555                2560                2565

Gln Lys Ser Leu Ser Leu Ser Pro Gly Lys
    2570                2575

<210> SEQ ID NO 7
<211> LENGTH: 11
<212> TYPE: PRT
<213> ORGANISM: Artificial Sequence
<220> FEATURE:
<223> OTHER INFORMATION: albumin-binding peptide

<400> SEQUENCE: 7

Asp Ile Cys Leu Pro Arg Trp Gly Cys Leu Trp
1               5                   10

<210> SEQ ID NO 8
<211> LENGTH: 32
<212> TYPE: PRT
<213> ORGANISM: Artificial Sequence
<220> FEATURE:
<223> OTHER INFORMATION: CTP peptide

<400> SEQUENCE: 8

Asp Pro Arg Phe Gln Asp Ser Ser Ser Lys Ala Pro Pro Pro Ser
1               5                   10                  15

Leu Pro Ser Pro Ser Arg Leu Pro Gly Pro Ser Asp Thr Pro Ile Leu
            20                  25                  30

<210> SEQ ID NO 9
<211> LENGTH: 28
<212> TYPE: PRT
<213> ORGANISM: Artificial Sequence
<220> FEATURE:
<223> OTHER INFORMATION: CTP Peptide

<400> SEQUENCE: 9

Ser Ser Ser Ser Lys Ala Pro Pro Pro Ser Leu Pro Ser Pro Ser Arg
1               5                   10                  15

Leu Pro Gly Pro Ser Asp Thr Pro Ile Leu Pro Gln
            20                  25

<210> SEQ ID NO 10
<211> LENGTH: 20
<212> TYPE: PRT
<213> ORGANISM: Artificial Sequence
<220> FEATURE:
<223> OTHER INFORMATION: PAS peptide

<400> SEQUENCE: 10

Ala Ser Pro Ala Ala Pro Ala Pro Ala Ser Pro Ala Ala Pro Ala Pro
1               5                   10                  15

Ser Ala Pro Ala
            20

<210> SEQ ID NO 11
<211> LENGTH: 20
<212> TYPE: PRT
<213> ORGANISM: Artificial Sequence
<220> FEATURE:
<223> OTHER INFORMATION: PAS peptide
```

```
<400> SEQUENCE: 11

Ala Ala Pro Ala Ser Pro Ala Pro Ala Ala Pro Ser Ala Pro Ala Pro
1               5                   10                  15

Ala Ala Pro Ser
            20

<210> SEQ ID NO 12
<211> LENGTH: 20
<212> TYPE: PRT
<213> ORGANISM: Artificial Sequence
<220> FEATURE:
<223> OTHER INFORMATION: PAS peptide

<400> SEQUENCE: 12

Ala Pro Ser Ser Pro Ser Pro Ser Ala Pro Ser Ser Pro Ser Pro Ala
1               5                   10                  15

Ser Pro Ser Ser
            20

<210> SEQ ID NO 13
<211> LENGTH: 19
<212> TYPE: PRT
<213> ORGANISM: Artificial Sequence
<220> FEATURE:
<223> OTHER INFORMATION: PAS peptide

<400> SEQUENCE: 13

Ala Pro Ser Ser Pro Ser Pro Ser Ala Pro Ser Ser Pro Ser Pro Ala
1               5                   10                  15

Ser Pro Ser

<210> SEQ ID NO 14
<211> LENGTH: 20
<212> TYPE: PRT
<213> ORGANISM: Artificial Sequence
<220> FEATURE:
<223> OTHER INFORMATION: PAS peptide

<400> SEQUENCE: 14

Ser Ser Pro Ser Ala Pro Ser Pro Ser Ser Pro Ala Ser Pro Ser Pro
1               5                   10                  15

Ser Ser Pro Ala
            20

<210> SEQ ID NO 15
<211> LENGTH: 24
<212> TYPE: PRT
<213> ORGANISM: Artificial Sequence
<220> FEATURE:
<223> OTHER INFORMATION: PAS peptide

<400> SEQUENCE: 15

Ala Ala Ser Pro Ala Ala Pro Ser Ala Pro Pro Ala Ala Ala Ser Pro
1               5                   10                  15

Ala Ala Pro Ser Ala Pro Pro Ala
            20

<210> SEQ ID NO 16
<211> LENGTH: 20
<212> TYPE: PRT
<213> ORGANISM: Artificial Sequence
<220> FEATURE:
<223> OTHER INFORMATION: PAS peptide
```

```
<400> SEQUENCE: 16

Ala Ser Ala Ala Ala Pro Ala Ala Ala Ser Ala Ala Ala Ser Ala Pro
1               5                   10                  15

Ser Ala Ala Ala
            20
```